(12) United States Patent
Blum et al.

(10) Patent No.: US 12,702,862 B2
(45) Date of Patent: Aug. 11, 2026

(54) FILTERING EYEWEAR AND OPTICS FOR OCULAR PHOTO-BIO-STIMULATION

(71) Applicant: NeuroRays, LLC, Atlanta, GA (US)

(72) Inventors: Ronald Blum, Atlanta, GA (US); Jack Loeb, Fisher Island, FL (US); Anita Broach, Christiansburg, VA (US)

(73) Assignee: NEURORAYS, LLC, Atlanta, GA (US)

( * ) Notice: Subject to any disclaimer, the term of this patent is extended or adjusted under 35 U.S.C. 154(b) by 0 days.

(21) Appl. No.: 18/914,202

(22) Filed: Oct. 13, 2024

(65) Prior Publication Data

US 2025/0082959 A1 Mar. 13, 2025

Related U.S. Application Data

(63) Continuation of application No. 18/827,786, filed on Sep. 8, 2024, now Pat. No. 12,409,338, and a continuation of application No. 18/827,782, filed on Sep. 8, 2024, now Pat. No. 12,409,337.

(60) Provisional application No. 63/697,560, filed on Sep. 22, 2024, provisional application No. 63/684,509, filed on Aug. 19, 2024, provisional application No. 63/676,855, filed on Jul. 29, 2024, provisional (Continued)

(51) Int. Cl.

*A61N 5/06* (2006.01)
*G16H 40/63* (2018.01)

(52) U.S. Cl.

CPC .......... *A61N 5/0622* (2013.01); *G16H 40/63* (2018.01); *A61N 2005/0627* (2013.01); *A61N 2005/063* (2013.01); *A61N 2005/0648* (2013.01); *A61N 2005/0653* (2013.01); *A61N 2005/0654* (2013.01); *A61N 2005/0656* (2013.01); *A61N 2005/0663* (2013.01); *A61N 2005/0667* (2013.01)

(58) Field of Classification Search

CPC .......... A61N 5/0622; A61N 2005/0648; A61N 2005/0663; A61N 2005/0667; A61N 2005/0647; A61N 2005/0657; A61N 2005/0662; A61N 5/0618; A61N 2005/0627; A61N 2005/063; A61N 2005/0653; A61N 2005/0654; A61N 2005/0656; G16H 40/63

See application file for complete search history.

(56) References Cited

U.S. PATENT DOCUMENTS 3,826,751 A 7/1974 Laliberte
5,083,858 A 1/1992 Girerd (Continued)

FOREIGN PATENT DOCUMENTS

CN 103926710 A 7/2014
CN 111938911 A 11/2020

(Continued)

OTHER PUBLICATIONS

Cardinal Intellectual Property Patent Search Report dated Nov. 4, 2024.

(Continued)

*Primary Examiner* — Niketa Patel
*Assistant Examiner* — Sebastian X Lukjan
(74) *Attorney, Agent, or Firm* — Woods Rogers Vandeventer Black PLC; Nathan A. Evans

(57) ABSTRACT

A device providing ocular photo-bio-stimulation therapy.

28 Claims, 90 Drawing Sheets

Related U.S. Application Data application No. 63/674,219, filed on Jul. 22, 2024, provisional application No. 63/673,746, filed on Jul. 21, 2024, provisional application No. 63/671,237, filed on Jul. 14, 2024, provisional application No. 63/654,566, filed on May 31, 2024, provisional application No. 63/648,098, filed on May 15, 2024, provisional application No. 63/639,892, filed on Apr. 29, 2024, provisional application No. 63/569,005, filed on Mar. 22, 2024, provisional application No. 63/561,266, filed on Mar. 4, 2024, provisional application No. 63/553,693, filed on Feb. 15, 2024, provisional application No. 63/553,226, filed on Feb. 14, 2024, provisional application No. 63/550,852, filed on Feb. 7, 2024, provisional application No. 63/627,703, filed on Jan. 31, 2024, provisional application No. 63/623,253, filed on Jan. 20, 2024, provisional application No. 63/617,363, filed on Jan. 3, 2024, provisional application No. 63/609,306, filed on Dec. 12, 2023, provisional application No. 63/603,258, filed on Nov. 28, 2023, provisional application No. 63/600,139, filed on Nov. 17, 2023, provisional application No. 63/548,204, filed on Nov. 12, 2023, provisional application No. 63/546,848, filed on Nov. 1, 2023, provisional application No. 63/541,243, filed on Sep. 28, 2023, provisional application No. 63/540,090, filed on Sep. 24, 2023, provisional application No. 63/537,021, filed on Sep. 7, 2023.

(56) References Cited

U.S. PATENT DOCUMENTS

| | | | | |
|---|---|---|---|---|
| 5,243,460 | A | 9/1993 | Kornberg | |
| 5,838,419 | A * | 11/1998 | Holland | G02C 7/02 623/4.1 |
| 5,923,398 | A | 7/1999 | Goldman | |
| 6,350,275 | B1 | 2/2002 | Vreman et al. | |
| 8,469,512 | B2 | 6/2013 | Croft et al. | |
| 8,833,937 | B2 | 9/2014 | Shehadeh et al. | |
| 8,911,082 | B2 | 12/2014 | Ambler | |
| 9,028,064 | B2 | 5/2015 | Harris | |
| 9,138,595 | B2 | 9/2015 | Savage et al. | |
| 9,720,228 | B2 | 8/2017 | Harrison et al. | |
| 9,885,884 | B2 | 2/2018 | Drobe | |
| 10,073,283 | B2 | 9/2018 | Legerton | |
| 10,152,906 | B2 | 12/2018 | Gutierrez | |
| 10,219,944 | B2 | 3/2019 | Tedford et al. | |
| 10,386,654 | B2 | 8/2019 | Marshall et al. | |
| 10,444,505 | B2 | 10/2019 | Rousseau et al. | |
| 10,884,246 | B2 | 1/2021 | Blum et al. | |
| 10,884,264 | B2 | 1/2021 | Hones et al. | |
| 10,895,735 | B1 | 1/2021 | Feinbloom et al. | |
| 10,942,373 | B2 | 3/2021 | Barrau et al. | |
| 11,029,540 | B2 | 6/2021 | To et al. | |
| 11,048,103 | B2 | 6/2021 | Saylor et al. | |
| 11,061,255 | B2 | 7/2021 | Lau et al. | |
| 11,065,468 | B2 | 7/2021 | Barrau et al. | |
| 11,086,145 | B2 | 8/2021 | Flinders | |
| 11,099,408 | B2 | 8/2021 | McCabe et al. | |
| 11,131,869 | B2 | 9/2021 | Marshall et al. | |
| 11,420,072 | B2 | 8/2022 | He et al. | |
| 11,446,514 | B2 | 9/2022 | Bahmani et al. | |
| 11,701,315 | B2 | 7/2023 | Ishak et al. | |
| 11,711,600 | B2 | 7/2023 | Han et al. | |
| 11,774,784 | B2 | 10/2023 | Barrau et al. | |
| 12,055,797 | B2 | 8/2024 | Newman et al. | |
| 12,336,937 | B2 | 6/2025 | Tedford et al. | |
| 2002/0198577 | A1 | 12/2002 | Jaillet | |
| 2010/0033830 | A1 | 2/2010 | Yung | |
| 2010/0103371 | A1 | 4/2010 | Sarver et al. | |
| 2010/0152849 | A1 | 6/2010 | Degenaar et al. | |
| 2012/0200823 | A1 | 8/2012 | Bandhauer et al. | |
| 2013/0211178 | A1 | 8/2013 | Brigatti et al. | |
| 2014/0176898 | A1 | 6/2014 | Yi et al. | |
| 2014/0247423 | A1 | 9/2014 | Drobe | |
| 2015/0088231 | A1 | 3/2015 | Rubinfeld et al. | |
| 2015/0142086 | A1 | 5/2015 | Narita | |
| 2015/0234207 | A1 | 8/2015 | Koifman | |
| 2016/0022225 | A1 | 1/2016 | Palmer et al. | |
| 2016/0026005 | A1* | 1/2016 | Flinders | G02C 7/10 351/159.63 |
| 2016/0067086 | A1 | 3/2016 | Tedford et al. | |
| 2016/0216537 | A1 | 7/2016 | Drobe | |
| 2016/0270656 | A1 | 9/2016 | Samec et al. | |
| 2016/0361437 | A1 | 12/2016 | Lucas et al. | |
| 2017/0299898 | A1 | 10/2017 | Gallina et al. | |
| 2018/0035101 | A1* | 2/2018 | Osterhout | G02B 27/0172 |
| 2019/0204624 | A1 | 7/2019 | Barrau et al. | |
| 2019/0212581 | A1 | 7/2019 | Scherlen et al. | |
| 2019/0258086 | A1 | 8/2019 | Barrau et al. | |
| 2021/0031051 | A1* | 2/2021 | Kubota | A61N 5/0622 |
| 2021/0132416 | A1* | 5/2021 | Newman | B29D 11/00144 |
| 2021/0157172 | A1 | 5/2021 | Barrau et al. | |
| 2021/0382325 | A1 | 12/2021 | Kubota et al. | |
| 2022/0047887 | A1 | 2/2022 | Honold et al. | |
| 2022/0057651 | A1 | 2/2022 | Segre et al. | |
| 2022/0062634 | A1 | 3/2022 | Masko et al. | |
| 2022/0075211 | A1* | 3/2022 | Schmeder | G02C 7/022 |
| 2022/0082860 | A1 | 3/2022 | Guillot et al. | |
| 2022/0111228 | A1 | 4/2022 | Schoutens | |
| 2022/0187628 | A1 | 6/2022 | Valentine et al. | |
| 2022/0233878 | A1 | 7/2022 | Lee et al. | |
| 2022/0252904 | A1 | 8/2022 | Hones, Jr. et al. | |
| 2022/0397774 | A1 | 12/2022 | Barrau et al. | |
| 2022/0413318 | A1 | 12/2022 | Kubota et al. | |
| 2023/0132952 | A1 | 5/2023 | Youngblood et al. | |
| 2023/0204982 | A1* | 6/2023 | Boyles | G02C 7/104 351/159.65 |
| 2023/0248937 | A1 | 8/2023 | Blair et al. | |
| 2023/0248993 | A1 | 8/2023 | Bahmani et al. | |
| 2023/0338742 | A1* | 10/2023 | Pang | A61N 5/0616 |
| 2023/0389161 | A1 | 11/2023 | Coleman | |
| 2024/0036357 | A1 | 2/2024 | Schianchi et al. | |
| 2024/0272454 | A1 | 8/2024 | Zheleznyak et al. | |
| 2024/0359031 | A1 | 10/2024 | Marshall et al. | |

FOREIGN PATENT DOCUMENTS

| | | | |
|---|---|---|---|
| CN | 212973238 | U | 4/2021 |
| EP | 2772794 | A1 | 9/2014 |
| EP | 3528036 | A1 | 8/2019 |
| EP | 3528037 | A1 | 8/2019 |
| EP | 4248925 | A2 | 9/2023 |
| EP | 4296762 | A1 | 12/2023 |
| KR | 20130006766 | U | 11/2013 |
| KR | 102195466 | B1 | 12/2020 |
| KR | 102436963 | B1 | 8/2022 |
| WO | 2019109125 | A1 | 6/2019 |
| WO | 2021105979 | A1 | 6/2021 |
| WO | 2021116449 | A1 | 6/2021 |
| WO | 2021252319 | A1 | 12/2021 |
| WO | 2022094678 | A1 | 5/2022 |
| WO | 2022187279 | A1 | 9/2022 |
| WO | 2022219441 | A1 | 10/2022 |
| WO | 2022258572 | A1 | 12/2022 |
| WO | 2023186146 | A1 | 10/2023 |
| WO | 2024094884 | A1 | 5/2024 |

OTHER PUBLICATIONS

Chakraborty, R., et al.; Axial length reduction and choroidal thickening with short-term exposure to cyan light in human subjects; Ophthalmic Physiol Opt. 2024;00:1-19. https://doi.org/10.1111/opo.13390.

National Academies of Sciences, Engineering, and Medicine. 2024. Myopia: Causes, Prevention, and Treatment of an Increasingly Common Disease. Washington, DC: The National Academies Press. https://doi.org/10.17226/27734.

(56) References Cited

OTHER PUBLICATIONS

Visible Bandpass Filters; Optical Filter Shop; retrieved at https://opticalfiltershop.com/product-category/bandpass-filter/visible-bandpass-filters-390nm-to-750nm/?srsltid=AfmBOoq17fx_K3qa6-4IEMggf0z4wh0-EXqLU41U1dkCunEv0lyDQzcw on Nov. 8, 2024.
Application No. PCT/US2024/051175, International Search Report and Written Opinion dated Nov. 25, 2024.
Application No. PCT/US2024/053151, International Search Report and Written Opinion dated Jan. 2, 2025.
Application No. PCT/US2024/056407, International Search Report and Written Opinion dated Jan. 17, 2025.
Application No. PCT/US2024/045750, International Search Report and Written Opinion dated Dec. 16, 2024.
Application No. PCT/US2024/045751, International Search Report and Written Opinion dated Dec. 16, 2024.
Application No. PCT/US2024/057354, International Search Report and Written Opinion dated Feb. 3, 2025.
Application No. PCT/US2025/012142, International Search Report and Written Opinion dated Mar. 5, 2025.
Capovilla, G.; Effectiveness of a particular blue lens on photoparoxysmal response in photosensitive epileptic patients; Ital J. Neurol Sci (1999) 20:161-166.
www.dopavision.com/product/, visited Sep. 11, 2024.
Akerman, D., Predicting the Onset of Myopia in Children, Review of Myopia Management, Jul. 15, 2024, https://reviewofmm.com/predicting-the-onset-of-myopia-in-children/, downloaded May 30, 2025.
Liu, Z., et al., The Effects of Repeated Low-Level Red-Light Therapy on the Structure and Vasculature of the Choroid and Retina in Children with Premyopia, Ophthalmol Ther 13:739-759 (2024), https://doi.org/10.1007/s40123-023-00875-x, downloaded Jun. 6, 2025 from https://link.springer.com/article/10.1007/s40123-023-00875-x.
Lumivision & Wellbeing: Myproclear webpage; https://lumivisionandwellbeing.co.uk/red-light-therapy-for-myopical-control/; downloaded May 19, 2025.
Mutti, D., et al., Predicting the onset of myopia in children by age, sex, ethnicity: Results from the Cleere Study, Optom Vis Sci. Apr. 1, 2024;101(4):179-186, https://pmc.ncbi.nlm.nih.gov/articles/PMC11060695/, downloaded May 30, 2025.

* cited by examiner

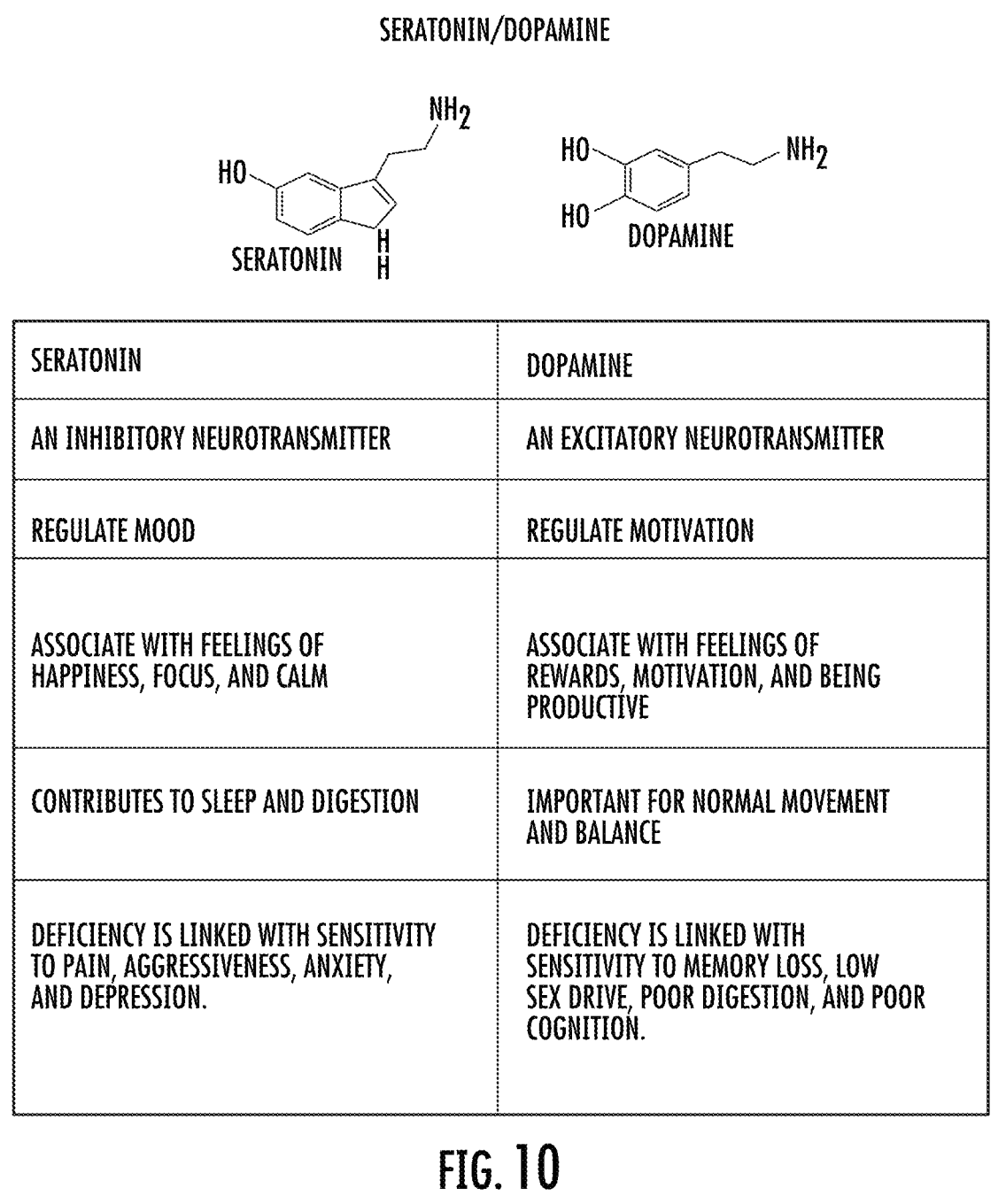

SERATONIN/DOPAMINE

| SERATONIN | DOPAMINE |
|---|---|
| AN INHIBITORY NEUROTRANSMITTER | AN EXCITATORY NEUROTRANSMITTER |
| REGULATE MOOD | REGULATE MOTIVATION |
| ASSOCIATE WITH FEELINGS OF HAPPINESS, FOCUS, AND CALM | ASSOCIATE WITH FEELINGS OF REWARDS, MOTIVATION, AND BEING PRODUCTIVE |
| CONTRIBUTES TO SLEEP AND DIGESTION | IMPORTANT FOR NORMAL MOVEMENT AND BALANCE |
| DEFICIENCY IS LINKED WITH SENSITIVITY TO PAIN, AGGRESSIVENESS, ANXIETY, AND DEPRESSION. | DEFICIENCY IS LINKED WITH SENSITIVITY TO MEMORY LOSS, LOW SEX DRIVE, POOR DIGESTION, AND POOR COGNITION. |

FIG. 10

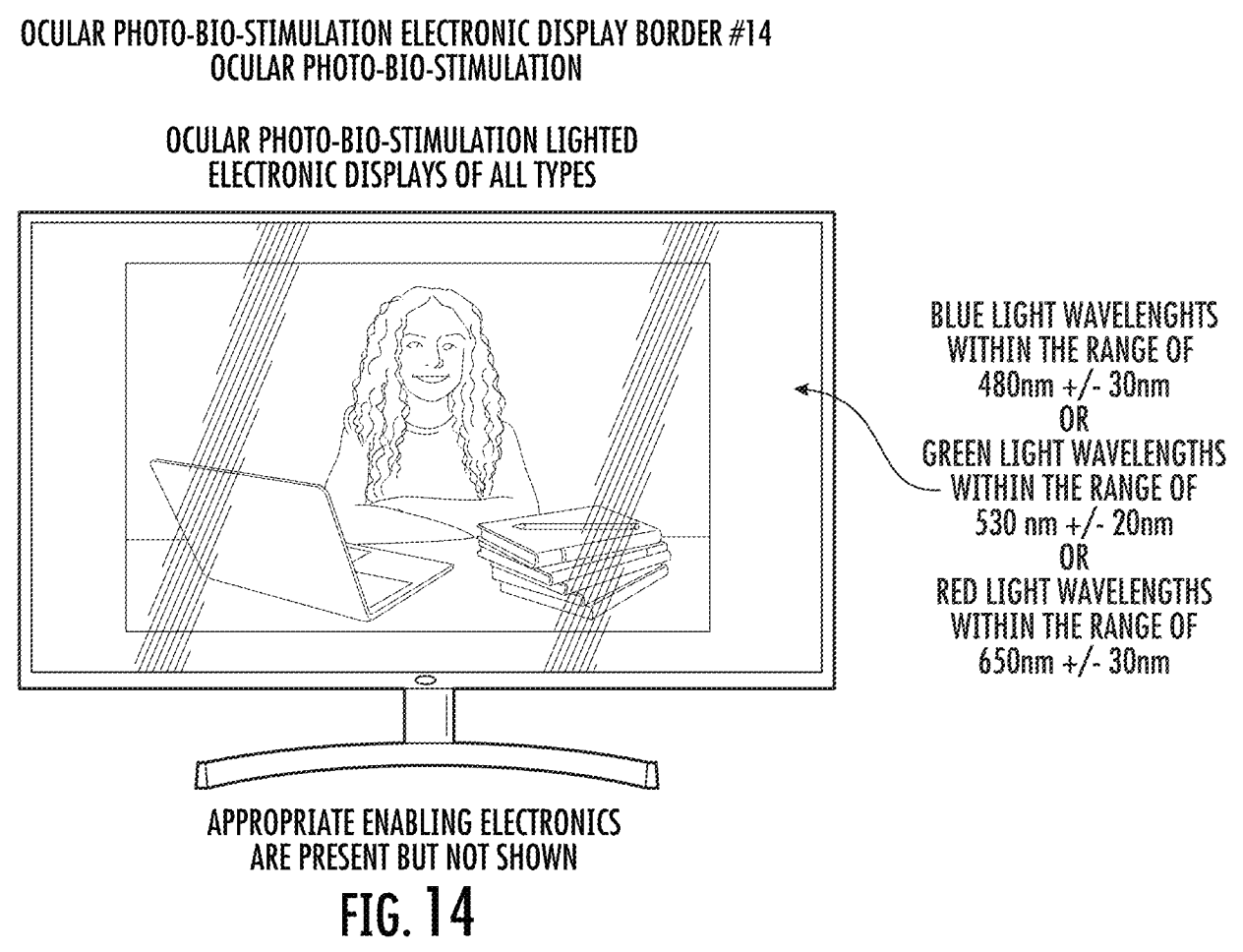

OCULAR PHOTO-BIO-STIMULATION ELECTRONIC DISPLAY BORDER #14
OCULAR PHOTO-BIO-STIMULATION

OCULAR PHOTO-BIO-STIMULATION LIGHTED
ELECTRONIC DISPLAYS OF ALL TYPES

BLUE LIGHT WAVELENGHTS
WITHIN THE RANGE OF
480nm +/- 30nm
OR
GREEN LIGHT WAVELENGTHS
WITHIN THE RANGE OF
530 nm +/- 20nm
OR
RED LIGHT WAVELENGTHS
WITHIN THE RANGE OF
650nm +/- 30nm

APPROPRIATE ENABLING ELECTRONICS
ARE PRESENT BUT NOT SHOWN

FIG. 14

OCULAR PHOTO-BIO-STIMULATION ATTACHABLE DISPOSABLE EYEWEAR FILTERED OPTICS*

OCULAR PHOTO-BIO-STIMULATION ELECTRONIC EYEWEAR INSERTS
— FITS BEHIND LENSES OR IN PLACE OF LENSES

ROLLABLE OCULAR PHOTO-BIO-STIMULATION DISPOSABLE FILTERED OPTICS

OCULAR PHOTO-BIO-STIMULATION FILTERED FIT-OVER EYEWEAR COMPRISING DEFOCUS OPTICS

A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450nm – 500nm, 470nm +/- 20nm, 480nm +/- 30nm, OR 530nm +/- 10nm, 530nm +/- 15nm, 530nm +/- 20nm, 510nm TO 550nm, OR 630nm +/-20nm, 650nm +/- 30nm, OR 600nm – 700nm WHILE AT THE SAME TIME FILTERING AND BLOCKING WAVELENGTHS WITHIN THE RANGE OF LIGHT WAVELENGTHS OF ONE OR MORE OF; 449nm – 421nm AND 419nm – 400nm.

FILTERED LENS OR OPTIC WITH DEFOCUS

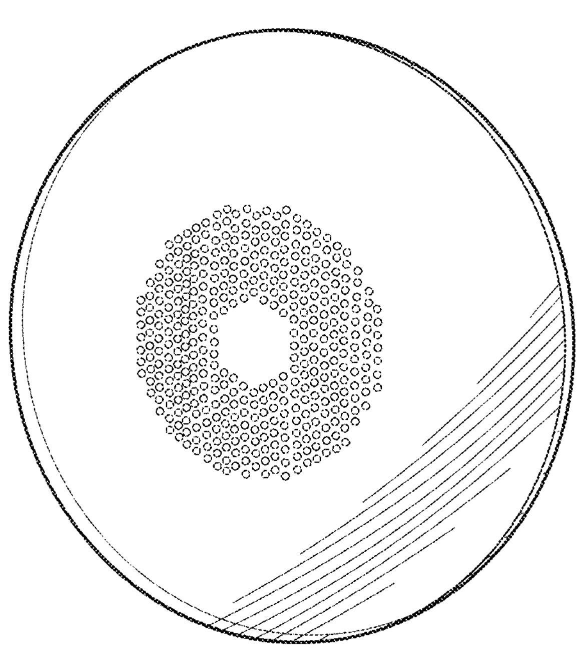

A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450NM – 500NM, 470NM +/- 20NM, 480NM +/- 30NM, OR 530NM +/- 10NM, 530NM +/- 15NM, 530NM +/- 20NM, 510NM TO 550NM, OR 630NM +/-20NM, 650NM +/- 30NM, OR 600NM – 700NM WHILE AT THE SAME TIME FILTERING AND BLOCKING WAVELENGTHS WITHIN THE RANGE OF LIGHT WAVELENGTHS OF ONE OR MORE OF; 449NM – 421NM AND 419NM – 400NM.

FIG. 28

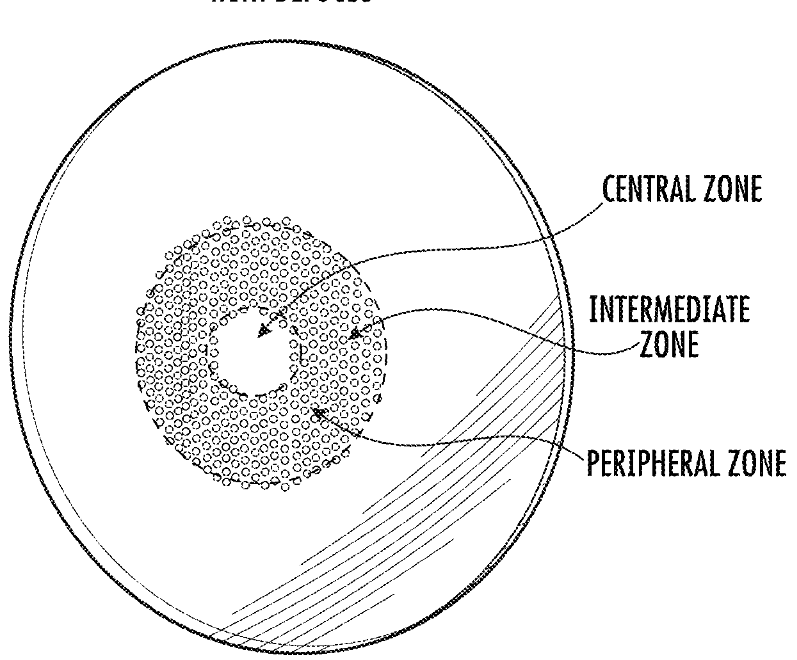
A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450NM – 500NM, 470NM +/- 20NM, 480NM +/- 30NM, OR 530NM +/- 10NM, 530NM +/- 15NM, 530NM +/- 20NM, 510NM TO 550NM, OR 630NM +/-20NM, 650NM +/- 30NM, OR 600NM – 700NM WHILE AT THE SAME TIME FILTERING AND BLOCKING WAVELENGTHS WITHIN THE RANGE OF LIGHT WAVELENGTHS OF ONE OR MORE OF; 449NM – 421NM AND 419NM – 400NM.
FIG. 29

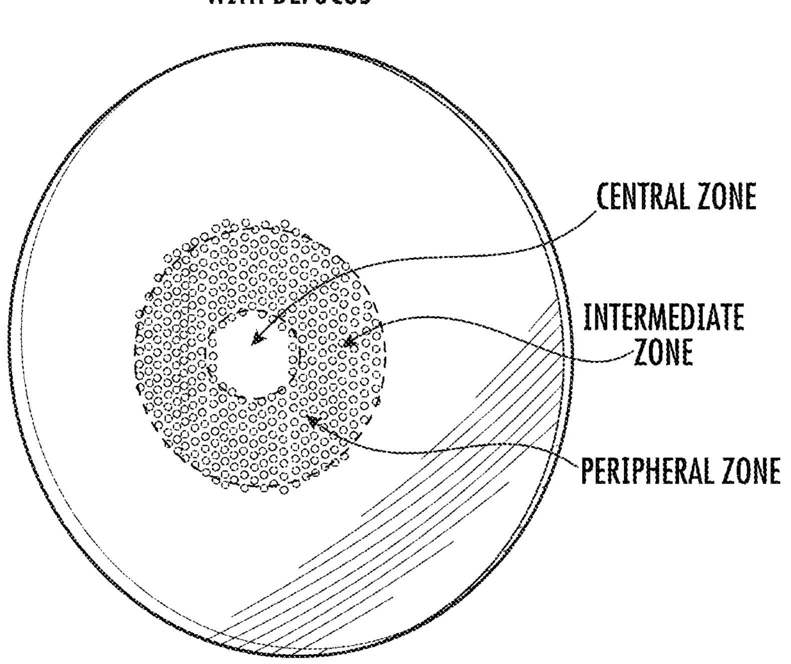
A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450NM – 500NM, 470NM +/- 20NM, 480NM +/- 30NM, OR 530NM +/- 10NM, 530NM +/- 15NM, 530NM +/- 20NM, 510NM TO 550NM, OR 630NM +/-20NM, 650NM +/- 30NM, OR 600NM – 700NM WHILE AT THE SAME TIME FILTERING AND BLOCKING WAVELENGTHS WITHIN THE RANGE OF LIGHT WAVELENGTHS OF ONE OR MORE OF; 449NM – 421NM AND 419NM – 400NM.
FIG. 30

FIG. 34

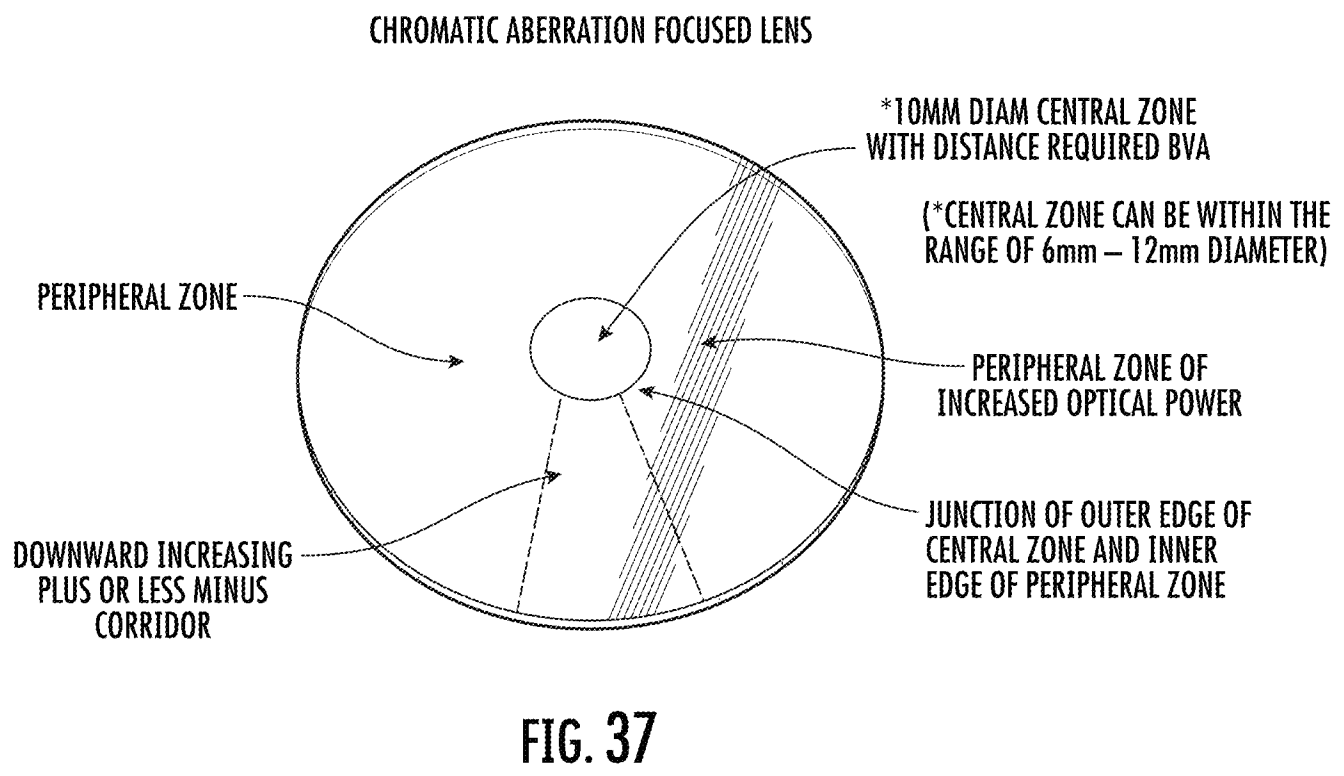

CHROMATIC ABERRATION FOCUSED LENS

*10MM DIAM CENTRAL ZONE WITH DISTANCE REQUIRED BVA (*CENTRAL ZONE CAN BE WITHIN THE RANGE OF 6mm – 12mm DIAMETER)

PERIPHERAL ZONE OF INCREASED OPTICAL POWER

JUNCTION OF OUTER EDGE OF CENTRAL ZONE AND INNER EDGE OF PERIPHERAL ZONE

PERIPHERAL ZONE

DOWNWARD INCREASING PLUS OR LESS MINUS CORRIDOR

FIG. 37

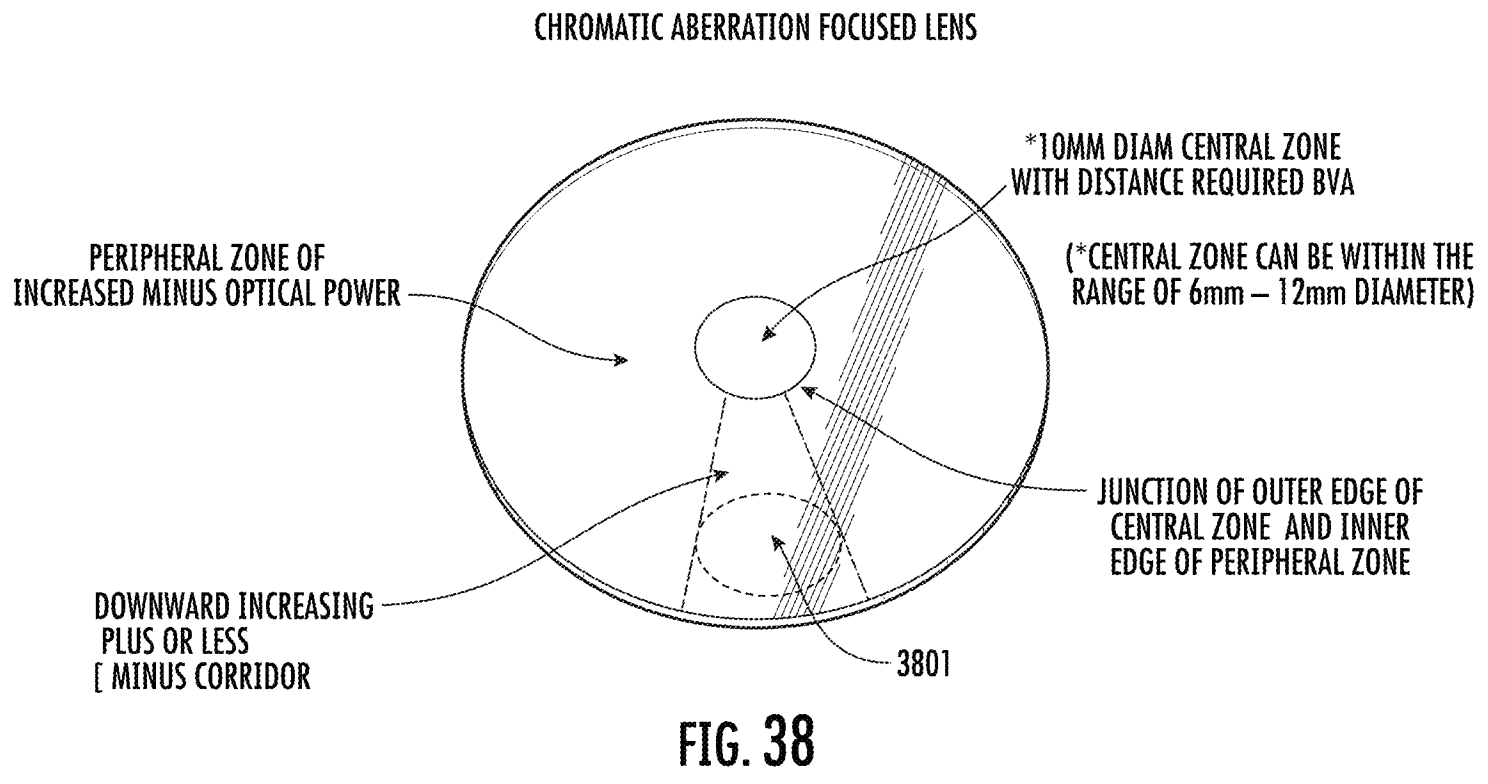

CHROMATIC ABERRATION FOCUSED LENS

*10MM DIAM CENTRAL ZONE
WITH DISTANCE REQUIRED BVA (*CENTRAL ZONE CAN BE WITHIN THE
RANGE OF 6mm – 12mm DIAMETER)

JUNCTION OF OUTER EDGE OF
CENTRAL ZONE AND INNER
EDGE OF PERIPHERAL ZONE

3801

PERIPHERAL ZONE OF
INCREASED MINUS OPTICAL POWER

DOWNWARD INCREASING
PLUS OR LESS
[ MINUS CORRIDOR

FIG. 38

*"LENSLETS ONLY" IN INTERMEDIATE ZONE PRODUCE MORE MINUS OR LESS PLUS COMPARED TO CENTRAL ZONE. PERIPHERAL TO THE INTERMEDIATE ZONE THE LENS POWER CONTRIBUTES MORE MINUS OR LESS PLUS COMPARED TO THE CENTRAL ZONE.

*LENSLETS AND MORE MINUS OR LESS PLUS LENS POWER IN INTERMEDIATE ZONE "TOGETHER" PRODUCES MORE MINUS OR LESS PLUS COMPARED TO CENTRAL ZONE. PERIPHERAL TO THE INTERMEDIATE ZONE THE LENS POWER CONTRIBUTES MORE MINUS OR LESS PLUS COMPARED TO THE CENTRAL ZONE.

SUNGLASS CATEGORIES

| CATEGORY | VLT RANGE | DESCRIPTION | USE | DAY DRIVING | NIGHT DRIVING |
|---|---|---|---|---|---|
| 0 | 100% - 80% | VERY LOW REDUCTION OF VISIBLE LIGHT | | ✓ | ✓ |
| 1 | 80% - 43% | LIMITED REDUCTION OF VISIBLE LIGHT | | ✓ | X |
| 2 | 43% - 18% | MEDIUM REDUCTION OF VISIBLE LIGHT | | ✓ | X |
| 3 | 18% - 8% | HIGH REDUCTION OF VISIBLE LIGHT | | ✓ | X |
| 4 | 8% - 3% | VERY HIGH REDUCTION OF VISIBLE LIGHT | | X | X |

FIG. 44

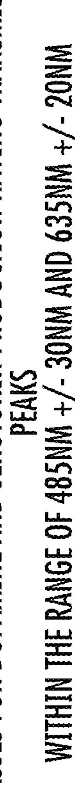
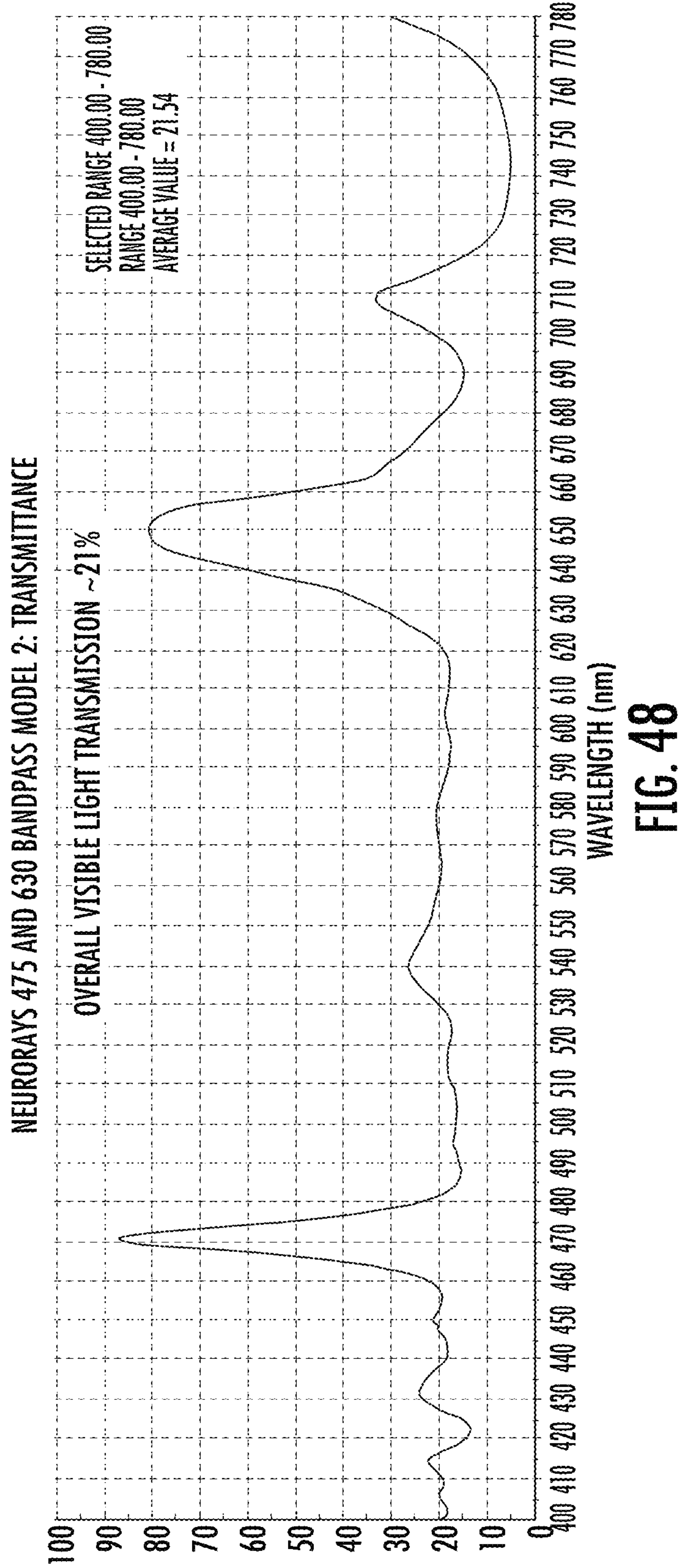
FIG. 48

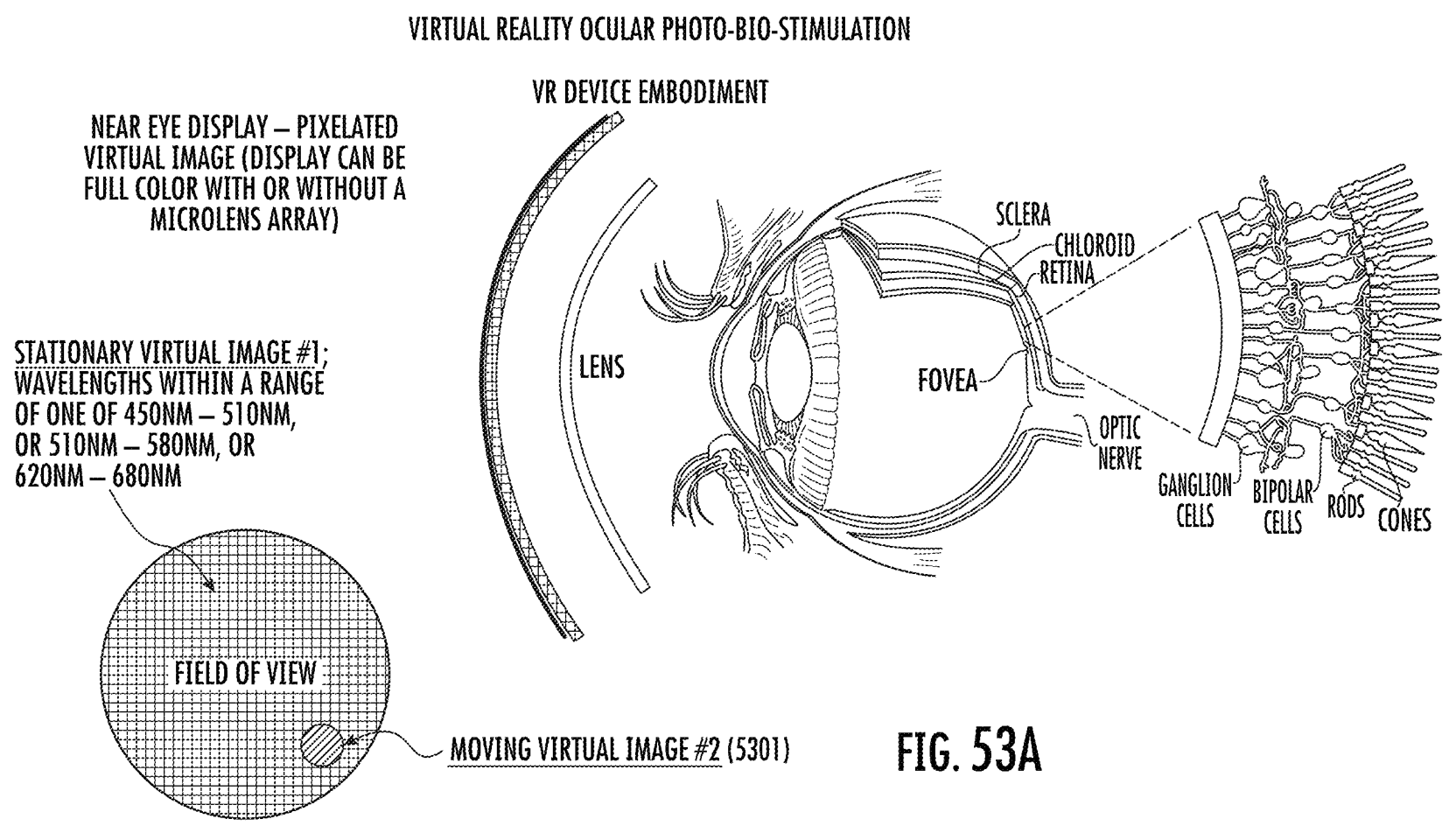

VIRTUAL REALITY OCULAR PHOTO-BIO-STIMULATION

VR DEVICE EMBODIMENT

NEAR EYE DISPLAY – PIXELATED VIRTUAL IMAGE (DISPLAY CAN BE FULL COLOR WITH OR WITHOUT A MICROLENS ARRAY)

LENS

SCLERA

CHLOROID

RETINA

FOVEA

OPTIC NERVE

GANGLION CELLS

BIPOLAR CELLS

RODS

CONES

STATIONARY VIRTUAL IMAGE #1: WAVELENGTHS WITHIN A RANGE OF ONE OF 450NM – 510NM, OR 510NM – 580NM, OR 620NM – 680NM

FIELD OF VIEW

MOVING VIRTUAL IMAGE #2 (5301)

FIG. 53A

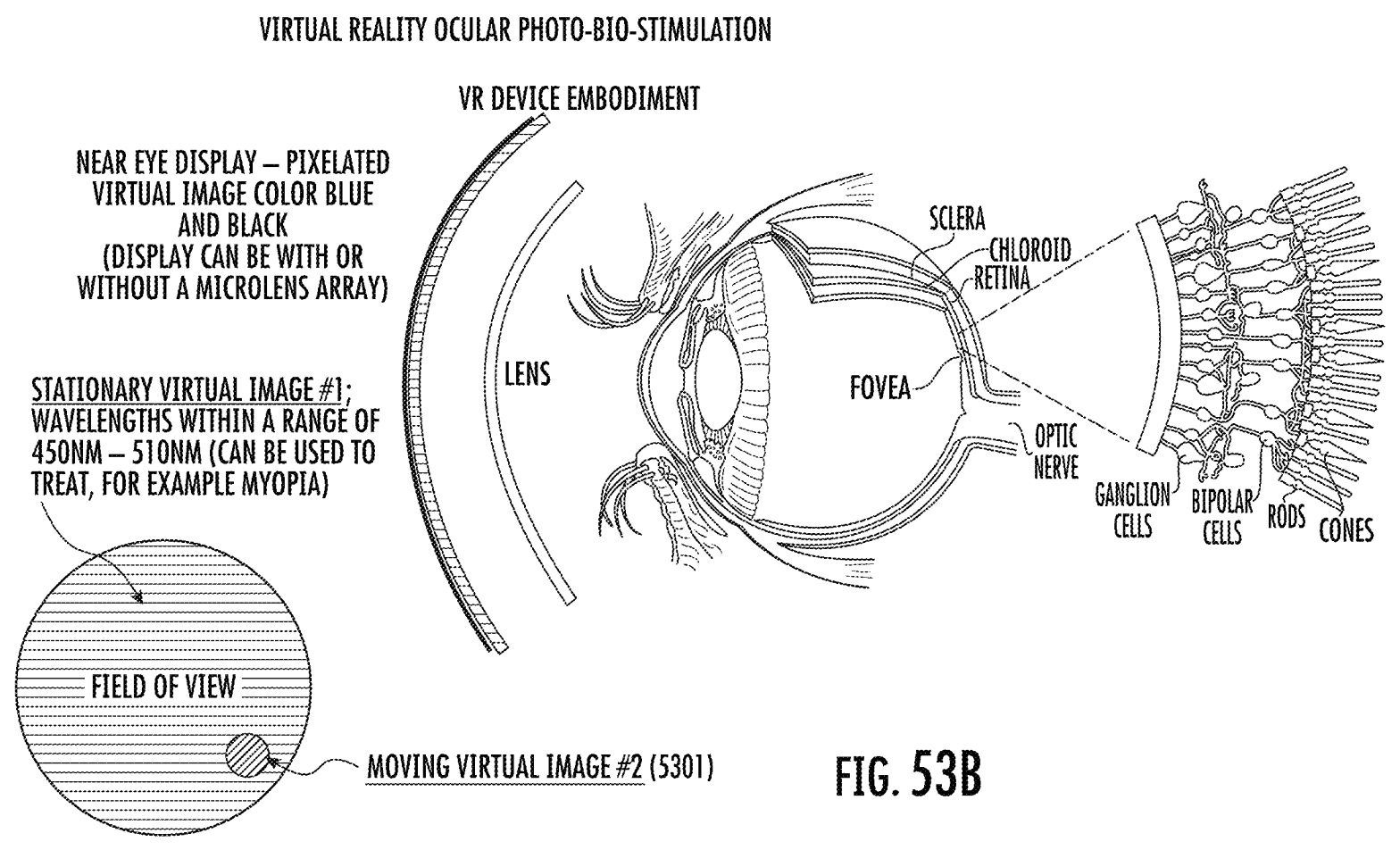

VIRTUAL REALITY OCULAR PHOTO-BIO-STIMULATION

VR DEVICE EMBODIMENT

NEAR EYE DISPLAY – PIXELATED VIRTUAL IMAGE COLOR BLUE AND BLACK (DISPLAY CAN BE WITH OR WITHOUT A MICROLENS ARRAY)

STATIONARY VIRTUAL IMAGE #1; WAVELENGTHS WITHIN A RANGE OF 450NM – 510NM (CAN BE USED TO TREAT, FOR EXAMPLE MYOPIA)

FIELD OF VIEW

MOVING VIRTUAL IMAGE #2 (5301)

LENS

SCLERA

CHLOROID

RETINA

FOVEA

OPTIC NERVE

GANGLION CELLS

BIPOLAR CELLS

RODS

CONES

FIG. 53B

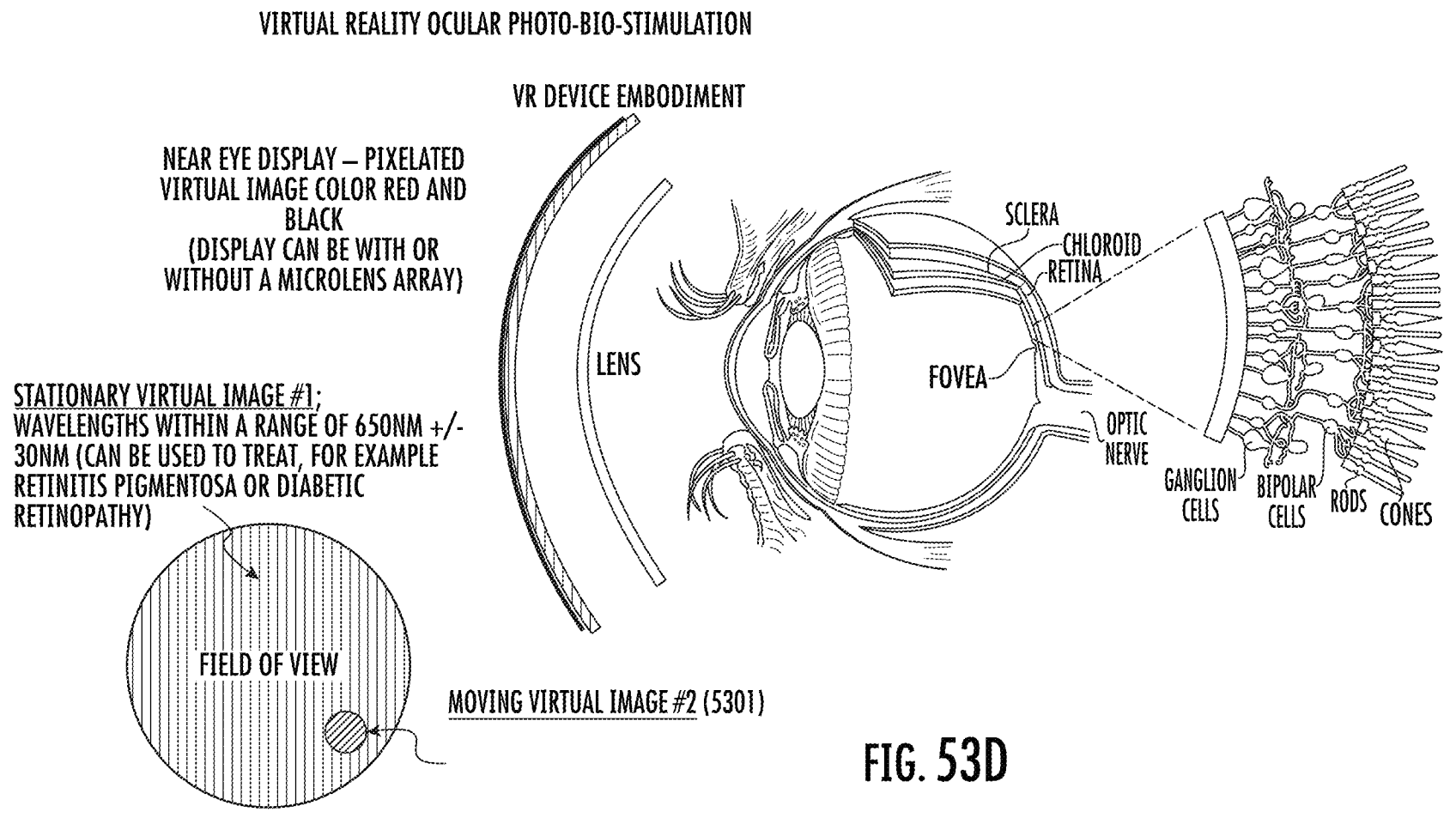

VIRTUAL REALITY OCULAR PHOTO-BIO-STIMULATION

VR DEVICE EMBODIMENT

NEAR EYE DISPLAY – PIXELATED VIRTUAL IMAGE COLOR RED AND BLACK (DISPLAY CAN BE WITH OR WITHOUT A MICROLENS ARRAY)

LENS

SCLERA

CHLOROID

RETINA

FOVEA

OPTIC NERVE

GANGLION CELLS

BIPOLAR CELLS

RODS

CONES

STATIONARY VIRTUAL IMAGE #1; WAVELENGTHS WITHIN A RANGE OF 650NM +/- 30NM (CAN BE USED TO TREAT, FOR EXAMPLE RETINITIS PIGMENTOSA OR DIABETIC RETINOPATHY)

FIELD OF VIEW

MOVING VIRTUAL IMAGE #2 (5301)

FIG. 53D

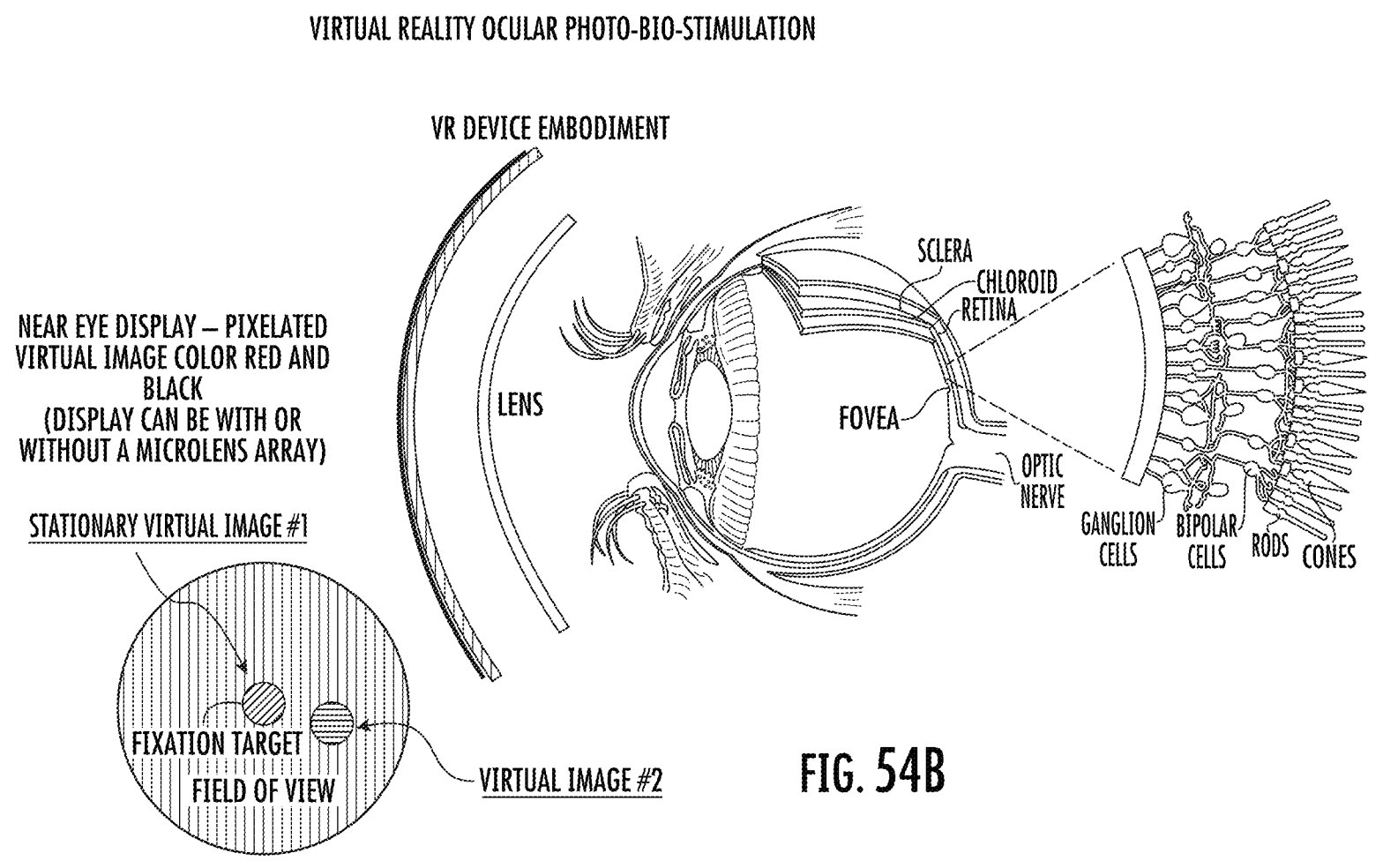

VIRTUAL REALITY OCULAR PHOTO-BIO-STIMULATION

VR DEVICE EMBODIMENT

NEAR EYE DISPLAY – PIXELATED VIRTUAL IMAGE COLOR RED AND BLACK
(DISPLAY CAN BE WITH OR WITHOUT A MICROLENS ARRAY)

STATIONARY VIRTUAL IMAGE #1

FIXATION TARGET

FIELD OF VIEW

VIRTUAL IMAGE #2

LENS

SCLERA

CHLOROID

RETINA

FOVEA

OPTIC NERVE

GANGLION CELLS

BIPOLAR CELLS

RODS

CONES

FIG. 54B

FILTERING EYEWEAR AND OPTICS FOR OCULAR PHOTO-BIO-STIMULATION

CROSS-REFERENCE TO RELATED APPLICATIONS

The present application relies on the disclosures of and claims priority to and the benefit of the filing dates of the following U.S. patent applications:

- U.S. Appl. No. 63/546,848, filed Nov. 1, 2023, titled Improved Eyewear or Optic Providing Blue Light Alertness, Myopia Control, Green Light Pain Relief, and Red-Light Calming
- U.S. Appl. No. 63/548,204, filed Nov. 12, 2023, titled Neuro-Light Therapy
- U.S. Appl. No. 63/600,139, filed Nov. 17, 2023, titled Enhanced Neuro-Light Therapy
- U.S. Appl. No. 63/603,258, filed Nov. 28, 2023, titled Optimized Neuro-Light Therapy
- U.S. Appl. No. 63/609,306, filed Dec. 12, 2023, titled Neuro-Light Therapy Improved
- U.S. Appl. No. 63/617,363, filed Jan. 3, 2024, titled Neuro-Light Therapy Optimized
- U.S. Appl. No. 63/623,253, filed Jan. 20, 2024, titled Neuro-Light Therapy Further Optimized
- U.S. Appl. No. 63/627,703, filed Jan. 31, 2024, titled Neuro-Light Optogenetic Therapy
  - U.S. Appl. No. 63/550,852, filed Feb. 7, 2024, titled Enhanced Neuro-Light Optogenetic Therapy
  - U.S. Appl. No. 63/553,226, filed Feb. 14, 2024, titled Neuro-Light Optogenetic Therapy Enhanced
  - U.S. Appl. No. 63/553,693, filed Feb. 15, 2024, titled Enhanced Neuro-Light Optogenetic Therapy
  - U.S. Appl. No. 63/561,266, filed Mar. 4, 2024, titled Ocular Neuro-Light Therapy
  - U.S. Appl. No. 63/569,005, filed Mar. 22, 2024, titled Ocular Neuro-Light Therapy Improved
  - U.S. Appl. No. 63/639,892, filed Apr. 29, 2024, titled Ocular Optogenetic Neuro Therapy
  - U.S. Appl. No. 63/648,098, filed May 15, 2024, titled Ocular Optogenetic Therapy
  - U.S. Appl. No. 63/654,566, filed May 31, 2024, titled Optogenetic Lens Designs
  - U.S. Appl. No. 63/671,237, filed Jul. 14, 2024, titled XR Optogenetic Stimulation of the Human Eye and Sunglasses Allowing Dopamine Production
  - U.S. Appl. No. 63/673,746, filed Jul. 21, 2024, titled Enhanced XR Optogenetic Stimulation of the Human Eye and Sunglasses Allowing Dopamine Production
  - U.S. Appl. No. 63/674,219, filed Jul. 22, 2024, titled Advanced XR Optogenetic Stimulation of the Human Eye and Sunglasses Allowing Dopamine Production
  - U.S. Appl. No. 63/676,855, filed Jul. 29, 2024, titled XR Optogenetic Stimulation U.S. Appl. No. 63/684,509, filed Aug. 19, 2024, titled Refined Optogenetic Lens Designs
  - U.S. Appl. No. 63/684,509, filed Aug. 19, 2024, titled Refined Optogenetic Lens Designs
  - U.S. application Ser. No. 18/827,782, filed Sep. 8, 2024, titled Ocular Photo-Bio-Stimulation Optics
  - U.S. application Ser. No. 18/827,786, filed Sep. 8, 2024, titled Ocular Photo-Bio-Stimulation Optics
  - U.S. Appl. No. 63/697,560, filed Sep. 22, 2024, titled Filtering Eyewear and Optics for Ocular Photo-Bio-Stimulation
- U.S. application Ser. Nos. 18/827,782, and 18/827,786 rely on the disclosures of and claim priority to and the benefit of the filing dates of U.S. Appl. No. 63/537,021, filed Sep. 7, 2023, titled Device Providing Blue Light for Alertness and Red Light for Calming, U.S. Appl. No. 63/540,090, filed Sep. 24, 2023, titled Enhanced Device Providing Blue Light for Alertness and Red Light for Calming, and U.S. Appl. No. 63/541,243, filed Sep. 28, 2023, titled Device Providing Blue Light Alertness and/or Red Light Calming The disclosures of those applications are hereby incorporated by reference herein in their entireties.

BACKGROUND OF THE INVENTION

Field of the Invention

The current invention relates, in part, to ocular photo-bio-stimulation therapy, a biological technique to control or influence the activity of neurons or other cell types in, on or about the eye with light. As used herein ocular photo-bio-stimulation is an umbrella category of which photobiomodulation, optogenetics and phototherapy are forms thereof. The current invention relates, in part, to photobiomodulation therapy, which includes the utilization of non-ionizing electromagnetic energy to trigger photochemical changes within cellular structures. The current invention relates, in part, to optogenetics. Optogenetics is a biological technique to control the activity of neurons or other cell types with light. The current invention relates, in part, to phototherapy, also known as light therapy or bright light therapy, which is a treatment that uses controlled exposure to artificial or natural light to treat medical conditions.

A description of the anatomy of the eye will help understand the invention described herein.

The Eye's Retinal Layer

In reference to FIG. 1, retinal cones are photoreceptor cells in the retina that give humans color vision and help them see fine details. They are cone-shaped, with a pointed tip at the top and a circular bottom, and are concentrated in the center of the retina, in an area called the macula, the center of which is called the fovea. There are ~6M cones.

In further reference to FIG. 1, retinal Rods make up more than 95% of the photoreceptors. There are ~125M rods, and they pool signals to provide high sensitivity for dark-adapted vision, say starlight, which appears monochromatic. A lack of color vision is the hallmark of rod-mediated vision. Rods are absent within 350 μm of the fovea but reach a peak density in an annular region at about 20 degrees eccentricity.

In further reference to FIG. 7, rodopsin is the opsin of the rod cells in the retina and a light-sensitive receptor protein that triggers visual phototransduction in rods.

In further reference to FIG. 1, intrinsically photosensitive retinal ganglion cells (ipRGCs), also called photosensitive retinal ganglion cells that contain melanopsin (ipRGC) or called (mRGcs), are retinal ganglion cells (RGCs), which are neurons in the retina that transmit visual information from the eye to the brain. They are located near the inner surface (the ganglion cell layer) of the retina of the eye. It receives visual information from photoreceptors via two intermediate neuron types: bipolar cells and amacrine cells. Retinal ganglion cells collectively transmit image-forming and non-image forming visual information from the retina to several regions in the thalamus, hypothalamus, and mesencephalon, or midbrain. There are about 1.2 to 1.5 million retinal ganglion cells in the human retina. The melanopsin-containing retinal ganglion cells (mRGCs) represent only between 0.3% and 0.8% of the total ganglion cells of the retina.

In further reference to FIG. 7, melanopsin, a G family coupled receptor, is found within the ganglion cell layer in the retina and plays an important role in non-image-forming visual functions, including hormone secretion, entrainment of circadian rhythms, cognitive and affective processes.

In further reference to FIG. 9, melatonin is a natural hormone that is mainly produced by your pineal gland in your brain. It plays a role in managing your sleep wake cycle and circadian rhythm.

In further reference to FIG. 1, Amacrine cells are nerve cells in the vertebrate retina that act as interneurons, or local circuit neurons, to connect two projection neurons. They are located in the inner nuclear layer of the retina and are the first neurons in the visual system to fire action potentials. Amacrine cells are named for their presumed lack of an axon. They come in many shapes and sizes and are synaptically active in the inner plexiform layer (IPL).

In further reference to FIG. 1, dopaminergic amacrine cells (DACs) serve as the sole source of retinal dopamine, and dopamine release in the retina follows a circadian rhythm and is modulated by light exposure. Dopaminergic amacrine cells (DACs) make up less than 1% of all amacrine cells in the retina. DACs are the main source of dopamine in the retina and are one of the rarest cell types in the retina, with a density of about 10-100 per mm. DACs are the first retinal neurons to be identified neurochemically. They have long primary dendrites, a sparse dendritic arbor, and an axon that usually emerges from the soma or primary dendrite. Their dendritic fields are irregular, often elongated or asymmetric.

In further reference to FIG. 1, the optic nerve head (optic disk) is composed of neural, vascular, and connective tissues. The convergence of axons of retinal ganglion cells (RG) at the optic disc creates the neuroretinal rim that surrounds the cup, a central shallow depression in the optic disc.

In further reference to FIG. 2, the macula is a small, round area in the center of the retina, the light-sensitive layer of tissue at the back of the eye. It is about 5 millimeters across and a quarter of a millimeter thick, and is responsible for central vision, color vision, and fine detail. The macula is the part of the retina used when looking directly at objects, such as when reading or recognizing faces at a distance.

In further reference to FIG. 2, the fovea centralis, or fovea, is a small depression within the neurosensory retina where visual acuity is the highest. The fovea itself is the central portion of the macula, which is responsible for central vision.

In reference to FIG. 1, retinal rods & cones are photoreceptors in the retina that detect light and convert it into signals that the brain can use for vision.

In reference to FIG. 4, it shows the eyes retina diameter and retinal zones of the retina relative to the center of the fovea: posterior zone (or central zone) (radius<10 mm), midperiphery zone (radius=10-15 mm), and far-periphery zone (radius>15 mm.

In reference to FIG. 5, it shows pupil size relative to ambient light, by way of example only, a pupil size can be 3.5 mm at 550 lux, 4.2 mm at 350 lux, 5.2 mm at 150 lux, 5.03 mm at 40 lux, and 5.4 mm at 2 lux.

In reference to FIG. 11, myopia (nearsightedness or shortsightedness), is a common eye disease that causes light rays to bend and focus in front of the retina instead of on it. This makes distant objects appear blurry, while nearby objects appear normal. There is a silent epidemic of myopia in the world. It is forecasted that by 2050 approximately 50% of the world's population will be myopic. The number of myopes forecasted is approximately 5 billion. Hyperopia (farsightedness) is a common vision condition in which you can see distant objects clearly, but objects nearby may be blurry. With hyperopia the eye focus of the light rays is behind the retina. Astigmatism is a common eye problem that occurs when the cornea or lens of the eye is an abnormal shape, causing light to bend differently as it enters the eye. This refractive error results in distorted or blurred vision at any distance and can make it difficult to see fine details. Presbyopia is a refractive error that causes the eye to lose its ability to focus on close objects as it ages. It is also known as age-related farsightedness. Presbyopia occurs when the eye's lens loses its elasticity and can no longer focus light correctly on the retina. This makes it harder to read, thread a needle, or do other close-up tasks. Symptoms include blurry close-up vision, eyestrain, headaches, difficulty focusing on crafts and hobbies, and needing brighter lighting for clearer near vision. Dry macular degeneration (AMD) is a common eye disorder that affects the macula, the part of the retina that gives the eye clear vision. It is a chronic condition that usually develops in both eyes and is caused by a metabolic disorder, genetics, and environmental factors. As people age, the macula thins and the light-sensitive cells in it slowly break down, causing blurred or reduced central vision. AMD is referred to as age related macular degeneration and as such begins centrally within the macular area of the retina. Diabetic retinopathy (DR) is a chronic eye condition that occurs when high blood sugar from diabetes damages the retina's blood vessels. The damaged blood vessels can swell, leak, or bleed, which can lead to blurry vision, dark areas, and difficulty seeing colors. This usually begins peripheral to the macular area of the retina. Retinitis pigmentosa (RP) is a rare genetic disorder that affects the retina, the light-sensitive part of the eye at the back. RP causes the retina's photoreceptor cells to gradually break down over time, leading to vision loss. Symptoms often start in childhood or adolescence and include night blindness and peripheral vision loss. This may begin in the far and mid periphery of the retina and progresses centrally from the peripheral retina.

In reference to FIG. 6, the visible light wavelength spectrum is the segment of the electromagnetic spectrum that the human eye can view. More simply, this range of wavelengths is called visible light. Typically, the human eye can detect wavelengths from 380 to 700 nanometers.

In reference to FIG. 7, light sensitivity spectrum for melanopsin, rhodopsin is shown. Regarding the spectral sensitivity of human vision, the maximum spectral sensitivity of the human eye under daylight conditions is ~555 nm (yellow/green arrowhead), while at night the peak shifts to ~507 nm (green arrowhead), near the peak of rhodopsin (dashed blue-green line with a peak at 505 nm). Circadian photoreception mediated by melanopsin-expressing, intrinsically photosensitive ganglion cells integrate light information, but is most sensitive to a distinct blue portion of the spectrum (dashed blue line). The human retina also contains macular xanthophylls (X), yellow pigments found to be composed of two chromatographically separable components (i) lutein and (ii) zeaxanthin, whose absorption spectrum is a broad band (~100 nm width) with a spectral center between the short and medium-long wavelength photoreceptor pigments of the retina (peak ~460 nm). Rhodopsin, a visual pigment found in photoreceptor rods, has a peak sensitivity to blue-green light at around 500 nanometers (nm). This means that rhodopsin absorbs green-blue light most strongly, which gives it a reddish-purple appearance. The peak for melanopsin is ~480 nm. In addition, between 25 and 33% of all light entering the eye is absorbed by pigment granules in the RPE and the choroid. The naturally occurring pigment melanin, contained within pigment granules in the RPE and the choroid, and to a lesser extent hemoglobin in red blood cells, absorbs excess and scattered light to improve visual acuity. This serves to protect photoreceptors from photic injury and is thought to function as a quencher of free radicals and suppressor of photosensitized molecules.

In reference to FIG. 8, longitudinal chromatic aberration (LCA) is a lens's inability to focus on different color wavelengths in the same focal plane. It occurs when different wavelengths of light disperse from a lens at different points along the optical axis, creating a circle of confusion. This results in unintentional color fringes, even in the center of an image, and colored areas where not all three colors are in focus. The eye's natural longitudinal chromatic aberration (LCA) is an optical imperfection in the human eye that causes images projected onto the retina to blur. It occurs because the eye's refractive index varies with wavelength, causing the eye's focal power to change by almost 2 diopters (D) across the visible spectrum. This chromatic difference of focus causes short wavelengths to focus in front of long wavelengths, which is known as LCA. Optical lens material's longitudinal chromatic aberration (LCA) decreases as Abbe number increases. Abbe number is a measure of how much light a lens disperses, and lenses with higher Abbe numbers disperse less light and produce less chromatic aberration. Chromatic aberration is inversely proportional to the Abbe number, meaning that as Abbe number decreases, chromatic aberration increases.

In reference to FIG. 9, Brain—melatonin, serotonin, dopamine, studies show that dopamine production and release increases with light and decreases with darkness, while melatonin does the opposite. Seasonal Affective Disorder (SAD) is a type of depression that occurs in a seasonal pattern, often during the fall and winter months when there is less sunlight.

In reference to FIG. 10, serotonin and dopamine are neurotransmitters that act as chemical messengers between nerve cells in the brain and other parts of the body. They are often called "happy hormones" because they both play a role in positive mood and emotion. Brain Serotonin (5-HT) is a chemical messenger that the body produces naturally and acts as a neurotransmitter and hormone. It is involved in many physiological functions, including the central nervous system: mood, memory, anger, fear, appetite, stress, addiction, sexual pleasure, sleep, pain perception, and central respiratory drive and pupil dilation. Serotonin is a chemical messenger that affects wellbeing and happiness. Many antidepressants increase serotonin levels in the brain. Serotonin is found in the eye, where it acts as a neuromodulator in the retina and is present in human tears. Eye serotonin is found in the A17 cell, where it co-exists with GABA. Serotonin receptor signaling pathways are specific to the retina, and activating these receptors can help prevent photoreceptor degeneration. Serotonin is also involved in retinal physiology, physiopathology, and photoreceptor survival. Sunlight entering the eyes can stimulate the retina, which then signals the brain to produce serotonin. Brain dopamine is a chemical messenger in the brain that helps nerve cells communicate with each other. It is produced in the brain and acts on cells in other parts of the brain. Dopamine plays a role in many body functions, including motivation, pleasure, movement, memory, and mood. Dopamine is known as the feel-good hormone. Dopamine levels that are too high or too low can be associated with diseases like Parkinson's disease, restless legs syndrome, and attention deficit hyperactivity disorder (ADHD). Low dopamine levels can also lead to symptoms like anxiety, sadness, difficulty sleeping, and low sex drive. Eye dopamine (DA) is a neurotransmitter in the retina that plays a role in visual signaling, development, and refractive development. It is found in the retinas of all vertebrates, including humans, and is released from dopaminergic amacrine cells in the retina's inner plexiform layer. DA levels are dependent on light and retinal image contrast. Attention-deficit/hyperactivity disorder (ADHD) is one of the most common and most studied neurodevelopmental disorders in children. "Neuro" means nerves in cases. Scientists have discovered there are differences in the brain, nerve networks and neurotransmitters of people with ADHD. ADHD is a long-term (chronic) brain condition that causes executive dysfunction, which means it disrupts a person's ability to manage their own emotions, thoughts and actions. ADHD makes it difficult for people to: manage their behavior, pay attention, control overactivity, regulate their mood, stay organized, concentrate, and/or follow directions and sit still. Kids usually receive a diagnosis during childhood and the condition often lasts into adulthood. However, effective treatment is available. Left untreated, ADHD can cause serious, lifelong complications. According to the Centers for Disease Control and Prevention, almost 11% of U.S. children between the ages of 2 and 17 have received an ADHD diagnosis representing an estimated 6 million children ages 3 to 17 years. Worldwide, 7.2% of children have received an ADHD diagnosis. It is estimated that adult ADHD affects more than 8 million adults (or up to 5% of Americans). Many medical conditions are linked to low levels of dopamine including attention deficit hyperactivity disorder (ADHD), Parkinson's disease, Alzheimer's, restless legs syndrome, depression, schizophrenia, brain fog, mood swings, chronic fatigue and muscle spasms. Low levels of serotonin may be associated with many health conditions including depression and other mood problems such as anxiety, sleep problems, digestive problems, suicidal behavior, obsessive-compulsive disorder, post-traumatic stress disorder and panic disorders.

Exposure to blue light wavelengths stimulates the body's production of serotonin and dopamine, both in the eye and possibly the brain. Also, very bright intense red light has been found to stimulate serotonin and dopamine. Serotonin is an inhibitory neurotransmitter that affects mood, appetite, sleep, temperature regulation, and some social behavior. 95% of the body's serotonin is generated in the intestine. Dopamine is an excitatory neurotransmitter that regulates motivation. A low dopamine level can contribute to ADHD, as well as memory loss, low sex drive, poor digestion, muscle spasms, restless legs syndrome, Parkinson's Disease, poor cognition, as well as an increase in myopia. Dopamine is produced in serval areas of the brain. Some dopamine is generated in the retina of the eye by the rods and/or ganglion cells more so than the cones.

Research findings suggest that green light wavelengths can alleviate or reduce pain by stimulating cone cells, which then initiate a signaling pathway that results in the activation of opioid receptors in the DRN. It is believed that green lighting can stimulate the release of endogenous endorphins and stimulate the cannabinoid system which results in improved moods and higher pain tolerance. By way of example, it is thought that green light can reduce the pain associated with migraines and other types of pain.

Description of Related Art

While ocular photo-bio-stimulations have been tested before, a need for improvement exists within the art. For example, U.S. Pat. No. 10,444,505 B2 teaches a head mounted display comprising a light emitting source and an optical waveguide adapted to collect light emitting from the light emitting source and to guide the collected light to the eye. U.S. Pat. No. 10,444,505 B2 further teaches the use of blue green wavelengths of light within the range of 460 nm and 520 nm directly targeting intrinsically photosensitive retinal ganglion cells (ipRGC), more specifically the melanopsin ganglion cells, and indirectly targeting rods. However, U.S. Pat. No. 10,444,505 B2 does not teach a means for maximizing the number or ganglion cells and rods stimulated. The larger number of melanopsin ganglion cells and rods that are stimulated the greater the physiological response. This prior art is silent as to how to stimulate certain areas of the mid peripheral and far peripheral retina that are not normally stimulated when light is shined into an eye. The teachings included herein will show that an estimated 20%-30% of each eye's retina is not normally stimulated when looking straight ahead. U.S. Pat. No. 5,923,398 teaches off axis photon stimulation of a person's eye, provided by a light field which provides biological or psychological benefits. This art teaches embedded or fixed light delivery elements such as fiber optic members that deliver off axis stimulation to peripheral areas of the retina. The cosmetics of the device leave much to be desired. Furthermore, anyone looking at an individual wearing such a device would look bizarre as the wearer's eye lids, and eyes, would appear lighted. Both U.S. Pat. Nos. 10,444,505 B2 and 5,923,398 teach the use of eye tracking for the purpose of identifying the location of the pupil of the eye. Thus, there is a need for a simplified and more cosmetically desirable way to provide photo-bio-stimulation to the eye or eyes of a user. The inventive embodiments taught herein solve that need. The invention disclosed herein teaches various embodiments of electronic displays, optics, lenses, extended reality and modified extended reality that are not taught by any known art.

SUMMARY OF THE INVENTION

Embodiments disclosed herein can provide ocular photo-bio-stimulation through light stimulation of specific wavelengths to the eye's retina, and, in some embodiments, to the entire eye's retina, the retina peripheral to the fovea, and/or the retina peripheral to the macula. In certain embodiments, the light stimulation is targeted at or to the rods. In other embodiments, the light stimulation is targeted at or to the ganglion cells. In still other embodiments, it is targeted at or to the rods and the ganglion cells. When ganglion cells are mentioned herein, the ganglion cells targeted or stimulated are the melanopsin containing ganglion cells (ipRGCs) or can also be called mRGCs.

Embodiments herein teach the stimulation of the rods and/or ipRGCs with specific light wavelengths. The retina of the human eye contains 100+M rods, 1M ganglion cells but fewer than 7,000 ipRGCs which are the ganglion cells that contain melanopsin. ipRGCs are less sensitive to photic stimulation and their response kinetics are slow compared to that of rods and cones. Response latency is inversely related to stimulus intensity and under dim light conditions ipRGCs can take many seconds to reach a peak response; the response may also persist for minutes after stimulus termination. However, ipRGCs are similar to rods and cones in that they show adaptation by adjusting their sensitivity according to lighting conditions. While slow to respond to dim light conditions, ipRGCs appear capable of responding to the capture of a single photon of light. It has been estimated that the membrane density of melanopsin is about a thousand times lower than that of photopigments in the outer segments of rod and cone photoreceptors; this relatively low density may account for the poor absorption rate of ipRGCs. The capture of a single photon in an ipRGC generates a large and prolonged membrane current, greater than that recorded in rod photoreceptors but also 20-fold slower.

Melanopsin photopigment expressed in intrinsically photosensitive retinal ganglion cells (ipRGCs) plays a crucial role in the adaptation of mammals to their ambient light environment through non-image-forming (NIF) visual responses. ipRGCs are stmucturally and functionally distinct from classical rod/cone photoreceptors and have unique properties including single-photon response, long response latency, photon integration over time, and slow deactivation.

Embodiments disclosed herein that are directed to increasing dopamine in an individual's eye's retina or dopamine in the brain of the individual whose eye was stimulated attempt to use wavelength ranges that cover the peak sensitivities for melanopsin (480 nm) and also for rhodopsin (500 nm). Given that rhodopsin of Rods is 20 times faster to react than melanopsin of ipRGCs, but that melanopsin has much longer reactive staying power than the reaction of rhodopsin, combined with the fact that rods are 10+ times the number of ipRGCs, is the reason various embodiments disclosed herein use light wavelengths within the light wavelength ranges of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm. The lower level of 480 nm+/−30 nm is to capture direct stimulation of melanopsin by ipRGCs and indirect stimulation of melanopsin by rods.

In certain embodiments when generating dopamine in the eye or the brain via the eye light, the invention utilizes light wavelengths that strike the eye's retina which fall within the wavelength range of the following at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, which would include blue, bluish green and green wavelengths. These light wavelength ranges can be generated by light emitters, filtered optics or filtered lenses.

As used herein, in embodiments when light wavelengths are generated by way of filtered optics or filtered lenses, the peak spectral curve of the wavelength range that strike the eye's retina fall within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In certain embodiments disclosed herein, when a filtered optic or filtered lens is used, the overall light transmission through the filtered optic or filtered lens can be 50% or less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments disclosed herein, when a filtered optic or filtered lens is used, the overall light transmission through the filtered optic or filtered lens can be 40% or less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In certain embodiments disclosed herein, when a filtered optic or filtered lens is used, the overall light transmission through the filtered optic or filtered lens can be 30% or less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens.

As used herein, in embodiments when light wavelengths are generated by way of a light emitter(s) if in a dark room with no ambient lighting the wavelength range that strikes the eye's retina fall within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

As used herein, in embodiments when light wavelengths are generated by a light emitter(s) if ambient lighting is present (including that of artificial light or sun light) the blended light wavelengths of the light emitter(s) and also the ambient light comprises wavelengths of light that strike the eye's retina falling within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

It should be understood that when interpreting embodiments utilized herein unless total darkness is specified, it should be assumed that there is ambient light and thus the light wavelengths striking the retina are blended by the light from the light emitter and the ambient light. The same is true with a filtered optic or filtered lens. In most but not all cases the filtered optic or filtered lens is located 12+mm from the eye of the wearer unless the filtered optic or filtered lens is that of a contact lens or intraocular lens. An exception to this interpretation would be that of the use of a virtual reality device or a modified reality device whereby the device is sealed from ambient light.

In still other embodiments, a light wavelength(s) from either a filtered optic, filtered lens, light emitter(s), and/or light emitter(s), combined with ambient light that strikes the retina of the eye, are selected so that the radiation peak of these wavelengths falls between the peak melanopsin sensitivity (480 nm, and rhodopsin sensitivity (500 nm)). Thus, the spectral curve peak of these wavelengths falls within the range of 480 nm and 500 nn. In these embodiments this occurs whether the wavelengths were generated by a filtered optic, filtered lens, light emitter, and/or light emitter, combined with ambient light.

In still other embodiments, the light stimulation is targeted at or to the cones, rods and ganglion cells. In certain embodiments the objective of ocular photo-bio-stimulation is to increase dopamine within the eye. In certain embodiments the objective of ocular photo-bio-stimulation is to increase dopamine within the eye's retina. When increasing dopamine in the eye and/or retina, ocular photo-bio-stimulation blue light or blue green light having wavelengths within the range of 450 nm to 510 nm can be used, or, for increasing dopamine in the eye and/or retina, ocular photo-bio-stimulation red light wavelengths of 650 nm+/−30 nm or 700 nm+/−30 nm can be utilized. In certain embodiments the objective of ocular photo-bio-stimulation is to increase dopamine within the eye's retina and the brain. In still other embodiments the objective of ocular photo-bio-stimulation is to reduce pain. In still other embodiments the objective of ocular photo-bio-stimulation is to reduce the severity of a headache. When reducing pain by ocular photo-bio-stimulation, green light having wavelengths within the range of 530 nm+/−20 nm can be utilized. In still other embodiments the use of light wavelengths in the range of 650 nm+/−30 nm or 700 nm+/−30 nm can improve mitochondria function and/or reduce age related inflammation in the eye of the user. In other embodiments the objective is to improve mitochondria function and/or reduce age related inflammation in the eye's retina of the user.

In still other embodiments, the objective of ocular photo-bio-stimulation is to increase the number or healthy mitochondria present within the ocular photo-bio-stimulation, the area of the retina in which the ocular photo-bio-stimulation has targeted. When increasing healthy mitochondria by way of ocular photo-bio-stimulation, red light having wavelengths within the range of one of 650 m to 700 nm, 650 nm+/−30 nm, 700 nm+/−30 nm, or 830 nm+/−30 nm, can be utilized. Such ocular photo-bio-stimulation, according to the present invention, increases retinal mitochondrial function and attenuates oxidative stress thus increasing the number of healthy mitochondria within the area of the retina being treated. This can be important for treating, by way of example only, diabetic retinopathy, macular degeneration, and/or retinitis pigmentosa.

In still other embodiments, the objective of ocular photo-bio-stimulation is to increase the alertness of the individual being treated with ocular photo-bio-stimulation. When increasing alertness by way of ocular photo-bio-stimulation, blue light having wavelengths within the range of 450 nm to 510 nm can be utilized. In still other embodiments the objective of ocular photo-bio-stimulation is to increase the slowing down, to slow the progressing of, or to stop myopia of the individual being treated with ocular photo-bio-stimulation. When slowing down or stopping myopia by way of ocular photo-bio-stimulation, blue light having wavelengths within the range of 450 nm to 510 nm, or red light within the wavelength range of 650 nm+/−30 nm or 700 nm+/−30 nm can be utilized. Such ocular photo-bio-stimulation wavelengths can be applied to a large portion of the eye's retina to stimulate the ipRGC ganglion cells and/or rods, or to the ganglion axons of the optic nerve head for the purposes of generating increased retinal dopamine.

In still other embodiments, the objective of ocular photo-bio-stimulation is to treat or correct a neurological abnormality of the individual being treated with the ocular photo-bio-stimulation. When correcting a neurological abnormality by way of ocular photo-bio-stimulation, blue light having wavelengths within the range of 450 nm to 510 nm can be utilized. Neurological abnormalities that may be treatable by ocular photo-bio-stimulation are by way of example only: Alzheimer's, cognitive disorders, ADD, ADHD, depression, anxiety, and/or Parkinson's disorder.

In still other embodiments the objective of ocular photo-bio-stimulation is to prevent myopia from occurring with the individual being treated with the ocular photo-bio-stimulation. In still other embodiments the objective of ocular photo-bio-stimulation is to treat or correct an ocular abnormality of the individual being treated with ocular photo-bio-stimulation. When correcting an ocular abnormality, the use of the appropriate light wavelengths must be employed when treating with ocular photo-bio-stimulation. Ocular abnormalities that may be treatable by ocular photo-bio-stimulation are by way of example only: myopia, AMD, dry AMD, diabetic retinopathy, retinal degenerative disease, glaucoma, optic neuropathy, cataract, and/or meibomian gland disfunction leading to dry eye.

For all embodiments provided herein for providing ocular photo-bio-stimulation, light wavelengths predominantly fall within the wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, which can be utilized in addition to what is stated within the embodiment description. The desired wavelength band of the above will depend upon the type of ocular photo-bio-stimulation that is desired to produce the desired physiological response. Thus, for any embodiment disclosed within this invention disclosure, any of the above ranges of wavelengths can be applied over and beyond what may be stated.

In embodiments, a second eyewear to be worn by a wearer, wherein the second eyewear when worn is in optical communication with a first eyewear worn by a wearer, wherein the second eyewear comprises a filtered lens or filtered optic, wherein the filtered lens or filtered optic of the second eyewear predominantly transmits light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, to an eye of the wearer, wherein the first eyewear comprises a first eyewear lens for optically correcting the distance vision of the wearer, and wherein the filtered lens or filtered optic of the second eyewear is distinct from first eyewear lens. The overall transmission of the first and second eyewear filtered lens or filtered optic being such to cause an enlargement of the pupil of the eye of the wearer. The transmission of light wavelengths is within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, providing ocular photo-bio-modulation to the retina of the eye of the wearer.

In embodiments, biofeedback can be utilized to confirm that increased dopamine and/or serotonin is being produced within the brain of a patient having ocular photo-bio-stimulation therapy. Such biofeedback can be comparing one or more of: increased blink rate of the eye(s) of the patient being treated, increased diameter of pupil(s) of the patient being treated, and/or increased heart rate of the patient being treated to that of a base line for the same activity prior to the ocular photo-bio-stimulation therapy.

In embodiments, one or more of a timer, an alarm (such as by way of example only, sound, vibration, light, or image), and/or wireless or wired communication to notify a remote third party, can be incorporated or associated with eyewear providing ocular photo-bio-stimulation therapy.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention.

FIG. 10 shows background information for purposes of explaining the invention herein.

FIG. 14 shows an embodiment of the current invention as described herein.

FIG. 28 shows an embodiment of the current invention as described herein.

FIG. 29 shows an embodiment of the current invention as described herein.

FIG. 30 shows an embodiment of the current invention as described herein.

FIG. 34 shows an embodiment of the current invention as described herein.

FIG. 37 shows an embodiment of the current invention as described herein.

FIG. 38 shows an embodiment of the current invention as described herein.

FIG. 44 shows categories of sunglasses.

FIG. 48 shows information related to the invention described herein.

FIG. 53A-D shows an embodiment of the current invention as described herein.

FIG. 54A-B shows an embodiment of the current invention as described herein.

DETAILED DESCRIPTION OF THE INVENTION

Definitions

Figure 1:
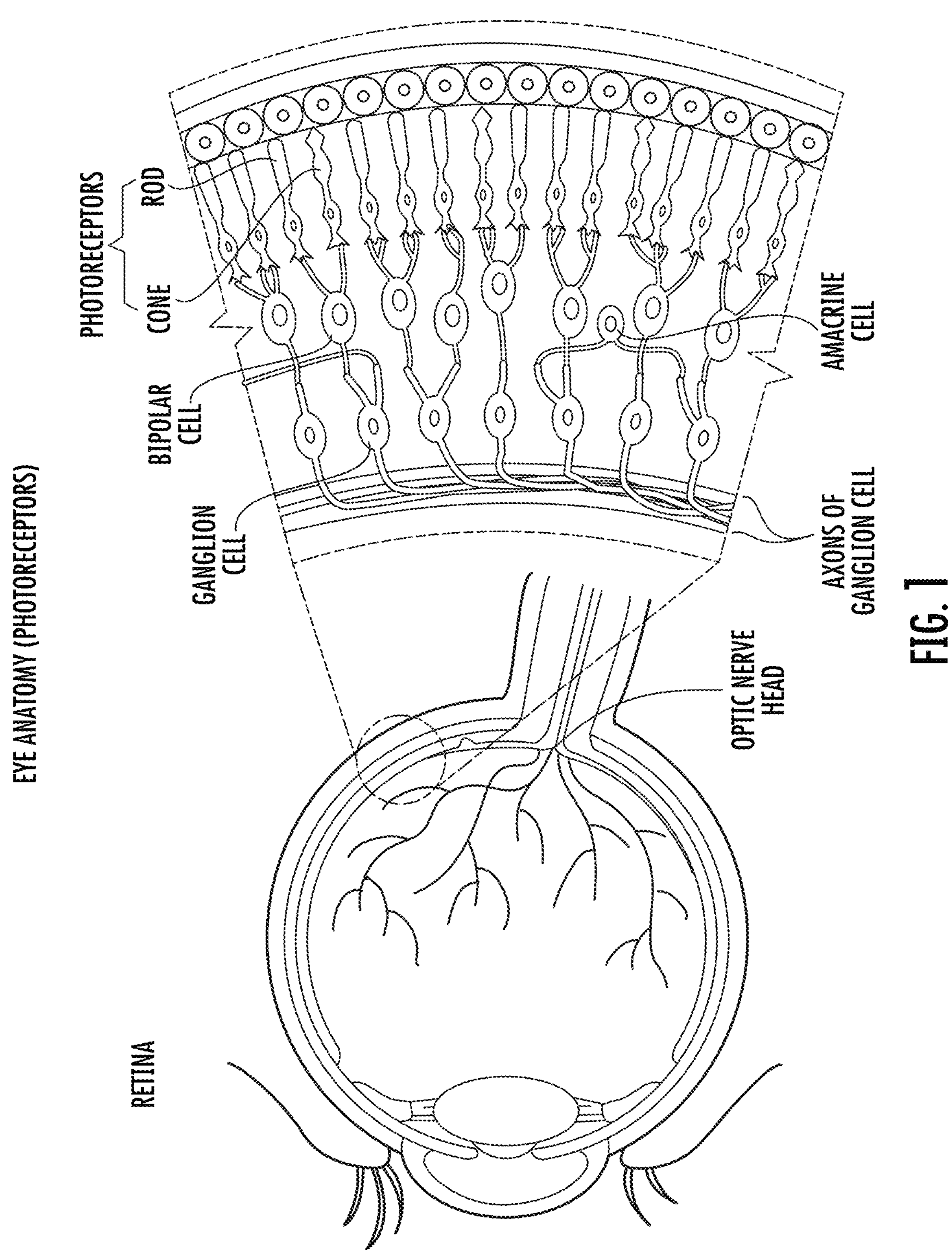
FIG. 1 shows background information for purposes of explaining the invention herein.
Figure 2:
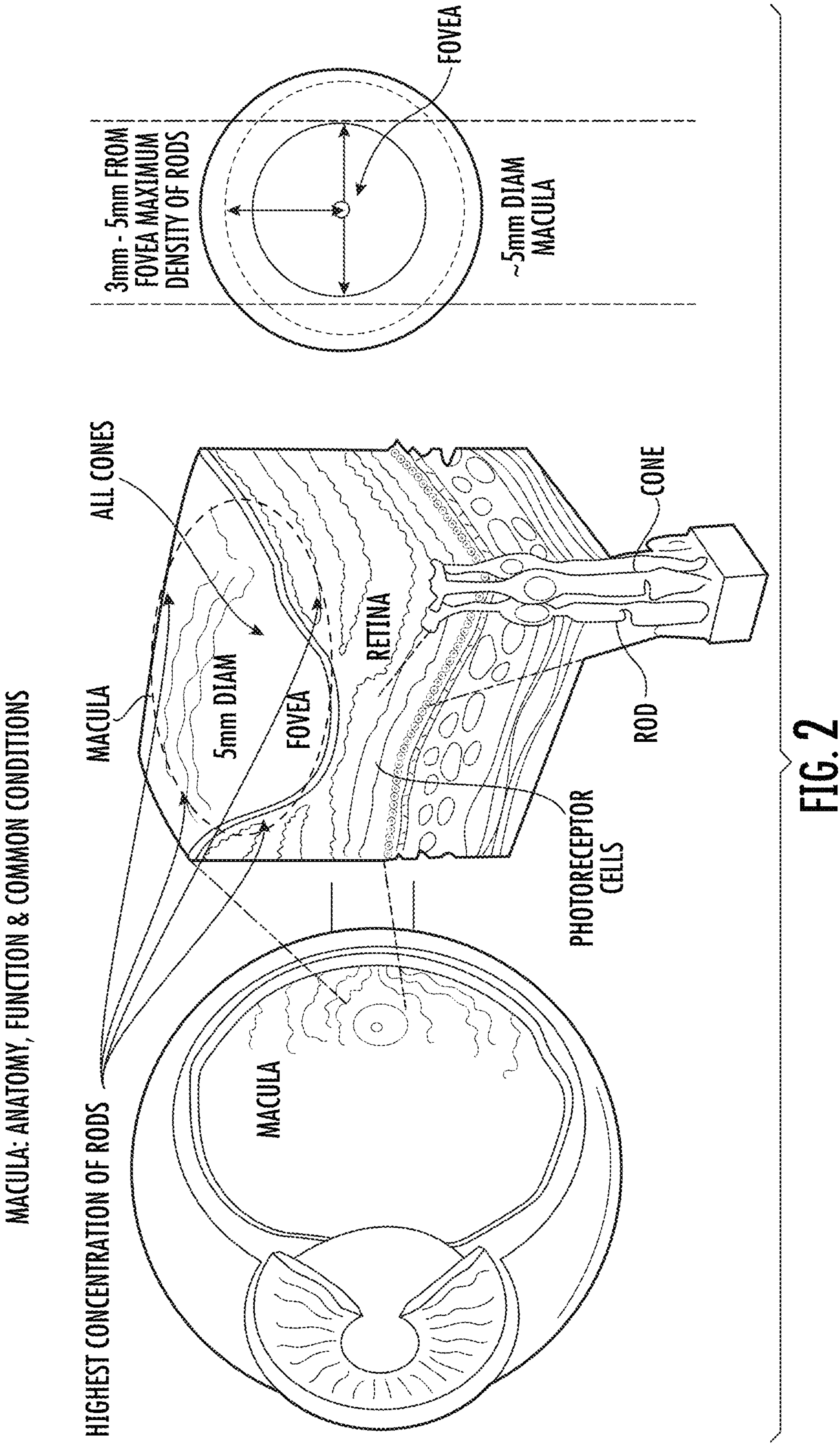
FIG. 2 shows background information for purposes of explaining the invention herein.
Figure 3:
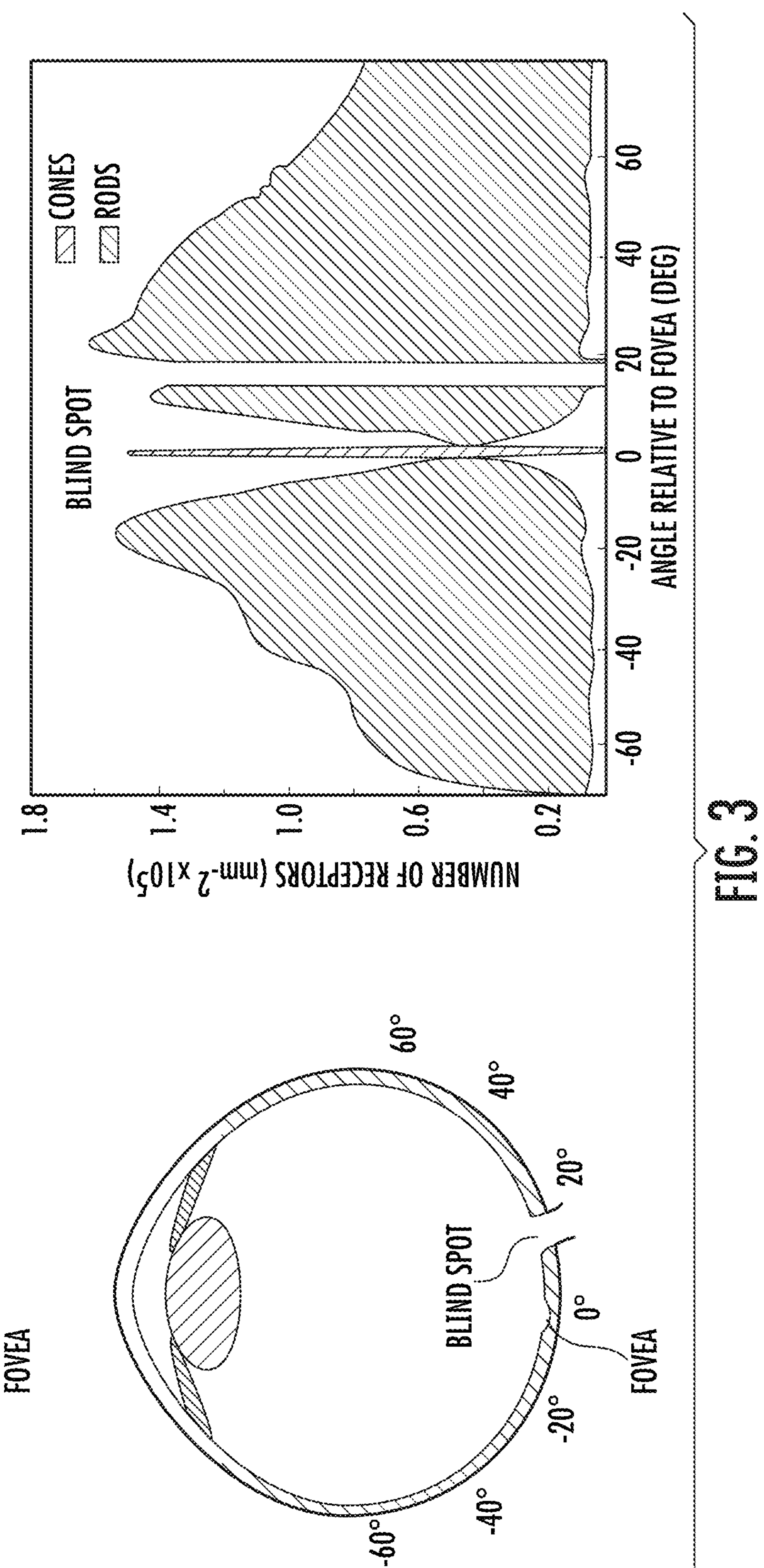
FIG. 3 shows background information for purposes of explaining the invention herein.
Figure 4:
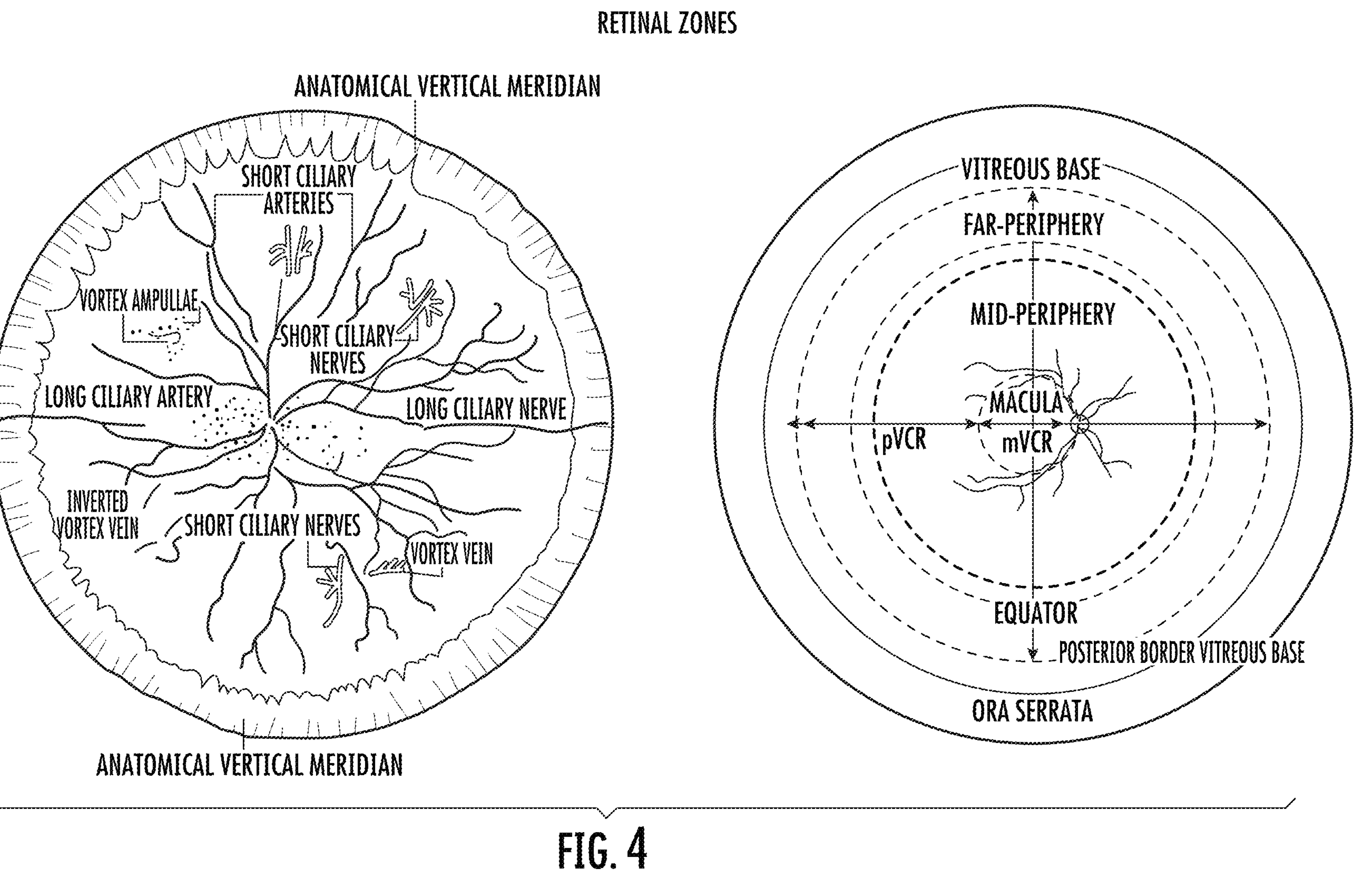
FIG. 4 shows background information for purposes of explaining the invention herein.
Figure 5:
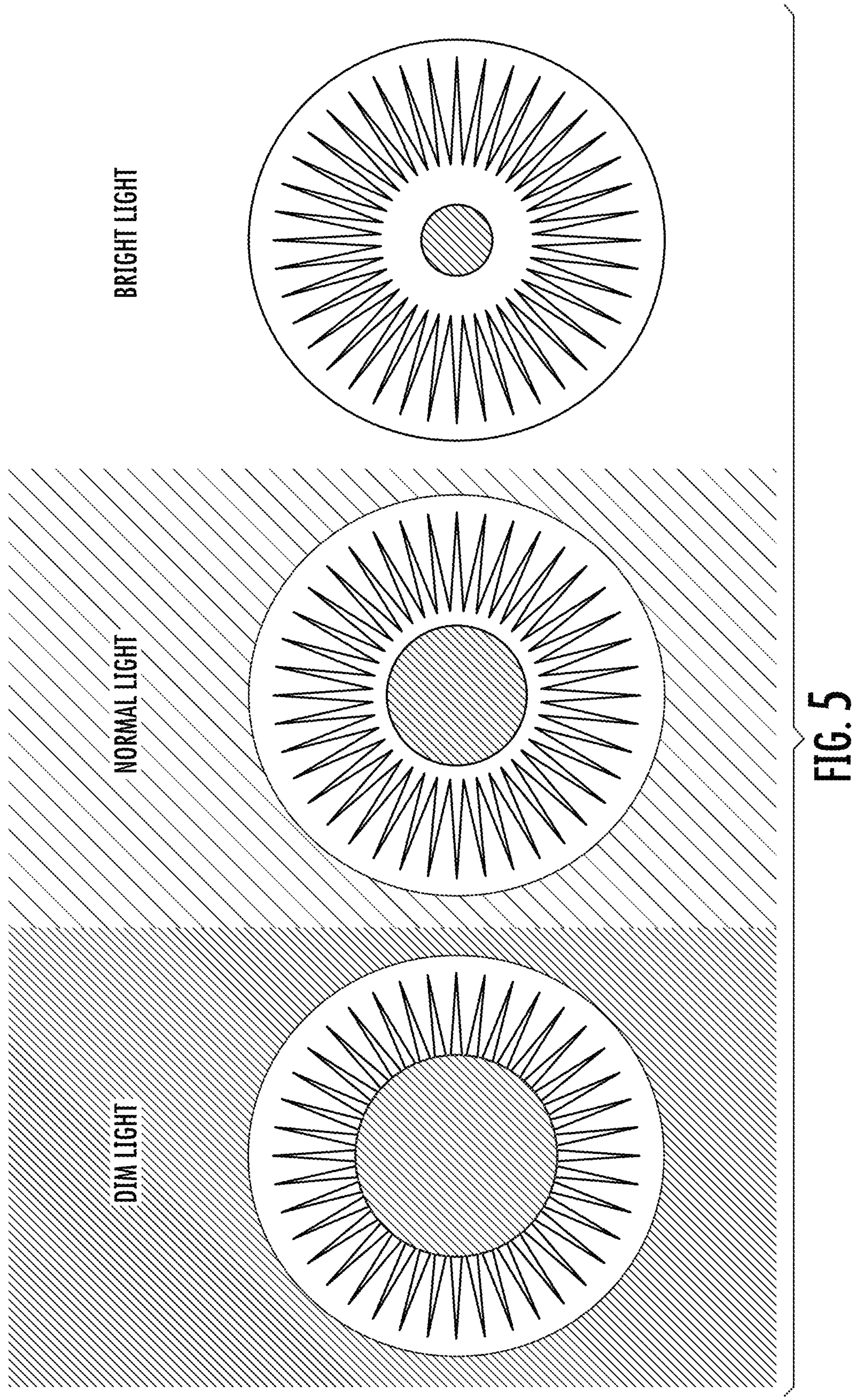
FIG. 5 shows background information for purposes of explaining the invention herein.
Figure 6:
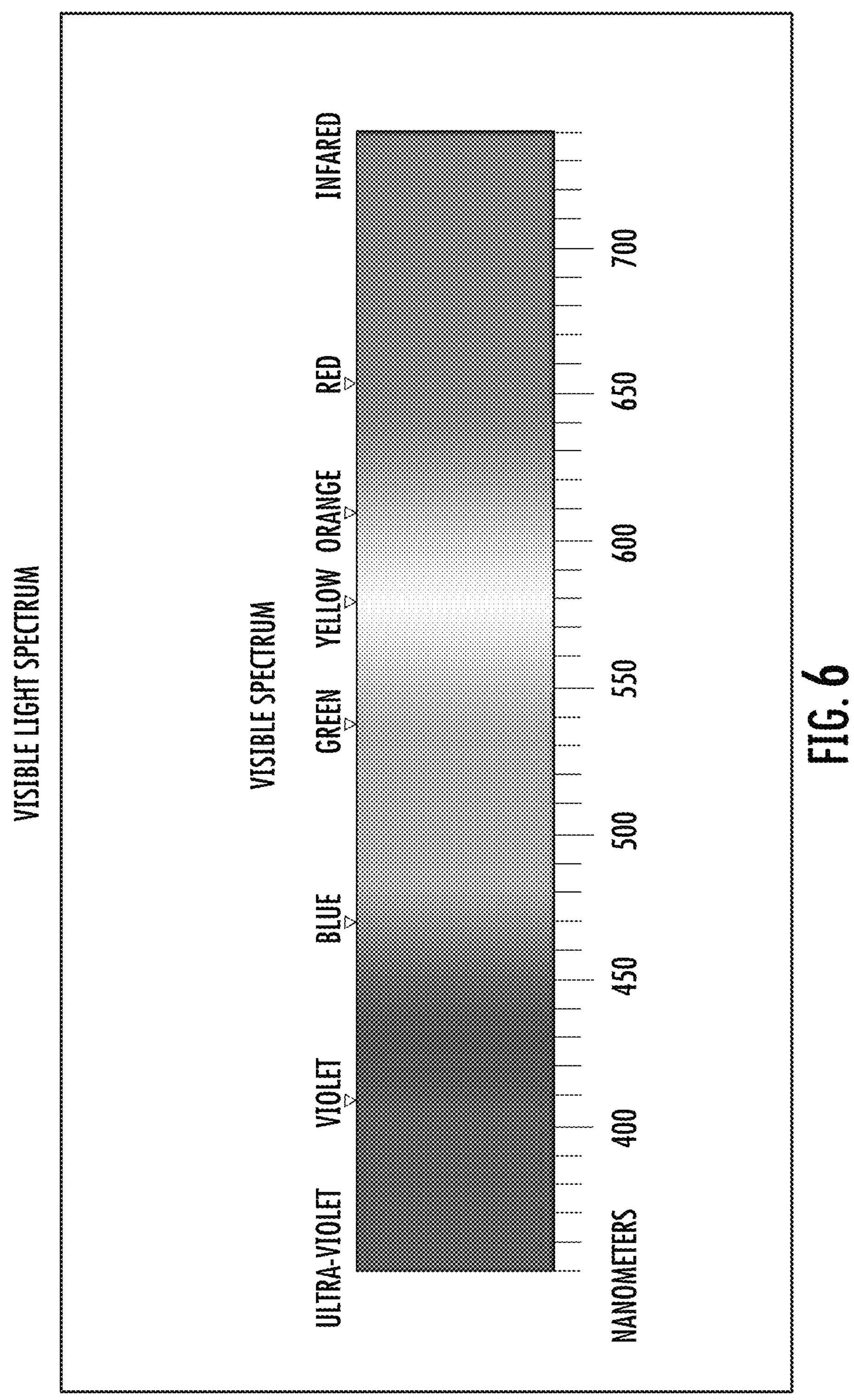
FIG. 6 shows background information for purposes of explaining the invention herein.
Figure 7:
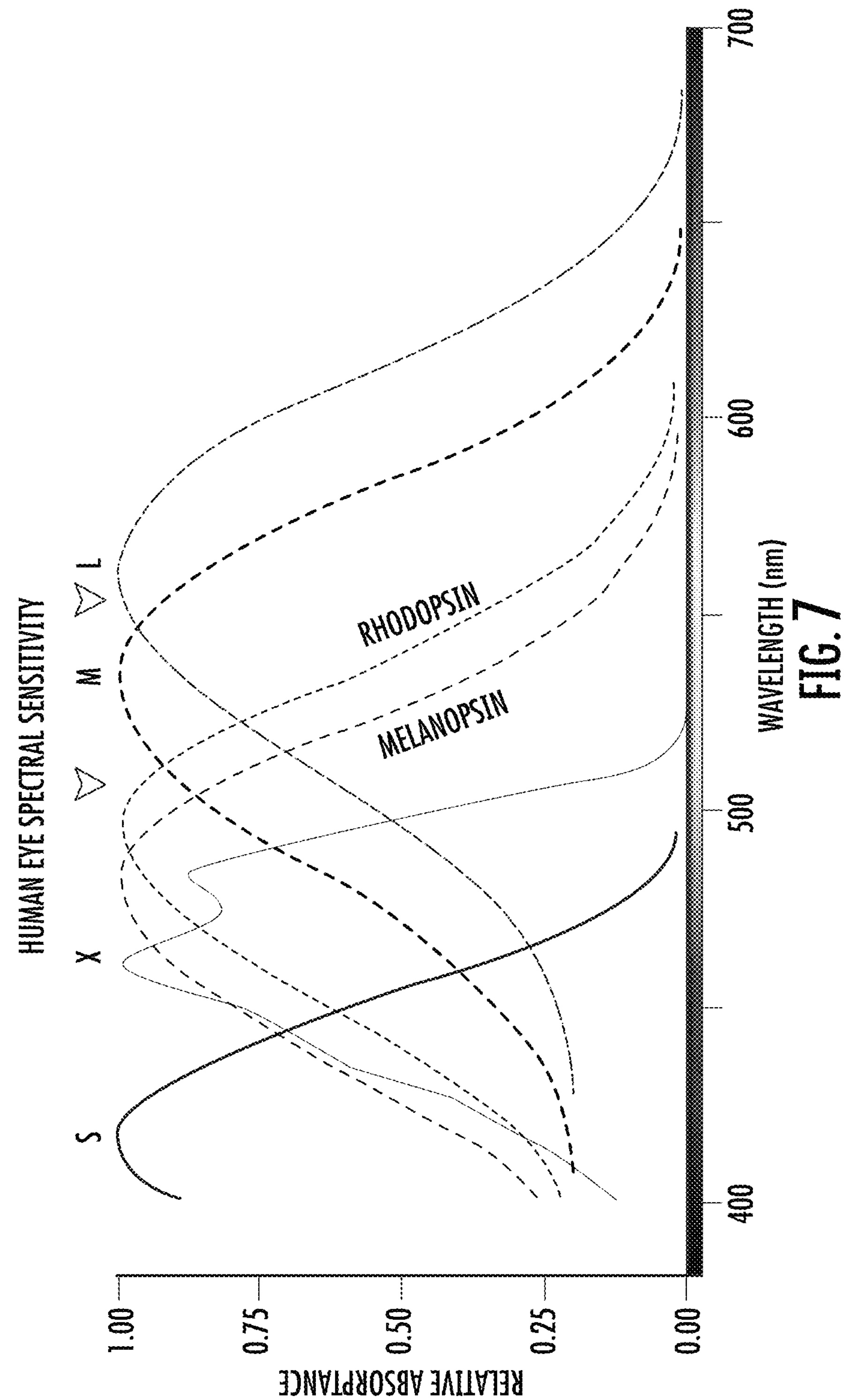
FIG. 7 shows background information for purposes of explaining the invention herein.
Figure 8:
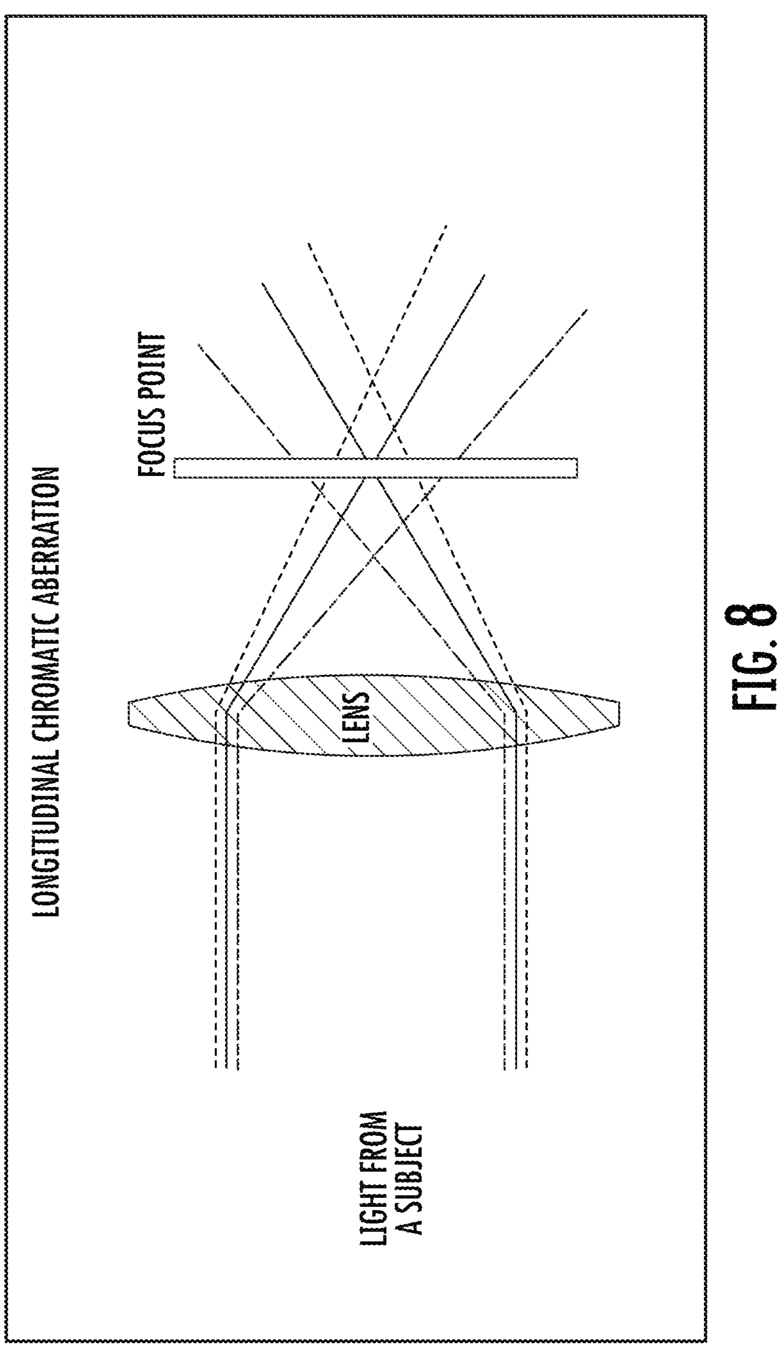
FIG. 8 shows background information for purposes of explaining the invention herein.
Figure 9:
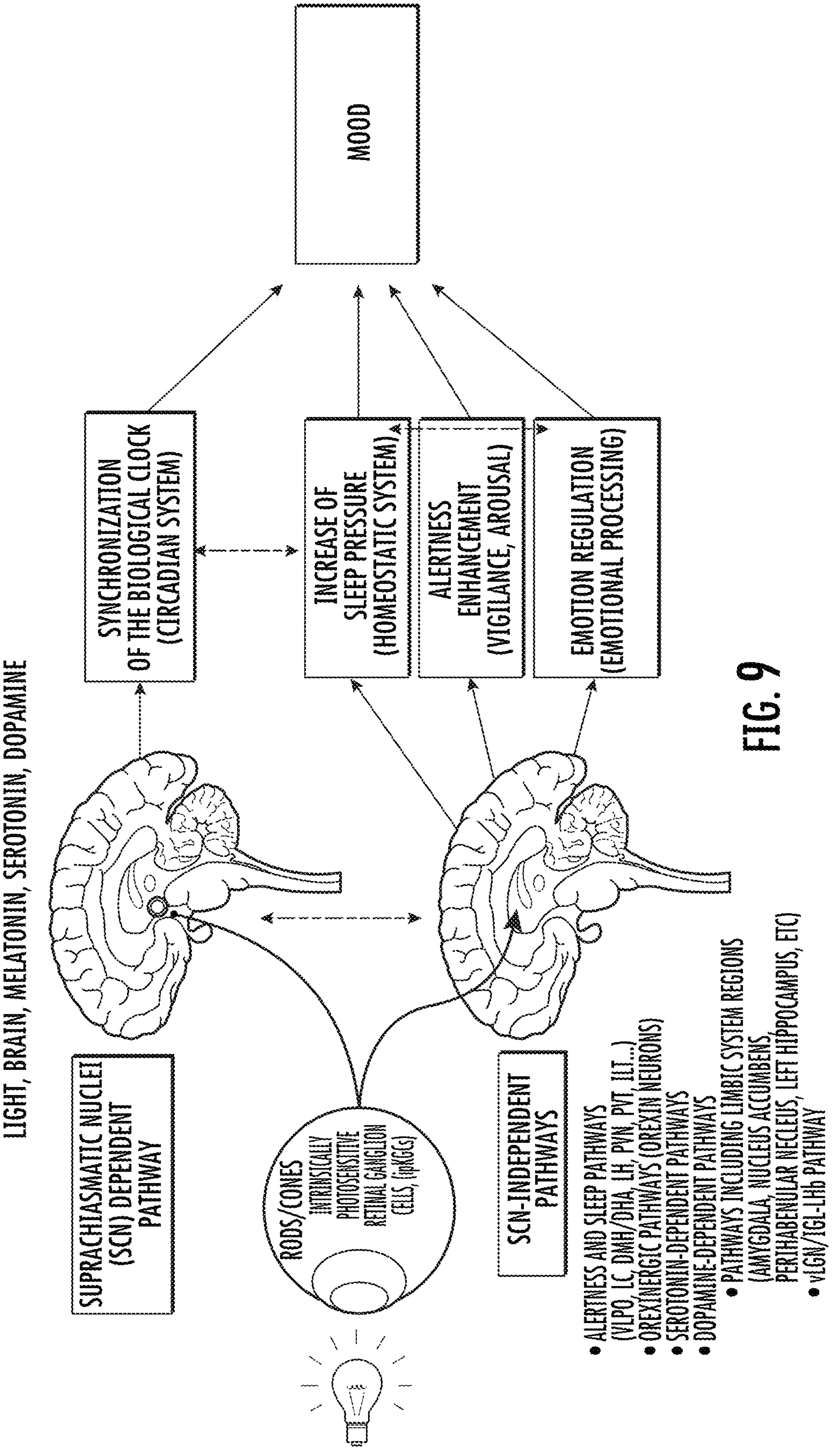
FIG. 9 shows background information for purposes of explaining the invention herein.
Figure 11:
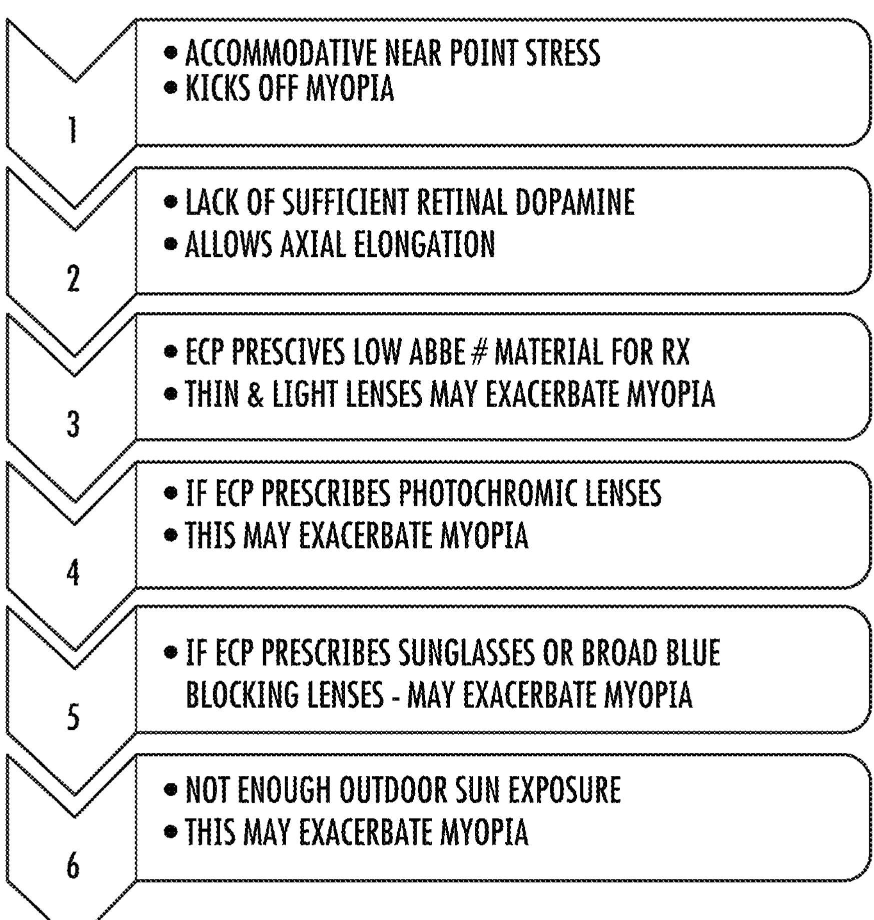
FIG. 11 shows background information for purposes of explaining the invention herein.

As used herein, ambient light can be that of indoor artificial light or sunlight. Ambient light as used herein can be that which would be in addition to that of a light emitter.

As used herein, ECP stands for Eye Care Professional.

As used herein, ocular photo-bio-stimulation is an umbrella term. Ocular photo-bio-stimulation is a biological non-invasive technique of using light to stimulate a neuron(s) or other cells within, on, or about the eye for the purpose of generating a physiological response within the human body. Such stimulation can directly or indirectly amount to stimulation or inhibition of a biological, neurological or chemical process within the human body.

As used herein optogenetic therapy is broadly defined as a form of photo-bio-stimulation.

As used herein, photo-bio-modulation is broadly defined as a form of photo-bio-stimulation.

As used herein, painting the retina, is defined as causing a light that is providing ocular photo-bio-stimulation of the retina to project its wavelengths of light onto the retina of an eye in such a manner that the light paints, covers, or affects, different portions or different neurons of the retina with light wavelengths as the light moves relative to the retina or the retina moves relative to the light.

As used herein, the visible light spectrum is as follows: Visible Light Spectrum (electromagnetic radiation spectrum) can be divided by color; blue/violet (400 nm-450 nm), blue (451 nm-489), bluish green (490-520 nm), green (521 nm-556 nm), yellow (556 nm-590 nm), orange (590 nm-625 nm), and/or red (625 nm-700 nm). However, in a general sense as used herein blue can be from 400 nm-520 nm.

As used herein, BVA stands for the level of vision when considering the best visual correction of a patient's distance vision needs. For example, that of 20/25, 20/20, or 20/15.

As used herein, a wavelength within the range of; by way of example only, 480 nm+/−30 nm means any single wavelength or wavelengths found within the range of 480 nm+/−30 nm.

As used herein, a wavelength within the range of; by way of example only, 530 nm+/−20 nm means any single wavelength or wavelengths found within the range of 530 nm+/−30 nm.

As used herein, a wavelength within the range of; by way of example only, 650 nm+/−30 nm means any single wavelength or wavelengths found within the range of 650 nm+/−30 nm.

As used herein, a wavelength band or wavelengths band, means one or more wavelengths of light within a certain range.

As used herein, predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to the eye(s) of the wearer, means at least one of the preceding ranges of wavelengths includes the predominant (or most) light wavelengths within that wavelength range transmitted to the eye(s) of the wearer.

As used herein, when referring to wavelengths within the range of X, this is meant to convey that any two or more wavelengths that are within the given range of wavelengths are predominantly or solely emitted or transmitted wavelengths (within the light wavelength range given) for the optic, filter, lens, and/or system, when discussing lighting or transmission. In certain cases, the word predominantly may be omitted, however in all cases the word predominantly should be read in to express the meaning.

As used herein a wavelength band is a band of light wavelengths that run concurrent with a beginning wavelength and ending wavelength.

As used herein, a transmission peak is the peak light wavelength or wavelengths having the highest light transmission that fall within a band of light wavelengths. A transmission peak can be that of a curve or a plateau.

As used herein an image can be generated by light or by the absence of light when surrounded by a lighted image (in the case of a black image). A black image can also be generated by the colors of: blue, magenta, and yellow.

As used herein, a light emitter can be any a component that converts an electrical signal into a light signal. Light emitters can be, for example only, LEDs, OLEDs, TOLEDs. micro-OLEDs, micro-LEDs, micro-ileds, iLEDs, quantum dots, florescent lights, incandescent lights, and/or the sun.

As used herein, a light source can be any artificial light source that comprises a light emitter or light emitters or a light source can be that of the sun.

As used herein, an electronic display screen can be that of any electronic display screen. By way of example only, cell phone display screen, tablet display screen, laptop computer display screen, desktop computer display screen, or television display screen.

As used herein, an optical filter is any device or material that changes the spectral distribution of a light beam spectrally selectively or non-selectively.

As used herein, an optic is a material that transmits light. An optic can be part of an optical system. However, a lens can also be an optic. As used herein, an optic can be any kind of optic. Furthermore, a lens can be an optic, or an optic can be a lens.

As used herein, a lens is an optic that focuses or defocuses light. A lens is a transmissive optical device that focuses or disperses a light beam by means of refraction. As used herein, a lens can be any kind of lens. Furthermore, a lens can be of any optical power including plano, unless that an optical power is specified in the disclosure.

As used herein, an eyeglass lens can include or be a transparent optical component designed to enhance visual clarity and provide corrective vision for individuals with refractive errors, such as myopia, hyperopia, astigmatism, or presbyopia. It can be made from various materials, including glass and plastic, and may incorporate special features such as coatings for anti-reflective properties, ultraviolet ("UV") protection, or light filtration. Eyeglass lenses can be customized to fit a wide range of frame styles and can also include specialized lenses for conditions like photophobia or low vision, catering to diverse visual needs and preferences.

As used herein, the Abbe value, also known as the V-number or constringence, is a numerical value that measures how much light disperses into individual wavelengths as it passes through a transparent material.

As used herein, eyewear means any device used on, in, or about the eye that transmits or directs light into the eye of the wearer of such eyewear. By way of example only, one of: spectacles, sunglasses, disposable eyewear, goggles, dress eyewear, safety eyewear, sports eyewear, clip on eyewear, fit over eyewear, magnetic attachable eyewear, military eyewear, smart eyewear, XR eyewear, AR eyewear, VR eyewear, MR eyewear, modified reality eyewear, contact lens, intra-ocular lenses, corneal implant, lens or lenses that are housed, supported, attached to eyewear or a frame worn around the eye or eyes of the wearer.

As used herein, optical finishing can be the application of any finish, coating, tinting, to a lens. Such a coating can be by way of example only, hard scratch resistant coat, antireflection coat, spin coat, dip coat, vacuum deposition coat, surface cast.

As used herein a semi-finished lens blank is a lens blank that has one of its surfaces polished.

As used herein a finished lens blank is a lens blank that has both of its surfaces polished and further that optical power can be measured.

As used herein, a filtered optic, is an optic or lens that comprises one or more filters or is in optical alignment with one or more filters. Such filters can be by way of example only one or more of, interference filter, bandpass filter, absorption filter, notch filter, selective wavelength(s) filter, and/or neutral density filter.

As used herein, a filtered lens is a lens or optic that comprises one or more filters or is in optical alignment with one or more filters. Such filters can be by way of example only one or more of, interference filter, bandpass filter, absorption filter, notch filter, selective wavelength(s) filter, and/or neutral density filter.

As used herein, optical alignment means that two optics (such as, two optics, two lenses, and/or one optic and one lens) are aligned so that a light ray can pass through each of the two optics.

As used herein, chromatic aberration is aberration caused by the differences in refraction of the colored rays of the spectrum.

As used herein, longitudinal chromatic aberration (LCA) is a lens's inability to properly focus different color wavelengths in the same focal plane.

As used herein, the central retina (macula) is a circular area of the retina that is about 5 mm-6 millimeters in diameter with the fovea in the center, which is a small area in the center of the retina. The retina is between 30 mm to 40 mm in diameter.

As used herein, the peripheral retina is any area of the retina that is outside of the central retina.

As used herein, the mid peripheral retina is located between the far peripheral retina and the central retina.

As used herein the far peripheral retina is located between the ora serrata and the mid periphery of the retina.

As used herein, a biomarker (short for biological marker) is an objective measure that captures what is happening in a cell or an organism at a given moment As used herein, a physiological response is a bodily response that can be the result of direct or indirect neural simulation. The physiological response can be immediate or delayed. By way of example only, slowing myopia may result from stimulating retinal rods and/or ganglion cells with an ocular photo-bio-stimulation light comprising blue light wavelengths within the range of 480 nm+/−30 nm. The immediate response, in aspects, can be the increase of dopamine in the eye produced by the amacrine cells, while the delayed response could, for example, be that of slowing myopia. For the purposes of this invention disclosure, both the increasing dopamine and slowing of myopia would be considered physiological responses. Another example would be stimulating dopamine and/or serotonin in the brain.

As used herein, intrinsically photosensitive retinal ganglion cells (ipRGCs), also called photosensitive retinal ganglion cells (pRGC) are ganglion cells containing melanopsin and are a type of neuron in the retina of the human eye.

As used herein, melanopsin-containing retinal ganglion cells (mRGCs) are specialized ganglion cells that contain melanopsin and are a type of neuron in the retina of the human eye.

As used herein, scotopic light is a type of light that is used to describe vision in dim or dark conditions, also known as scotopic vision or night vision. Scotopic light can be below 0.4 lux.

As used herein, mesopic light or mesopic vision, sometimes also called twilight vision, is a combination of photopic and scotopic vision under low-light (but not necessarily dark) conditions. An example of mesopic light is low light level light provided by public lighting of 0.4 lux up to 10 lux (about 0.6 cd/m2).

As used herein, photopic light, also known as daytime vision, is the visual perception that occurs when the eyes are light-adapted and there is enough brightness. A candle at 1 meter distance gives 1 photopic lux of light. Typical room illumination is in the order of 300-500 lux, whereas outdoor light varies from 1,500 lux on a cloudy day to 100,000 lux on a sunny day.

As used herein, light intensity or luminous intensity is measured in lumens per square foot (footcandles) or lumens per square meter (lux). Lumens measure the intensity of light emitted by a luminaire, while lux is a measurement of the light that is achieved and perceived. Lux, in some cases, is a more important measurement because it relates brightness to distance from the light source.

As used herein, light transmission is the percentage of all visible light transmission through a lens or optic.

As used herein, overall visible light transmission includes all visible light transmission through a lens or optic.

As used herein, the transmission of light wavelengths (within a range of given wavelengths) is the transmission percentage measured within a given range of light wavelengths through a lens or optic of the overall visible light that is transmitted through the lens or optic. By way of example only, if the overall transmission of visible light through the lens or optic was 2,000 lux and only 1,000 lux of light was transmitted through and measured within 480 nm+/−30 nm, then the transmission percentage through the wavelength range of 480 nm+/−30 nm would be 50%.

As used herein within a range of wavelengths or within a wavelength range means one or more wavelengths within the given range.

As used herein, dopamine deficiency disorders are any disorder caused by a lack of the appropriate amount of dopamine. Low levels of dopamine can affect both physical and mental health.

As used herein, serotonin deficiency disorders are any disorder caused by a lack of the appropriate amount of serotonin. Low levels of serotonin can affect one's mental, behavioral, and emotional health.

As used herein, Extended Reality (XR) is an umbrella term to refer to augmented reality (AR), virtual reality (VR), mixed reality (MR), modified reality (MoR), and combinations thereof. The technology is intended to combine or mirror the physical world with a "digital world" able to interact with it, giving users an immersive experience by being in a virtual or augmented environment.

Virtual Reality (VR) is a computer-generated environment with scenes and objects that appear to be real, making the user feel they are immersed in their surroundings. This environment is perceived through a device known as a Virtual Reality headset or helmet.

Mixed Reality (MR) combines Augmented Reality (AR) and Virtual Reality (VR). While AR overlays digital content onto the real world, and VR immerses the user in a completely virtual environment, MR blends these two, creating interactive environments where physical and digital objects coexist and interact.

Augmented reality (AR) is an interactive experience that visually combines the real world and computer-generated 3D content.

The distinctions between VR and AR come down to the devices they require and the experience itself: AR uses a real-world setting while VR is completely virtual.

As used herein, Modified Reality is a modified version of extended reality which results in any deviation from Augmented Reality, Mixed Reality, or Virtual Reality, where a portion of one, two or more lighted images are seen with an eye or eyes of a user merged or intertwined or overlapped. Such modified reality can be a modified form of augmented reality, virtual reality or mixed reality.

As used herein, a near eye display is an electronic display that is within 30 mm or less (in most cases 20 mm or less) of the cornea of the eye of the user. A near eye display can comprise or be aligned and in optical communication with a micro-lens array. The use of a micro-lens array allows for the user to see a clear virtual image from said near eye display. However, in certain cases the near eye display is used to provide defocused light and in these cases a micro-lens array is not utilized.

As used herein, a see-through near eye display is an electronic near eye display that the eye of the user can see a real image by looking through. In most cases, the use of a micro-lens array allows for the user to see a clear virtual image from said near eye display. However, a micro-lens array can be fabricated to defocus light or diffuse light.

As used herein, a non-see-though near eye display is an electronic near eye display that the eye of the user cannot see a real image through. In most cases the use of a micro-lens array allows for the user to see a clear virtual image from said near eye display. However, a micro-lens array can be fabricated to defocus light or diffuse light.

As used herein, an eyewear apparatus includes any device or apparatus described herein that filters, treats, changes, enhances, diffuses, focuses, defocuses, transmits, generates, or otherwise is capable of producing or affecting light in such a way that the light can be used for ocular photo-biostimulation purposes.

As used herein, a micro-lens array is a structure made up of many small lenses, or microlenses, that are arranged in a patterned manner. A micro-lens array can comprise hundreds, thousands or millions of micro-lenses. A micro-lens array as used herein can be for one or more of, providing focused light, defocused light, diffused light, and/or filtered light.

As used herein, a chromatic aberration focused lens or optic can be that of a peripheral refocused chromatic aberration lens or optic. A chromatic aberration focused lens is a lens or optic where a portion or all of the lens peripheral to the central zone of the lens, focuses one or more of the chromatic aberration wavelength bands (blue, green, red)

farther away from the lens or optic. Said another way, while the central zone maintains its normal focus of chromatic aberration wavelength bands, the chromatic aberration wavelength bands peripheral to the central zone focuses farther from the lens or optic than those of the central zone.

As used herein defocused light can be that of one or more of: light that focuses in front of the retinal, behind the retina, is scattered light, and/or dispersed or diffused light.

As used herein when discussing enlarging the pupil diameter it is meant to enlarge the pupil diameter relative to what the pupil diameter would have been if all light (without being filtered or blocked) was permitted to strike the retina of the wearer/user's eye(s).

As used herein, a vehicle can be that of any vehicle. By way of example only, a vehicle can be an airplane, car, truck, bus, trolley, ship, train, subway, or tram.

As used herein, the frame of an electronic display can be the other edge or a frame that goes around the outer edge of the display.

As used herein, programmable means software, memory, or an electrical component that was one or more of, programed during the fabrication of the device, can be programmed after fabrication, can be programed after fabrication remotely, and/or can be programed by the consumer after purchase.

All embodiments disclosed herein, when appropriate, can utilize one or more of the following: bandpass filter, notch filter, selective filter, absorption filter, interference filter, neutral density filter, coating, and/or dye, to achieve the desired wavelength transmission results. When more than one filter is used, it can be referred to herein as a hybrid filter. In certain embodiments a film or optic comprising the appropriate filter can be applied over or in front of the front of an electronic display or optic to allow for the desired wavelengths of light to be transmitted. The film or optic comprising the filter can be attachable and removable from the display screen or built into the screen (or optic).

Myopia, Prevention and Control:

According to the current invention, it is believed that juvenile-onset myopia (nearsightedness) occurs due to accommodative near point stress that generates a force causing an increase in the axial length of the eye. The resulting axial elongation occurs when the eye's ocular structure is unable to provide an offsetting force equal to or larger than that of the force causing axial elongation. The weakness of the opposing ocular structural is due to a deficiency of dopamine present in the retina.

Figure 12:
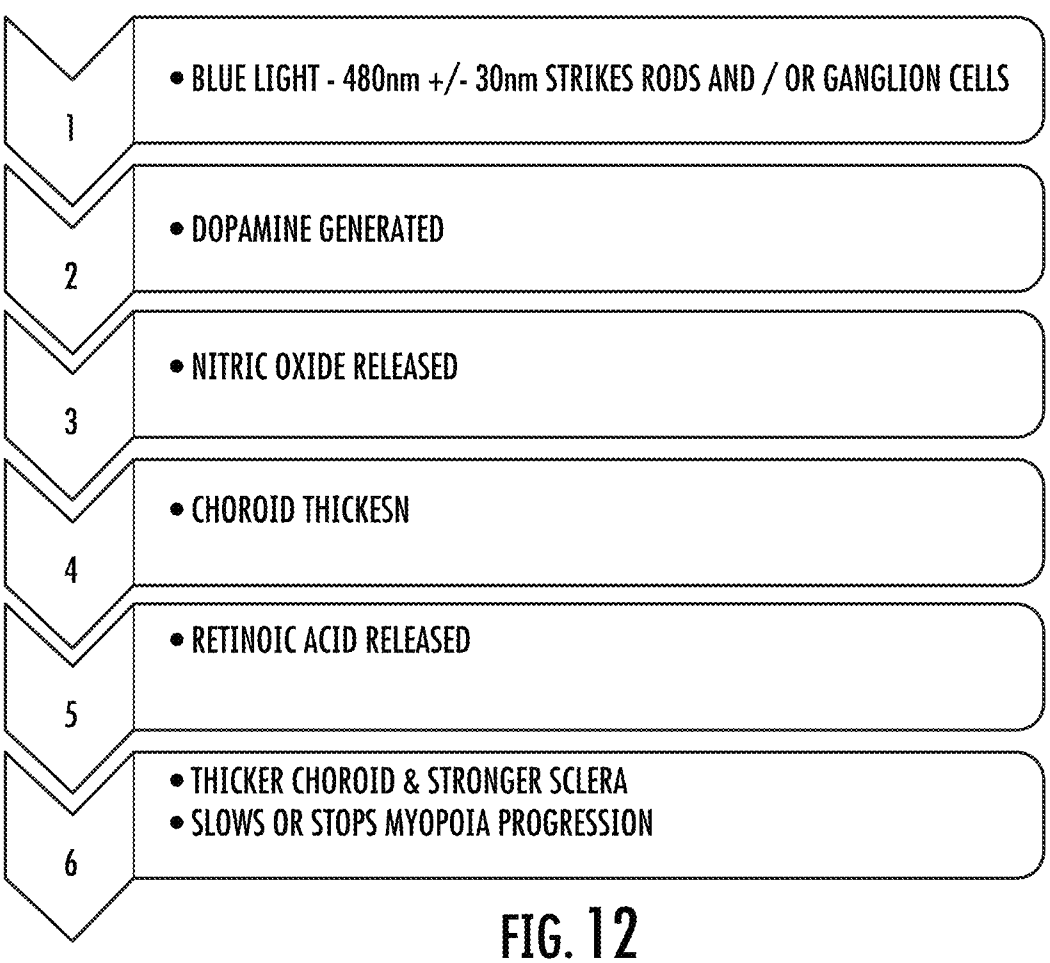
FIG. 12 shows an embodiment of the current invention as described herein.

In reference to FIG. 12, ample retinal dopamine is required to increase choroid thickness and maintain a healthy sclera, both of which generate an offsetting force of resistance to axial elongation of the eye. Thus, the following embodiment provides for the prevention of myopia or slowing or stopping myopia progression.

An embodiment of the invention is that of identifying children susceptible to myopia and treating them before their myopia develops. A diagnostic test can be performed to determine the level of dopamine in the eye or eyes of a child. By way of example only an ERG (electroretinogram) test can be performed at an early age, (for example) 6 years and older. When such a test is performed one can identify if a child has a dopamine deficiency disorder. Following this, a refractive examination can be performed, whether subjective or objective, using a retinoscope, automatic refractor, or phoropter. Accordingly, the results can be used to identify those children who have 0.75D of hyperopia or less of hyperopia. Such children would include emmetropes. The result of these two tests (electroretinogram and refraction) can then identify which children are susceptible to becoming myopic. Upon identifying a child that is susceptible of becoming myopic, one can begin treatment for ocular dopamine generation. Such means of treatment are identified in this invention disclosure. By improving the level of dopamine in the retina of the child's eye, one can offset the development of ocular axial elongation (or myopia).

Said another way, an embodiment for the prevention of myopia is:

1) Identify those children 6 years old or older (or even younger) who have low levels of dopamine in their retina;
2) Test those children to identify their BVA (best distance visual acuity) refractive status; and
3) If the refractive status of the child is +0.75D or less hyperopia and their ocular dopamine test indicates low dopamine, begin therapy to increase retinal dopamine.

For those children who already have myopia it is important to stop or slow the progression of myopia as the child ages. Thus, it is important to increase the level of retinal dopamine in those children. Embodiments for increasing dopamine in the eye's retina are disclosed herein.

An embodiment of the current invention can be that of a device that is capable of determining a level of dopamine in the eye's retina of a patient, while also determining a refractive status of the eye. By way of example only, such a device can measure if the patient's eye comprises dopamine at a level that meets or exceeds "X", wherein X represents the level of dopamine deficiency, and also measure if the same eye comprises a refractive status that is less than "Y" diopters of hyperopia or is emmetropia or myopic. Another example would be that such a device can measure if the patient's eye comprises dopamine at a level that meets or exceeds "X", wherein X represents the level of dopamine deficiency, and also measure if the same eye comprises a best distance refractive correction that measures +0.75D or less of hyperopia.

An embodiment can be an instrument for identifying a child or young adult that is susceptible to developing myopia, wherein the child or young adult is 25 years or younger, wherein the instrument determines if the child or young adult's eye comprises dopamine at a level that meets or exceeds "X", wherein X represents the level of dopamine deficiency, and wherein the instrument can also determine if the same eye's distance refractive correction (being that of the best distance correction optical power) is that of +0.75D or less.

An embodiment can be an instrument for identifying a child or young adult that is susceptible for developing myopia, wherein the child or young adult is 25 years or younger, wherein the instrument determines if the child or young adult's eye comprises dopamine at a level that meets or exceeds "X", wherein X represents the level of dopamine deficiency, and wherein the instrument can also measure if the same eye's refractive correction, being that of the best distance correction optical power, is that of a spherical equivalent that is +0.75D or less hyperopic.

Such a device could determine both the level of dopamine in the retina or eye and the refractive status simultaneously or in succession. Such a device could be one of, handheld, a tabletop instrument, attachable to a slit lamp bio microscope, or attachable to a phoropter stand. By way of example only, such a device could be a combination ERG instrument and an autorefractor.

An embodiment can be that of an instrument for identifying a child or young adult that is susceptible for developing myopia, wherein the child or young adult is 25 years or younger, wherein the instrument determines if the child or young adult's eye comprises dopamine at a level that exceeds "X", wherein X represents the level of dopamine deficiency, and wherein the instrument can also determine if the same eye's distance refractive correction (being that of the best distance correction optical power) is that of +0.75D or less.

An embodiment can be that of an instrument for treating myopia progression, wherein the instrument can determine a level of dopamine in the eye, wherein the instrument can also determine if the eye's refraction requires an increase in minus optical power. Such an instrument can be that of an electroretinogram (ERG). Such an instrument can be handheld, or table mounted. For testing children, the use of a handheld ERG instrument that uses electrodes connected to the skin of the patient is recommended as opposed to corneal electrodes. By measuring the B wave amplitude, it is possible to determine a level of dopamine in the retina of the eye. A reduction in the B wave amplitude can indicate a dopamine deficiency.

An embodiment can be that of an instrument for preventing or treating myopia, wherein the instrument can determine a level of dopamine in the eye's retina, wherein the instrument can also determine if the eye's best distance refraction is +0.75D or less of plus optical power or if the eye requires an increase in minus optical power to maintain its best corrected distance vision.

An embodiment can be that of an instrument for preventing or treating myopia, wherein the instrument can determine a level of dopamine in a patient's eye's retina, wherein the instrument can also determine the optical power required to achieve for the same eye of the patient its best distance vision correction or best distance visual acuity.

An embodiment can be that of an instrument for preventing and/or treating myopia, wherein the instrument can determine a level of dopamine in a patient's eye's retina, wherein the instrument can also determine the optical power required to achieve for the same eye of the patient its best distance vision correction or best distance visual acuity, and wherein the instrument can apply photo-bio-stimulation.

As disclosed herein, a means for determining an indication of the level of dopamine in the retina of the eye of a patient one or more of the following can be measured; the B wave amplitude of an electroretinogram, the thickness of the choroid and/or sclera. Such thickness can be measured (by way of example only) by a Cirrus HD-OCT 5000.

An embodiment for slowing or preventing myopia can comprise modulation of the image or light source. Such modulation can be within the range of 5 Hz-15 Hz, 10 Hz to 20 Hz, or 40 Hz+/−20 Hz.

An embodiment can comprise a light source or light emitter having a light intensity of at least one of: 300 lux or greater, 500 lux or greater, 1,000 lux or greater, or 5,000 lux or greater. An embodiment can comprise light that strikes the eye of the user or wearer of at least one of: 300 Lux or greater, 500 lux or greater, 1,000 lux or greater, or 5,000 lux or greater.

An embodiment can comprise an ocular-photo-bio-stimulation time of 1 minute to 5 minutes, 5 minutes to 30 minutes, or one hour or less. With certain embodiments of eyewear disclosed herein such an ocular-photo-bio-stimulation time can be that of normal daily wear of the eyewear.

Another embodiment of the invention can be a diagnostic test to determine the thickness of the choroid and/or scleral thickness of the eye or eyes of a child. By way of example only an OCT test can be performed at an early age, (for example) 6 years and older. When such a test is performed one can identify if a child has a dopamine deficiency disorder by way of measuring the choroidal and/or scleral thickness. Following this, a refractive examination can be performed, whether subjective or objective, using a retinoscope, automatic refractor, or phoropter. Accordingly, the results can be used to identify those children who have 0.75D of hyperopia or less of hyperopia. Such children would include emmetropes. The result of these two tests (electroretinogram and refraction) can then identify which children are susceptible to becoming myopic. Upon identifying a child that is susceptible to becoming myopic, one can begin treatment for ocular dopamine generation. Such means of treatment are identified in this invention disclosure. By utilizing ocular photo-bio-stimulation therapy one can stimulate dopamine production in the retina of the eye or eyes and also increase the thickness of the choroid and or sclera of the child's eye(s), thus offsetting the development of ocular axial elongation (or myopia).

Said another way, an embodiment for the prevention of myopia is:

4) Identify those children 6 years old or older (or even younger) who have low levels of dopamine in their retina.
5) Test those children to identify their BVA (best distance visual acuity) refractive status; and
6) If the refractive status of the child is +0.75D or less hyperopia and their choroidal and/or scleral thickness indicates a low dopamine level, begin therapy to increase retinal dopamine and choroidal and/or scleral thickness.

For those children who already have myopia it is important to stop or slow the progression of myopia as the child ages. Thus, it is important to increase the level of retinal dopamine in those children. Embodiments for increasing dopamine in the eye's retina are disclosed Ocular Photo-Bio-Stimulation with Inventive Embodiments Embodiments disclosed herein can provide ocular photo-bio-stimulation through light stimulation of specific wavelengths to the eye's retina, and, in some embodiments, to the entire eye's retina, the retina peripheral to the fovea, and/or the retina peripheral to the macula. In certain embodiments, the light stimulation is targeted at or to the rods. In other embodiments, the light stimulation is targeted at or to the ganglion cells. In still other embodiments, it is targeted at or to the rods and the ganglion cells. When ganglion cells are mentioned herein, the ganglion cells targeted or stimulated are the melanopsin containing ganglion cells (ipRGCs) or can also be called mRGCs.

Embodiments herein teach the stimulation of the rods and/or ipRGCs with specific light wavelengths. The retina of the human eye contains 100+M rods, 1M ganglion cells but fewer than 7,000 ipRGCs which are the ganglion cells that contain melanopsin. ipRGCs are less sensitive to photic stimulation and their response kinetics are slow compared to that of rods and cones. Response latency is inversely related to stimulus intensity and under dim light conditions ipRGCs can take many seconds to reach a peak response; the response may also persist for minutes after stimulus termination. However, ipRGCs are similar to rods and cones in that they show adaptation by adjusting their sensitivity according to lighting conditions. While slow to respond to dim light conditions, ipRGCs appear capable of responding to the capture of a single photon of light. It has been estimated that the membrane density of melanopsin is about a thousand times lower than that of photopigments in the outer segments of rod and cone photoreceptors; this relatively low density may account for the poor absorption rate of ipRGCs. The capture of a single photon in an ipRGC generates a large and prolonged membrane current, greater than that recorded in rod photoreceptors but also 20-fold slower.

In still other embodiments, the light stimulation is targeted at or to the cones, rods and ganglion cells. In certain embodiments the objective of ocular photo-bio-stimulation is to increase dopamine within the eye. In certain embodiments the objective of ocular photo-bio-stimulation is to increase dopamine within the eye's retina. When increasing dopamine in the eye and/or retina, ocular photo-bio-stimulation blue light having wavelengths within the range of 450 nm to 510 nm can be used, or, for increasing dopamine in the eye and/or retina, ocular photo-bio-stimulation red light wavelengths of 650 nm+/−30 nm can be utilized. In certain embodiments the objective of ocular photo-bio-stimulation is to increase dopamine within the eye's retina and the brain. In still other embodiments the objective of ocular photo-bio-stimulation is to reduce pain. In still other embodiments the objective of ocular photo-bio-stimulation is to reduce the severity of a headache. When reducing pain by ocular photo-bio-stimulation, green light having wavelengths within the range of 530 nm+/−20 nm can be utilized. In still other embodiments the use of light wavelengths in the range of 650 nm+/−30 nm can improve mitochondria function and/or reduce age related inflammation in the eye of the user. In other embodiments the objective is to improve mitochondria function and/or reduce age related inflammation in the eye's retina of the user.

In still other embodiments, the objective of ocular photo-bio-stimulation is to increase the number or healthy mitochondria present within the ocular photo-bio-stimulation, the area of the retina in which the ocular photo-bio-stimulation has targeted. When increasing healthy mitochondria by way of ocular photo-bio-stimulation, red light having wavelengths within the range of one of 650 m to 700 nm, 650 nm+/−30 nm, 700 nm+/−30 nm or 830 nm+/−30 nm, can be utilized. Such ocular photo-bio-stimulation, according to the present invention, increases retinal mitochondrial function and attenuates oxidative stress thus increasing the number of healthy mitochondria within the area of the retina being treated. This can be important for treating, by way of example only, diabetic retinopathy, macular degeneration, and/or retinitis pigmentosa.

For most if not all embodiments provided herein for providing ocular photo-bio-stimulation, light wavelengths predominantly fall within one of the wavelength ranges of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, and can be utilized in addition to what is stated within the embodiments. The exact wavelength band of the above will depend upon the type of ocular photo-bio-stimulation that is desired to produce the desired physiological response.

Embodiments when light wavelengths are generated by way of filtered optics or filtered lenses, the peak spectral curve of the wavelength range that strike the eye's retina falls within the wavelength range of one: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

Melanopsin photopigment expressed in intrinsically photosensitive retinal ganglion cells (ipRGCs) plays a crucial role in the adaptation of mammals to their ambient light environment through non-image-forming (NIF) visual responses. ipRGCs are structurally and functionally distinct from classical rod/cone photoreceptors and have unique properties including single-photon response, long response latency, photon integration over time, and slow deactivation.

Embodiments disclosed herein that are directed to increasing dopamine in an individual's eye's retina or dopamine in the brain of the individual whose eye was stimulated, attempt to use wavelength ranges that cover the peak sensitivities for melanopsin (480 nm) and also for rhodopsin (500 nm). Given that rhodopsin of Rods is 20 times faster to react than melanopsin of ipRGCs, but that melanopsin has much longer reactive staying power than the reaction of rhodopsin, combined with the fact that rods are 10+ times the number of ipRGCs, is the reason various embodiments disclosed herein use light wavelengths within the light wavelength ranges of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, and/or 700 nm+/−30 nm. The lower level of 480 nm+/−30 nm is to capture direct stimulation of melanopsin by ipRGCs and indirect stimulation of melanopsin by Rods.

In certain embodiments, when generating dopamine in the eye or the brain via the eye light, the invention utilizes light wavelengths that strike the eye's retina, which fall within at least one of the wavelength ranges of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm which would include blue, bluish green and green wavelengths. These light wavelength ranges can be generated by light emitters, filtered optics or filtered lenses.

In embodiments when light wavelengths are generated by way of filtered optics or filtered lenses, the transmission peak of the wavelength range that strike the eye's retina fall within one of the wavelength ranges of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by way of a light emitter(s) if in a dark room with no ambient lighting, the wavelength range that strike the eye's retina fall within at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

It should be understood that when interpreting the embodiments utilized herein unless total darkness is specified, it should be assumed that there is ambient light and thus the light wavelengths striking the retina are blended by the light from the light emitter and the ambient light. The same is true with a filtered optic or filtered lens. In most but not all cases the filtered optic or filtered lens is located 12+mm from the eye of the wearer unless the filtered optic or filtered lens is that of a contact lens or intraocular lens. An exception to this interpretation would be that of the use of a virtual reality device or a modified reality device whereby the device is sealed or mostly sealed from ambient light.

In still other embodiments, light wavelength from either a filtered optic, filtered lens, and/or light emitter(s), that strikes the retina of the eye are selected so that the radiation peak of these wavelengths falls between the peak melanopsin sensitivity (480 nm, and rhodopsin sensitivity (500 nm)). Thus, the transmission peak of these wavelengths falls within the range of 480 nm and 500 nm.

In certain embodiments when a filtered optic or filtered lens is used, the overall light transmission through the filtered optic or filtered lens can be 50% or less, 40% or less, or 30%/o or less, while the light transmission within the predominant transmitted filtered wavelength range being transmitted to the eye can be 50% or more. In certain cases, the pupil of the eye enlarges when looking through the filtered optic or filtered lens and constricts when not looking through the filtered optic or filtered lens.

In still other embodiments, the objective of ocular photo-bio-stimulation is to increase the alertness of the individual being treated with ocular photo-bio-stimulation. When increasing alertness by way of ocular photo-bio-stimulation, blue light having wavelengths within the range of 450 nm to 510 nm can be utilized. In still other embodiments the objective of ocular photo-bio-stimulation is to increase the slowing down, to slow the progressing of, or to stop myopia of the individual being treated with ocular photo-bio-stimulation. When slowing down or stopping myopia by way of ocular photo-bio-stimulation, blue light having wavelengths within the range of 450 nm to 510 nm, or red light within the wavelength range of 650 nm+/−30 nm or 700 nm+/−30 nm, can be utilized. Such ocular photo-bio-stimulation wavelengths can be applied to a large portion of the eye's retina to stimulate the ipRGC ganglion cells and/or rods, or to the ganglion axons of the optic nerve head for the purposes of generating increased retinal dopamine.

In still other embodiments, the objective of ocular photo-bio-stimulation is to treat or correct a neurological abnormality of the individual being treated with the ocular photo-bio-stimulation. When correcting a neurological abnormality by way of ocular photo-bio-stimulation, blue light having wavelengths within the range of 450 nm to 510 nm can be utilized. Neurological abnormalities that may be treatable by ocular photo-bio-stimulation are by way of example only: Alzheimer's, cognitive disorders, ADD, ADHD, depression, anxiety, and/or Parkinson's disorder.

In still other embodiments the objective of ocular photo-bio-stimulation is to prevent myopia from occurring with the individual being treated with the ocular photo-bio-stimulation. In still other embodiments the objective of ocular photo-bio-stimulation is to treat or correct an ocular abnormality of the individual being treated with ocular photo-bio-stimulation. When correcting an ocular abnormality, the use of the appropriate light wavelengths must be employed when treating with ocular photo-bio-stimulation. Ocular abnormalities that may be treatable by ocular photo-bio-stimulation are by way of example only: myopia, AMD, dry AMD, diabetic retinopathy, retinal degenerative disease, glaucoma, optic neuropathy, cataract, and/or meibomian gland disfunction leading to dry eye.

In embodiments, biofeedback can be utilized to confirm that increased dopamine and/or serotonin is being produced within the brain of a patient having ocular photo-bio-stimulation therapy. Such biofeedback can be comparing one or more of: increased blink rate of the eye(s) of the patient being treated, increased diameter of pupil(s) of the patient being treated, and/or increased heart rate of the patient being treated comparted to that of a base line for the same activity prior to the ocular photo-bio-stimulation therapy.

An embodiment for ocular photo-bio-stimulation can comprise modulation of the image or light source. Such modulation can be within the range of 5 Hz-15 Hz, 10 Hz to 20 Hz, or 40 Hz+/−20 Hz.

An embodiment can comprise a light source or light emitter having a light intensity of one of: 300 lux or greater, 500 lux or greater, 1,000 lux or greater, or 5,000 lux or greater. An embodiment can comprise light that strikes the eye of the user or wearer of one of: 300 Lux or greater, 500 lux or greater, 1,000 lux or greater, or 5,000 lux or greater.

An embodiment can comprise an ocular-photo-bio-stimulation time of 1 minute to 5 minutes, 5 minutes to 30 minutes, or one hour or less. With certain embodiments of eyewear disclosed herein such an ocular-photo-bio-stimulation time can be that of normal daily wear of the eyewear.

Figure 13:
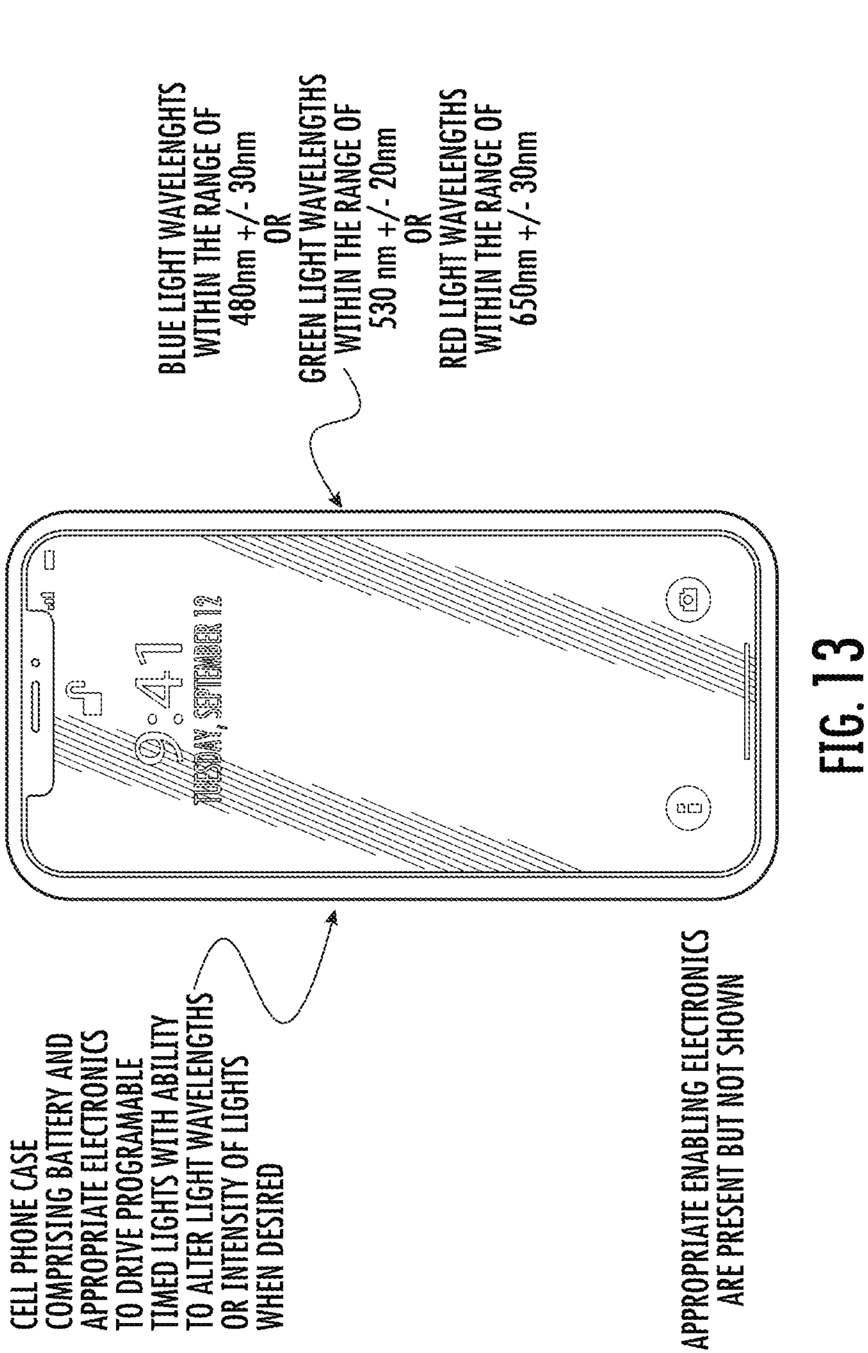
FIG. 13 shows an embodiment of the current invention as described herein.

Electronic Devices for Ocular Photo-Bio-Modulation or Ocular Photo-Bio-Stimulation Ocular Photo-Bio-Stimulation Cell Phone Case FIG. 13 shows an embodiment of the current invention. It shows a cell phone case, which can comprise, among other things, enabling electronics and a blue lighted border that circumvents all or part of the cell phone. The lighted border of the cell phone case can be programmed for one or more light intensity, wavelength, modulation or flicker, start time, and/or end time. The cell phone case can comprise a sensor to measure the distance from a user to the case and the light intensity can be automatically or manually adjusted to provide that appropriate level of light intensity required for the ocular photo-bio-stimulation therapy.

In embodiments, the electronic display screen or the housing device which houses the electronic display screen can identify the distance from the eye of the user and can automatically adjust the intensity of the blue, green, or red-light border to be appropriate for such a distance. In a certain embodiment the electronic display screen or the housing of the electronic display screen can comprise a distance sensor and optionally facial recognition. In addition, the border light intensity can be adjusted automatically or manually depending upon the ambient lighting available in the room or space.

The lighted border can comprise wavelengths within the range of one or more of: 441 nm or greater, 460 nm+/−20 nm, 470 nm+/−20 nm, 460 nm-520 nm, or 480 nm+/−30 nm. The ocular photo-bio-stimulation effect targeted can be one or more of (by way of example only), increased dopamine in the eye; the prevention of, slowing down of, or stopping of myopia; increasing dopamine in the brain; increasing alertness; and/or reducing depression severity.

Embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina falling within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In certain embodiments, the range of wavelength band includes the peaks of the most sensitive spectral points of rhodopsin (500 nm) and melanopsin (480 nm). This way both rhodopsin and melanopsin can be stimulated or excited. By way of example, by utilizing a filtered optic or lens, that predominantly transmits within the wavelength range of at least one of 460 nm-520 nm or 470 nm to 520 nm, or by utilizing a light source or light emitter that predominately transmits within the wavelength range of at least one of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

The light border can have an intensity of 300 lux or greater. The light border can have an intensity of 400 lux or greater. The light border can have an intensity of 1,000 lux or greater. The light border can have an intensity of 5,000 lux or greater. The time of ocular photo-bio-stimulation treatment can be 5 minutes to 10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more.

The lighted border can comprise wavelengths within the range of one of: wavelengths of 530 nm+/−10 nm, 530 nm+/−15 nm, 530 nm+/−20 nm, or 500 nm to 550 nm. The ocular photo-bio-stimulation effect targeted can be one or more of (by way of example only), reduced pain severity, reduced frequency of headaches, and/or reduced frequency of migraines.

The same embodiment can be provided for a red-light border within the wavelengths of 630 nm+/−20 nm, 650 nm+/−30 nm, or 650 nm-700 nm or 700 nm+/−30 nm. The ocular photo-bio-stimulation effect targeted can be that of one or more of (by way of example only), increased mitochondrial health or mitochondrial numbers within the retina of the eye for the purposes of reducing the severity or improving a retinal disease/disorder, such as one or more (by way of example only), dry AMD, retinitis pigmentosa, and/or diabetic retinopathy. In certain cases, the red wavelength border light can also treat or help treat dry eye conditions whereby the tear layer evaporates too quickly.

The border of treatment (e.g., blue light treatment) can appear for a certain time interval that can be programed or preset. The intensity of this blue light border can be adjustable or programed to a setting. The intensity can modulate. The intensity can be adjustable or fixed. The light wavelength can be adjusted or fixed. By way of example only, such a border can appear on one's electronic display screen at 7:00 am and remain there until 8:00 am when it will disappear/stop. The blue light can cause the user of the electronic display to become more alert. The cell phone case border can act as a design feature allowing for different colored lights that can be programmable during the day or at night. In most, but not all, cases, the lighted border is in the front periphery (that faces the user) of the cell phone case that surrounds the cell phone. The light can modulate or flicker. The light can be programmable with regards to one or more of: light intensity, wavelength, modulation or flicker, start time, and/or end time. The light can modulate by way of example only, within the range of 5 Hz to 15 Hz, 10 Hz to 20 Hz, or 40 Hz+/−20 Hz.

In another embodiment a cell phone case comprises the appropriate enabling electronics and comprises a green light border. The green light can be comprised of wavelengths of green light, for example within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, 650 nm+/−30 nm, or 700 nm+/−30 nm. The border of green light can appear for a certain time interval that can be programed or preset. The intensity of this green light border can be adjustable or programed to a setting. The intensity can modulate. The intensity can be adjustable or fixed. The light wavelength can be adjusted or fixed. By way of example only, such a border can appear on one's electronic display screen at 7:00 am and remain there until 8:00 am when it will disappear. The green light can cause the user of the electronic display to have, by way of example only, reduced pain. The cell phone case border can act as a design feature allowing for different colored lights that can be programmable during the day or at night. In most, but not all cases the lighted board is in the front periphery (that faces the user) of the cell phone case that surrounds the cell phone. The light can modulate or flicker. The light can be programmable with regards to one or more of: light intensity, wavelength, modulation or flicker, start time, and/or end time. In certain embodiments a diffuser can be placed over the light emitters. In certain embodiments a filter or filters are used so as to permit a higher concentration of wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to be transmitted from the light source.

In another embodiment a cell phone case comprises the appropriate enabling electronics and comprises a red-light border. The red light can be comprised of wavelengths of red light, for example only, 660 nm+/−10 nm or 650 nm+/−30 nm. The border of red-light can appear for a certain time interval that can be programed or preset. The intensity of this red-light border can be adjustable or programed to a setting. The intensity can modulate. The light can modulate or flicker. The intensity can be adjustable or fixed. The light wavelength can be adjusted or fixed. By way of example only, such a border can appear at 10:00 pm and be turned off prior to the user when going to sleep. The red light can cause the user of the electronic display to become more relaxed before going to sleep. The cell phone case border can act as a design feature allowing for different colored lights that can be programmable during the day or at night. In most, but not all cases the lighted board is in the front periphery (that faces the user) of the cell phone case that surrounds the cell phone. The light can be programmable with regards to one or more of: light intensity, wavelength, modulation or flicker, start time, and/or end time. The light can modulate by way of example only, within the range of one of, 5 Hz to 15 Hz, 10 Hz to 20 Hz, or 40 Hz+/−20 Hz.

An embodiment can be that of a phone case that can provide ocular photo-bio-stimulation therapy, wherein a plurality of light emitters encircle part or all of the cell phone screen, wherein the ocular photo-bio-stimulation light emitters provide one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein the plurality of light emitters are controllable, manually or automatically, with regards to one or more of: intensity, on and/or off time, and/or wavelengths band(s), and wherein the intensity of the ocular photo-bio-stimulation light can be automatically adjusted depending upon one or more of: distance from the face of the user or ambient light of the room or space. The ocular photo-bio-stimulation light can comprise a timer to provide the appropriate level of ocular photo-bio-stimulation therapy.

Ocular Photo-Bio-Stimulation Electronic Display Screen with Controllable Lighted Border In reference to FIG. 14, in embodiments, the border of any electronic display provides a lighted ocular photo-bio-stimulation therapy border. Such an electronic display can be, by way of example only, one of cell phone display screen, tablet display screen, laptop computer display screen, desktop computer display screen, or television display screen. By way of example only, in certain embodiments the display can be programed to provide for an outer peripheral zone (the lighted border) that provides ocular photo-bio-stimulation wavelengths of light while the central zone provides visual content, which can be in form or illustrations, letters, numbers or visual images (motion or still). The ocular photo-bio-stimulation border light can be programmable with regards to one or more of: light intensity, wavelength, modulation or flicker, start time, and/or end time. The light can modulate by way of example only, within the range of one of 5 Hz to 15 Hz, 10 Hz to 20 Hz, or 40 Hz+/−20 Hz. The display can comprise a sensor to measure the distance from a user to the display and the light intensity can be automatically or manually adjusted to provide that appropriate level of light intensity required for the ocular photo-bio-stimulation therapy.

The light border can have an intensity of 400 lux or greater. The light border can have an intensity of 1,000 lux or greater. The light border can have an intensity of 5,000 lux or greater. The time of ocular photo-bio-stimulation treatment can be 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more.

In embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In embodiments when light wavelengths are generated by a light emitter(s) if ambient lighting is present (including that of artificial light or sun light), the blended light wavelengths of the light emitter(s) and also the ambient light comprise wavelengths of light that strike the eye's retina, which fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

By way of example only, when the border light is part of the lighted electronic display, the electronic display can be programed for (by way of example only) 8:00 am so that a peripheral lighted border, having a light intensity and light wavelength band, within the electronic display area shows up while the central (non-peripheral border) becomes smaller in overall size. And this lighted border can be programed to turn off at (for example only) 11:00 am so that the central zone which is displaying the content and image(s) for the electronic display increases back to its original size. In this embodiment the electronic display screen or the housing device which houses the electronic display screen can identify the distance from the eye of the user and can automatically adjust the intensity and size and shape of the blue, green, or red-light border to be appropriate for such a distance. In a certain embodiment the electronic display screen or the housing of the electronic display screen comprises a distance sensor and optionally facial recognition. In addition, the border light intensity can be adjusted automatically or manually depending upon the ambient lighting available in the room or space. In certain embodiments a diffuser can be placed over the light emitters. In certain embodiments a filter or filters are used so to permit a higher concentration of wavelengths within the range of one of 480 nm+/−30 nm, 530 nm+/−20 nm, or 650 nm+/−30 nm, to be transmitted from the light source.

The lighted border can comprise wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The ocular photo-bio-stimulation effect targeted can be one or more of (by way of example only), increased dopamine in the eye; prevention of myopia; slowing or stopping myopia; healing myopia; improving myopia diagnosis; increasing dopamine in the brain; increasing alertness; and/or reducing depression severity.

The lighted border can comprise wavelengths within the range of at least one of: 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The ocular photo-bio-stimulation effect targeted can be one or more of (by way of example only), reduced pain severity, reduced frequency of headaches, and/or reduced frequency of migraines.

The same can be provided for a red-light border within the wavelengths 630 nm+/−20 nm or 650 nm+/−30 nm, or 650 nm-700 nm, or 700 nm+/−30 nm. The ocular photo-bio-stimulation effect targeted can be one or more of (by way of example only), increased mitochondrial health or mitochondrial numbers within the retina of the eye for the purposes of reducing the severity or improving a retinal disease/disorder such as one or more (by way of example only), dry AMD, retinitis pigmentosa, and/or diabetic retinopathy. In certain cases, the red wavelength border light can also be of help with dry eye conditions whereby the tear layer evaporates too quickly by way of stimulating the lids meibomian glands.

In certain embodiments the range of wavelength band includes the peaks of the most sensitive spectral points of rhodopsin (500 nm) and melanopsin (480 nm). This way both rhodopsin and melanopsin can be stimulated or excited. By way of example, by utilizing a filtered optic or lens that predominantly transmits within the wavelength range of at least one of 460 nm-520 nm or 470 nm to 520 nm, or by utilizing a light source or light emitter that predominately transmits within the wavelength range of at least one of 460 nm to 520 nm or 470 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

An embodiment can be of an electronic display screen, wherein the electronic display screen comprises a programmable ocular photo-bio-stimulation light border within the display screen, wherein the programmable ocular photo-bio-stimulation light border provides one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein the plurality of light emitters that generate the programmable ocular photo-bio-stimulation light border are controllable, manually or automatically, with regards to one of intensity, on and/or off time, and/or wavelength band, and wherein one of the intensity of the ocular photo-bio-stimulation light border, or size of the ocular photo-bio-stimulation light border can be automatically adjusted depending upon one of distance from the face of the user or ambient light of the room or space. Further the programmable border can be of any shape and can partially or fully surround a central area of the electronic display. The ocular photo-bio-stimulation light can comprise a timer to provide the appropriate level of ocular photo-bio-stimulation therapy.

Another embodiment can be that of an lighted electronic display screen frame, wherein the electronic display screen frame comprises an ocular photo-bio-stimulation light border around the display screen, wherein the programmable ocular photo-bio-stimulation light border provides one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein the plurality of light emitters that generate the programmable ocular photo-bio-stimulation light border are controllable, manually or automatically, with regards to one or more of intensity, on and/or off time, and/or wavelength band, and wherein the intensity of the ocular photo-bio-stimulation light border is automatically adjusted depending upon one of distance from the face of the user or ambient light of the room or space. Further the programmable border can be of any shape and can partially or fully surround a central area of the electronic display. The ocular photo-bio-stimulation light border can be one or more of, attachable to the display screen frame, attachable and detachable to the display screen frame, or built into and integral with the display screen frame.

The light border can have an intensity of 300 lux or greater. The light border can have an intensity of 400 lux or greater. The light can have an intensity of 1,000 lux or greater. The light can have an intensity of 5,000 lux or greater. The time of ocular photo-bio-stimulation treatment can be 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more.

Figure 15:
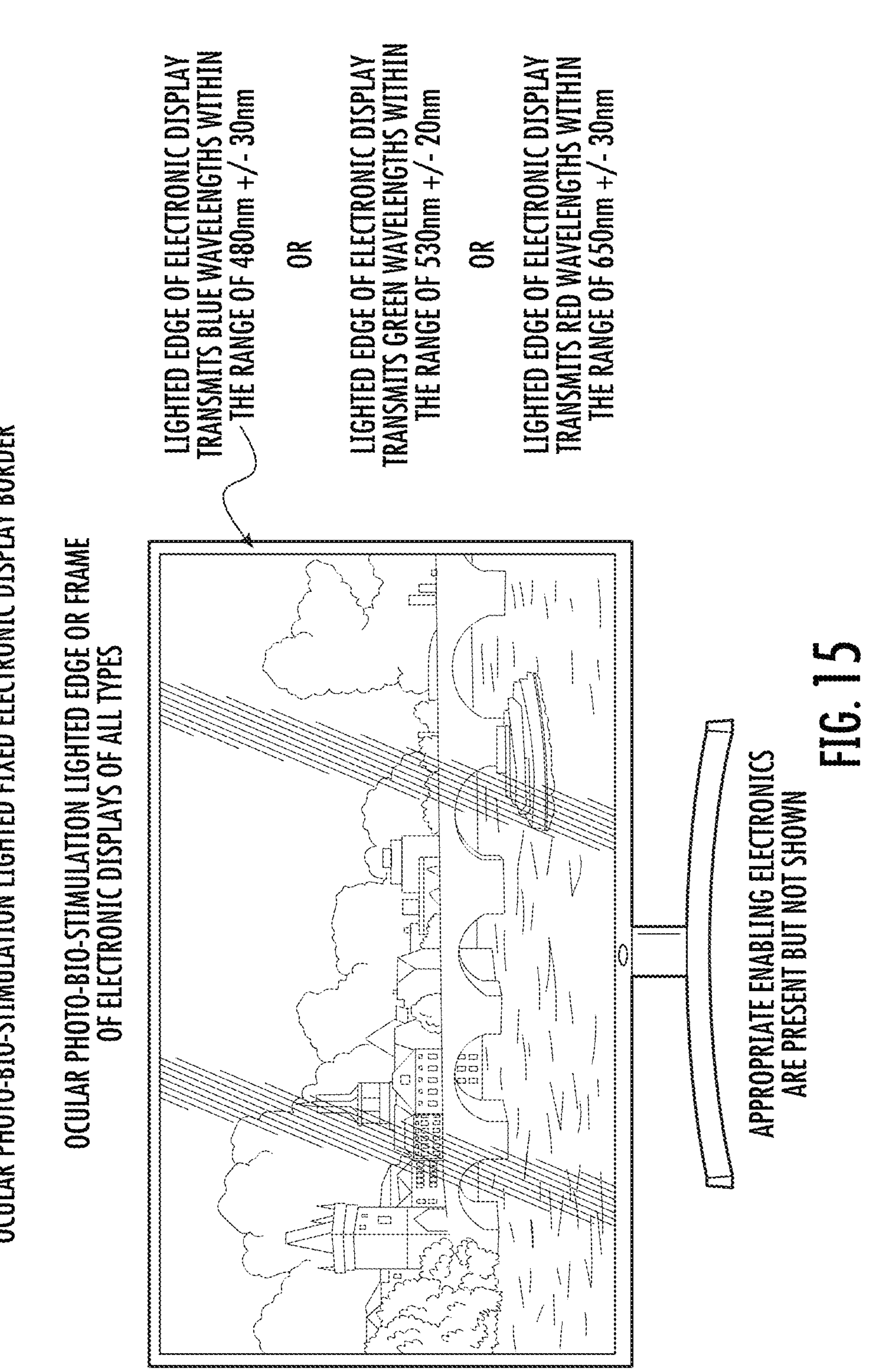
FIG. 15 shows an embodiment of the current invention as described herein.

Ocular Photo-Bio-Stimulation Electronic Display Screen with Fixed Lighted Border Edge In reference to FIG. 15, in certain embodiments, the border of any electronic display provides a lighted ocular photo-bio-stimulation therapy border. The embodiment can be a normal viewing screen with programmable content that can be shrunken down to allow for an ocular photo-bio-stimulation border to be provided. By way of example only, an embodiment can be a blue light border comprising light wavelengths within the wavelength range of 480 nm+/−30 nm, with the media content being displayed centrally. Said another way the blue light border was fully or partially around the central media that was being displayed. The lighting effect provided can be automatic and timed to occur for certain periods of usage time or manually set by the user. It can be programed to a provide desired light wavelength and intensity for providing ocular photo-bio-stimulation therapy. Such an electronic display can be, by way of example only, a cell phone display screen, tablet display screen, laptop computer display screen, desktop computer display screen, or television display screen. Such a lighted border can be that of a lighted frame itself that houses the display, or a light that attaches to the display screen's outer frame. The photo-bio-stimulation border light can be programmable with regards to one or more of: light intensity, wavelength, modulation or flicker, start time, and/or end time. If the border light is fixed to the frame of the electronic display or built into the frame of the electronic display, the size of the border light will be of a fixed size. The ocular photo-bio-stimulation light can comprise a timer to provide the appropriate time for photo-bio-stimulation therapy In embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprise wavelengths of light that strike the eye's retina, which fall within the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm.

For the purposes of this disclosure, the frame of the display screen can be the outer edge or a frame that goes around the outer edge. In certain embodiments a diffuser can be placed over the light emitters. In certain embodiments a filter or filters are used so to permit a higher concentration of wavelengths within the range of one of 480 nm+/−30 nm, 530 nm+/−20 nm, or 650 nm+/−30 nm, to be transmitted from the light source. The photo-bio-stimulation light can modulate. The photo-bio-stimulation light can be comprised of a plurality of light emitters.

The lighted border can comprise wavelengths within the range of at least one of: 441 nm or greater, or 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm. The ocular photo-bio-stimulation effect targeted can be one or more of (by way of example only), increased dopamine in the eye, prevention of myopia, slowing or stopping myopia, increasing dopamine in the brain, increasing alertness, and/or reducing depression severity.

The lighted border can comprise wavelengths within the range of at least one of: 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. The ocular photo-bio-stimulation effect targeted can be one or more of (by way of example only), reduced pain severity, reduced frequency of headaches, and/or reduced frequency of migraines.

The same can be provided for a red-light border within the wavelengths 630 nm+/−20 nm or 650 nm+/−30 nm, or 650 nm-700 nm. The ocular photo-bio-stimulation effect targeted can be one or more of (by way of example only), increased mitochondrial health or mitochondrial numbers within the retina of the eye for the purposes of reducing the severity or improving a retinal disease/disorder such as one or more (by way of example only), dry AMD, retinitis pigmentosa, and/or diabetic retinopathy. In certain cases, the red wavelength border light can also be of help with dry eye conditions whereby the tear layer evaporates too quickly.

In certain embodiments the range of wavelength band includes the peaks of the most sensitive spectral points of rhodopsin (500 nm) and melanopsin (480 nm). This way both rhodopsin and melanopsin can be stimulated or excited. By way of example, by utilizing a filtered optic or lens, that predominantly transmits within the wavelength range of 460 nm-520 nm or 470 nm to 520 nm, or by utilizing a light source or light emitter that predominately transmits within the wavelength range of 460 nm to 520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In embodiments, to stimulate the production of serotonin and/or dopamine in the brain, light wavelengths within the range of 700 nm+/−30 nm can be utilized. Wavelengths of 710 nm LED light has been shown to not have any detrimental effect on dopamine neurons in substantia nigra of the brain.

Ocular Photo-Bio-Stimulation Steering Wheel, Dashboard, or Instrument Panel

Figure 16:
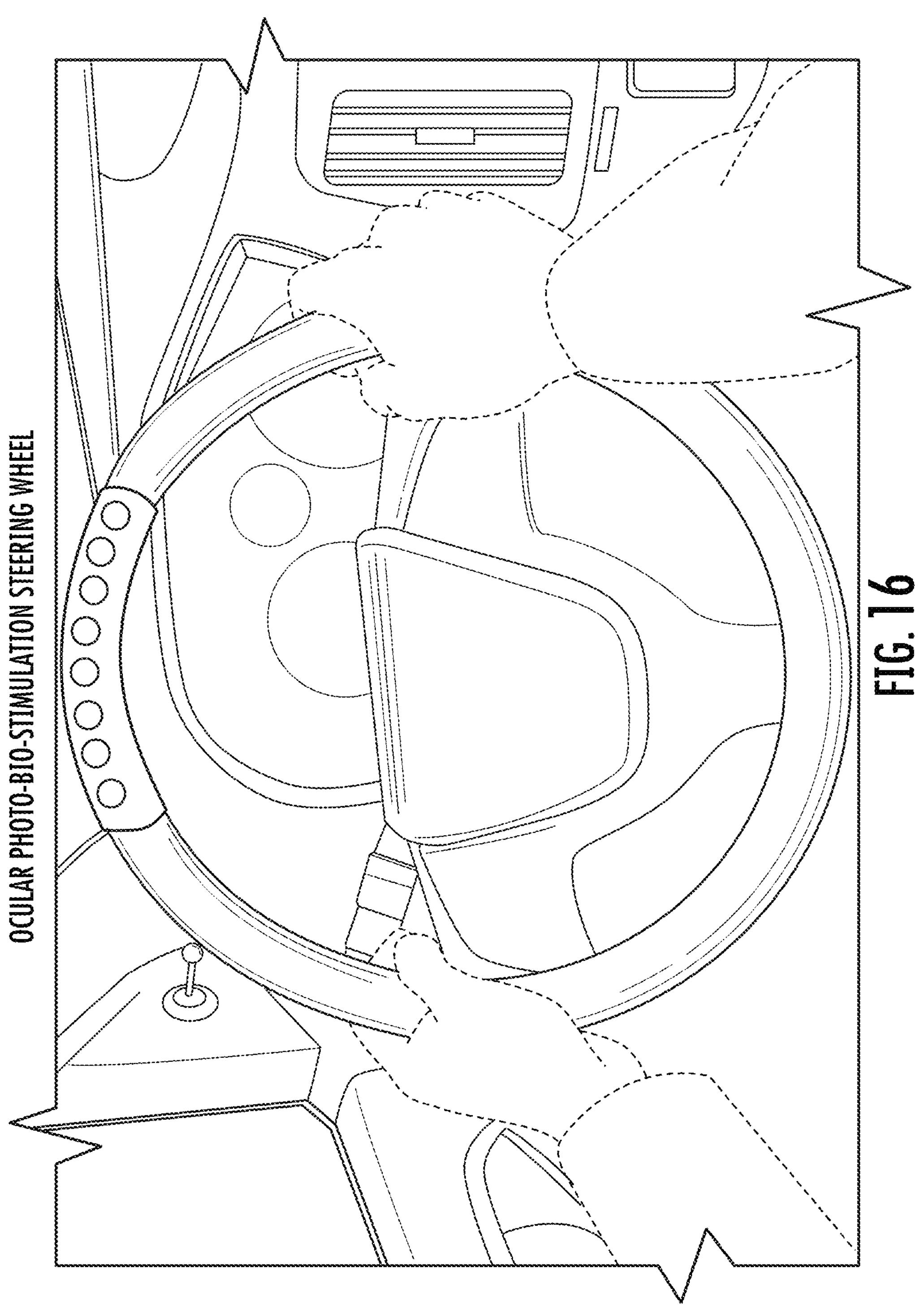
FIG. 16 shows an embodiment of the current invention as described herein, with the invention shown at the top of the steering wheel.

In reference to FIG. 16, embodiments include an ocular photo-bio-stimulation approach that can be implemented to keep a driver of a vehicle alert when driving day or night. A photo-bio-stimulation light source for a steering wheel having wavelengths of light within the wavelength range of 480 nm+/−30 nm can be included. It can be attachable, detachable, or permanently built into the steering wheel. The device can comprise its own power source. It can be programed to come on after a timed period of driving. It can be timed to remain on for a timed period. The control can be automatic or manual. The light can be modulated or flicker when being used if desired. The ocular photo-bio-stimulation effect targeted is, in aspects, increased alertness of the driver. The light source can comprise a sensor to measure the distance from a user to the light source and the light intensity can be automatically or manually adjusted to provide that appropriate level of light intensity required for the ocular photo-bio-stimulation effect.

Such an ocular photo-bio-stimulation approach can be that of utilizing a blue, bluish green, or green light emitter(s), having one or more blue wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. Such a light can be built into, by way of example only, the steering wheel or steering device of the vehicle. In certain other cases it can be built into the dashboard or instrument panel of the vehicle, such as directly in front of the steering wheel. In embodiments a sensor can identify the distance from the eye of the user and can automatically adjust the intensity of the blue light to be appropriate for such a distance.

In embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In addition, the blue light intensity can be automatically or manually adjusted depending upon the ambient lighting available within the vehicle (or outside the vehicle). Further, the time for the lighted ocular photo-bio-stimulation stimulation can be set manually or automatically for the driver of the car. In certain embodiments facial recognition can be utilized. By way of example only, the blue light can be programmed to turn on after a driver has driven for one hour and can remain on for 30 minutes. It further can be programmed (by way of example only) to come on every hour and off every hour. The light can also be programmed to modulate or flicker. In addition, vibration and or sound can be programmed to occur at certain intervals when the blue light is either on or off. The light can be further programmed to turn on if the car senses the driver is not alert. In certain embodiments a diffuser can be placed over the light emitters. In certain embodiments a filter or filters are used to permit a higher concentration of wavelengths within the range of 480 nm+/−30 nm to be transmitted from the light source.

The light can have an intensity of 300 lux or greater. The light can have an intensity of 400 lux or greater. The light can have an intensity of 1,000 lux or greater. The light can have an intensity of 5,000 lux or greater. The time of ocular photo-bio-stimulation treatment can be 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more. The light can modulate. The light can flicker. The light can modulate within the range of one of 5 Hz to 15 Hz, 10 Hz to 20 Hz, or 40 Hz+/−20 Hz.

An embodiment can be that of an ocular photo-bio-stimulation light within a vehicle, wherein the ocular photo-bio-stimulation light provides blue wavelengths of light predominantly within the wavelength range of 480 nm+/−30 nm, and wherein one of, the intensity of the ocular photo-bio-stimulation light, or the size or location of the ocular photo-bio-stimulation light, is automatically adjusted depending upon one of distance from the face of the user or ambient light of the vehicle (and/or outside the vehicle). The ocular photo-bio-stimulation light can comprise a timer to provide the appropriate level of ocular photo-bio-stimulation therapy.

An embodiment of the invention which can be utilized to improve the alertness of any pilot, driver, or steerer of a vehicle, and can be a system that employs blue, bluish green or green light of the wavelengths predominantly within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, and wherein the blue light strikes the retina of the eye(s) of the pilot, driver, or steerer of the vehicle, is hereby disclosed. Such a vehicle can be that of any vehicle, for example only, car, automobile, truck, bus, subway, trolley, tram, train, aircraft, spaceship, boat, ocean liner, cargo ship, or ship. The blue light can be releasably attachable and detachable to the steering wheel or integrated into the steering wheel. The blue light can paint the retinas of the wearer's eyes as the steering wheel is rotated or turned while driving. The blue light can be releasably attachable and detachable to the dashboard or integrated into the dashboard. The blue light emitter can be any light emitter that emits blue light predominantly within the wavelength range of 450 nm to 510 nm or 480 nm+/−30 nm. The blue lights can be programed to turn on automatically when the pilot, driver, or steerer of the vehicle shows signs of fatigue. The blue lights can be turned on manually when the pilot, driver, or steerer of the vehicle feels signs of fatigue. The blue lights can be modulated to turn on for X period of time and turn off for Y period of time. The lights can be set to turn on for, by way of example, only 2 minutes every 2 hours of driving time and then turned off until it is time for them to be turned on. This timing sequence can be set manually by the driver or automatically programmed. The intensity of the blue lights can become brighter during daytime and less bright during nighttime. The lights can be controlled by a dimmer or programed to maintain a certain intensity depending upon ambient light in the vehicle. The blue lights can be manually adjusted towards the eyes of pilot, driver, or steerer of the vehicle.

While the above discusses using blue light predominantly within the wavelength range of 450 nm-510 nm, red light within the wavelength range of 650 nm+/−30 nm or 700 nm+/−30 nm. can be used in place of the blue light, or a combination of blue light and red-light wavelengths predominantly within the range of 450 nm-510 nm and of 650 nm+/−30 nm can be utilized. This is due to the fact that the light wavelengths predominantly within the ranges of 450 nm-500 nm, of 650 nm-700 nm, or of 700 nm+/−30 nm, produce dopamine and increase alertness. In certain cases, for morning hours the blue light of wavelengths predominantly within the range of 450 nm to 500 nm are used and for afternoon hours red light predominantly within the wavelength ranges of 620 nm-700 nm or of 700 nm+/−30 nm are used.

The steering wheel can comprise one or more pressure sensor(s) such that when the pilot, driver, or steerer feels tired or desires to manually set such a hand pressure sensitive system, it can be set to the pressure threshold as desired by the pilot, driver, or steerer. So long as the pilot, driver, or steerer exerts the set hand pressure, the system (within certain limits) will function as if it is dormant, however, should the pressure become relaxed, and an established relaxed pressure threshold become met, an alert system within the car can cause the driver to become more awake or alert. Such a system can use, by way of example only, sound, light, electrical shock, and/or vibration to increase the alertness of the pilot, driver, or steerer. In certain embodiments for use with blue lighting of the wavelengths within the range of 450 nm-510 nm for a vehicle as disclosed above, or for the steering wheel pressure system disclosed, a vision system can also be utilized to further identify the lack of alertness on the part of the pilot, driver, or steerer. In certain other embodiments for use with red lighting of the wavelengths within the range of 650 nm+/−30 nm for a vehicle as disclosed herein, or for the steering wheel pressure system disclosed, a vision system can also be utilized to further identify the lack of alertness on the part of the pilot, driver, or steerer.

Ocular Photo-Bio-Stimulation Light or Lamp.

Figure 17:
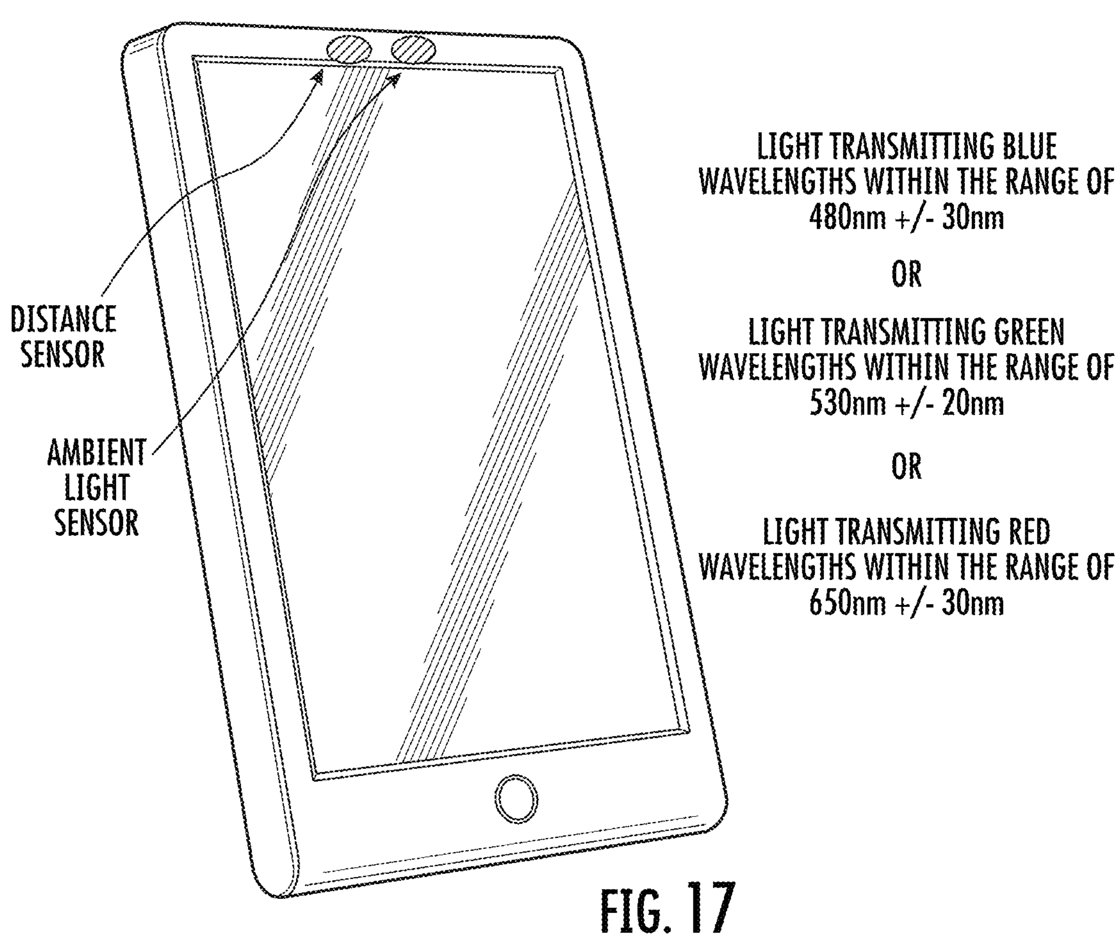
FIG. 17 shows an embodiment of the current invention as described herein.
Figure 18:
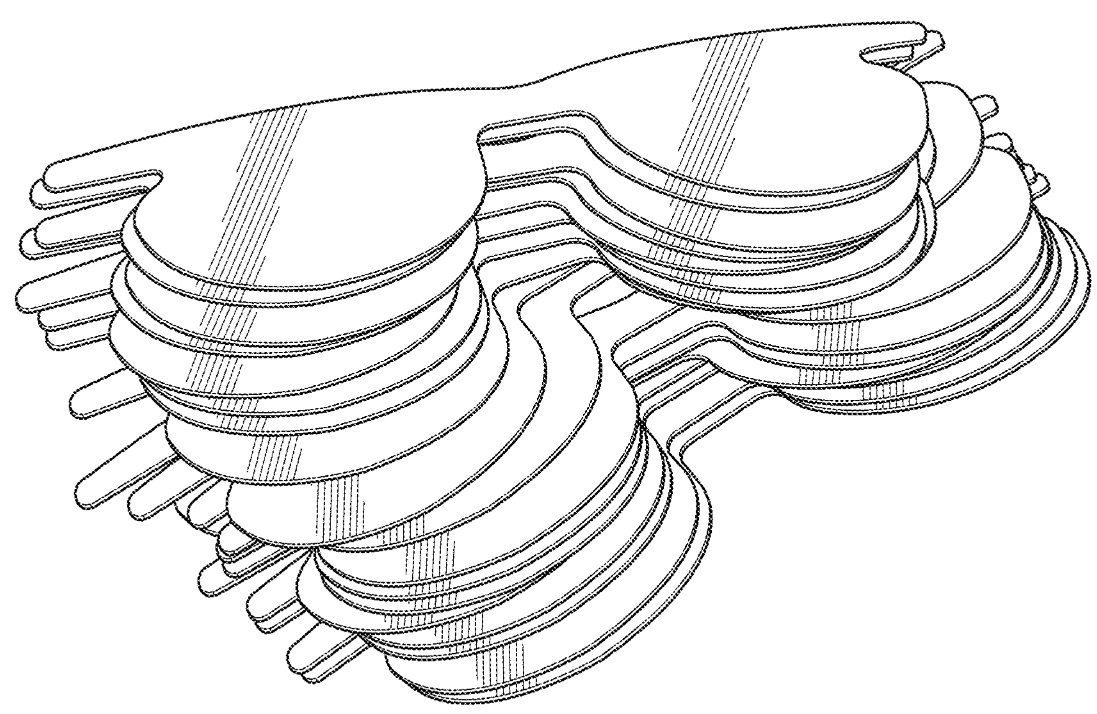
FIG. 18 shows an embodiment of the current invention as described herein.
Figure 19A:
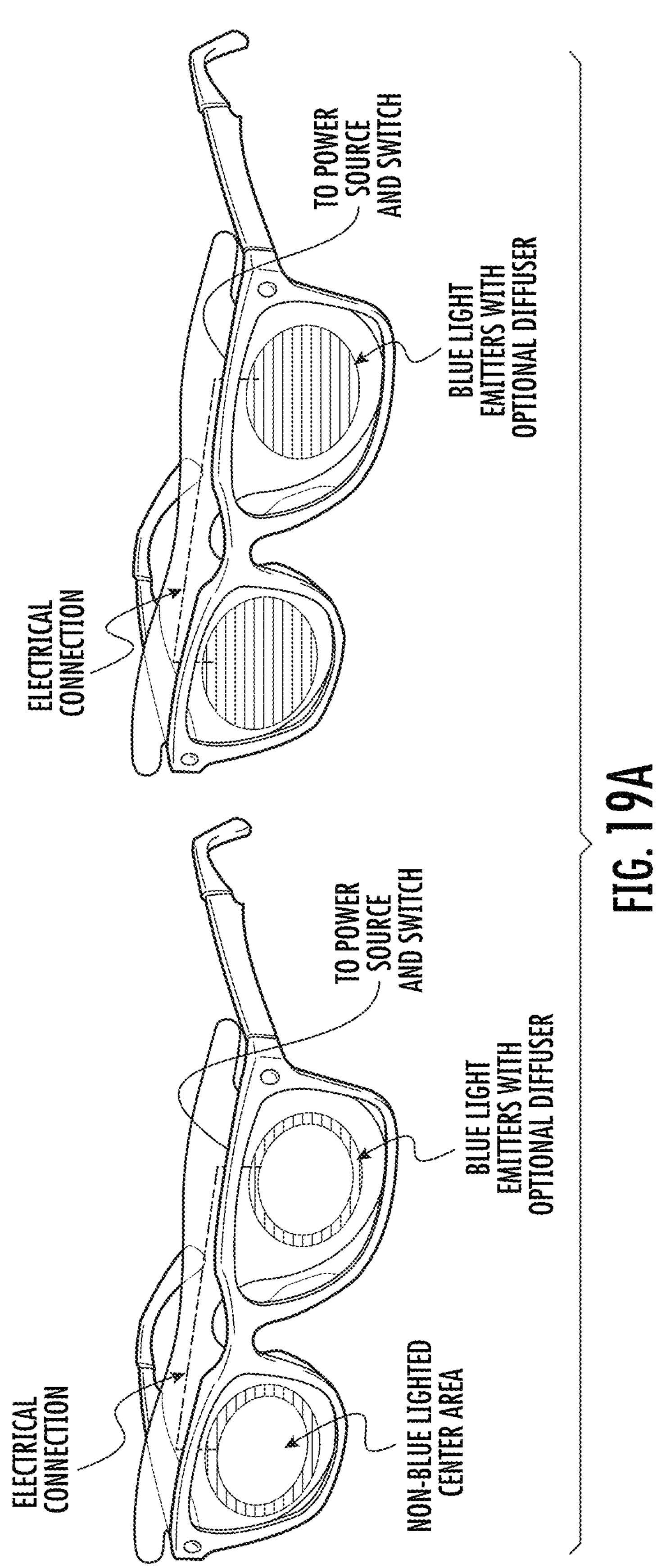
FIG. 19A-F shows an embodiment of the current invention as described herein.
Figure 19B:
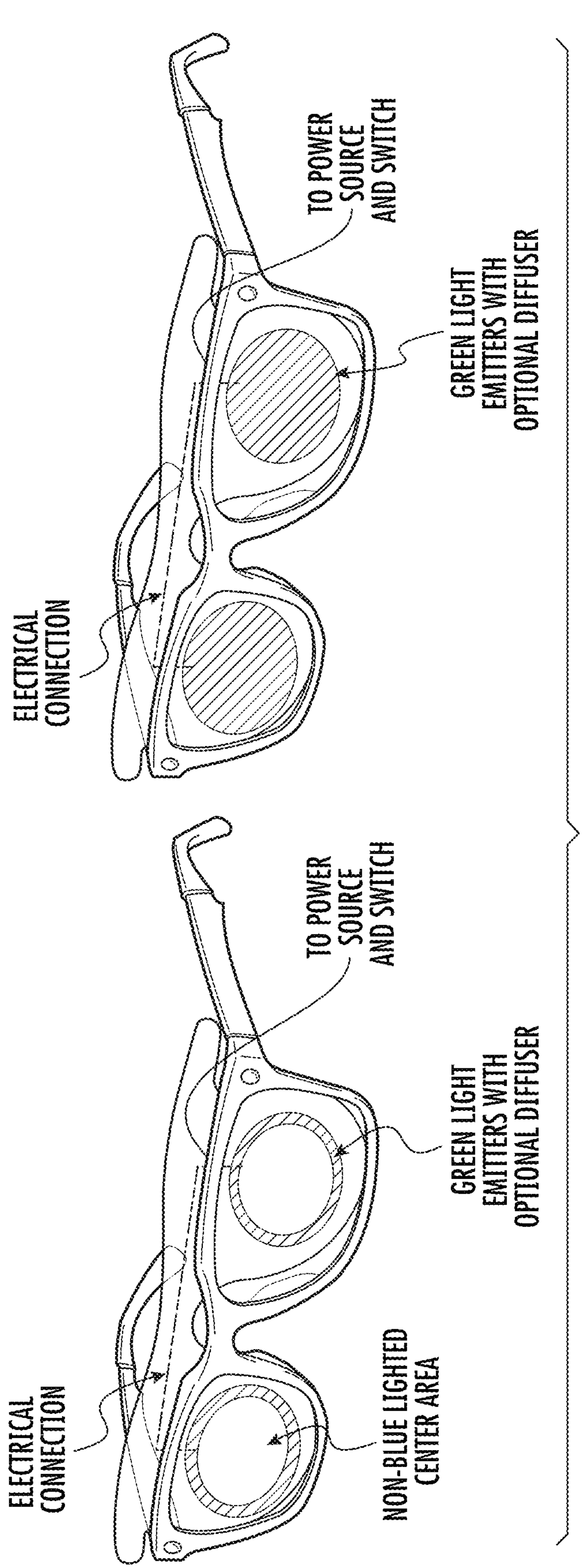
Figure 19C:
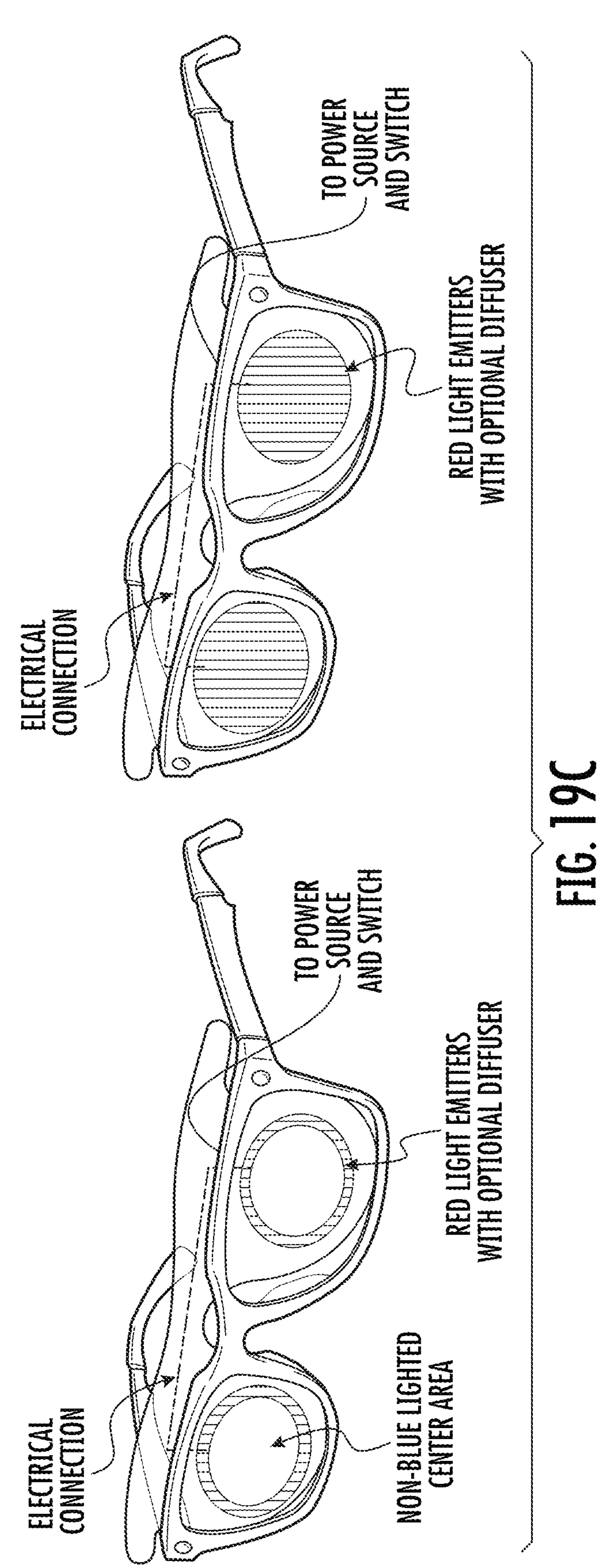
Figure 19D:
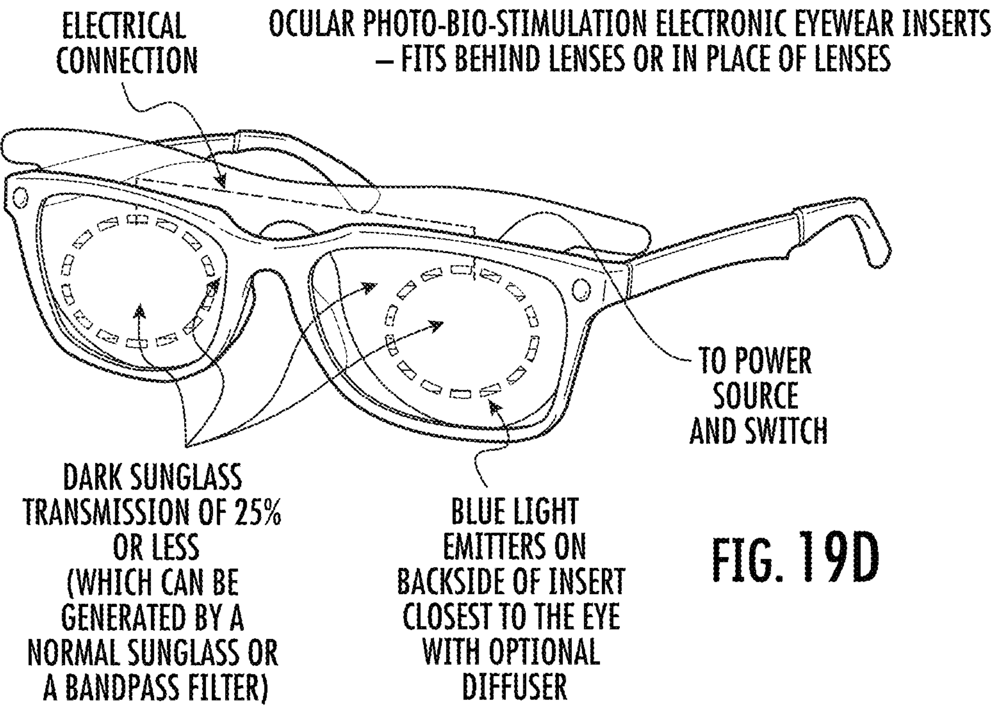
Figure 19E:
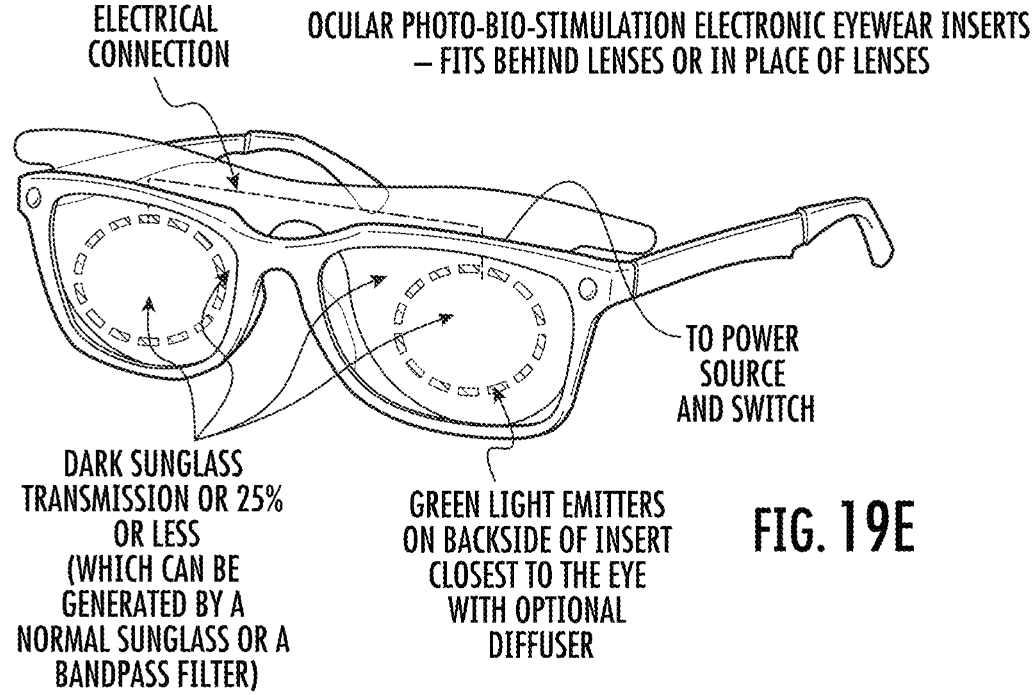
Figure 19F:
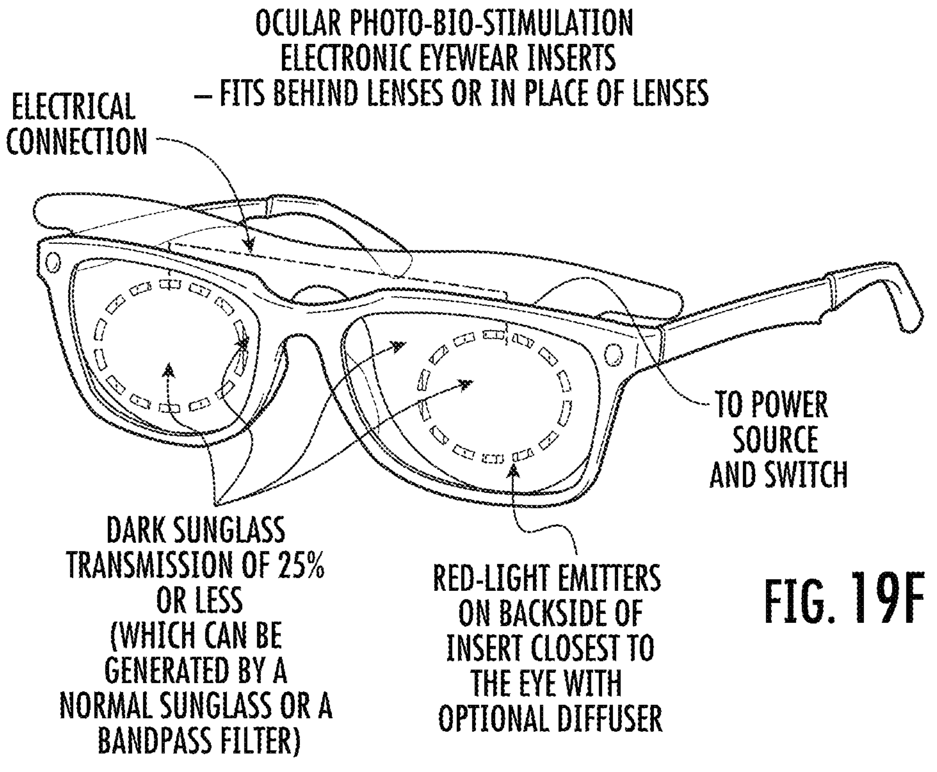

In reference to FIG. 17, embodiments include an ocular photo-bio-stimulation therapy lamp, wherein the ocular photo-bio-stimulation therapy lamp comprises an ocular photo-bio-stimulation light(s), wherein the lamp can be programmable, wherein the lamp can provide one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein one or a plurality of light emitters that generate the programmable ocular photo-bio-stimulation light or lamp can be controllable, manually or automatically, with regards to one or more of intensity, on and/or off time, and/or wavelength band, and wherein the intensity of the ocular photo-bio-stimulation therapy lamp's light or lamp can be automatically adjusted depending on distance from the face of the user or ambient light of the room or space. The light or lamp can comprise a distance sensor. The ocular photo-bio-stimulation light or lamp can be comprised of one light emitter or a plurality of light emitters.

Embodiments when light wavelengths are generated by way of filtered optics or filtered lenses the transmission peak of the wavelength range that strike the eye's retina falls within the wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina fall within wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens, which predominantly transmits within the wavelength range of at least one of 460 nm-520 nm or 470 nm to 520 nm, and/or by utilizing a light source or light emitter that predominately transmits within the wavelength range of at least one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

The light or lamp can have an intensity of 300 lux or greater. The light or lamp can have an intensity of 400 lux or greater. The light can have an intensity of 1,000 lux or greater. The light can have an intensity of 5,000 lux or greater. The time of ocular photo-bio-stimulation treatment can be 1 minute-5 minutes, 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more. The light can flicker. The light can modulate. The light can modulate, by way of example only, within the range of one of 5 Hz and 15 Hz, 10 Hz to 20 Hz, or 40 Hz+/−20 Hz.

In embodiments, the ocular photo-bio-stimulation light or lamp can identify the distance from the eye of the user and can automatically adjust the intensity of the blue, green, or red-light to be appropriate for such a distance. In a certain embodiment the ocular photo-bio-stimulation light or lamp comprises a distance sensor and optionally facial recognition. In addition, the light intensity can be adjusted automatically or manually depending upon the ambient lighting available in the room or space. In certain embodiments a diffuser can be placed over the light emitters. In certain embodiments a filter or filters are used so as to permit a higher concentration of wavelengths within the range of at least one of: 480 nm+/−30 nm, 480 nm+/−20 nm, 500 nm+/−30 nm, 500 nm+/−20 nm, 510 nm+/−30 nm, 510 nm+/−20 nm, 530 nm+/−20 nm, 650 nm+/−30 nm 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to be transmitted from the light source. The ocular photo-bio-stimulation light or lamp can modulate or flicker. The ocular photo-bio-stimulation light or lamp can comprise a timer to provide the appropriate level of ocular photo-bio-stimulation therapy.

The ocular photo-bio-stimulation light or lamp can comprise wavelengths within the range of 441 nm or greater, or 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The ocular photo-bio-stimulation effect targeted can be one or more of (by way of example only), increased dopamine in the eye, prevention of myopia, slowing or stopping myopia, increasing dopamine in the brain, increasing alertness, and/or reducing depression severity.

The ocular photo-bio-stimulation light or lamp can comprise wavelengths within the range of 530 nm+/−10 nm, or 530 nm+/−15 nm, or 530 nm+/−20 nm, or 500 nm to 550 nm. The ocular photo-bio-stimulation effect targeted can be one or more of (by way of example only), reduced pain severity, reduced frequency of headaches, and/or reduced frequency of migraines.

The ocular photo-bio-stimulation light or lamp can comprise wavelengths within the range of 630 nm+/−20 nm or 650 nm+/−30 nm, or 650 nm-700n or 700 nm+/−30 nm. The ocular photo-bio-stimulation effect targeted can be one or more of (by way of example only), increased mitochondrial health or mitochondrial numbers within the retina of the eye for the purposes of reducing the severity or improving a retinal disease/disorder such as one or more (by way of example only), dry AMD, retinitis pigmentosa, and/or diabetic retinopathy. In certain cases, the ocular photo-bio-stimulation light or lamp can also be of help with dry eye conditions whereby the tear layer evaporates too quickly.

Eyewear and Optics for Providing Ocular Photo-Bio-Stimulation

Eyewear embodiments for ocular photo-bio-stimulation can comprise a lens or optic that permits a wearer to view an image, wherein certain light wavelengths that pass from the eyewear or the optic stimulates dopamine or serotonin of the wearer, wherein certain of the light wavelengths are of the blue light, and wherein the highest concentration of blue, bluish green, or green light, that reach the eye of the wearer falls within the wavelengths range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, and wherein light wavelengths are filtered or blocked so to cause the overall light transmission of the lens or optic to be less than 50%. Blue, bluish green, green light radiation wavelengths can be within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, and can increase alertness and concentration, by way of example, upon waking in the morning or during the day when tired and less alert. This occurs by way of increasing dopamine production. In other embodiments wavelengths within the range of 650 nm+/−30 nm or 650 nm-700 nm, or 700 nm+/−30 nm, can be used. It is further known that low levels of dopamine can be associated, by way of example only, with ADHD, myopia and Parkinson disease.

Embodiments when light wavelengths are generated by way of filtered optics or filtered lenses the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In other embodiments for ocular photo-bio-stimulation, the eyewear or optic can comprise green light within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. Green light wavelengths can, in aspects, reduce the sensation of pain. In still other embodiments the eyewear or an optic can comprise red light within the range of 660 nm+/−20 nm, 650 nm+/−30 nm, or 600 nm to 700 nm. Red light wavelengths within the range of 660 nm+/−20 nm, 600 nm to 700 nm, or 700 nm+/−30 nm, can be soothing, calming and relaxing to the brain, thereby assisting with (by way of example) going to sleep. The eyewear and/or optic can be any type of eyewear or optic known to one of ordinary skill in the art. The eyewear and/or optic can be disposable. The eyewear and/or optic can be an insert that can be inserted or attached to existing eyewear. In most, but not all cases, the insert is positioned behind the corrective eyeglass lenses and is supported by the eye glass frame (see FIGS. 18, 19A, 19B, 19C, 19E, and 19F). The eyewear and/or optic can be a component that is removable or permanently attached to existing eyewear. As used herein an optic can be a lens. A lens can be an optic. A lens or optic can comprise optical power. A lens or optic can comprise no optical power. As used herein an optic can be any item that transmits light, such as a lens, flat sheet of transparent plastic or glass, film, light diffuser, window, etc., as would be understood by one of ordinary skill in the art.

The optic can comprise a single bandpass filter to provide for the transmission of the desired light wavelengths. The optic can comprise a double bandpass filter to provide for the transmission of the desired light wavelengths. The level of transmission of light to the eye's retina used in the various embodiments disclosed herein can be provided at one of scotopic, mesopic, and/or photopic light levels. In embodiments the light level is above 400 lux and is in the higher end of mesopic and most of the time photopic.

In embodiments, ambient light can be filtered or engineered by the design of the optic or lens to spread or focus over the retina, including that of the optic nerve head. In certain embodiments the blue wavelength band of chromatic aberration is engineered by way of the optic design or optic power to focus on or within the retina peripheral to the macula. The optic can be an ophthalmic lens. The optic can be a thin plastic or glass section or part having no optical power that transmits light. An optic can be a window. An optic can be a light diffuser. An optic can be a film. The optic can comprise optical power. The optic can comprise prescription optical power. The optic can comprise no optical power. The optic can be a spectacle lens. The optic can be a contact lens. The optic can be an intra ocular lens.

In some embodiments the highest concentration of blue light radiation or blue wavelengths falls within the range of 460 nm+/−20 nm or 470 nm+/−20 nm or 480 nm+/−30 nm. In some embodiments the highest concentration of blue light radiation or blue wavelengths falls within 460 nm+/−35 nm. In some embodiments the highest concentration of blue light radiation or blue wavelengths falls within the range of 460 nm+/−20 nm. In some embodiments the highest concentration of blue light radiation falls within the range of 470 nm+/−15 nm. In some embodiments the highest concentration of blue light radiation or blue wavelengths falls within the range of 470 nm+/−20 nm. In some embodiments the highest concentration of blue light radiation or blue wavelengths falls within the range of 470 nm+/−25 nm. In some embodiments the highest concentration of blue light radiation falls within the range of 480 nm+/−10 nm. In some embodiments the highest concentration of blue light radiation falls within the range of 480 nm+/−15 nm. In some embodiments the highest concentration of blue light radiation or blue wavelengths falls within the range of 480 nm+/−20 nm. In some embodiments the highest concentration of blue light radiation or blue wavelengths falls within the range of 480 nm+/−30 nm. In some embodiments the highest concentration of blue light radiation or blue wavelengths falls above 449 nm. In some embodiments the highest concentration of blue light radiation or blue wavelengths falls above 454 nm. In some embodiments the highest concentration of blue light radiation or blue wavelengths falls above 459 nm.

The eyewear or optic can cause the wearer to be, by way of example only, more alert and/or have better concentration. In aspects, light wavelengths within the range 460 nm+/−10 nm or 470 nm+/−20 nm, more specifically within the range of 480 nm+/−30 nm, are known to produce dopamine within the human eyes' retina and brain. In other embodiments wavelengths within the range of 650 nm-700 nm can be used to increase alertness by increasing dopamine production. Light wavelengths within the wavelength range of 480 nm+/−30 nm and 650 nm+/−30 nm can excite the melanopsin containing ipRGC and/or rods so as to cause an increase in dopamine and/or serotonin production in the retina of an eye. Light wavelengths within the wavelength range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, can excite the melanopsin containing ipRGC and/or rods so as to cause an increase in dopamine and/or serotonin production in the eye, eye's retina, and/or brain.

In some embodiments, blue light wavelengths below 450 nm are blocked or filtered. In certain embodiments the blue light wavelengths below 450 nm and above 490 nm are blocked or filtered. In certain embodiments all light wavelengths below 450 nm and above 490 nm are blocked or filtered. In certain embodiments the blue light wavelengths below 450 nm and above 480 nm are blocked or filtered. In certain embodiments all light wavelengths below 450 nm and above 480 nm are blocked or filtered. In certain embodiments all light wavelengths below 450 nm and above 510 nm are blocked or filtered. As used herein a filter is intended to filter light and affect the transmission thereof. In embodiments, a filter can affect/block or reduce the transmission of certain ranges of light wavelengths. In certain embodiments the filter blocks and/or filters certain light wavelengths while transmitting others.

The optic can be an ophthalmic lens. The optic can be a thin plastic, film, or glass section or part having non-optical power that transmits light. An optic can be a light diffuser. The optic can be antireflection coated. The optic can be slightly tinted. The optic can be without a color or tint. The optic can be mostly clear of color. The optic can be scratch resistant coated. The optic can be surface treated like any ophthalmic lens. In certain embodiments the optic can be an electrochromic lens.

Eyewear can be of any type of eyewear worn around or in the eye. Eyewear as used herein can comprise any eyewear, by way of example only: spectacles, sunglasses, disposable eyewear, goggles, dress eyewear, safety eyewear, sports eyewear, clip-on eyewear, fit-over eyewear, military eyewear, smart eyewear, XR eyewear, AR eyewear, VR eyewear, MR eyewear, contact lens, intra-ocular lenses, or corneal implant. When required the eyewear can comprise a power source and the appropriate electronics needed. Non-prescription can mean non optical power. Plano means no optical power. Optical power can mean all optical powers. The optic can be made of plastic or glass. The use of the word filter means in most cases reducing, but not fully eliminating. However, in some cases, filtering can mean eliminating. The use of the word blocking means eliminating. Diffusing means to spread out. Defocus means not focusing on the retina of the eye of the user. The eyewear or optic can comprise one or more of: a notch filter, bandpass filter, selective blue light filter, absorptive filter, interference filter, a plurality of filters, or a combination of any one or more.

A bandpass filter can be a type of interference filter. An interference filter can be a bandpass filter. The filter can be used in association with one or more lenses, lens blank, optic, and/or optical blank. The filter can be in optical communication with one or more of: a lens, lens blank, optic, optical blank, or another filter. The filter can be applied to one or more of: the concave surface, convex surface, or buried or embedded within the lens, lens blank, optic, or optical blank. The filter can be separated and/or distance separated and in optical communication with one or more of: the lens, lens blank, optic, and/or optical blank. A filter can be used in combination with another filter. A filter can be used in optical communication with a distance separated filter.

A filtered optic or filtered lens can be that of an optic or lens that comprises one or more of: an interference filter, bandpass filter, neutral density filter, notch filter, absorption filter, absorber(s), dyes, and/or selective blue light filter.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 40% of less or 30% or less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

The eyewear or optic can comprise one or more of blue light emitter(s), green light emitter(s), and/or red-light emitter(s). Examples of light emitters can be, by way of example only, LEDs, OLEDs, micro-OLEDs, micro-LEDs, quantum dots, iLEDs, fluorescent, incandescent, and/or the sun. As used herein a light emitter and be any light source that gives off light radiation. By way of example only: an LED, OLEDs, micro-OLED, micro-LED, quantum dots, diode, or the sun. In certain embodiments a light ring is utilized to minimize pupil constriction. This occurs as the eye being treated can fixate on a distant object through the center of the light ring while the light of the light ring is stimulating the photoreceptors of the eye. This further allows for providing light exposure to the peripheral retina of the eye. When an electrical light emitter is utilized, the light can flicker. The light can modulate. The light can modulate within the modulation range of 5 Hz and 15 Hz. Depending upon the type of light source, the light intensity utilized can be 300 lux or greater, 400 lux or greater, 1000 lux or greater, or 10,000 lux or greater.

In certain embodiments, eyewear can comprise blue or red-light emitters facing towards the eye of the wearer, facing inward and reflecting off the optic supported by the eyewear, and/or facing towards the wearer's pupil(s). In other embodiments a band of blue, green, or red-light wavelengths can be varied in intensification of light radiation. The highest concentration of blue, green, or red-light radiation being transmitted can be varied in terms of light radiation. The blue, bluish green or green light emitters can comprise a wavelength within 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. The blue light emitters can comprise a wavelength greater than 449 nm but less than 510 nm. The eyewear or optic can comprise a diffuser for the purposes of diffusing light. The green light emitters can comprise wavelengths within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. The redlight emitters can comprise wavelengths within the range of 630 nm+/−20 nm, 650 nm+/−30 nm, or 600 nm to 700 nm, or 700 nm+/−30 nm. In embodiments disclosed herein, the light emitters can (optionally) be pulsed or modulated on and off to permit the pupil of the wearer/user to open more (enlarge) before it reduces in diameter. In cases, by using red light, the pupils of the eye will constrict less. Also, by causing the eye to focus on a distant object as opposed to a near object, the pupil of the eye will constrict less. In embodiments disclosed herein, a filter can be utilized to reduce the transmission of non-essential light wavelengths so as to cause the pupil diameter to enlarge compared to what the diameter would have been if all the light was permitted to enter the eye.

Embodiments when light wavelengths are generated by way of filtered optics or filtered lenses the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina can fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm or by utilizing a light source or light emitter that predominately transmits within the wavelength range of 460 nm-520 nm, 470 nm to 520 nm, or 480 nm+/−30 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In embodiments, the blue or green or red-light emitters can be located around the periphery of a clear or lightly tinted optic permitting the center of the optic to be free of most, but not all, blue or green or red light. In embodiments the blue or green or red-light light emitters can be located around the periphery of a clear or lightly tinted optic permitting the center of the optic to be free of all blue or green or red-light light. The blue or green or red-light light emitters can be located around the backside of the eye-wire of an eyeglass frame closest to the eye of the wearer, thereby permitting the center of the optic to be free of most, but not all, blue or green or red-light light. The blue or green or red-light light emitters can be covered by a diffuser.

The emitted light wavelengths can strike or mostly strike the non-macular area of the retina, while mostly visible light wavelengths that pass through the center of the optic can strike or mostly strike the macular area of the retina. The optic can be tinted, by way of example only, blue, and blue light emitters can shine through the blue tinted optic. The wavelengths range being transmitted to the eye of the wearer can be within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The blue, bluish green, or green light emitters can excite one or more of, the retinal cones, rods and melanopsin containing ipRGCs. In a preferred case the blue light emitters excite the rods and melanopsin containing ganglion cells. The green light emitters can excite one or more of, the macula cones, retinal rods and melanopsin containing ipRGCs. Certain green light emitters within the wavelength range 500 nm and 530 nm can excite rhodopsin and melanopsin. Certain green light emitters within the wavelength range 500 nm and 530 nm can increase dopamine in the eye. Certain green light emitters within the wavelength range 500 nm and 530 nm can increase dopamine in the brain. The red-light emitters can excite one or more of, the macula cones, retinal rods and melanopsin containing ipRGCs. Certain blue light wavelengths increase alertness, focus, and cause the generation of dopamine in the eye and the brain. Certain blue light wavelengths can slow or stop myopia progression. Certain blue light wavelengths can prevent myopia from occurring in the first place. Certain green light wavelengths decrease pain. Certain red-light wavelengths increase calmness and relaxation. Certain red-light wavelengths increase dopamine production and increase alertness. Certain red-light wavelengths of 650 nm+/−30 nm or 700 nm+/−30 nm can improve the health of mitochondria.

In certain embodiments the range of wavelength band includes the peaks of the most sensitive points from rhodopsin (500 nm) and melanopsin (480 nm). This way both rhodopsin and melanopsin can be stimulated or excited. By way of example, the range of 460 nm-520 nm or 470 nm-520 nm, or 480 nm-520 nm, can be used. This would include blue, bluish green and green wavelengths.

The intensity of the light intensity of the ocular photo-bio-stimulation light can be in certain cases, by way of example only, 300 lux or greater. In other cases, by way of example it is less than 500 lux. In still other cases it can be greater than 500 lux. In still other cases it can be 1,000 lux or greater. In certain cases, by way of example, the time of light exposure is within the range of 1-5 minutes. In other cases, by way of example, it is 10 minutes or less. In still other cases, by way of example, it is greater than 10 minutes.

In embodiments for eyewear, the light emitter can have blue light wavelengths within the range of 460 nm+/−20 nm or 470 nm+/−20 nm or 450 nm to 510 nm and can be blended with white light such as providing a blue wavelength enhanced or enriched by or with white light. By way of example only, certain fluorescent light that provides indoor warm white lighting can provide blue light wavelengths within the range of 460 nm+/−20 nm or 470 nm+/−20 nm or 450 nm to 510 nm. In examples a white florescent light can be used with a blue light emitter. In other examples, certain incandescent light that provides indoor lighting can also provide blue light wavelengths within the range of 460 nm+/−20 nm or 470 nm+/−20 nm or 450 nm to 510 nm. In other examples, certain incandescent light that florescent light that provides indoor lighting can be used with an LED having blue light wavelengths within the range of 460 nm+/−20 nm or 470 nm+/−20 nm or 450 nm to 510 nm. And in still other embodiments, by way of example only, a white LED can be provided in combination with a blue LED having wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, or 495 nm+/−30 nm. And in still other embodiments, by way of example only, a white light emitter can be provided in combination with a blue light emitter having wavelengths within the range of 460 nm+/−20 nm or 470 nm+/−20 nm or 450 nm to 510 nm. And in still other embodiments, by way of example only, a blue LED can provide a level of blue light within the wavelength range of 460 nm+/−20 nm or 470 nm+/−20 nm or 450 nm to 510 nm.

In embodiments for eyewear, the light emitter can have green wavelengths within the range of 500 nm-520 nm, 510 nm to 540 nm, or 530 nm+/−20 nm, and be blended with white light such as providing a green wavelength enhanced or enriched by or with white light. By way of example only, certain fluorescent light that provides indoor warm white lighting can also provide green wavelengths within the range of 500 nm to 540 nm. In examples a white florescent light can be used with a green light emitter. In other examples, certain incandescent light that provides indoor lighting can also provide green light wavelengths within the range 510 nm to 540 nm. In other examples, certain incandescent light that florescent light that provides indoor lighting can be used with by way of example, an LED having green light wavelengths within the range of 500 nm-520 nm, 520 nm+/−10 nm, 530 nm+/−20 nm, or 510 nm to 540 nm. And in still other embodiments, by way of example only, a white LED can be provided in combination with a green LED having wavelengths within the range of 530 nm+/−20 nm, 530 nm+/−20 nm, or 510 nm to 540 nm. And in still other embodiments, by way of example only, a white light emitter can be provided in combination with a green light emitter having wavelengths within the range of 500 nm+/−10 nm, 520 nm+/−10 nm, 530 nm+/−20 nm, or 510 nm to 540 nm.

In embodiments for eyewear, the light emitter can have red wavelengths within the range of 630 nm+/−20 nm, 650 nm+/−30 nm, or 600 nm to 700 nm, and be blended with white light such to provide a red wavelength enhanced or enriched white light. By way of example only, certain fluorescent light that provides indoor warm white lighting can also provide red wavelengths within the range of range of 630 nm+/−20 nm, 650 nm+/−30n, or 600 nm to 700 nm. In examples a white florescent light can be used with a red-light emitter. In other examples, certain incandescent light that provides indoor lighting can also provide red-light wavelengths within the range of 630 nm+/−20 nm, 650 nm+/−30 nm, or 600 nm to 700 nm. In other examples, certain incandescent light that florescent light that provides indoor lighting can be used with an LED having red-light wavelengths within the range of range of 660 nm+/−20 nm, 650 nm+/−30 nm, or 600 nm to 700 nm. And in still other embodiments, by way of example only, a white LED can be provided in combination with a red LED having wavelengths within the range of range of 630 nm+/−20 nm, 650 nm+/−30 nm, or 600 nm to 700 nm. And in still other embodiments, by way of example only, a white light emitter can be provided in combination with a red-light emitter having wavelengths within the range of range of 630 nm+/−20 nm, 650 nm+/−30 nm or 600 nm to 700 nm, or 700 nm+/−30 nm.

In embodiments, the blue light emitters can be located around the periphery of a clear or lightly tinted optic permitting the center of the optic to be free of most, but not all, blue light. In embodiments the blue light emitters can be located around the periphery of a clear or lightly tinted optic permitting the center of the optic to be free of all blue light. The blue light emitters can be located around the backside of the eye-wire of an eyeglass frame closest to the eye of the wearer permitting the center of the optic to be free of most, but not all, blue light. The blue light emitters can be covered by a diffuser. The blue light wavelengths can strike or mostly strike the non-macular area of the retina, while mostly visible light wavelengths that pass through the center of the optic can strike or mostly strike the macular area of the retina. The optic can be tinted blue and blue light emitters can shine through the tinted optic. The optic can be tinted blue and blue light emitters can reflect off the surface of the optic. The optic can be tinted blue and white light emitters can shine through the blue tinted optic. In certain embodiments the blue light emitters which are located on the backside of the eyewear can be pointed towards the pupil of the eye of the wearer. In other embodiments the blue light emitters are perpendicular to the backside of the eyewear and can point towards the face of the wearer.

In embodiments the green light emitters can be located around the periphery of a clear or lightly tinted optic permitting the center of the optic to be free of most, but not all, green light. In embodiments the green light emitters can be located around the periphery of a clear or lightly tinted optic permitting the center of the optic to be free of all green light. The green light emitters can be located around the backside of the eye-wire of an eyeglass frame closest to the eye of the wearer permitting the center of the optic to be free of most, but not all, green light. The green light emitters can be covered by a diffuser. The green light wavelengths can strike or mostly strike the macular and non-macular area of the retina, while mostly visible light wavelengths that pass through the center of the optic can strike or mostly strike the macular area of the retina. The optic can be tinted green and green light emitters can shine through the green tinted optic. The optic can be tinted green and green light emitters can reflect off one of the surfaces of the optic. The optic can be tinted green and white light emitters can shine through the green tinted optic. In certain embodiments the green light emitters which are located on the backside of the eyewear can be pointed towards the pupil of the eye of the wearer. In other embodiments the green light emitters are perpendicular to the backside of the eyewear and can point towards the face of the wearer.

In embodiments, the red-light emitters can be located around the periphery of a clear or lightly tinted optic permitting the center of the optic to be free of most, but not all, red light. In embodiments the red-light emitters can be located around the periphery of a clear or lightly tinted optic permitting the center of the optic to be free of all red light. The red-light emitters can be located around the backside of the eye-wire of an eyeglass frame closest to the eye of the wearer permitting the center of the optic to be free of most, but not all, red light. The red-light emitters can be covered by a diffuser. The red-light wavelengths can strike or mostly strike the macular and non-macular area of the retina, while mostly visible light wavelengths that pass through the center of the optic can strike or mostly strike the macular area of the retina. The optic can be tinted red and red-light emitters can shine through the red tinted optic. The optic can be tinted red and red-light emitters can reflect off of one of the surfaces of the optic. The optic can be tinted red and white light emitters can shine through the red tinted optic. In certain embodiments the red-light emitters which are located on the backside of the eyewear can be pointed towards the pupil of the eye of the wearer. In other embodiments the red-light emitters are perpendicular to the backside of the eyewear and can point towards the face of the wearer.

In embodiments, the eyewear houses or supports an optic which can comprise optical power. A defocusing lens can be utilized with the eyewear or optic. Such a defocusing lens can be housed within the eyewear, attached to the eyewear or optic, or worn behind the eyewear or optic. In cases, the defocusing lens is on the backside of a Bandpass Filter between the filter and the eye of the wearer or user. In certain embodiments the eyewear houses or supports an optic which can comprise non-optical power. In certain embodiments the eyewear houses or supports an optic which can comprise an eyeglass prescription. In certain embodiments the eyewear houses or supports an optic which can comprise an eyeglass lens that is non-prescription. In certain embodiments, by way of example, the eyewear can be disposable, comprising a colored optic such that when viewing a bright light source transmits light wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm, to the eye of the wearer. In certain embodiments the eyewear can be disposable, comprising a colored optic such that when viewing a bright light source transmits light wavelengths within the range of 500 nm-520 nm or 530 nm+/−20 nm to the eye of the wearer. In certain embodiments the eyewear can be disposable, comprising a colored optic such that when viewing a distant separated bright light source transmits light wavelengths within the range of 630 nm+/−20 nm, 650 nm+/−30 nm, or 600 nm to 700 nm, or 700 nm+/−30 nm, to the eye of the wearer.

In certain embodiments the eyewear houses or supports an optic that comprises blue light emitters having blue light wavelengths within the range of 441 nm to 500 nm, or 460 nm+/−20 nm or 470 nm+/−20 nm or 480 nm+/−30 nm. In certain embodiments, by way of example only, the eyewear houses or supports an optic that comprises a blue color having blue wavelength within the range of 441 nm to 500 nm, or 460 nm+/−20 nm or 470 nm+/−20 nm or 480 nm+/−30 nm, while, in aspects, filtering or blocking blue light wavelengths of 440 nm or below. In certain embodiments the eyewear houses or supports an optic that comprises a blue color having blue light wavelengths within the range of 441 nm to 500 nm, or 460 nm+/−20 nm or 470 nm+/−20 nm or 480 nm+/−30 nm, and wherein the blue light wavelengths transmitted below 441 nm have been reduced in number or intensity. In still other embodiments a bandpass filter transmits wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. In certain embodiments the eyewear houses or supports an optic that comprises green light emitters having green light wavelengths within the range of 510 nm-540 nm or 530 nm+/−20 nm or 520 nm+/−10 nm. In certain embodiments the eyewear houses or supports an optic that comprises a green color having green light wavelengths within the range of 510 nm-540 nm or 530 nm+/−20 nm.

In some embodiments the eyewear or optic can comprise red-light emitters. In certain other embodiments the eyewear or optic can comprise blue, bluish green, green, and/or red-light emitters. In such cases the light emitters are used for improving, by way of example only, increased alertness and cognitive ability. The light emitters can emit wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The optic can comprise a double bandpass filter that can be used to provide for these ranges of transmission.

The eyewear can comprise blue or red light provided by an electronic display, and wherein the electronic display is located within an optic, in front of an optic, behind an optic, on the surface of an optic, on the eyewear and transmitted or projected to an optic, and/or on the eyewear and transmitted or projected to or on the human eye(s). Such an electronic display used with eyewear can be for XR (extended reality), VR (virtual reality), AR (augmented reality), MR (mixed reality), Modified Reality and in some cases just to provide blue, or green, or red-light to or from an optic. The red-light can be of a red-light within the wavelength range of 660 nm+/−30 nm or 650 nm+/−30 nm or 660 nm+/−20 nm. The blue light can have wavelengths within the range of 441 nm to 500 nm, or 460 nm+/−20 nm or 470 nm+/−20 nm or 480 nm+/−30 nm, while if needed filtering or blocking within the range of 420 nm+/−20 nm. The green light can have wavelengths within the range of 510 nm-540 nm or 530 nm+/−20 nm. The red-light wavelengths can be within the range of 630 nm+/−20 nm, or 650 nm+/−30 nm, or 660 nm+/−30 nm, or 600 nm to 700 nm, or 700 nm+/−30 nm. A plurality of light emitters can be utilized to provide one or more of the preceding wavelength bands.

In certain embodiments the eyewear or optic can comprise white light emitters that shine on a blue colored lens or optic, or a green colored lens or optic, or a red colored lens or optic. Examples of light emitters can be, by way of example only: LEDs, OLEDs, micro-OLEDs, micro-LEDs, iLEDs, and/or quantum dots. A plurality of light emitters can be utilized. A clip-on optic or flip-up or down optic can attach to the eyewear (see, FIG. 21A-D). The eyewear can comprise a prescription lens or non-prescription lens. The eyewear can comprise a lens having optical power or having non-optical power (plano power).

In reference to FIG. 19, in embodiments, one or more lens housed or supported by the eyewear can comprise a blue color having blue wavelengths within the range 450 nm to 500 nm or 460 nm+/−20 nm, or 470 nm+/−20 nm, or 480 nm+/−30 nm, and can filter or block blue wavelengths below 450 nm. A lens having a green color can have wavelength transmission within the range of 510 nm-550 nm, or 530 nm+/−20 nm, or 520 nm+/−10 nm. A lens having a red color can have wavelength transmission within the range of 650 nm+/−30 nm, or 660 nm+/−20 nm or 600 nm to 700 nm, or 700 nm+/−30 nm.

In still other embodiments the lens housed by eyewear can be clear of color. The clip-on optic or flip-up or down optic can comprise a prescription lens or non-prescription lens. The housing of the clip-on optic or flip-up and down optic can attach to the eyewear, by way of example only, magnetically, mechanically, and/or by a tension mount. (See, FIGS. 21A-D and FIG. 22.) In certain other embodiments the optic can be attached to the lens housed by the eyewear by way of example only, with magnets, removable adhesive, and/or through static energy.

Other embodiments, by way of example, may include a ring, a band, or a section of blue or green or red-light emitters, which can be adhered to the lens or optic surface, attached to the lens or optic surface, or embedded within the lens or optic surface, wherein the lens or optic is supported or housed by an eyeglass frame or eyewear. In certain other embodiments by way of example only, a ring, band, or a section of blue or green or red-light emitters, can be adhered to the lens or optic surface, attached to the lens or optic surface, or embedded within the lens or optic surface, such that it can be inserted or such that it is supported or stabilized on an eyeglass frame or eyewear. In aspects, the filters and/or emitters and related embodiments can be removeable inserts, such as attached to a lens, attached to eyewear, inserted into a lens, or embedded in a lens. (See, FIG. 19A-F.)

Figure 20A:
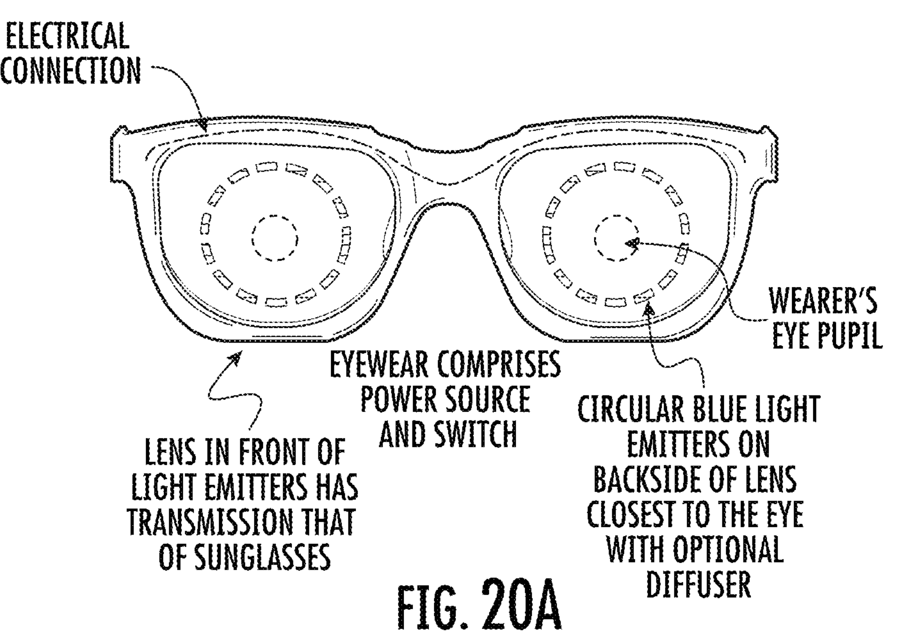
FIG. 20A-C shows an embodiment of the current invention as described herein.
Figure 20B:
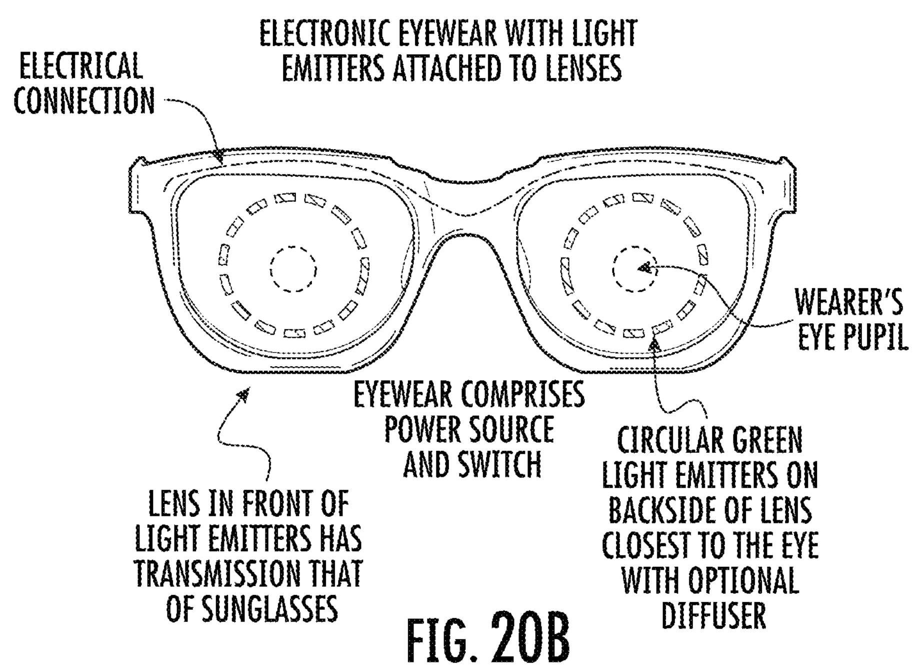
Figure 20C:
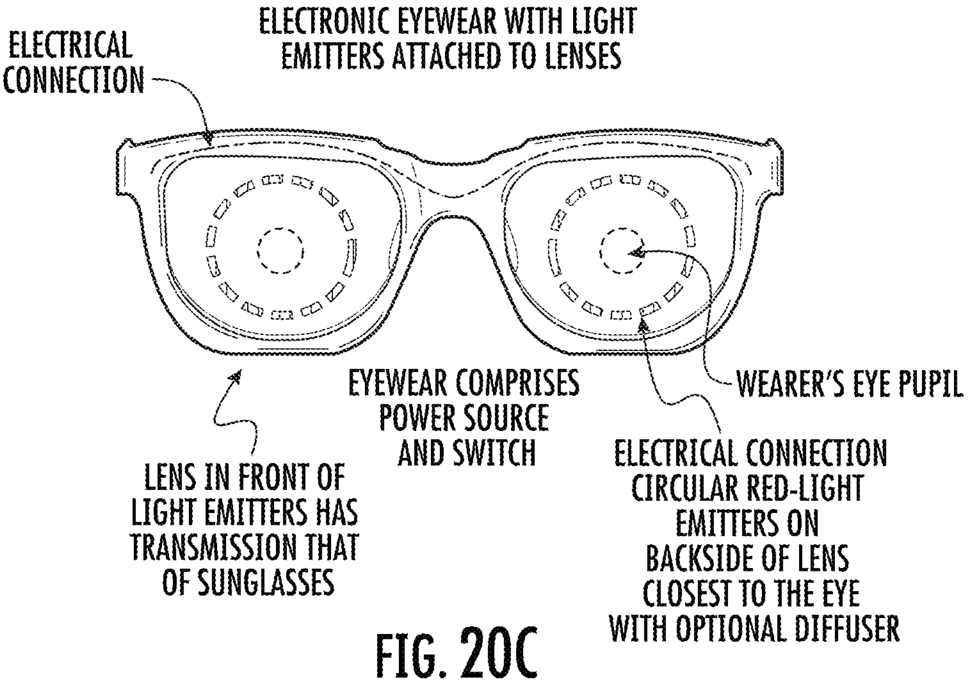

In reference to FIG. 20, in embodiments, the blue, or green, or red-light, or white light emitters, can provide light covering a central portion of the lens or optic. In other cases, the blue, green, or red-light, or white light emitters, can provide light covering a peripheral portion of the lens or optic leaving the center of the lens or optic mostly clear of blue, green, red, or white light. In still other embodiments the blue, green, red or white light emitters can provide light covering a portion of the lens or optic. (See, FIGS. 20A-C.)

In still other embodiments, the blue, or green, or red-light, or white light emitters, can be distance separated from the optic. The light emitters can be covered by a diffuser to spread and soften the light. The light can be directed towards the eye of the wearer. The light can be directed towards the pupils of the eyes of the wearer. In certain embodiments the light source or emitter can modulate for example, within the range of one of 5 Hz-15 Hz, 10 Hz to 20 Hz, or 40 Hz+/−20 Hz. In certain embodiments the light source or emitter can modulate, for example 10 times per second or less. In certain embodiments the light source or emitter can modulate (on and off), for example, 20 times per second or less. In other embodiments the light source or emitter can modulate, for example, 50 times per second or less. And in still other embodiments the light emitter or emitter can modulate, for example, 100 times per second or less. In still other embodiments the light does not modulate or flicker.

In embodiments utilizing blue light as the light source (wavelengths within the range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, or 500 nm+/−20 nm), can be of an intensity of 300 lux or more. In other embodiments the intensity can be of 500 lux or more. In other embodiments the intensity can be of 1,000 lux or more. In certain embodiments utilizing a blue light source, the time of treatment with the light source can be 1 hour or less. In other embodiments the time of treatment can be 30 minutes or less. In still other embodiments it can be 10 minutes or less. And in still other embodiments it can be 5 minutes or less.

In certain embodiments utilizing a green light source (e.g., wavelengths within the range of 530 nm+/−20 nm), the green light source can have an intensity of 250 lux or more. In other embodiments the intensity can be 500 lux or more. In other embodiments the intensity can be 1,000 lux or more. In certain embodiments, when utilizing a green light source, the time of treatment with the light source can be 1 hour or less. In other embodiments the time of treatment can be 30 minutes or less. In still other embodiments it can be 10 minutes or less. And in still other embodiments it can be 5 minutes or less.

In embodiments utilizing a red-light source (wavelengths within the range of 650 nm+/−30 nm or 700 nm+/−30 nm), the red-light source can have an intensity of 400 lux or more. In other embodiments the intensity can be of 500 lux or more. In other embodiments the intensity can be of 1,000 lux or more. In other embodiments the intensity can be of 5,000 lux or more. In certain embodiments utilizing a red-light source the time of treatment with the light source can be 1 hour or less. In other embodiments the time of treatment can be 30 minutes or less. In still other embodiments it can be 10 minutes or less. And in still other embodiments it can be 5 minutes or less. In reference to FIG. 21, an embodiment can include a clip-on optic or flip-up or down optic comprising a lens having optical power or having non-optical power (plano power). In embodiments the clip-on optic or flip-up or down optic can transmit blue wavelengths within the range of 441 nm-500 nm, or 460 nm+/−20 nm, or 470 nm+/−20 nm, or 480 nm+/−30 nm, such as, in cases, using a bandpass filter. (See, e.g., 2101 in FIG. 21*a*.) In still other embodiments the clip-on optic or flip-up or down optic can be clear of color and comprise blue light emitters having blue wavelengths predominately or solely within the range of 441 nm-500 nm, or 460 nm+/−20 nm, or 470 nm+/−20 nm, or 480 nm+/−30 nm, around its periphery of that of the housing that supports the optic. (See, e.g., FIG. 20A-C.) Such a housing can be a frame or an eyewear frame. In certain embodiments the clip-on optic or flip-up or down optic can transmit blue light (e.g., using one or more light emitter 2102) wavelengths within the range of 441 nm-500 nm, or 460 nm+/−20 nm, or 470 nm+/−20 nm, or 480 nm+/−30 nm, and the lens housed by the eyewear can filter or block blue wavelengths 440 nm or below. In certain embodiments the forward optic farthest away from the eye of the wearer can provide or emit a blue color having wavelengths within the range of 441 nm-500 nm, or 460 nm+/−20 nm, or 470 nm+/−20 nm, or 480 nm+/−30 nm. In certain embodiments the forward optic is that of the clip-on or flip down optic and the optic located behind the clip-on or flip down optic is that of the eyewear optic. In certain other embodiments the optic housed in the eyewear can be a stack of two optics with the forward optic comprising a blue color having wavelengths predominately or solely within the range of 441 nm-500 nm, or 460 nm+/−20 nm, or 470 nm+/−20 nm, or 480 nm+/−30 nm, and the optic closest to the eye of the wearer being the optic that either filters or blocks blue light wavelengths. The optic can be a clip on or flip down filter. The filter can be a bandpass filter. The filter can be an interference filter. The filter can be an absorption filter. Any of the clip-on optics or flip-up or down optics can be attachable and detachable to the eyewear, eyewear frame, or optic/lens; in other words, any of the clip-on optics or flip-up or down optics can be attachable and detachable to a frame, or any of the clip-on optics or flip-up or down optics can be integral with or embedded within the frame.

The clip-on optic or flip-up or down optic can comprise a lens having optical power or having non-optical power (plano power). In certain embodiments the clip-on optic or flip-up or down optic can comprise transmission of green light wavelengths predominately or solely within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. In still other embodiments the clip-on optic or flip-up or down optic can be clear of color and comprise green light emitters having wavelengths within the range of 500 nm-550 nm, or 530 nm+/−20 nm, around its periphery of that of the housing that supports the optic. Such a housing can be a frame or an eyewear frame. In certain embodiments the forward optic furthest away from the eye of the wearer can provide or emit green wavelengths within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. In certain embodiments the forward optic is that of the clip-on or flip down optic and the optic located behind the clip-on or flip down optic is that of the eyewear optic comprising an optical power. The optic can be a clip on or flip down filter. The filter can be a bandpass filter. The filter can be an interference filter. The filter can be an absorption filter.

The clip-on optic or flip-up or down optic can comprise a lens having optical power or having non-optical power (plano power). In certain embodiments the clip-on optic or flip-up or down optic can comprise transmission of red-light wavelengths predominately or solely within the range of 630 nm+/−20 nm, 650 nm+/−30 nm, or 600 nm-700 nm. In still other embodiments the clip-on optic or flip-up or down optic can be clear of color and comprise red light emitters having wavelengths within the range of 630 nm+/−20 nm, 650 nm+/−30 nm, or 600 nm-700 nm, or 700 nm+/−30 nm, around its periphery of that of the housing that supports the optic. Such a housing can be a frame or an eyewear frame. In certain embodiments the forward optic farthest away from the eye of the wearer can provide or emit red wavelengths within the range of 630 nm+/−20 nm, 650 nm+/−30 nm, or 600 nm-700 nm, or 700 nm+/−30 nm. In certain embodiments the forward optic is that of the clip-on or flip down optic and the optic located behind the clip-on or flip down optic is that of the eyewear optic comprising an optical power. The optic can be a clip on or flip down filter. The filter can be a bandpass filter. The filter can be an interference filter. The filter can be an absorption filter.

Figure 21A:
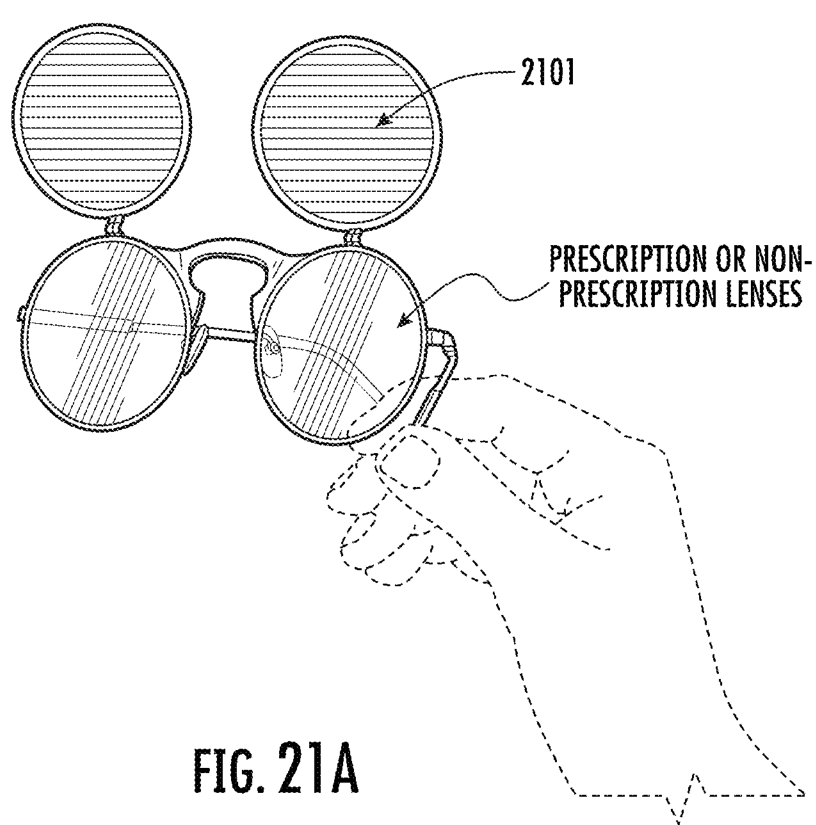
FIG. 21A-D shows an embodiment of the current invention as described herein.
Figure 21B:
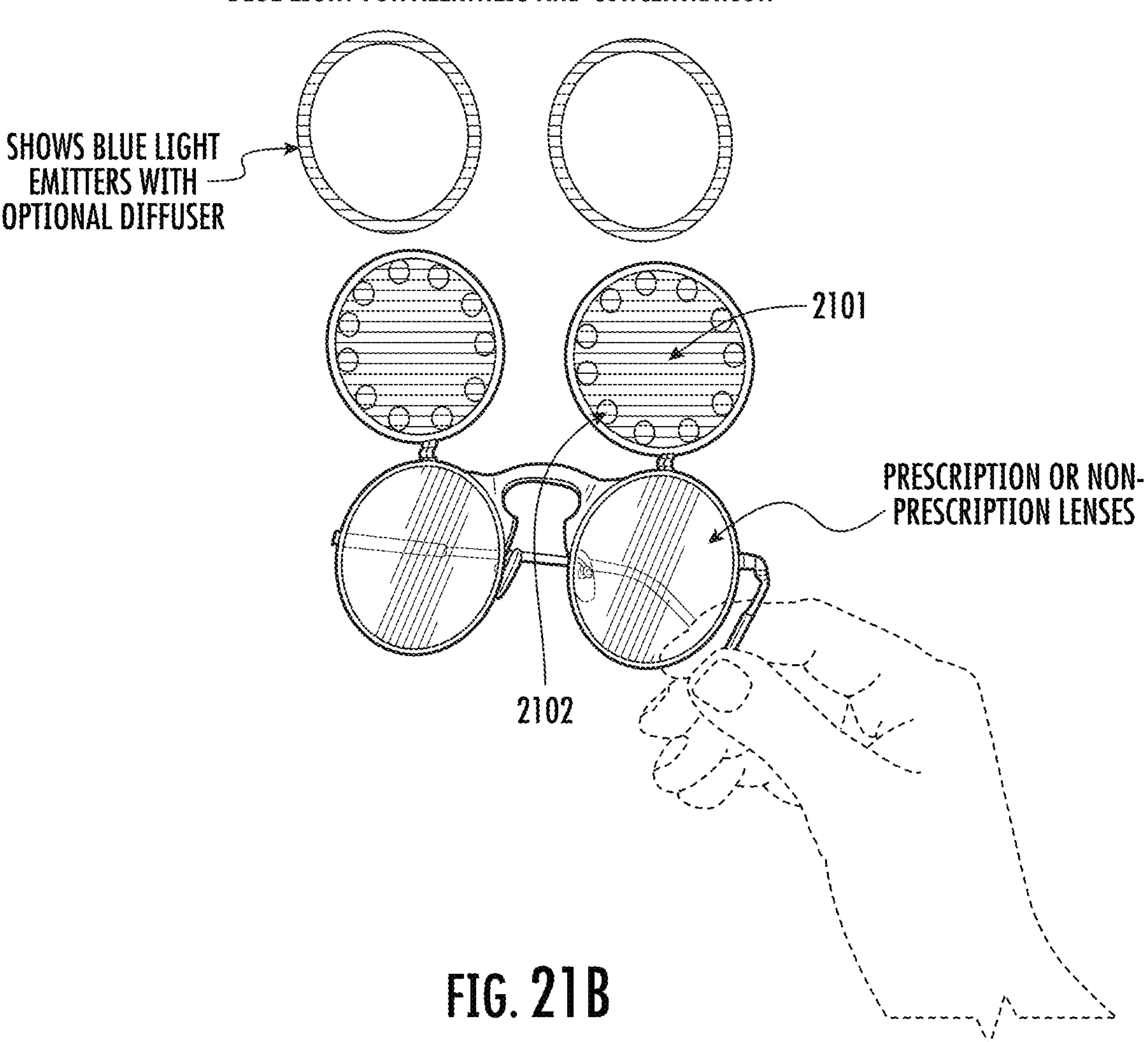
Figure 21C:
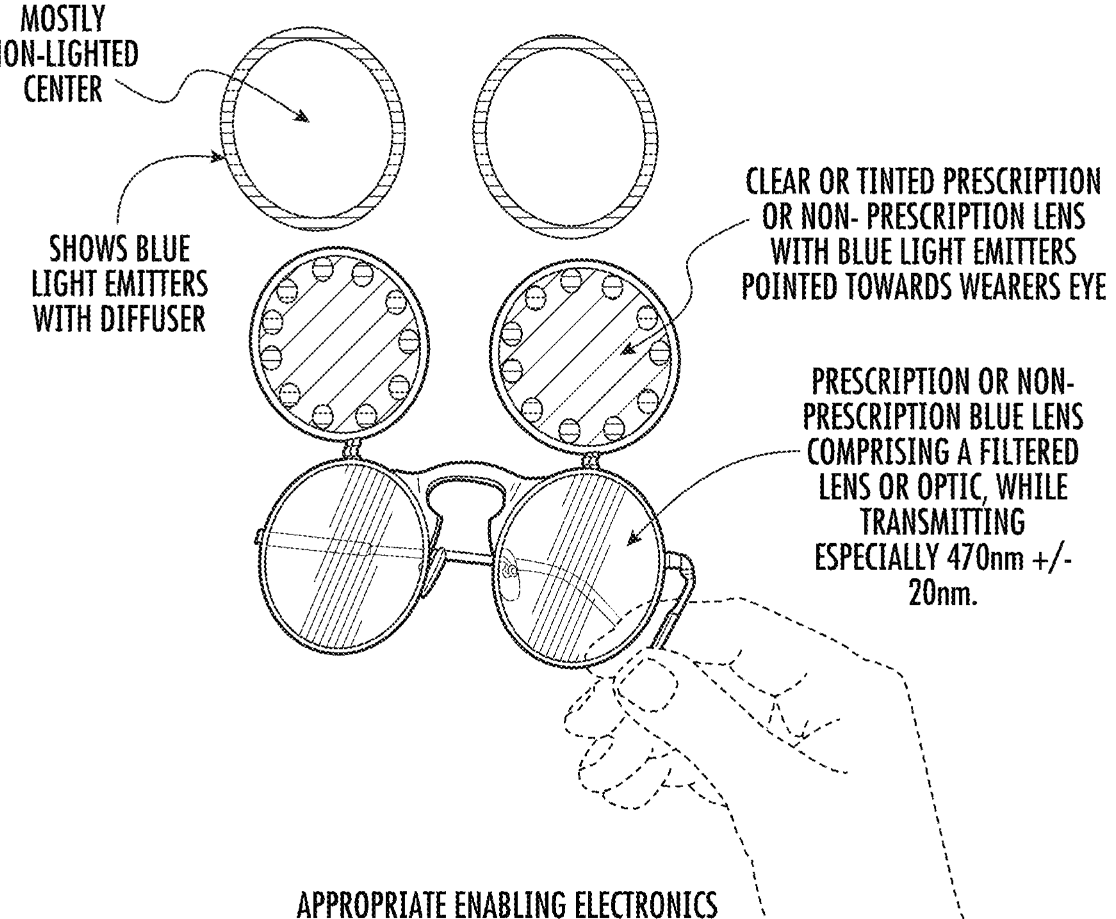
Figure 21D:
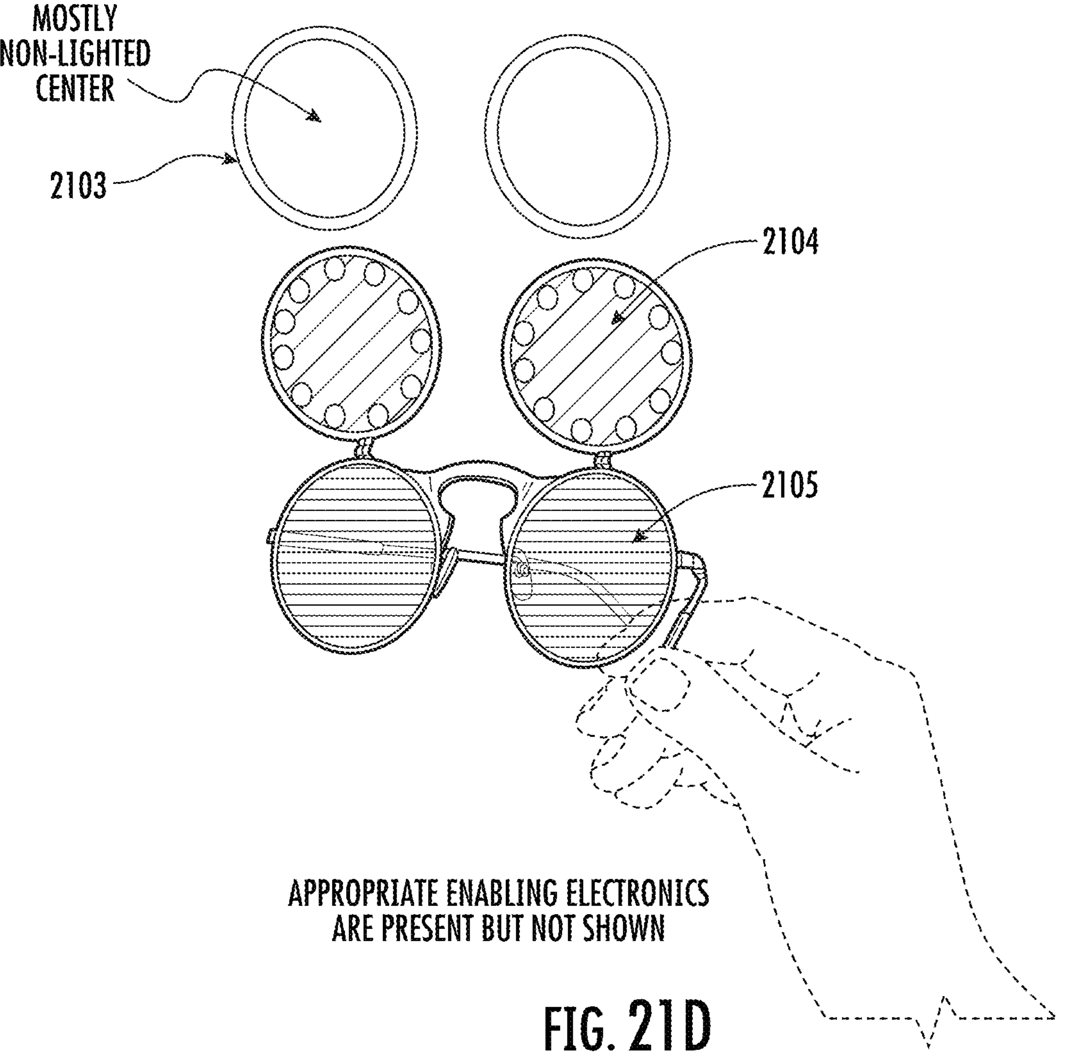

As shown in FIG. 21D, an embodiment can include white light emitters (with or without a diffuser) 2103. The clip-on optic or flip-up or down optic can be prescription, or not. The lenses can be tinted, or not 2104. The lenses can include one or more filter. In embodiments, white LEDs are pointed towards the eye of the wearer, and they can transmit trough a filter 2105 (e.g., blue lens comprising notch filter or bandpass filter while transmitting especially between 480+/−30 nm).

With all embodiments requiring electronics provided herein the appropriate enabling electronics to drive, power, control, modulate, dim or brighten the light emitters are part of or in association with the embodiments even if not identified within the illustrations. With any of the embodiments disclosed herein when appropriate, by way of example only, one or more of a bandpass filter, notch filter, interference filter, dye absorption filter, specialized filter, coating, and/or dye, can be utilized to achieve the desired wavelengths transmission results. In certain embodiments a plurality of filters is used such that each is in optical alignment with the other. The optic can be a clip on or flip down filter. The filter can be a bandpass filter. The filter can be an interference filter. The filter can be an absorption filter.

Figure 22:
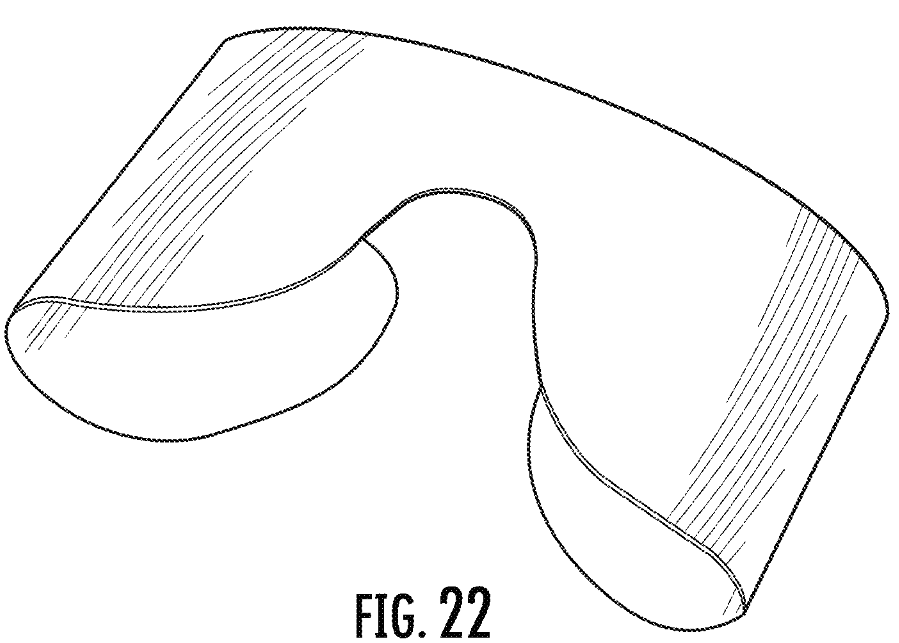
FIG. 22 shows an embodiment of the current invention as described herein.

In reference to FIG. 22, in embodiments, the eyewear and/or optic can be comprised of a non-prescription optic that can by way of example only, one or more of: disposable, repeatably rolled up when not in use and extends back out when in use such that it utilizes pressure to attach to and eyewear frame, rests by way of arms on existing eyewear that is being worn, fits over existing eyewear, and/or clips or snaps on to existing eyewear. The non-prescription eyewear or optic can further be comprised of either a light wavelength filtered material or a light wavelength bandpass material. The eyewear or optic can be largely darkened, only allowing the transmission of 20% or less of the light through. The eyewear or optic can be largely darkened, only allowing the transmission of 15% or less of the light through. The eyewear or optic can be largely darkened, only allowing the transmission of 10% or less of the light through.

Such a transmission will cause the pupil of the eye(s) to enlarge fully or slightly. This increase in the size of the pupil(s) then permits a larger area of the retina to be exposed to the light wavelengths that are being transmitted to the eye(s). In certain cases, light wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm are used. In aspects, a defocusing lens can be utilized with the eyewear or optic. Such a defocusing lens can be housed within the eyewear, attached to the eyewear or optic, or worn behind the eyewear or optic. In most, but not all cases, the defocusing lens is on the backside of the bandpass filter between the filter and the eye of the wearer or user.

In reference to FIG. 23, by largely acting as very dark sunglasses, embodiments can cause the pupil to partially or fully enlarge, thus allowing more of the retina to become exposed to the transmitted light wavelengths. This is especially helpful with blue light wavelengths of 460 nm or greater to 480 nm or greater, or 510 nm or less, where the blue light wavelength is intended to cause the wearer to become more alert or focused. This also is the case with red light within the range of 650 nm+/−30 nm or 650 nm-700 nm. The very dark sunglass effect of the eyewear or optic causes the pupil to partially or fully enlarge, which exposes more retinal rods and/or ipRGCs to the blue (or red) light wavelength being transmitted. This in turn increases dopamine production which then assists with making the wearer of the optic or eyewear more alert and focused. In addition, rods and cones are sensitive to green light wavelengths.

Thus, by partially or fully dilating the eye it is possible to expose more of the retinal rods in addition to the cones. When an embodiment comprising a bright light is shined on the retina of a wearer the pupil of the eye constricts and reduces the amount of retina that is stimulated. It is one of the purposes of the invention to stimulate a larger amount of the retina, thus increasing the amount of dopamine produced. This can be accomplished by way of one or more of: defocused light, reducing or eliminating accommodative pupil constriction by fixating on a distant object, utilizing dim light, utilizing red light when possible, and/or utilizing a bandpass filter thus reducing the overall light transmission by way of allowing only the desired light wavelengths to be transmitted. The bandpass filter can be a single bandpass filter or a double bandpass filter. The filter can be a hybrid filter. A bandpass filter can be an interference filter.

Figure 23A:
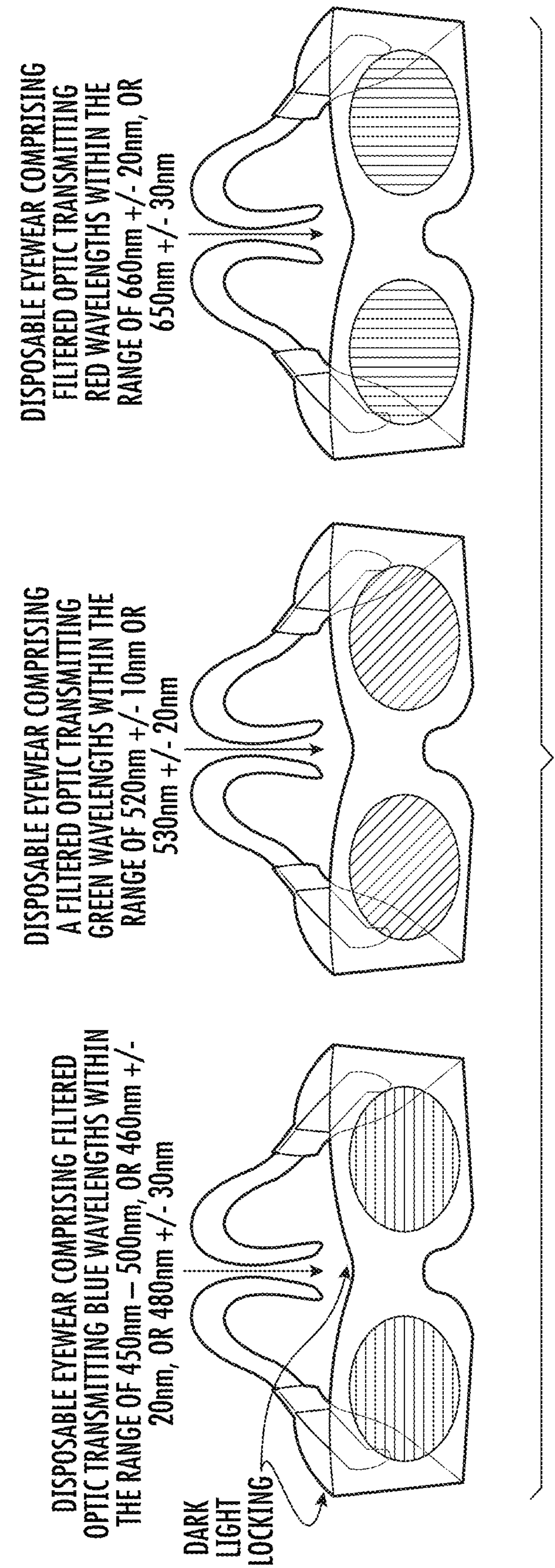
FIG. 23A-B shows an embodiment of the current invention as described herein.
Figure 23B:
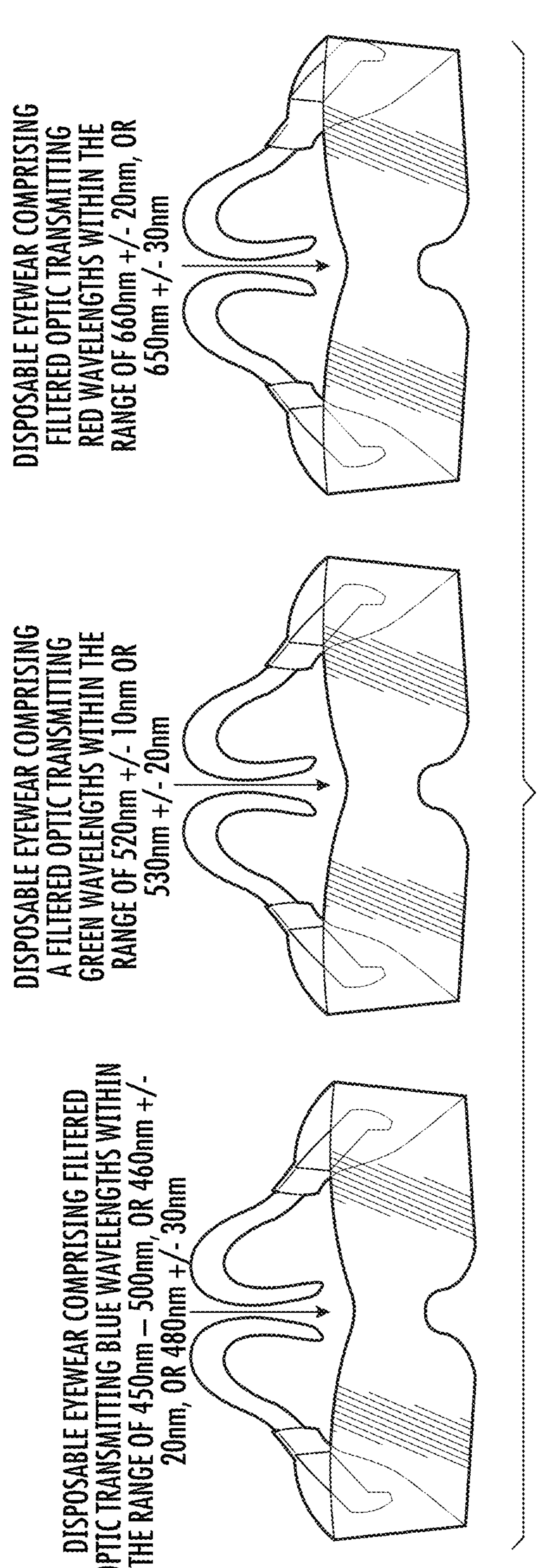

The degree of darkness of the sunglasses or treatment glasses can provide one of or more of: scotopic condition, reduced mesopic conditions, and reduced photopic conditions. FIG. 23A shows examples of ocular photo-bio-stimulation disposable (or non-disposable) light wavelength filtered optic eyewear; the disposable eyewear can be made, by way of example only, a darkly tinted or near opaque colored plastic material having plastic or paper arms that are supported by the wearer's ears, to wear over or around the user's conventional eyeglasses, if needed. The wearer can look at a distance separated bright light source while wearing the disposable eyewear for a time. Such a bright light source can be one of LED, OLED, iLED, quantum dots, fluorescent, incandescent, sun light, laser, plasma display, TV display, tablet display, cell phone display, computer display, or electronic display. A defocusing lens can be utilized with the eyewear or optic. Such a defocusing lens can be housed within the eyewear, attached to the eyewear or optic, or worn behind the eyewear or optic. In most, but not all cases, the defocusing lens is on the backside of the filter between the filter and the eye of the wearer or user. FIG. 23B shows examples of ocular photo-bio-stimulation disposable (or non-disposable) light wavelength filtered optic eyewear; the disposable eyewear can be made, by way of example only, a darkly tinted or near opaque colored plastic material having plastic or paper arms that are supported by the wearer's ears, to wear over or around the user's conventional eyeglasses, if needed. The wearer can look at a distance separated bright light source while wearing the disposable eyewear for a time. Such a bright light source can be one of LED, OLED, iLED, quantum dots, fluorescent, incandescent, sun light, laser, plasma display, TV display, tablet display, cell phone display, computer display, or electronic display. A defocusing lens can be utilized with the eyewear or optic. Such a defocusing lens can be housed within the eyewear, attached to the eyewear or optic, or worn behind the eyewear or optic. In most, but not all cases, the defocusing lens is on the backside of the filter between the filter and the eye of the wearer or user.

Figure 24:
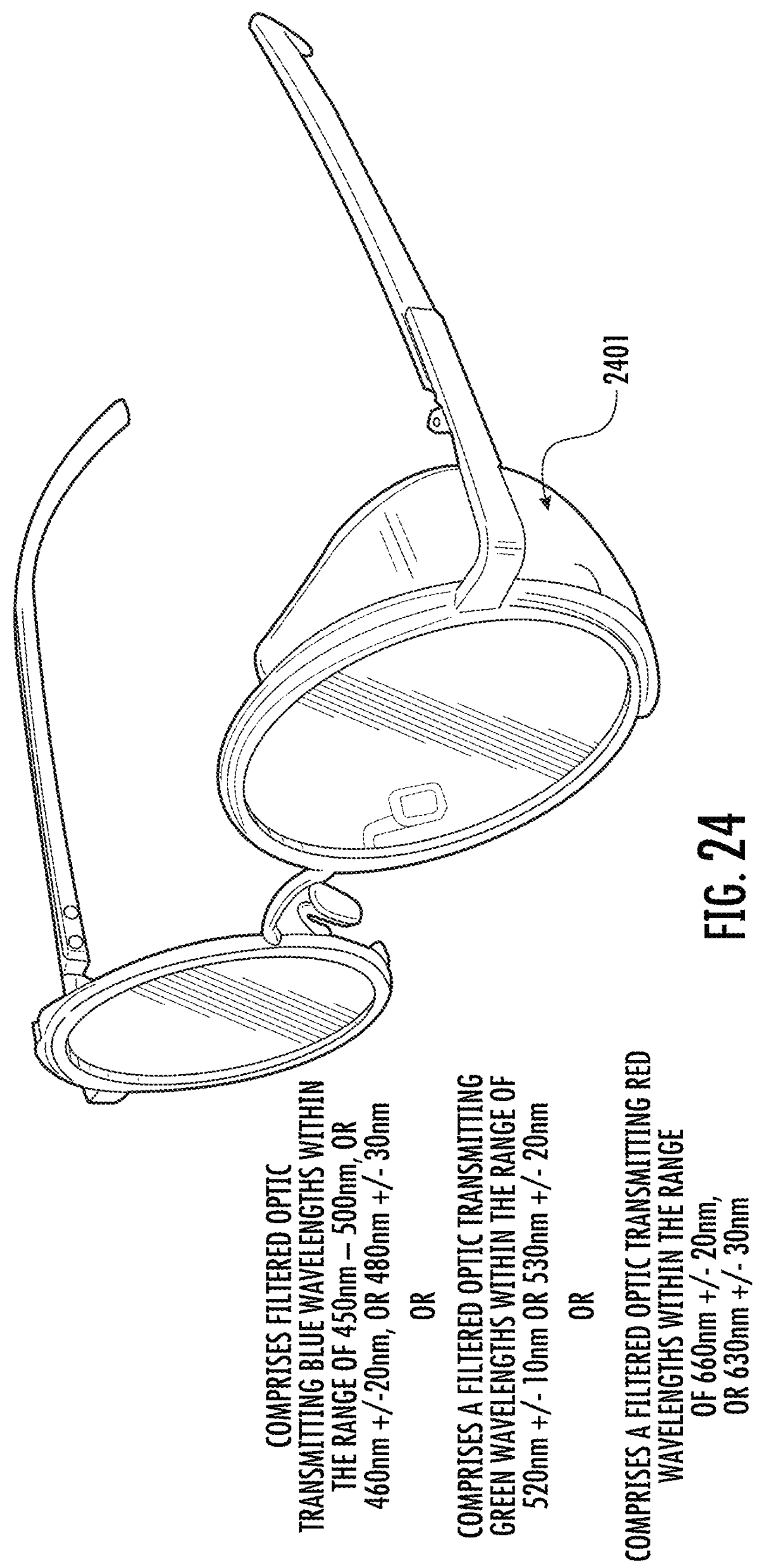
FIG. 24 shows an embodiment of the current invention as described herein.

If reference to FIG. 24, the embodiment can be eyewear comprising an optic, wherein the eyewear when worn causes the pupil of an eye to enlarge in diameter, wherein the optic transmits light radiation having wavelengths of light within the range of 450 nm and 510 nm and wherein the optic transmits 40% or less of visible light. Eyewear that comprises side shields can be used to assist in blocking light coming in from the periphery. The optic can comprise a filter or filters. The wavelengths of light that can be transmitted, by way of example only, are within the range of 460 nm+/−10 nm or 480 nm+/−30 nm. The optic can transmit 30% or less visible light. The optic can transmit 20% or less visible light. The optic can transmit 15% or less of visible light. The optic can transmit 10% or less visible light. The eyewear can be one of: rollable eyewear, clip-on eyewear, disposable eyewear, fit-over eyewear, or flip down or up eyewear. The eyewear can block or filter light from striking the eyes of the wearer by way of the sides and optics of the eyewear. (See, 2401.) The eyewear can block or filters light from striking the eyes of the wearer by way of the optics of the eyewear. The eyewear can comprise wrap around optics. The optics can have no optical power or can be of plano power. The optics can be non-prescription. The optics can comprise optical power. The eyewear can fit over or in front of prescription optics.

In another embodiment eyewear comprises an optic that comprises one or more of a bandpass filter, interference filter, absorption filter, selective wavelengths filter, neutral density filter, and/or notch filter, such that the optic can transmit either light wavelengths within the range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The optic can be used in conjunction with a light source of the appropriate light wavelength and intensity. The eyewear can be one of: rollable eyewear, clip-on eyewear, disposable eyewear, fit-over eyewear, or flip down or up eyewear. The eyewear blocks or filters light from striking the eyes of the wearer by way of the sides and optics of the eyewear. The eyewear blocks or filters light from striking the eyes of the wearer by way of the optics of the eyewear. The eyewear can comprise wrap around optics. The optics can have no optical power or can be of plano power. The optics can be non-prescription. The optics can comprise optical power. The eyewear can fit over or in front of prescription optics. The overall transmission of visible light through the optic of the eyewear can be 40% or less, 30% or less, 20% or less. One or both optic(s) of the eyewear can comprise optical power. One or both optic(s) of the eyewear can comprise no optical power (plano). The optic(s) can be comprised of one or more of: CR 39, Trivex, mid index, high index ophthalmic materials, polycarbonate, or glass. A filter can be added to an optic, in this case a lens or lens blank by way of, imbibed, coated, having an absorptive dye intermixed with the lens matrix material, or surface cast. The filter can be added, by one of: an outer layer, a separate filter that is adjacent to the lens or lens blank, and/or a separate filter that is distance separated but in optical alignment with the lens or lens blank.

When surface casting is utilized, a thin surface cast layer can be placed on the front convex surface of the lens or lens blank. Conventional finishing layers such as, by way of example only, hard scratch resistant coating or an anti-reflective layer or coating can be placed on top of the surface cast layer. For single vision lenses a spherical surface cast layer on the front surface works well with the concave surface providing the astigmatic curve and the curve that causes the spherical power to be what is required. Such a concave surface can be fabricated by way of surfacing or free forming. When fabricating a progressive addition lens, the same surface cast front convex surface can be utilized and the PAL surface can be free formed on the concave surface of the lens, lens blank or semi-finished lens blank.

In certain embodiments a filter or filters is/are applied to the convex side of the lens, lens blank, or semi-finished lens blank. In other cases, the filter or filters is/are applied to the concave side of the lens, lens blank, or semi-finished lens blank. In other cases, the filter or filters is/are applied to both sides of the lens, lens blank, or semi-finished lens blank. In still other cases the filter or filters is/are applied to matrix of the lens, lens blank, or semi-finished lens blank. And in still other cases the filter or filters is/are embedded within the lens, lens blank, or semi-finished lens blank. Still in other embodiments the filter or filters is/are separated and placed in optical alignment with the lens, lens blank or semi-finished lens blank.

In certain embodiments a filter or filters transmitting predominantly blue light wavelengths can be utilized in the morning hours and a filter or filters transmitting predominantly red-light wavelengths can be utilized in the afternoon hours. This can be accomplished by having an attachable, detachable front piece comprising or housing the bandpass filter that by way of example only, clips on and off or magnetically attaches to the front or sides of the eyewear, or that attaches by way of pressure on the sides of the eyewear, or that attach mechanically to the eyewear. This allows for swapping the bandpass filters based upon the time of day being used or the filter(s) desired. In this case the prescription optic or nonprescription (plano) optic (which can include defocus or that of a separate defocusing optic) is housed or supported by the base frame to which the detachable front piece is releasably attached.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of, 460 nm-520 nm, 470 nm to 520 nm, or 480 nm+/−30 nm, or by utilizing a light source or light emitter that predominately transmits within the wavelength range of at least one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Figure 25A:
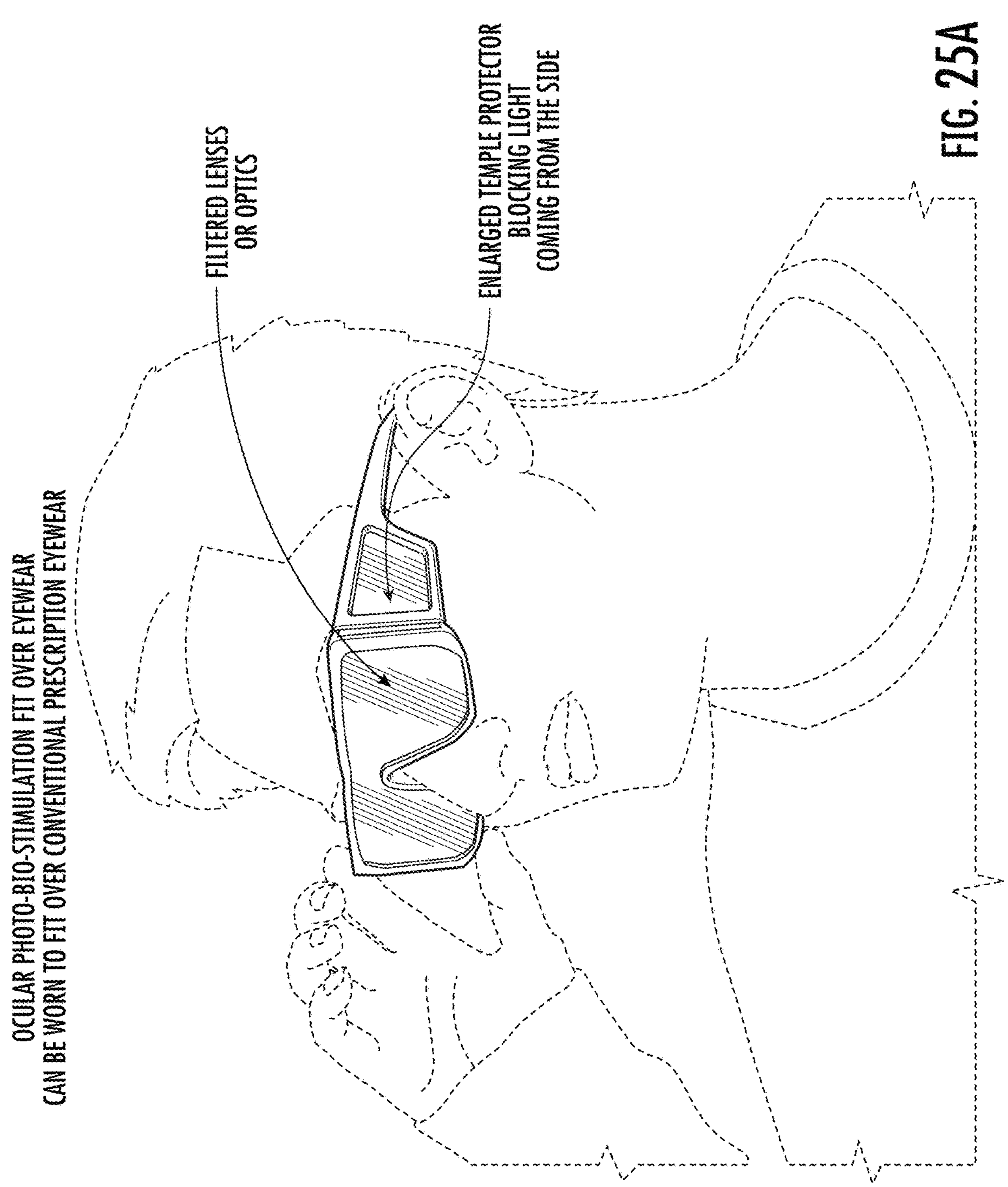
FIG. 25A-C shows an embodiment of the current invention as described herein.
Figure 25B:
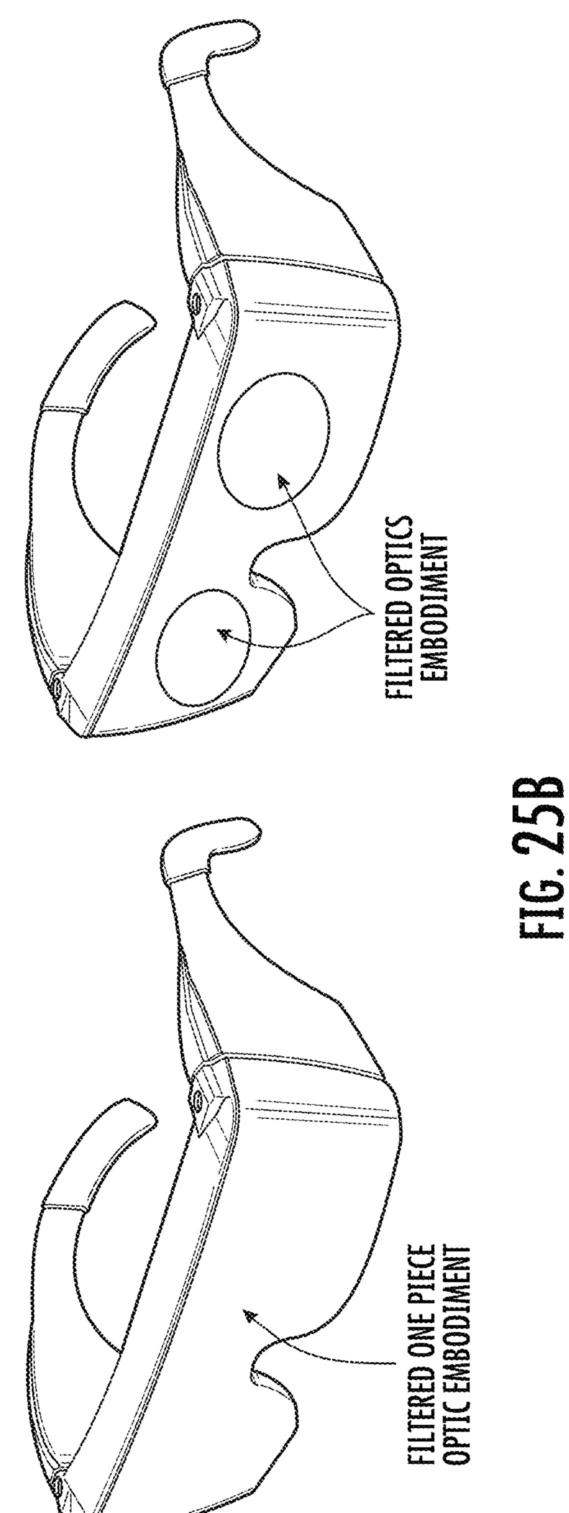
Figure 25C:
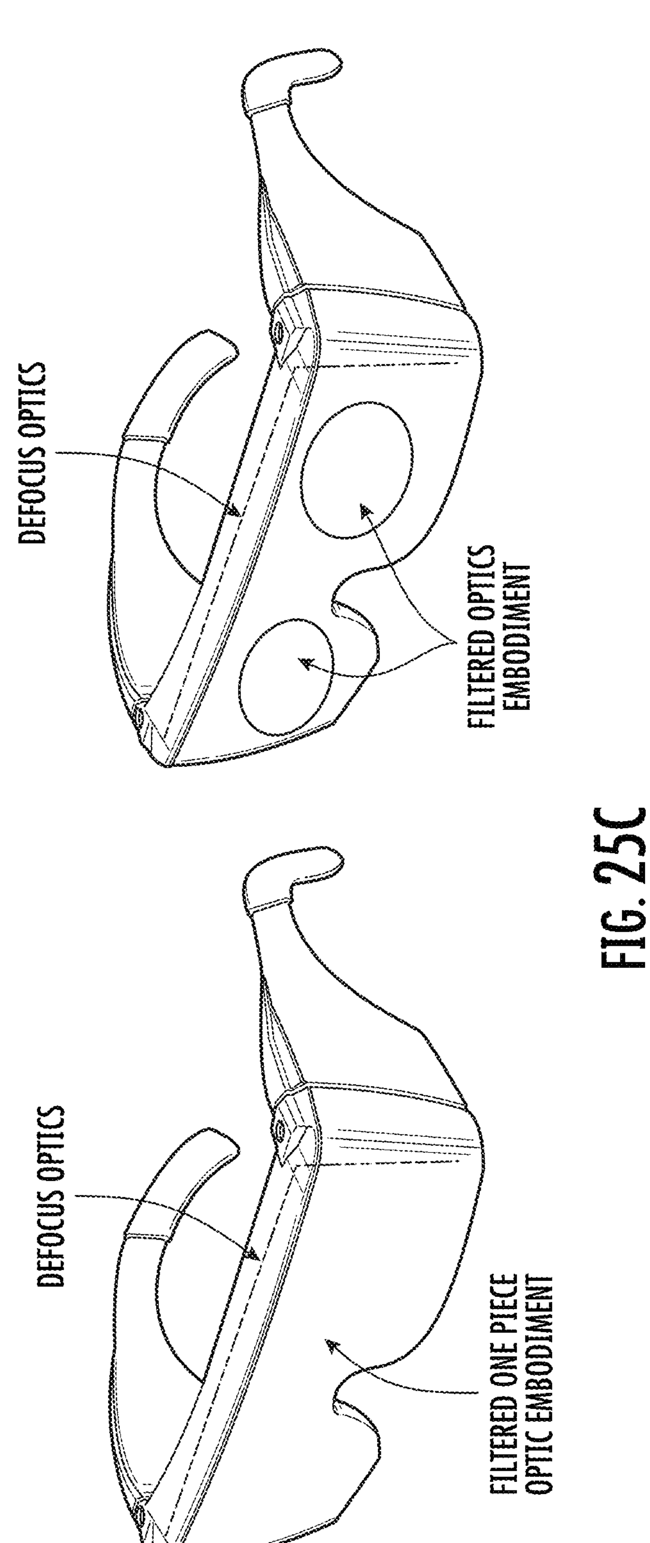

In reference to FIGS. 25*a-c*, an embodiment for ocular photo-bio-stimulation can be fit over eyewear that fits over the wearer's conventional vision correction eyewear. Such an embodiment can comprise:

Lens(es) or optic(s) that transmit predominately wavelengths within the range of, by way of example only, at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm, to the retina(s) of the user's eye(s).

Such lens(es) or optic(s) can comprise lens(es) or optic(s) comprising one or more filters, or the one or more filters can be separated and in optical alignment with the lens(es) or optic(s);

Such lens(es) or optic(s) can also comprise a defocusing optic or a light dispersion optic;

Such lens(es) or optic(s) can comprise optical power or no optical power; and/or Optionally, such lens(es) or optic(s) can comprise plus optical power or minus optical power for generating a defocus to enlarge the area of retina stimulated by the desired ocular photo-bio-stimulation therapy light wavelength(s).

Eyewear for ocular photo-bio-stimulation, wherein the eyewear fits over conventional eyewear worn by a wearer (see, e.g., FIGS. 25*a-c*), wherein the fit over eyewear predominantly transmits one or more light wavelengths within the range of at least one of: 450 nm-500 nm, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm, to the eye(s) of the wearer, wherein the fit over eyewear comprises a filter or filters, and wherein the conventional eyewear houses lenses for correcting the distance vision needs of the wearer.

Embodiments of the above inventive optical system as taught herein attempt to keep the user's eye pupil diameter as large as possible during treatment of the eye(s) by one or more of the following: 1) user distance viewing fixation—eliminates accommodative pupil constriction, 2) Lower Level of light intensity being transmitted, 3) utilization of a red wavelength light emitter or emitters), and/or 4) utilization of a red-light filter. While the inventive system will work with a mydriatic pharmaceutical, the inventive embodiments have been designed to work without the use of a mydriatic pharmaceutical, too.

An embodiment can be eyewear that fits over conventional eyewear worn by a wearer, wherein the fit-over eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the user, wherein the fit over eyewear comprises a filter or filters, and wherein the conventional eyewear houses lenses for correcting the distance vision needs of the wearer. The fit-over eyewear can also comprise one or more light emitters.

An embodiment can be eyewear that fits over conventional eyewear worn by a wearer, wherein the fit over eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the user, wherein the fit over eyewear comprises a filter or filters, and wherein the conventional eyewear houses lenses for correcting the distance vision needs of the wearer, and wherein the fit over eyewear comprises a defocusing lens or optic. The fit over eyewear can also comprise one or more light emitters.

An embodiment can be eyewear that fits over conventional eyewear worn by a wearer, wherein the fit over eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the user, wherein the fit-over eyewear comprises a filter or filters, and wherein the conventional eyewear houses lenses for correcting the distance vision needs of the wearer, and wherein the fit over eyewear comprises a light diffusing lens or optic. The fit-over eyewear can also comprise one or more light emitters.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm or 470 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye. Wavelengths within the range of 650 nm+/−30 nm or 700 nm+/−30 nm can also be utilized.

An embodiment for ocular photo-bio-stimulation can be by way of example only, one of a clip on, magnetic attachable, or pressure attachable eyewear that is attachable and detachable from the wearer's conventional vision correction eyewear. Such an embodiment can comprise:

Another embodiment includes a second eyewear to be worn by a wearer, wherein the second eyewear when worn is in optical communication with a first eyewear worn by a wearer, wherein the second eyewear comprises a filtered lens or filtered optic, wherein the filtered lens or filtered optic of the second eyewear predominantly transmits at a light wavelength transmission rate of 50% or more within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to an eye of the wearer, wherein the first eyewear comprises a first eyewear lens for optically correcting the distance vision of the wearer, and wherein the filtered lens or filtered optic of the second eyewear is distinct from first eyewear lens and wherein the overall visible light transmission through both the filtered lens or filtered optic and the first lens is 50% or less.

Each filtered lens or filtered optic can be comprised of two or more of: filters, absorbing dyes, light absorbers, or any combination thereof. The filtered lens or filtered optic can comprise one or more of: an interference filter, absorption filter, light absorber, neutral density filter, bandpass filter, notch filter, or selective blue light filter. The filtered lens or filtered optic can comprise two or more of interference filter, absorption filter, neutral density filter, bandpass filter, notch filter, or selective blue light filter. The second eyewear can be releasably attachable to the first eyewear. The second eyewear can be clip on eyewear, magnetic attachable eyewear, pressure mounted eyewear, rollable eyewear, or statically attachable eyewear. The second eyewear can be fit over eyewear which is reusable or disposable. The second eyewear can be disposable eyewear or insert eyewear. The filtered lens or filtered optic can have optical power or be plano (devoid of optical power).

The overall visible light transmission through a filtered lens or filtered optic and the first lens can be 40% or less. The overall visible light transmission through the filtered lens or filtered optic and the first lens can be 30% or less. The filtered lens or filtered optic can comprise a predominant light wavelength transmission that is within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, which can be 40% or greater. The filtered lens or filtered optic can increase choroidal thickness and reduce axial elongation of the wearer's eye. The filtered lens or filtered optic can slow down myopia progression of the wearer's eye. The filtered lens or filtered optic can comprise a peak light transmission spectral curve that falls within at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The first eyewear lens for correcting the distance vision of the wearer can comprise a central zone for correcting the distance vision needs of the wearer and an increased minus optical power zone peripheral to that of the central zone. The first eyewear lens can comprise optical power or optics that provide peripheral vision defocus. The first eyewear lens can comprise an optical power or optics that provide peripheral vision light diffusion or dispersion. The first eyewear lens can comprise optical power or optics that provide a reduction in peripheral vision contrast seen by the eye of a wearer.

The light transmitted by the filtered lens or filtered optic excites rhodopsin in the wearer's eye. The light transmitted by the filtered lens or filtered optic excites melanopsin in the wearer's eye. The light transmitted by the filtered lens or optic can increase dopamine or serotonin in the wearer's eye. The light transmitted by the filtered lens or optic increases dopamine or serotonin in the wearer's brain. The light transmitted by the filtered lens or filtered optic can increase retinal mitochondrial function.

The second eyewear can comprise one or more of timer, alarm, or wireless communication. The second eyewear can comprise a biofeedback component. The wearer's pupil of the second eyewear and the first eyewear can reduce in size absent of wearing the second eyewear and first eyewear when in ambient room light or sunlight. The filtered lens or filtered optic can generate defocused light. The filtered lens or filtered optic can generate dispersed light, diffused light, or light having less image contrast. The filtered lens or filtered optic can transmit the majority of their light wavelengths within a wavelength range to excite melanopsin and rhodopsin.

Lens(es) or optic(s) that transmit predominately wavelengths within the range of, by way of example only, at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, can be transmitted to or painted on the retina(s) of the user's eye(s).

Such lens(es) or optic(s) can comprise lens(es) or optic(s) comprising one or more filters, or the one or more filters can be separated and in optical alignment with the lens(es) or optic(s);

Such lens(es) or optic(s) can also comprise a defocusing optic or a light dispersion optic;

Such lens(es) or optic(s) can comprise optical power or no optical power; and/or Optionally, such lens(es) or optic(s) can comprise plus optical power or minus optical power for generating a defocus to enlarge the area of retina stimulated by the desired ocular photo-bio-stimulation therapy light wavelength(s).

Ocular photo-bio-stimulation embodiments of the above inventive optical system as taught herein attempt to keep the user's eye pupil diameter as large as possible during treatment of the eye(s) by one or more of the following; 1) user distance viewing fixation—eliminates accommodative pupil constriction, 2) Lower Level of light intensity being transmitted, 3) utilization of a red wavelength light emitter or emitters), and/or 4) utilization of a red-light filter. While the inventive system will work with a mydriatic pharmaceutical, the inventive embodiments have been designed to work without the use of a mydriatic pharmaceutical, too.

An embodiment can be that of eyewear that is attachable to conventional eyewear worn by a wearer/user, wherein the attachable eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the wearer, wherein the fit over eyewear comprises a filter or filters, and wherein the conventional eyewear houses lenses for correcting the distance vision needs of the wearer, and wherein the attachable eyewear comprises a defocusing lens or optic. The attachable eyewear can also comprise one or more light emitters.

As used herein, a light emitter and be any light source that gives off light radiation. By way of example only, one of: LEDs, OLEDs, TOLEDs. micro-OLEDs, micro-LEDs, micro-ileds, iLEDs, quantum dots, florescent lights, incandescent lights, ambient light, and the sun. In certain embodiments a light ring is utilized to minimize pupil constriction. This occurs as the eye being treated can fixate on a distant object through the center of the light ring while the light of the light ring is stimulating the photoreceptors of the eye. This further allows for providing light exposure to the peripheral retina of the eye.

As used herein, a defocusing lens or optic is a lens or optic that causes light to not focus on the retina of the wearer's eye. As used herein, dispersed light can be that of defocused light. In certain embodiments it focuses in front of the retina and in other embodiments it focuses behind the retina. And in still other embodiments it never focuses. In certain embodiments a defocusing lens can be utilized with a filter. In certain embodiments a defocusing lens can comprise a filter. In certain embodiments a defocusing lens can be utilized with a bandpass filter. In certain embodiments a defocusing lens can comprise a bandpass filter. In certain embodiments a defocusing lens can be utilized with an interference filter. In certain embodiments a defocusing lens can comprise an interference filter. In certain embodiments a defocusing lens can be utilized with an absorptive filter. In certain embodiments a defocusing lens can comprise an absorptive filter.

The defocus lens can comprise an optical power that can be one or more of the optical powers within the range of +0.35D to +5.00D or −0.35D to −5.00D. The defocus lens can comprise an optical power that can be one or more of the optical powers within the range of +0.35D to +10.00D or −0.35D to −10.00D. The defocusing lens can comprise central defocus. The defocusing lens can comprise peripheral defocus. The defocusing lens can comprise central focus and peripheral defocus. The defocusing lens can comprise defocus for the retina throughout the power of the defocusing lens.

In most, but not all cases, the defocusing lens is located between the filter and the eye of the wearer or user. The defocusing lens can be any optic that defocuses light so that the light after passing through the wearer or user eye's pupil spreads the light rays over a larger area of the retina of the wearer or user's eye as opposed to that of a focusing lens. The defocusing optic can be a minus lens power. The defocusing optic can be a positive lens power. The defocusing optic can be a Fresnel lens. The defocusing optic can be a multifocal lens. The multifocal lens can comprise a plano central zone having no optical power and a peripheral defocusing zone or zones having plus optical power. The multifocal lens can comprise a central zone having optical power that focuses light on the fovea/macular area and a peripheral defocusing zone or zones having plus optical power. The multifocal lens can comprise a central zone of clear vision and a peripheral zone(s) of defocused light. The defocusing optic can be an electronic display. The defocusing optic can be attached to a filter, or distance separated from a filter or a portion of a filter. The multifocal optic can be attached to a filter, or distance separated from a filter or a portion of the filter.

Embodiments when light wavelengths are generated by way of filtered optics or filtered lenses the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

An embodiment is that of eyewear worn by a wearer, wherein the eyewear is attachable to a different set of eyewear, wherein the attachable eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the wearer, wherein the eyewear comprises a filter or filters, wherein the eyewear comprises a minus optical power defocusing optic or lens that permits central vision clarity but peripheral defocus, and wherein the peripheral defocus is caused by one of: minus powered lenslets or minus peripheral defocusing power that is peripheral to the central zone of the lens or optic, and wherein the minus optical power defocus is within the range of −0.35D to −5.00D.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of 460 nm-520 nm or 470 nm to 520 nm, or by utilizing a light source or light emitter that predominately transmits within the wavelength range of 60 nm-520 nm or 470 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye. However, wavelengths within the range of 650 nm+/−30 nm or 70 nm+/−30 nm can also be utilized.

Another embodiment is that of eyewear worn by a wearer, wherein the eyewear is attachable to a different set of eyewear, wherein the attachable eyewear predominantly transmits one or more light wavelengths within the range of one of: 480 nm+/−30 nm, 530 nm+/−20 nm, or 650 nm+/−30 nm to the eye(s) of the wearer, wherein the eyewear comprises a filter or filters, wherein the eyewear comprises a plus optical power defocusing optic or lens that permits central vision clarity but peripheral defocus, and wherein the peripheral defocus is caused by one of: plus powered lenslets or plus peripheral defocusing power that is peripheral to the central zone of the lens or optic, and wherein the plus optical power defocus is within the range of −+0.35D-+5.00D.

Still another embodiment is eyewear worn by a wearer, wherein the eyewear is attachable to a different set of eyewear, wherein the attachable eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the wearer, wherein the eyewear comprises a filter or filters, wherein the eyewear comprises a minus defocusing optic or lens that permits central vision clarity but peripheral defocus, and wherein the peripheral defocus is caused by one of: aspheric lenslets or dispersion defocusing power that is peripheral to the central zone of the lens or optic.

In most but not all cases, a filter is located on the front convex surface of the optic. When the optic is devoid of optical power the filter can be on either surface or buried in between either surface. In certain embodiments a lens comprising the desired optical power for correcting the refractive power of the eye of the wearer is located between a filter (which can be on or in an optic) and the front of the eye of the wearer/user. In certain embodiments a lens comprising the desired optical power for correcting the refractive power of the eye of the wearer is attached to a filter (which can be on or in an optic) and the front of the eye of the wearer/user. A filter can be one of deposited, coated, or adhered to a substrate (being an optic) having optical power or no optical power. The substrate can be comprised of plastic or glass. The substrate can be a film. In certain cases, the filter or filters can be separated from the optic or lens but aligned to be in optical alignment with the lens or optic.

In certain embodiments the above bandpass filter optic or sunglasses can be utilized without a defocused optic or lens. In certain embodiments the above bandpass filter optic or sunglasses can be utilized in association with a defocused lens. Such a defocused lens can comprise one or more of a central zone of focusing power or no optical power, increasing plus power from the central zone outwards, multiple different plus power zones of optical power, multiple islands of plus optical power, multiple zones of plus defocus optical power, multiple zones of defocus, multiple islands of defocus optical power, and/or multiple zones of defocus. The zones or islands can be of the same plus optical power. The zones or islands can be of different plus optical power. The zones or islands can be of different optical power. The zones or islands can cause different defocus. The zones or islands can increase optical power. The zones or islands can increase in defocus. The zones or islands can decrease in defocus. The zones or islands can decrease in optical power. The zones or islands can remain constant in optical power. The zones or islands can remain constant in defocus. In certain embodiments a central zone can have focus, and the peripheral zones can have defocus.

Such a defocused lens can comprise one or more of a central zone of focusing power or no optical power, increasing minus optical power from the central zone outwards, multiple different plus power zones of optical power, multiple islands of minus optical power, multiple zones of minus defocus optical power, multiple zones of defocus, multiple islands of defocus optical power, and/or multiple zones of defocus. The defocus lens can comprise no optical power. The defocus lens can comprise optical power. The defocus can be caused by one or more of, of a single vision lens, multifocal lens, light scatter material, prism, applicator attached to lens surface, Fresnel optic, holographic optic, micro-lens array, and/or scratched surface of the optic. The defocusing element(s) can be located off center on or in the optic. The defocusing elements can be located centered on or in the optic. The defocusing elements can be located on or in the periphery of the optic. The defocusing elements can be embedded within the optic. The defocusing elements can be attached to the optic. The defocusing element can be attachable and detachable to the optic. The defocusing elements can be located peripheral to a central zone of the optic. When using the term defocusing optic in this disclosure document, it is meant that the light rays do not focus on the retina of the eye(s) of the wearer or user.

The light defocusing optic can comprise one or more of: a positive power convex lens design, negative power concave lens design, spherocylindrical lens design, prismatic lens design, aspheric lens design, Fresnel lens design, micro-lens array design, nano or micro-structure materials, concentric rings, grooves, scratches, and/or surface curves on the convex or concave side of the optic. The nano or micro-structure materials of a different index of refraction from the optic matrix material can be embedded within the optic matrix. The nano or micro-structure materials can be embedded within an optical coating and of a different index of refraction from an optic coating material that is applied to the optic. Such an optical coating can be by way of example only, a hard scratch resistant coating, a cushion coating, and/or a dielectric deposition coating. In certain embodiments the defocusing element is caused by dispersion of light. In such embodiments certain electrochromic optical materials or material properties cause light to disperse into blue, green and red wavelength bundles.

In one embodiment an electrochromic material layer can cause slight dispersion when electricity is applied and when no electricity is applied the electrochromic element returns the lens zone to a clear nondispersive lens zone. This allows for causing, by way of example only, white light to become dispersed when electrical power is applied, thus causing blue wavelengths of light to strike the retina for ocular photo-bio-stimulation light therapy and cease the retinal stimulation when the light therapy is no longer needed, and the electrical power is turned off. The electrochromic lens zone can be in the lens to coincide where light wavelengths can strike an area of the retina having a concentration of rods.

In another embodiment certain electroactive optical materials or material properties cause light to disperse into blue, green and red wavelength bundles. In this embodiment an electroactive liquid crystal layer can cause slight dispersion when electricity is applied and when no electricity is applied the electroactive element returns the lens zone to a clear nondispersive lens zone. This allows for causing when electrical power is applied, by way of example only, white light to become dispersed, thus causing blue wavelengths of light to strike the retina for ocular photo-bio-stimulation light therapy and cease the retinal stimulation when the light therapy is no longer needed, and the electrical power is turned off. The electroactive lens zone can be in the lens to coincide where light wavelengths can strike an area of the retina having a concentration of rods. In still other embodiments a zone comprising a plurality of prismatic surface features can be properly positioned to provide light wavelengths that will strike an area of the retina having a concentration of rods. In each of these embodiments, electrochromic, electroactive, or prismatic, the zone can be located around that of the central zone of the lens and at a location that optimizes dispersed light wavelengths of light striking an area of the retina peripheral to the macula having a high concentration of rods.

In certain embodiments nano or micro-structure particle materials can be used to disperse light. Examples of nano or micro-structure particle materials can be, by way of example only, polycrystalline ceramics like, by example, transparent alumina consisting of birefringent crystals. Additional examples are polystyrene (PS), copolymer polyacrylates (PMMA), polyolefins (PE, PP), titanium dioxide (TiO2), Zinc oxide (ZnO), or Zirconium oxide (ZrO2). Light passing through a transparent particle with a size comparable to the wavelength of incident light can be refracted or diffracted. Surface scratches or imperfections can cause light scattering. Each of the preceding lens designs, embedded particles in the optic matrix, coatings comprising particles, surface imperfections, surface refractive cures, quantum dots, or particles that fluoresce, can be utilized individually or in any combination to provide defocus. Once again it should be pointed out that the use of defocus as disclosed herein is causing or having the light rays to be defocused on the retina of the wearer or user of the optic. This maximizes the ability of the light wavelengths that strike the retina of the wearer or user of the optic within the wavelengths range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm or 600 nm-700 nm, or 700 nm+/−30 nm, to be spread out.

In certain embodiments the optic that creates the defocus can be rotated either manually or automatically. When automatically rotated the defocus optic can be rotated by a motor. The rotation can help spread the defocused light wavelengths over the retina painting the retina with the defocused light as the defocused optic is rotated. The optic area of defocus can be from the entire optic. The area of defocus can be from the central zone. The central zone can be 9 mm, 10 mm, or 11 mm in diameter. The defocus can be from the peripheral zone of the optic. The peripheral zone can be any area outside of the central zone. As used herein, defocus means the light rays do not focus to a point on the retina of the eye of the user. In certain embodiments the light rays focus in front of the retina. In other cases, the light rays focus behind the retina. In still other embodiments the light rays are dispersed or scattered.

Any of the eyewear, lamp, electronic display, and/or lighting embodiments disclosed herein, including those comprising a bandpass filter, can also comprise a neutral density filter. By utilizing a neutral density filter in addition to a band pass filter it is possible to adjust the light intensity transmission of the transmitted wavelengths to provide for an enlargement of the pupil(s) of the wearer. The neutral density filter can be separate from the bandpass filter. The neutral density filter can be built into the bandpass filter. The neutral density filter can be attached to the bandpass filter. The neutral density filter can be integral with the bandpass filter. Utilizing a neutral density filter is important when the intensity of the light that is being transmitted by the optic exceeds a threshold where it constricts the pupil of the eye of the wearer or user of the optic. Embodiments disclosed herein prefer for the pupil of the eye to be as large as possible when the desired light wavelengths are being exposed to the retina. In preferred embodiments the pupil(s) of the eye(s) of the wearer or user of the lens or optic would be 3 mm or larger in diameter. In preferred embodiments the pupil(s) of the eye of the wearer or user of the lens or optic would be 4 mm or larger in diameter. In preferred embodiments the pupil(s) of the eye(s) of the wearer or user of the optic would be 5 mm or larger in diameter.

In certain other embodiments, the light source providing wavelengths of light within the range of light wavelengths of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm or 600 nm-700 nm, or 700 nm+/−30 nm, can be moved relative to one of the eye, cornea, or pupil of the subject whose retina is being exposed to such light wavelengths, or the eye, cornea, or pupil of the subject can be moved relative to the light source. This allows for painting multiple large areas of retina of the subject with the light source. By moving the light source or moving the eyes of the subject the light radiation can intersect the cornea and pupil of the subject at multiple angles thus striking large and/or different areas of the retina as the eye and the light source move relative to one another. Such a device for accomplishing this can be a handheld instrument, tabletop or fixed spaced instrument, virtual reality device, mixed reality device, augmented reality device, eyewear, and/or helmet with a face shield. Ocular photo-bio-stimulation eyewear can be that of wrap around eyewear. Ocular photo-bio stimulation eyewear can comprise side shields for the purposes of blocking peripheral light rays.

A photo-bio-stimulation lens can filter and transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm, 419 nm-400 nm, or 399 nm-380 nm.

An embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within a light wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to an eye of a wearer of the wearable eyewear device, and wherein the filtered lens or filtered optic further provides an overall visible light transmission rate of 50% or less, 40% or less, or 30% or less.

Another embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within a light wavelength range of at least one of: 480 nm+/−30 nm or 500 nm+/−20 nm to an eye of a wearer of the wearable eyewear device, and wherein the filtered lens or filtered optic further provides an overall visible light transmission rate of 50% or less, 40% or less, or 30% or less.

By way of example only, if 2,000 lux is considered to be the overall visible transmission through the filtered lens or optic, and the light intensity is 1,000 lux that passes through and measured within the filtered wavelength range of 480 nm+/−30 nm, then the light transmission through and measured within the wavelength range of 480 nm+/−30 nm would be 50% of the overall visible light transmission. By way of another example only, if 1,200 lux is considered to be the overall visible transmission through the filtered lens or optic, and the light intensity is 400 lux through and measured within the filtered wavelength range of 480 nm+/−30 nm, then the light transmission through and measured within the wavelength range of 480 nm+/−30 nm would be ~33% of the total overall visible light transmission. And still by way of another example only, if 1,200 lux is considered to be the overall visible transmission through the filtered lens or optic, and the combined light intensity is 400 lux through and measured within the filtered wavelength ranges of 480 nm+/−30 nm and also that of 700 nm+/−30 nm, then the light transmission through and measured within the wavelength range of 480 nm+/−30 nm and 700 nm+/−30 nm would be ~33% of the total overall visible light transmission Another embodiment can be that of a wearable eyewear device comprising a filtered lens or filtered optic, wherein the filtered lens or filtered optic provides a light transmission rate of 50% or more, or 60% or more, of ocular photo-bio-stimulation light through and measured within light wavelength ranges of a combination of 450 nm+/−30 nm and 580 nm+/−20 nm to an eye of a wearer of the wearable eyewear device, and wherein the filtered lens or filtered optic further provides an overall visible light transmission rate of 50% or less, 40% or less, or 30% or less. Such a lens can be designed to have a greyish color.

Another embodiment can be that of a wearable eyewear device comprising a filtered lens or filtered optic, wherein the filtered lens or filtered optic provides a light transmission 50% or more or 60% or more of ocular photo-bio-stimulation light through and measured within light wavelength ranges of a combination of 450 nm+/−30 nm and 600 nm+/−30 nm to an eye of a wearer of the wearable eyewear device, and wherein the filtered lens or filtered optic further provides an overall visible light transmission rate of 50% or less, 40% or less, or 30% or less. Such a lens can be designed to have a reddish-brown color.

Another embodiment can be that of a wearable eyewear device comprising a filtered lens or filtered optic, wherein the filtered lens or filtered optic provides a light transmission rate of 50% or more or 60% or more of ocular photo-bio-stimulation light through and measured within a light wavelength range of 650 nm+/−30 nm to an eye of a wearer of the wearable eyewear device, and wherein the filtered lens or filtered optic further provides an overall visible light transmission rate of 50% or less, 40% or less, or 30% or less.

Another embodiment can be that of a wearable eyewear device comprising a filtered lens or filtered optic, wherein the filtered lens or filtered optic provides a light transmission rate of 50% or more or 60% or more of ocular photo-bio-stimulation light through and measured within a light wavelength range of 700 nm+/−30 nm to an eye of a wearer of the wearable eyewear device, and wherein the filtered lens or filtered optic further provides an overall visible light transmission rate of 50% or less, 40% or less, or 30% or less.

Ocular photo-bio-stimulation light can be transmitted by the filtered lens or filtered optic and increase the production of dopamine or serotonin in an eye and/or a brain of the wearer of the wearable eyewear device. The wearable eyewear device can be utilized on its own for daily wear, or wherein the wearable device fits over, behind, or around, a second eyewear frame or a lens of the second eyewear frame, or wherein the wearable eyewear device is supported by or releasably attachable to the second eyewear frame or the lens of the second eyewear frame.

The filtered lens or filtered optic can comprise two or more of: a filter, a filtered wafer, a surface cast filtered layer, an absorbing dye, a light absorber, or any combinations thereof. The filtered lens or filtered optic can comprise two or more of: an interference filter, an absorption filter, a light absorber, dye, a neutral density filter, a bandpass filter, a notch filter, or a selective blue light filter. The wearable eyewear device is one of: fit-over eyewear, disposable eyewear, clip-on eyewear, magnetically attachable eyewear, pressure-mounted eyewear, rollable eyewear, statically attachable eyewear, or eyewear. The wearable eyewear device can be dress glasses or sunglasses.

The filtered lens or filtered optic can comprise optical power or can be plano (devoid of optical power). The overall visible light transmission through the filtered lens or filtered optic and an eyeglass lens is 40% or less or 30% or less. The wearable eyewear device can be utilized in association with a light source, wherein the light source has an intensity of 2,000 lux or greater, and wherein a transmission intensity of light is within a wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, or wherein a light intensity of light within one of the wavelength ranges passing through a last surface of the filtered lens or filtered optic closest to an eye of the wearer is 300 lux or greater.

The ocular photo-bio-stimulation light transmitted through the filtered lens or filtered optic can increase choroidal thickness and/or reduce axial elongation of an eye of the wearer of the wearable eyewear device. The ocular photo-bio-stimulation light transmitted through the filtered lens or filtered optic can slow down myopia progression of an eye of the wearer of the wearable eyewear device.

The eyeglass lens of a second eyewear frame can comprise a central zone for correcting distance vision of the wearer of the wearable eyewear device, and the eyeglass lens of the second eyewear frame comprises an increased minus optical power zone peripheral to that of the central zone. The eyeglass lens of a second eyewear frame can comprise optical power, optics that provide peripheral vision defocus, or both. The eyeglass lens of a second eyewear frame can comprise one or more of: optical power, optics that provide peripheral vision light diffusion or dispersion, or both. The eyeglass lens of the second eyewear frame can comprise one or more of: optical power, optics that provide a reduction in peripheral vision contrast, or both.

The ocular photo-bio-stimulation light transmitted through the filtered lens or filtered optic can excite rhodopsin an eye of the wearer of the wearable eyewear device. The ocular photo-bio-stimulation light filtered that is transmitted through the filtered lens or filtered optic can excite melanopsin in an eye of the wearer of the wearable eyewear device. The ocular photo-bio-stimulation light transmitted through the filtered lens or filtered optic can increase retinal mitochondrial function in the wearer of the wearable eyewear device. The wearable eyewear device can comprise one or more of: a timer, an alarm, or a wireless communication component. The wearable eyewear device can comprise a biofeedback component. The filtered lens or filtered optic can cause a pupil of an eye of the wearer of the wearable eyewear device to increase in size when the wearable eyewear device is worn in ambient room light, sunlight, or both.

The filtered lens or filtered optic: defocuses light, disperses light, diffuses light, allows transmission of light having less or decreased image contrast, or combinations thereof. The filtered lens or filtered optic can comprise an imbibed tint or dye. The filtered lens or filtered optic can comprise a deposition coating or spin coating. The filtered lens or filtered optic can be a single vision lens or single vision optic. The filtered lens or filtered optic can comprise a surface cast layer that filters light. The surface cast layer can comprise one or more of a filter, dye, absorber, coating. The filtered lens or filtered optic can comprise a plurality of one or more of, dyes, filters, absorbers, coatings.

The filtered lens or filtered optic can comprise a progressive addition lens topography. The eyeglass lens of the second eyewear frame can comprise single vision lens. The eyeglass lens of the second eyewear frame can comprise a progressive addition lens topography. The wearable eyewear device can be one of spectacle eyewear, XR eyewear, a contact lens, an intraocular lens, or a corneal implant. The eyeglass lens of the second eyewear frame can comprise optical power, and the filtered lens or filtered optic of the wearable eyewear device can comprise a plano optical power.

Lenses or Optics Comprising a Defocus Zone for Ocular Photo-Bio-Stimulation Therapy Embodiments can be that of a filtered lens or a clear lens, either of which comprises a zone of defocus. The defocus can be in the form of optical defocus or defocus caused by light scatter or dispersion. With a filtered lens, the filtering effect and the defocus zone both provide for the desired photo-bio-stimulation effect. With a non-filtered lens (e.g., a clear lens) the defocus zone provides for the desired photo-bio-stimulation effect. Defocus can be utilized to cause light wavelengths to spread across the peripheral retina of the wearer/user. The peripheral retina is the retina peripheral to the central region of the retina, which is that of the macula. As used herein, defocus can be one or more of: optical defocus, light scattering, and/or light dispersion.

An embodiment is a lens that can be that of a filtered lens. The filtered lens can predominantly transmit light wavelengths predominantly within the range of wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm. The filtered lens can comprise a central zone and a defocus zone can be positioned peripheral to the central zone.

The defocus zone can begin at the junction of the outer central zone periphery and the start of a zone adjacent to the central zone. The defocus zone can be comprised of ringed optical power steps (see, FIG. 26). The defocus zone can be comprised of minus optical power. The defocus zone can be comprised of lenslets (see, FIGS. 27, 28, 29, and 30). The defocus zone can be comprised of light scatter elements. The defocus zone can be comprised of minus optical power being more minus optical power or less plus optical power than the central zone's optical power. The minus of optical power increase over that of the central zone's optical power can be within the range of −0.35D to −5.00D. Such a lens can comprise a downward channel or zone of increasing positive optical power offsetting some or all of the added minus power. Such a downward channel can connect to a reading zone of increased positive optical power within the range of +1.00D to +3.25D over that of the central zone's optical power.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

The lenslets can be comprised of −0.35D to −5.00D negative power. The lenslets can be aspheric. The defocus zone can be comprised of a microlens array. The defocus zone can be comprised of optical power steps. The defocus zone can be comprised of light scatter elements. The defocus zone can be comprised of liquid crystal. The liquid crystal can switch on and off by way of an electrical potential change. Such a defocus can be that of either light scatter or a change in the refractive optical power of the lens' defocus zone. The liquid crystal can be switched to increase or decrease optical power. The liquid crystal can be switched to cause light scatter. The liquid crystal can be switched to eliminate most or all of the light scatter or to eliminate any change of optical power. By utilizing a switchable liquid crystal defocus zone, the lens can provide the desired level of ocular photo-bio-stimulation which can then be turned on or off as needed. The ability to electrically switch liquid crystal for that of optical power generation or light scattering is known in the art.

Figure 26:
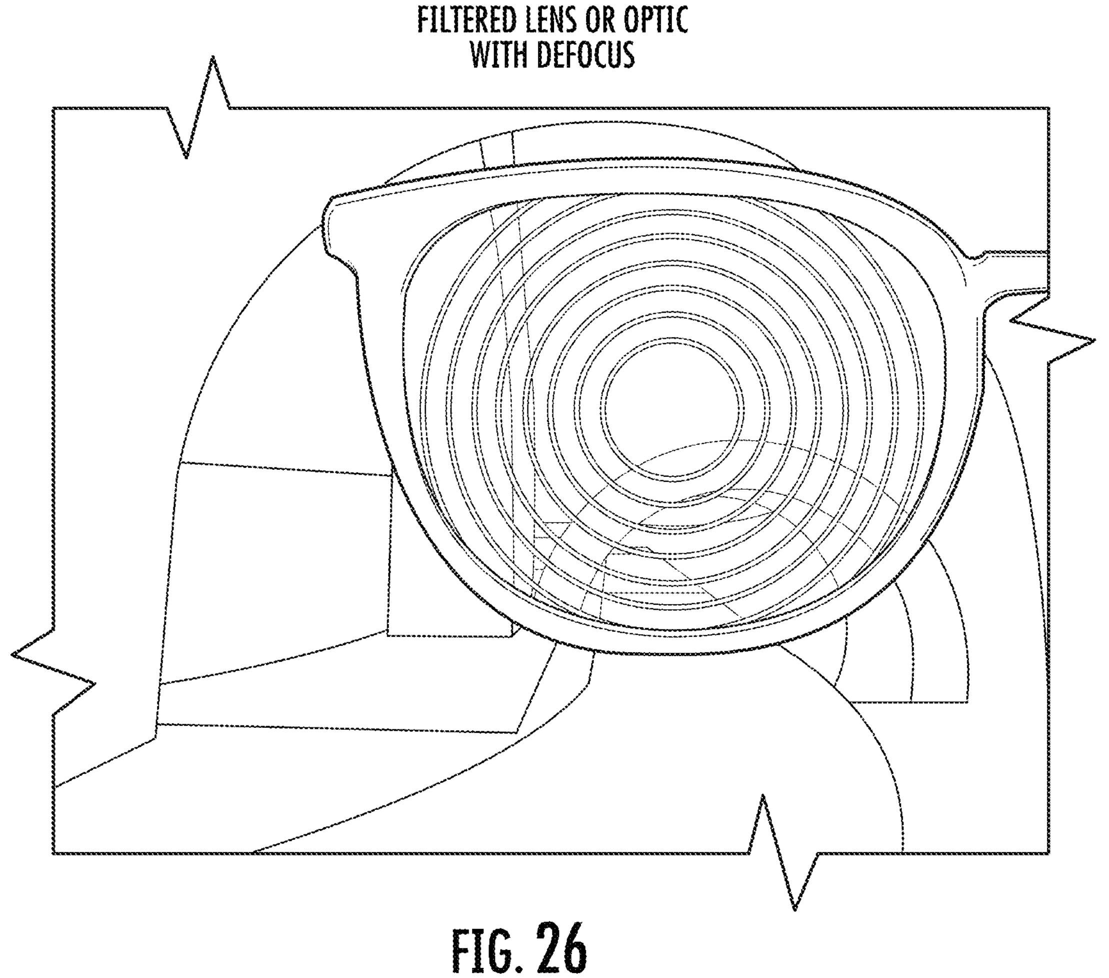
FIG. 26 shows an embodiment of the current invention as described herein.

In reference to FIG. 26, it shows an embodiment of a photo-bio-stimulation filtered defocused lens, which can be a lens that comprises:

a central zone for correcting distance focus for the wearer and small enough to establish an effective functional zone;

a selected fill factor to deliver high efficacy while preserving good wearability;

a central zone of 4 mm-6 mm; and added surface power within the range of +0.50D to +3.50D or −0.35D to −5.00D; and The filtering can predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

According to the embodiment, a photo-bio-stimulation lens can filter and predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Figure 27:
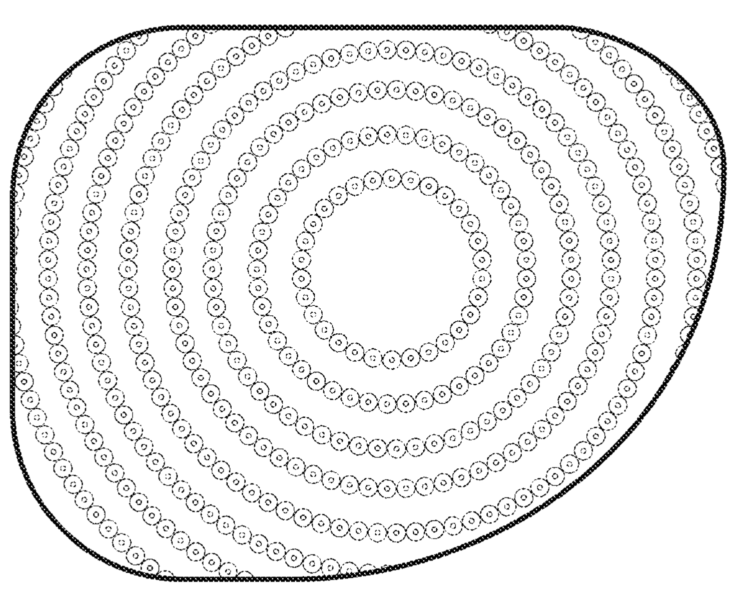
FIG. 27 shows an embodiment of the current invention as described herein.

In reference to FIG. 27, it shows an embodiment of a photo-bio-stimulation filtered defocused lens, which can be a lens that comprises: a spectacle lens for myopia correction and control with Highly Aspherical Lenslet Target (H.A.L.T.) Technology; a central optical zone (9 mm) for correcting distance refractive error of the wearer, with surrounding myopia control zone incorporating 1021 contiguous (touching) highly aspherical lenslets (each 1.12 mmø). Each lenslet does not have a single focal power, instead creating a 'volume of defocus' as a slow-down signal for eye growth. Each of the 11 rings of lenslets features contiguous lenslets of similar asphericity, with successive rings having lenslets with different asphericities. Spaces between the rings of lenslets provide single vision correction. Added optical power peripheral to the central zone being within the range +0.50D to +3.50D or −0.35D to −5.00D. The filtered lens can transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of 460 nm-520 nm or 470 nm to 520 nm, or by utilizing a light source or light emitter that predominately transmits within the wavelength range of at least one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In reference to FIG. 28, is shows an embodiment of a photo-bio-stimulation filtered defocused lens, which can be a lens that comprises: A spectacle lens for myopia correction and control with Defocus Incorporated Multiple Segments (DIMS) Technology; a central optical zone (9 mmø) for correcting distance refractive error of the wearer, and surrounding treatment zone with honeycomb array of lenslets (each 1.03 mm). The lenslets have a relative positive power within the range of +0.50D to +3.50D. The filtered lens can predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In reference to FIG. 29, it shows an embodiment of a photo-bio-stimulation filtered defocused lens, which can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb array of lenslets (each 1.03 mmø). The lenslets have a relative power within the range of +0.50D to +3.50D or −0.35D to −5.00D. There are spaces between the lenslets where the single vision correction is accessible. The filtered lens can predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of 460 nm-520 nm, 470 nm to 520 nm, or 480 nm-520 nm, or by utilizing a light source or light emitter that predominately transmits within the wavelength range of at least one o, 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye. In reference to FIG. 30, it shows an embodiment of a photo-bio-stimulation filtered defocused lens, which can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb micro-lens array of lenslets (each 1.03 mmø). The lenslets have a relative positive power within the range of +0.50D to +3.50D or −0.35D to −5.00D. There are spaces between the lenslets where the single vision correction is accessible. The filtered lens can predominantly transmit light wavelengths within the range of light wavelengths of one or more of the following 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of one of, 460 nm-520 nm, 470 nm to 520 nm, or 480 nm to 520 nm, or by utilizing a light source or light emitter that predominately transmits within the wavelength range of one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Similarly, another embodiment of the lens can be a non-filtered lens or a clear lens. The lens can comprise a central zone and a defocus zone (see, FIGS. 39, 40, 41, 42, and 43). A defocus zone can be positioned peripheral to the central zone. The defocus zone can begin at the junction of the outer central zone periphery and the start of a zone adjacent to the central zone. The defocus zone can be comprised of lenslets. The defocus zone can be comprised of light scatter elements. The defocus zone can be comprised of minus optical power. The defocus zone can be comprised of minus optical power being more minus optical power or less plus optical power than the central zone's optical power. The minus of optical power increase over that of the central zone's optical power can be within the range of −0.35D to −5.00D. Such a lens can comprise a downward channel or zone of increasing positive optical power offsetting some or all of the added minus power. Such a downward channel can connect to a reading zone of increased positive optical power within the range of +1.00D to +3.25D over that of the central zone's optical power.

The lenslets can be comprised of −0.35D to −5.00D negative power. The lenslets can be aspheric. The defocus zone can be comprised of a microlens array. The defocus zone can be comprised of optical power steps. The defocus zone can be comprised of light scatter elements. The defocus zone can be comprised of liquid crystal. The liquid crystal can switch on and off by way of an electrical potential change. Such a defocus can be that of either light scatter or a change in the refractive optical power of the lens' defocus zone. The liquid crystal can be switched to increase or decrease optical power. The liquid crystal can be switched to cause light scatter. The liquid crystal can be switched to eliminate most or all of the light scatter or to eliminate any change of optical power. By utilizing a switchable liquid crystal defocus zone, the lens can provide the desired level of ocular photo-bio-stimulation which can then be turned on or off as needed.

An embodiment can be that of a lens or optic for ocular photo-bio-stimulation, wherein the lens or optic comprises a central zone and a zone of defocus, wherein the zone of defocus is peripheral to the central zone, wherein the zone of defocus is comprised of liquid crystal, wherein the defocus is one of optical defocus, light scattering, or light dispersion, wherein the liquid crystal can be switched on or off to remove defocus or provide peripheral defocus, and wherein the central zone of the lens remains capable of providing a wearer with clear distance vision. Embodiments when light wavelengths are generated by way of filtered optics or filtered lenses have a the transmission peak of the wavelength range that strike the eye's retina fall within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of; 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

An embodiment can be that of a lens or optic for ocular photo-bio-stimulation, wherein the lens or optic comprises a central zone and a zone of defocus, wherein the zone of defocus is peripheral to the central zone, wherein the lens or optic is that of a filtered lens or optic, and wherein the lens or optic predominantly transmits light wavelengths within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, so as to strike the retina of an eye. The defocus can be that of either an optical power defocus or light scattering or light dispersion. When lenslets cause an optical power defocus, such lenslets can be of optical power within the optical power range of +0.35D to +5.00D or −0.35D to −5.00D.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens, that predominantly transmits within the wavelength range of one of 460 nm-520 nm, 470 nm to 520 nm, or 480 to 520 nm, or by utilizing a light source or light emitter that predominately transmits within the wavelength range of one of, 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

An embodiment can be that of a lens or optic for ocular photo-bio-stimulation, wherein the lens or optic comprises a central zone and a zone of defocus, wherein the zone of defocus is peripheral to the central zone, wherein the lens or optic further comprises an add power zone comprised of an increased positive optical power compared to one of the lens' or optic's peripheral zone or the central zone. The defocus can be that of either an optical power defocus or light scattering or light dispersion. When lenslets cause an optical power defocus, such lenslets can be of optical power within the optical power range of +0.35D to +5.00D or −0.35D to −5.00D.

Figure 39:
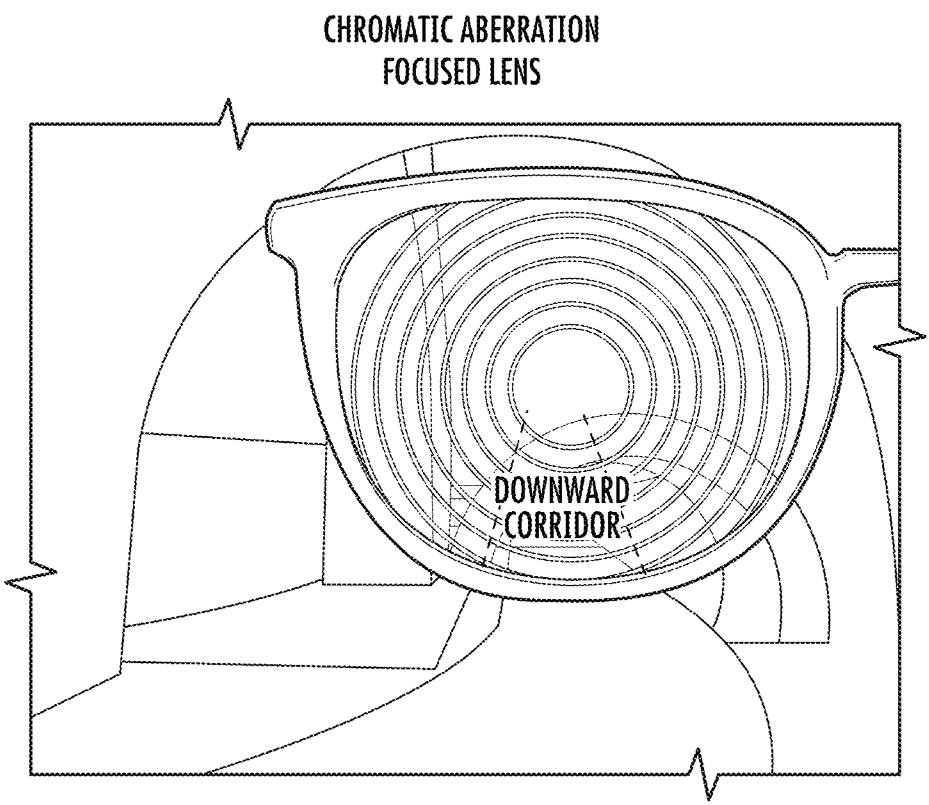
FIG. 39 shows an embodiment of the current invention as described herein.

In reference to FIG. 39, an embodiment of a photo-bio-stimulation filtered defocused lens can be a lens that comprises:

a central zone for correcting distance focus for the wearer and small enough to establish an effective functional zone;

a selected fill factor to deliver high efficacy while preserving good wearability;

a central zone of 4 mm-6 mm; and added Surface power within the range of −0.35D to −5.00D.

Figure 40:
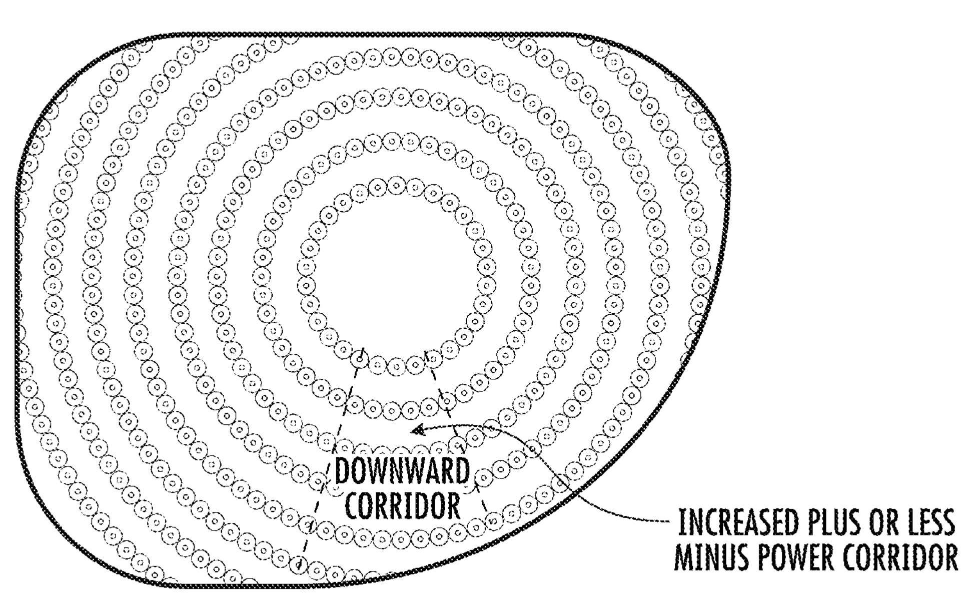
FIG. 40 shows an embodiment of the current invention as described herein.

In reference to FIG. 40, another embodiment of a photo-bio-stimulation filtered defocused lens can be a lens that comprises: a spectacle lens for myopia correction and control with Highly Aspherical Lenslet Target (H.A.L.T.) Technology; a central optical zone (9 mm) for correcting distance refractive error of the wearer, with surrounding myopia control zone incorporating 1021 contiguous (touching) highly aspherical lenslets (each 1.12 mmø). Each lenslet does not have a single focal power, instead creating a 'volume of defocus' as a slow-down signal for eye growth. Each of the 11 rings (or more or less rings) of lenslets features contiguous lenslets of similar asphericity, with successive rings having lenslets with different asphericities. Spaces between the rings of lenslets provide single vision correction. Added optical power peripheral to the central zone being within the range −0.35D to −5.00D.

Figure 41:
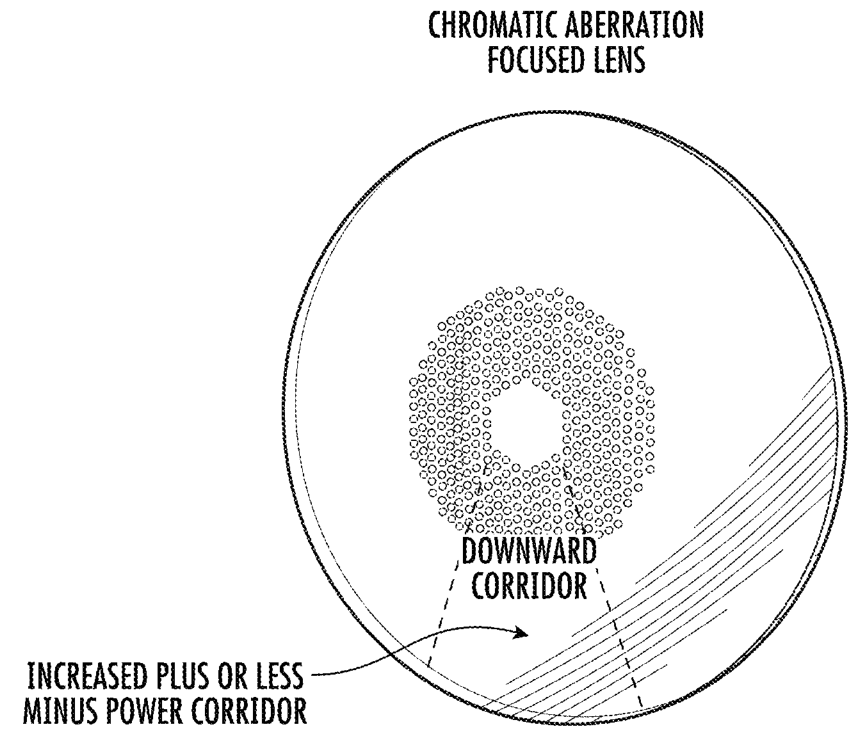
FIG. 41 shows an embodiment of the current invention as described herein.
Figure 42:
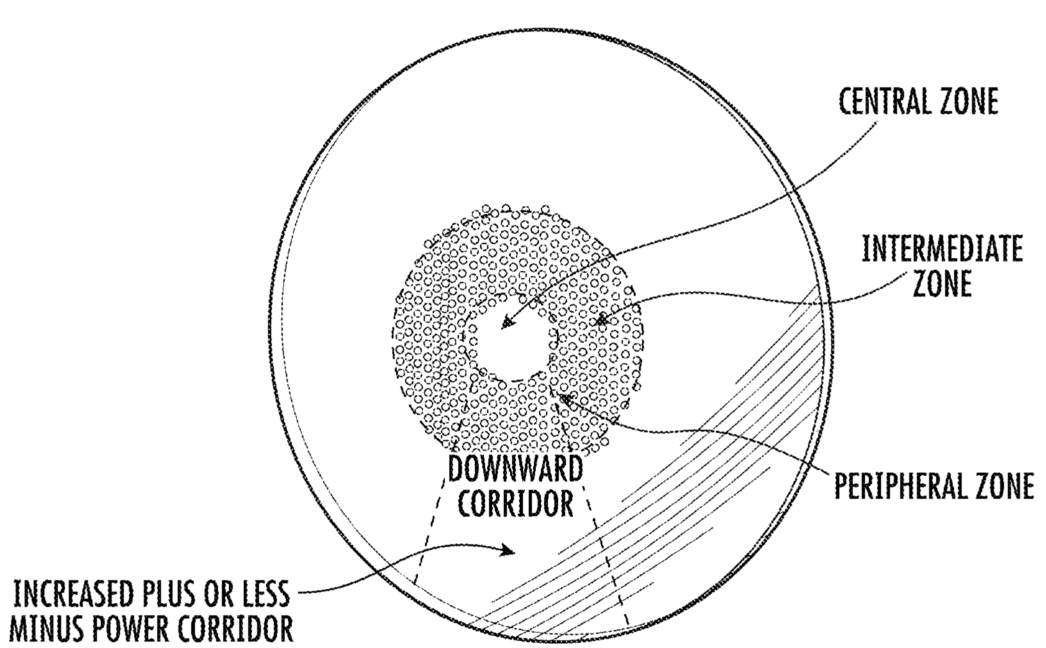
FIG. 42 shows an embodiment of the current invention as described herein.

In reference to FIGS. 41 and 42, still another embodiment of a photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and surrounding treatment zone with honeycomb array of lenslets (each 1.03 mm). The lenslets have a relative positive power within the range of −0.35D to −5.00D.

In reference to FIGS. 41 and 42, another embodiment of a photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb array of lenslets (each 1.03 mmø). The lenslets have a relative power within the range of −0.35D to −5.00D. There are spaces between the lenslets where the single vision correction is accessible.

Figure 43:
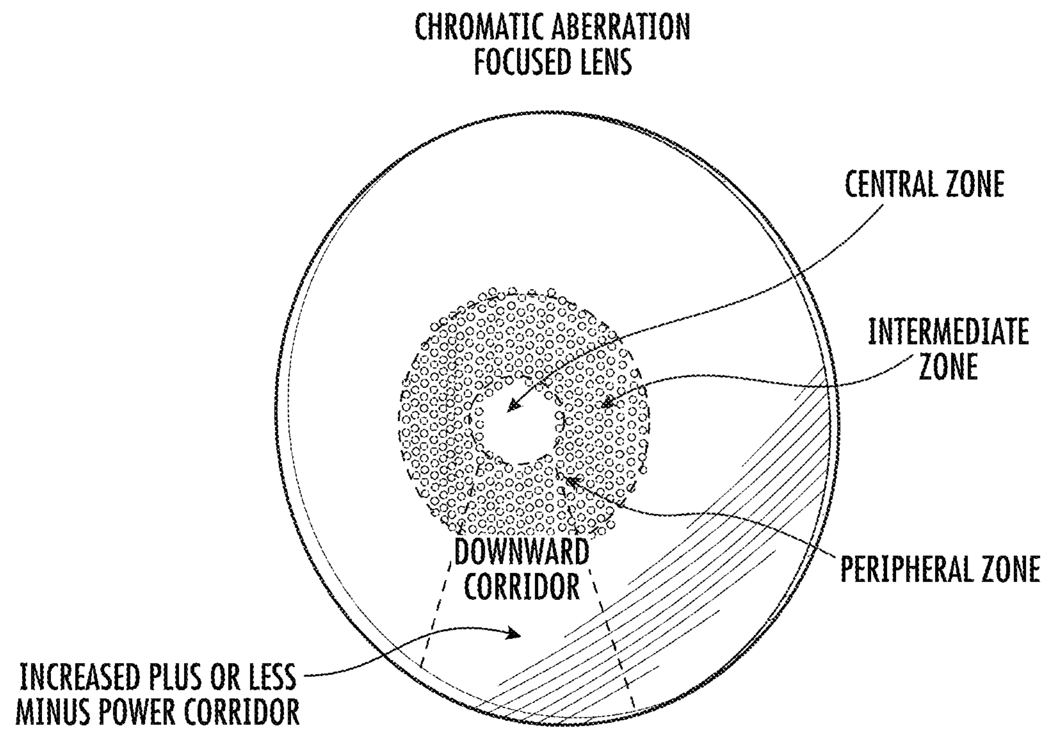
FIG. 43 shows an embodiment of the current invention as described herein.

In reference to FIG. 43, another embodiment of a photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb micro-lens array of lenslets (each 1.03 mmø). The lenslets have a relative positive power within the range of −0.35D to −5.00D. There are spaces between the lenslets where the single vision correction is accessible. The embodiment further comprises a downward channel of increasing plus optical power or reducing minus optical power.

Chromatic Aberration Focused Lens for Ocular Photo-Bio-Stimulation

Figure 31:
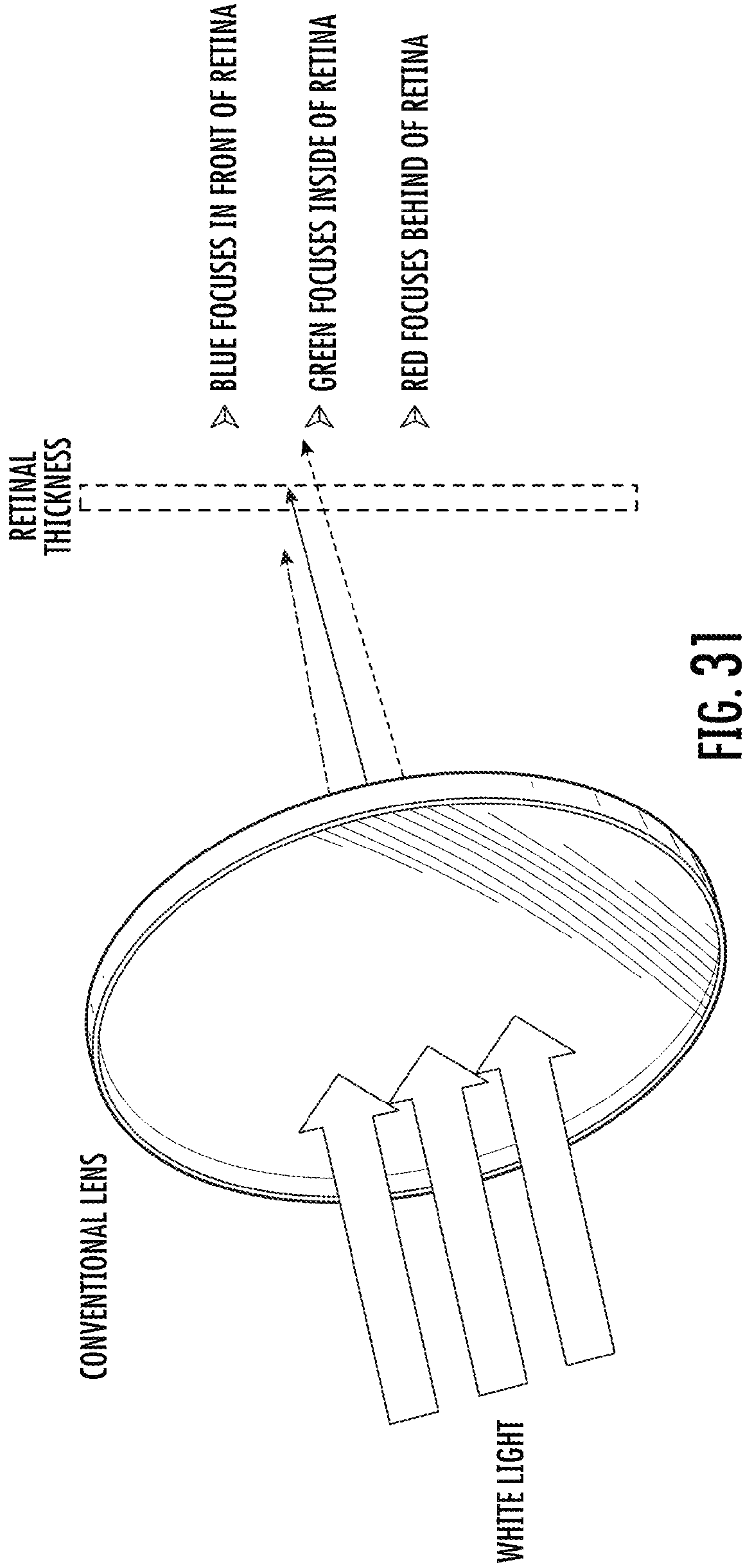
FIG. 31 shows an embodiment of the current invention as described herein.

In reference to FIG. 31, it shows an embodiment of having a conventional lens or optic comprising longitudinal chromatic aberration. The degree of chromatic aberration can be constant unless there is a power change, such as a multifocal. The multifocal area is that of an increase in plus power which pulls the blue wavelength of longitudinal chromatic aberration further in front of the retina. An embodiment of the invention is that of a chromatic aberration focused lens or optic. A chromatic aberration focused lens represents a new category of lenses. A chromatic aberration focused lens or optic for the purposes of this disclosure is a lens that comprises two or more sets of chromatic aberration; the first set of chromatic aberration comprises blue light wavelengths, green light wavelengths and red-light wavelengths, each of the bands of blue, green and red wavelengths are separated from each other after leaving the lens, and wherein the second set of chromatic aberration comprises blue light wavelengths, green light wavelengths and red-light wavelengths, each of the bands of blue, green and red wavelengths are separated from each other after leaving the lens, and wherein the second set of blue, green and red wavelengths of chromatic aberration are positioned farther away from the lens than the first set of blue, green and red wavelengths of chromatic aberration. As used herein, a band represents blue light wavelengths, green light wavelengths, or red-light wavelengths.

Figure 32:
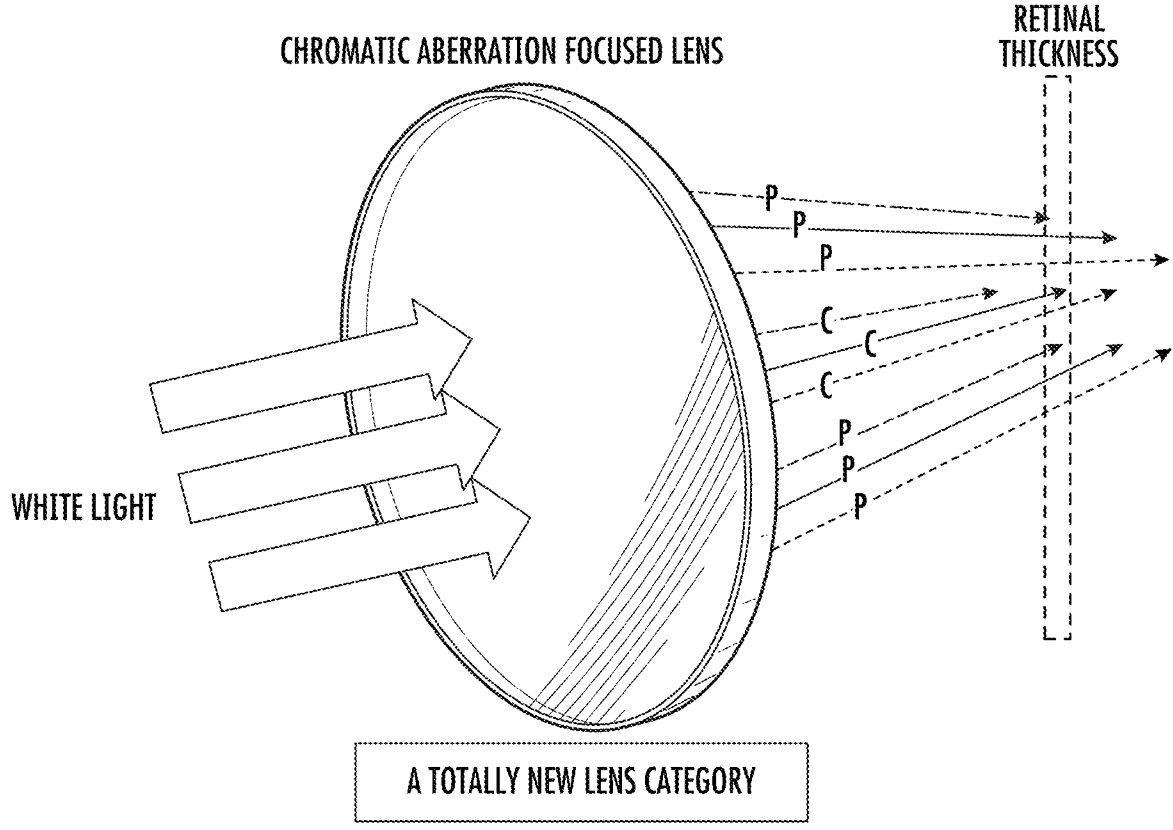
FIG. 32 shows an embodiment of the current invention as described herein.

In reference to FIG. 32, said another way, a chromatic aberration focused lens has two bands of blue wavelengths, two bands of green wavelengths and two bands of red wavelengths, wherein the one set of the blue bands when focusing is farther away from the lens than the other blue band, wherein one set of the green bands when focusing is farther away from the lens than the other green band, wherein one set of the red bands when focusing is farther away from the lens than the other red band. In FIG. 32, "C" refers to a central lens zone allowing transmission of light wavelengths, and in cases refracting the light wavelengths, so that their focus gives clear distance vision. In FIG. 32, "P" refers to a peripheral lens zone (the area outside of the central lens zone) transmitting light wavelengths that focus farther from the lens due to an increase in minus lens power found outside of the central lens zone of the lens. Said still another way, a chromatic focused lens has two bands of blue wavelengths, two bands of green wavelengths and two bands of red wavelengths, wherein the one set of the blue bands is refracted less upon leaving the lens than the other blue band, wherein one set of the green bands is refracted less upon leaving the lens than the other green band, wherein one set of the red bands is refracted less upon leaving the lens than the other red band. The bands of blue, green and red wavelengths that focus closest to the lens are transmitted by the central zone of the lens. The bands of blue, green and red wavelengths that focus farthest away from the lens are those transmitted by the peripheral zone of the lens. This is accomplished by keeping the central zone's optical power that of the BVA distance correction for the wearer. However, adding minus optical power to the lens outside of the central zone.

This then means that a chromatic aberration focused lens generates a minimum of 6 bands of colored light wavelengths upon light exiting the lens. Thus, a chromatic aberration focused lens comprises a minimum of 6 chromatic aberration produced bands. By utilizing a chromatic focused lens or optic it is possible with a single lens or optic to cause the chromatic aberration to spread its light wavelength bands throughout the thickness of the retina of an eye. The thickness of the retina of an eye range between 250 microns to 300 microns. By way of example only, in certain examples, the first band of blue light wavelengths can be focused just before the surface of the retina, while the second band of blue light wavelengths can be focused within the retina, the first bands of green light wavelengths can be focused within the middle of the retina, while the second bands of green light wavelengths can be focused within the back of the retina, and the first bands of red-light wavelengths can be focused just behind the retina, while the second band of red-light wavelengths can be focused further behind the retina.

In most chromatic aberration focused lenses, the central zone of the lens is optical power corrected for the wearer's best corrected distance vision. Thus, the central zone generates a first set of chromatic aberration bands where the blue light focuses usually in front of the retina and the red light usually behind the retina with the green band within the retina. By utilizing a chromatic aberration focused lens or optic, one of the two or more bands of blue light wavelengths can be caused to focus within the retina closer to the rods as opposed to today's conventional lenses where chromatic aberration causes a proper corrected optical powered lens used to correct one's vision (distance and/or near to 20/20 vision) to have the one blue band of wavelengths from chromatic aberration focus always in front of the retina, thus not focusing close to or on the rods of the retina for the generation of dopamine.

By utilizing a chromatic aberration focused lens or optic it is possible to excite the ganglion cells with blue light, as one of the bands of blue light wavelengths will pass through the ganglion cells as it travels and focuses deeper into the retina closer to the rods. Such a chromatic aberration focused lens or optic can be a single vision lens or optic, multifocal lens or optic, and/or progressive addition lens or optic. A chromatic aberration focused lens can be used for increasing the level of dopamine within the eye and brain of the wearer. By way of example only, a child that is suffering from myopia can wear a chromatic aberration focused lens to reduce the progression of myopia or said another way to reduce the increases in minus optical power of the child's myopia correcting lenses over time. Most individuals who are suffering from dopamine and/or serotonin deficiency can benefit from such a lens type. A chromatic aberration focused lens can be prescribed for all optical powers (plus, minus, cylindrical, including plano/no optical power) required for one or more of: myopes, hyperopes, astigmatism and presbyopia. A chromatic aberration focused lens can be prescribed for myopia, hyperopia, astigmatism, compound astigmatism, emmetropia, and/or presbyopia. A chromatic aberration focused lens can be filtered to transmit mostly wavelengths of light that are within the wavelength range of 480-nm+/−30 nm to further enhance the physiological response of the wearer.

In certain embodiments multiple sets of chromatic aberration bands of blue, green and red wavelengths can be found in the peripheral of the lens due to a plurality of zones of different refractive power. In most cases the first set of chromatic aberration bands is that of axial chromatic aberration, and the second set of chromatic aberration bands is also caused by axial chromatic aberration, and one or both are designed to focus deeper into the retina with the red-light band to focus further behind the retina, the green light band near the back of the retina, thus causing the blue light band to focus within the retina close to the rods. Thus, a chromatic aberration corrected lens allows the central vision of the wearer to remain as it appears with a conventional corrected distance vision lens, and for the peripheral retina (outside of the macular area) to be stimulated by the second set of chromatic aberration bands, wherein the blue band is focused within the retina increasing dopamine and/or serotonin production. In certain embodiments one set of bands of blue, green and red wavelengths, can be generated from the central zone of the lens, and a plurality of bands of blue, green and red wavelengths, can be generated from an area peripheral to the central zone. In still another embodiment, one set of bands of blue, green and red wavelengths, can be generated from the central zone of the lens, and a different set of bands of blue, green and red wavelengths, can be generated from an area peripheral to the central zone.

Another way of thinking about a chromatic aberration focused lens is to consider only the blue band of chromatic aberration. In aspects, there will be two blue bands (of blue wavelengths). One is caused by the chromatic aberration focus from the optical power of the central zone of the lens or optic. A second one is caused by the optical power chromatic aberration focus of an area peripheral to the central zone of the lens or optic. The focus of the first blue band will be focused in front of the retina if the central zone of the lens is providing the wearer with 20/20 distance vision or their corrected distance vision. The focus of the second blue band will be focused further away from the lens deeper into the retina. Because the second band, if generated by an area outside of the central zone of the lens, if thus is focused peripheral to the macular area of the eye, stimulating primary rods and ganglion cells of the wearer (visual clarity from the non-macular area is not of a prime concern). By way of example only, the second blue wave band can be located within the range of 100 microns to 500 microns further from the back of the lens than that of the first blue wave band. Said another way, with a chromatic aberration focused lens the second focused blue band is located between 100 microns to 500 microns from the first focused blue band. In certain embodiments it can be located within the range of 150 microns to 350 microns farther from the back of the lens than that of the first blue wave band. Said another way, in these embodiments, with a chromatic aberration focused lens, the second focused blue band is located between 150 microns to 350 microns from the first focused blue band.

Figure 33:
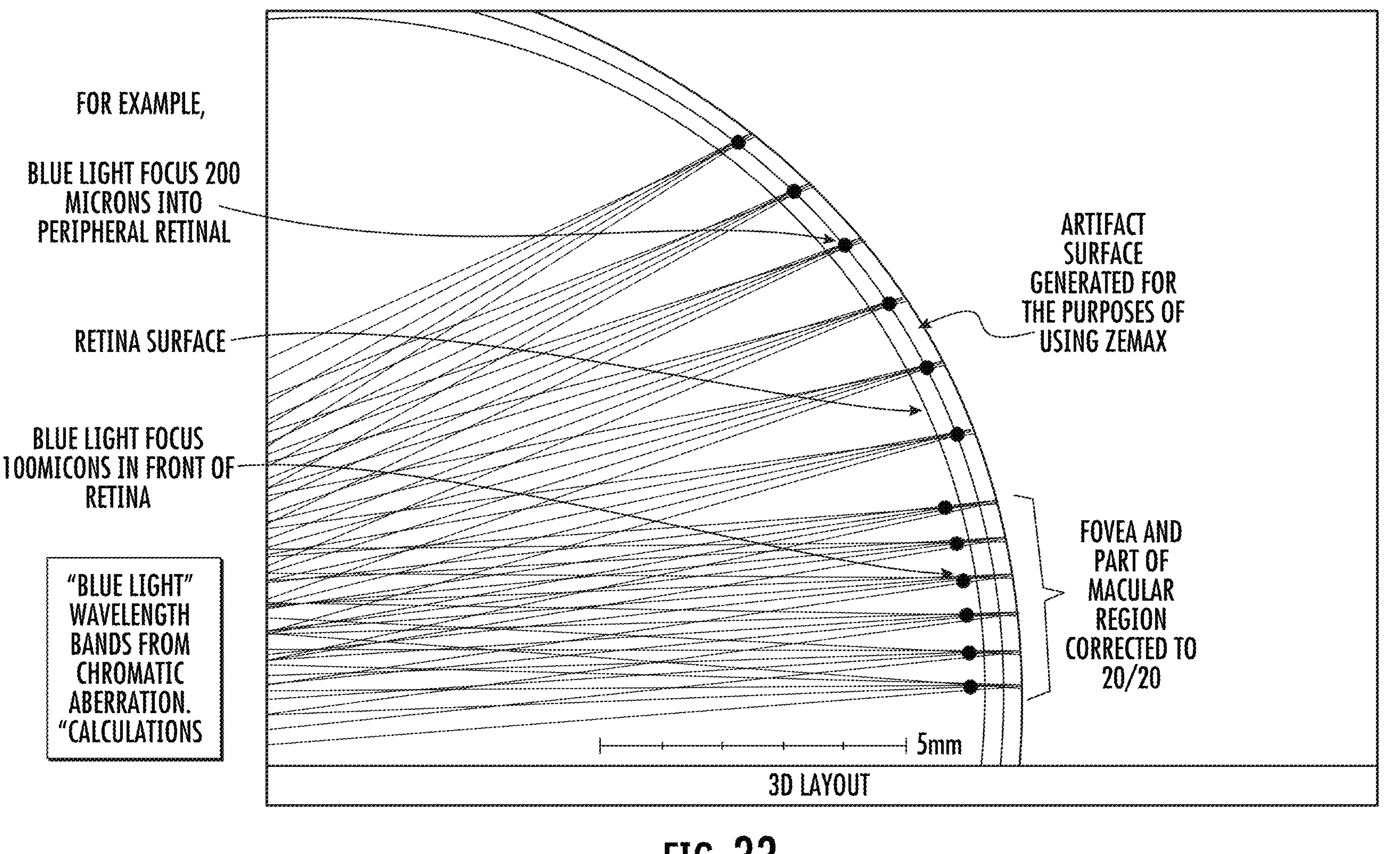
FIG. 33 shows an embodiment of the current invention as described herein.

In reference to FIG. 33, it shows an embodiment of the current invention. In examples, wherein the eye's retina (excluding the foveal area) is within the range of 200 microns to 300 microns thick, the eye's power in diopters may be 1000/16.6=60.24D. If the focal plane were shifted 0.25 microns back, the device might need a focal length of 16.6+0.25=16.85 mm. And the power in diopters would be 1000/16.85=59.35D. Thus, a corrector of size 60.24-59.35D=0.89D is required in this example. Therefore, for the peripheral area of a lens (outside of the central zone) to cause a second chromatic aberration band of blue light wavelengths to be located within the retina closer to the rods, a minus increase in optical power of approximately −0.90D more than the optical power found in the central zone of the lens is needed in this example. In certain other embodiments the increase in minus power can range between 0.50D and 2.00D (more minus optical power or less plus optical power). In embodiments of a chromatic aberration focused lens in the central zone can comprise an optical power to correct the distance vision requirements of the wearer and the zone peripheral to the central zone can comprise an optical power that is more minus (when the central zone is plano or a minus power) or less plus (when the central zone is of a plus power).

Figure 34:
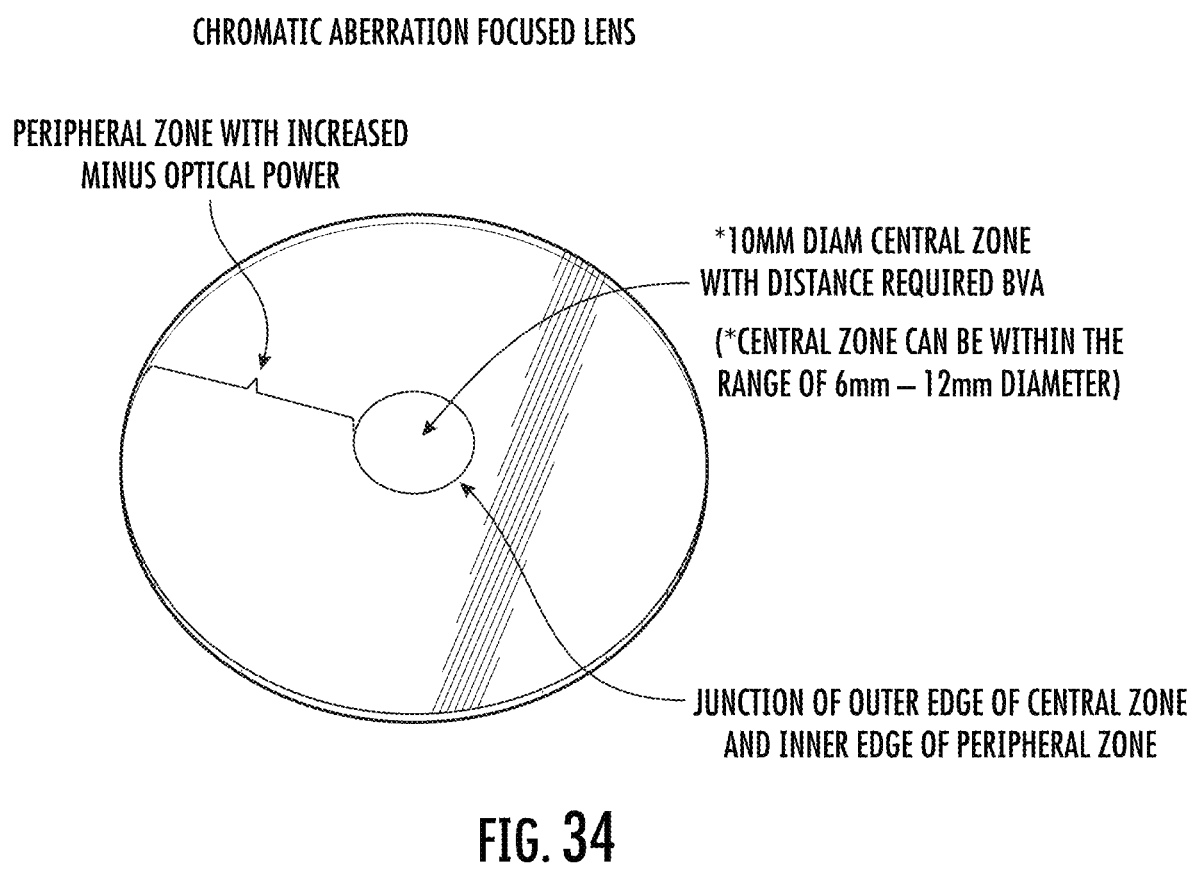

In reference to FIG. 34, by way of example, the peripheral zone can be of an optical power that is within the range of 0.50D to 2.00D more minus (when the central zone is of a minus power) or the peripheral optical power can be within the range of 0.50D to 2.00D less plus optical power (when the central zone is of a plus optical power). By way of another example, the peripheral zone can be of an optical power that is within the range of 0.50D to 1.25D more minus (when the central zone is plano or minus power), or the peripheral optical power can be within the range of 0.50D to 1.25D less plus optical power (when the central zone is of a plus optical power). In certain embodiments the power outside of the central zone can be that a spherical equivalent optical power which is more minus optical power than that of the central zone. In some embodiments the central zone of the lens, by way of example only, can be 10 mm in diameter and there can be an intermediate zone where the optical power of the central zone's optical power changes to that of the peripheral zones increase in minus optical power or less plus optical power. In examples, with this embodiment, one surface of this peripheral zone can be that of a smooth continuous curve. In certain embodiments, the optical power is constant within the tolerance of +/−0.12D and in other embodiments the optical power can vary. In aspects, the central zone can be of any distance optical power required by an emmetrope, hyperope, myope, astigmat, or any combination thereof. The lens further can comprise an additional positive power for the correction of presbyopia. The additional optical power can be a lined bifocal, trifocal or progressive addition zone. In aspects, a peripheral zone can comprises "increased" Minus Optical Power (or "less" Plus Optical Power) within the range of 0.35D to 5.00D compared to that of the Distance Corrected BVA, which is the optical power of the central zone. If the central zone power is plano the peripheral zone would be within the range of −0.50D and −5.00D.

Figure 35:
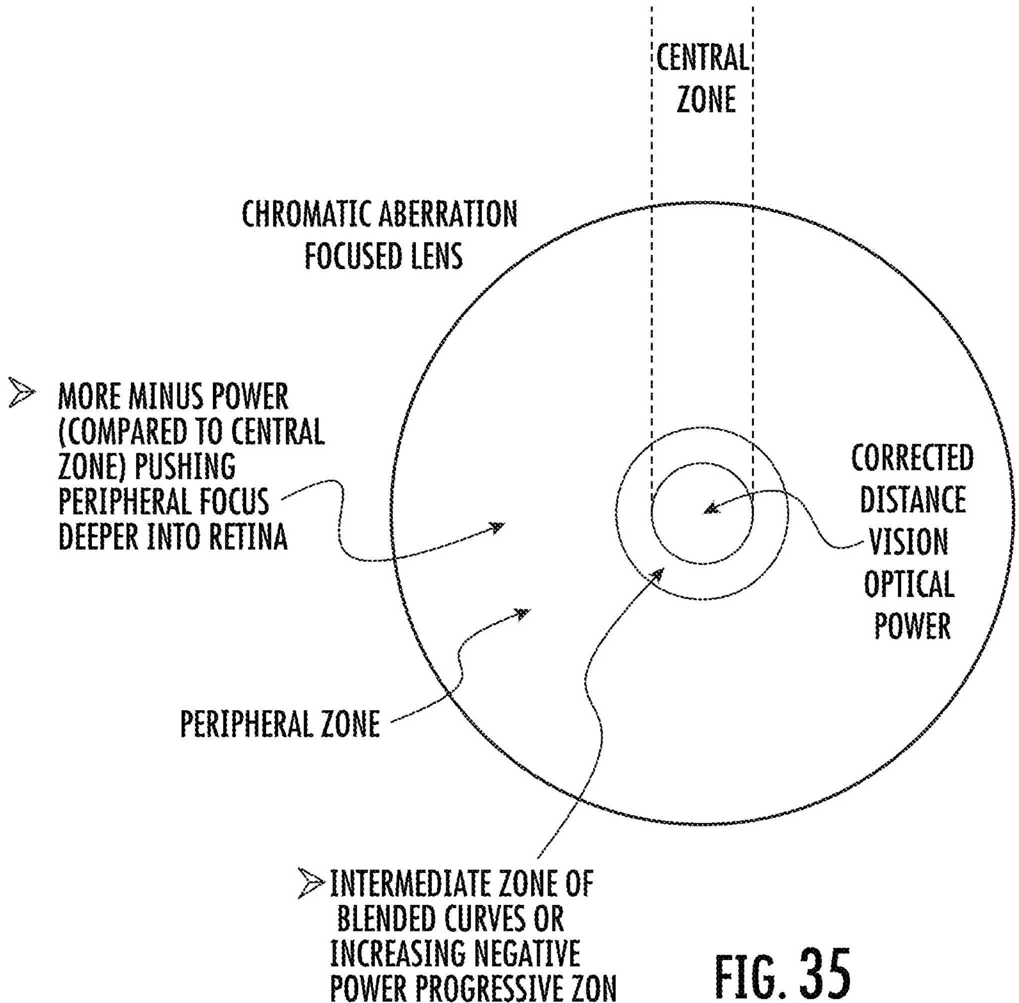
FIG. 35 shows an embodiment of the current invention as described herein.

In reference to FIG. 35, the central zone diameter can be within the range of 5 mm-15 mm, more preferably 6 mm-10 mm. In certain embodiments the intermediate zone can comprise one or more optical power steps. In other embodiments the intermediate zone can comprise one or more continuous curves that alter the optic power as it changes from the central zone's optical power to the peripheral zone's optical power. In still other embodiments the intermediate zone can comprise a blended zone of optical power where the optical power transitions in optical power. In certain other embodiments the intermediate zone can comprise one or more of optical power step(s), continuous curve(s), and/or blended power area(s). In each of these cases the peripheral zone can be of more minus optical power compared to the central zone or less plus optical power compared to the central zone. In still other embodiments the change in optical power can occur over a larger area with a plurality of one or more of, smaller optical power changes in optical steps, continuous curves, or blended regions. In aspects, the lens can have 1.59 refractive index matrix, 30 Abbe, and be of 2.0 mm in thickness.

In embodiments the lower the Abbe number of the lens material the higher the increase in minus optical power in the non-central zone of the lens compared to the central portion. And the higher the Abbe number the lower the increase in minus optical power required in the non-central zone of the lens compared to the central zone of the lens.

In certain embodiments the peripheral thickness (outside of the central zone can increase beyond what it would be in a conventional lens or optic.) This increase in thickness of the lens material can provide for moving the second set of chromatic aberration bands farther away from the lens than those from the central zone of the lens. In still other embodiments, both the peripheral thickness (outside of the central zone can increase beyond what would be in a conventional lens or optic), and the optical power can be increased in minus compared to a central zone of plano or minus optical power, or a less plus compared to a central zone of plus optical power.

In certain embodiments of a chromatic aberration focused lens as described herein, the optical power of the periphery is the same as the optical power of the central zone, but the Abbe number of the periphery can be lower than the Abbe number of the central zone. This can be caused by way of a coating not being present in the central zone, however being present in periphery to the central zone. Such a coating can be, by way of example only, a coating, an AR coating (antireflection coating), or a vacuum deposition coating. When the Abbe of the peripheral zone is of a lower Abbe than the central zone, the chromatic aberration of the peripheral zone can cause the second set of bands of blue light wavelengths (generated by the peripheral zone) to focus deeper into the retina as compared to the first set of blue light bands associated with and generated by the central zone of the lens.

In aspects, a chromatic aberration focused lens can be that of a lens or optic wherein there are 6 chromatic aberration bands, wherein there are two sets of blue wavelength bands, green wavelength bands, and red wavelength bands, wherein a first set of bands is generated from a central zone of a lens, wherein a second set of bands is generated from an area peripheral to the central zone, and/or wherein each band of the second set focuses further from the lens when compared to their counterpart band of the first set. The blue wavelength band of the first set can focus in front of the retina when the optical power of the lens comprises the wearer's distance refractive correction. The blue wavelength band of the second set can focus closer to the rods of the retina compared to the blue wavelength band of the first set. The blue wavelength band of the second set can focus farther away from the lens than the blue wavelength band of the first set. The green wavelength band of the second can focus farther away from the lens than the green wavelength band of the first set. The red wavelength band of the second set can focus farther away from the lens than the red wavelength band of the first set.

The lens can comprise a central zone and a peripheral zone, wherein the surface refractive index of the central zone is higher than the surface refractive index of a peripheral zone. The surface of the peripheral zone can comprise a different coating material as compared to the central zone. Such coating can be by way of example only, an antireflection coating, hard scratch resistant coating, or cushion coating. The lens can comprise a central zone and a peripheral zone, wherein the surface Abbe number of the central zone is higher than the surface Abbe number of a peripheral zone. The surface of the peripheral zone can comprise a different coating material as compared to the central zone. Such coating can be by way of example only, an antireflection coating, hard scratch resistant coating, or cushion coating. The lens can comprise a central zone and a peripheral zone, wherein the optical power of the central zone is of less minus power or more plus power than the optical power of a peripheral zone.

The optical power of a peripheral zone can be within the range of −0.35D to −2.00D more minus optical power or less plus optical power when compared to the optical power of the central zone. The optical power of a peripheral zone can be within the range of −0.50D to −5.00D more minus optical power or less plus optical power when compared to the optical power of the central zone. The optical power of a peripheral zone can be −1.00D+/−0.50D more minus optical power or less plus optical power when compared to the optical power of the central zone. The lens can comprise a central zone, intermediate zone, and peripheral zone. The intermediate zone can comprise a blended region of optical powers or a continuous surface contributing to reducing optical power. The lens can comprise a peripheral zone comprised of zones of lower optical power compared to the central zone of the lens.

The lens can be a single vision, multifocal, or progressive addition lens. The lens can be comprised of any suitable ophthalmic material, by way of example only, CR39, polycarbonate, Trivex, High Index, Cyclic olefin polymers (COP) and cyclic olefin copolymers (COC) that are amorphous, and/or transparent thermoplastics composed of cyclic olefin monomers (norbornene) and linear olefins (e.g. ethene). The lens can be coated, treated, and finished like any other ophthalmic lens. The lens can be first in the form of a semi-finished lens blank before it becomes a lens. The lens can be provided to individuals having one of a dopamine deficiency and/or serotonin deficiency.

An embodiment can be generated by altering the lens focus power between the central zone, an optional intermediate Zone, and a peripheral zone, in such a way that the focus power in the optical intermediate zone and non-optional peripheral zone is more minus focus power or less plus focus power that the central zone. Another embodiment can be generated by altering the index of refraction of the central zone, optional intermediate zone and non-optional peripheral zone. In this case the refractive index would be less in the optional intermediate zone and non-optional peripheral zone of the lens or lens blank as compared to the central zone. And still another embodiment can be caused by a combination of both altering the focal power and the index of refraction. In embodiments, these innovative lens embodiments are comprised of two or more sets of chromatic aberration bands (each comprising blue, green, and red wavelengths of light).

The embodiment can utilize the two or more chromatic aberration sets of bands, so that the first set of chromatic aberration bands is that of a conventional lens with regards to the central area which comprises the distance power focus needed for the wearer of the lens or lens blank. The other chromatic aberration bands which are peripheral to the central set of bands are focused deeper into the retina and/or behind the retina of the eye of the wearer. The retina being 200-300 microns thick. An embodiment can be one of a lens, lens blank, or optic, wherein the lens, lens blank, or optic, which comprise two or more sets of chromatic aberration, wherein one set focuses farther away from the lens, lens blank, or optic than the other set, wherein a first set is caused by an optical power of the lens that provides the proper distance correction for the wearer and a second set that focuses light farther from the lens, lens blank, or optic than the first set.

In embodiments of a chromatic aberration focused lens, the movement of the focus of the second set of chromatic aberration bands farther from the lens than those of the focus of the first set of chromatic aberration bands, can be caused by way of one or more of the following: lower abbe number of the lens peripheral zone compared to the lens central zone, lower refractive index of the lens peripheral zone compared to the lens central zone, increased thickness of the lens peripheral zone compared to the lens central zone, or more minus or less plus optical power of the lens peripheral zone compared to the lens central zone. While all lens materials can be used to fabricate a chromatic aberration focused lens, the lower the abbe number and/or higher index lenses work well in terms of small changes generating larger movement of the focus of the second chromatic aberration bands relative to that of the focus of the first chromatic aberration bands. Thus, while glass or plastic CR39 can be used, polycarbonate or other thin and light high index lenses work well in embodiments. In most embodiments when fabricating (by way of example only), one or more of, free forming, grinding and polishing, casting, molding, stamping, surface casting, and/or coating a chromatic aberration focused lens, once the proper optical power of the central zone of the lens is created so that it delivers the (BVA) best corrected distance vision for the lens (for example, 20/20 distance vision), the optical power of the peripheral zone (compared to the optical power of the central zone) can be of the same increase in minus power or decrease in plus optical power for, by way of example only, all lenses, lens materials, identical lens materials, and/or lens types. Thus, a look up table or software table can be constructed for, by way of example, each lens material or lens type.

In certain embodiments of a chromatic aberration focused lens, the front surface convex curve of the lens is preset when producing a lens blank and the back concave surface is fabricated to provide the proper optical powers. In other embodiments of a chromatic aberration focused lens, the back surface concave curve of the lens is preset when producing a lens blank and the front convex surface is fabricated to provide the proper optical powers. In still other embodiments of a chromatic aberration focused lens, the back surface concave curve of the lens and the front convex surface are fabricated to provide the proper optical powers. In certain embodiments of a chromatic aberration focused lens, the peripheral zone optical power can be an increase in minus optical power compared to the central zone. In other embodiments of a chromatic aberration focused lens, the peripheral zone optical power can be a decrease in plus optical power compared to the central zone. In still other embodiments, the peripheral zone optical power can be that of a spherical equivalent such that it is more minus compared to the central zone optical power when the central zone is plano or minus optical power. In still other embodiments of a chromatic aberration focused lens, the peripheral zone optical power can be that of a spherical equivalent, such that it is less plus compared to the central zone optical power when the central zone is of a plus optical power.

Figure 36:
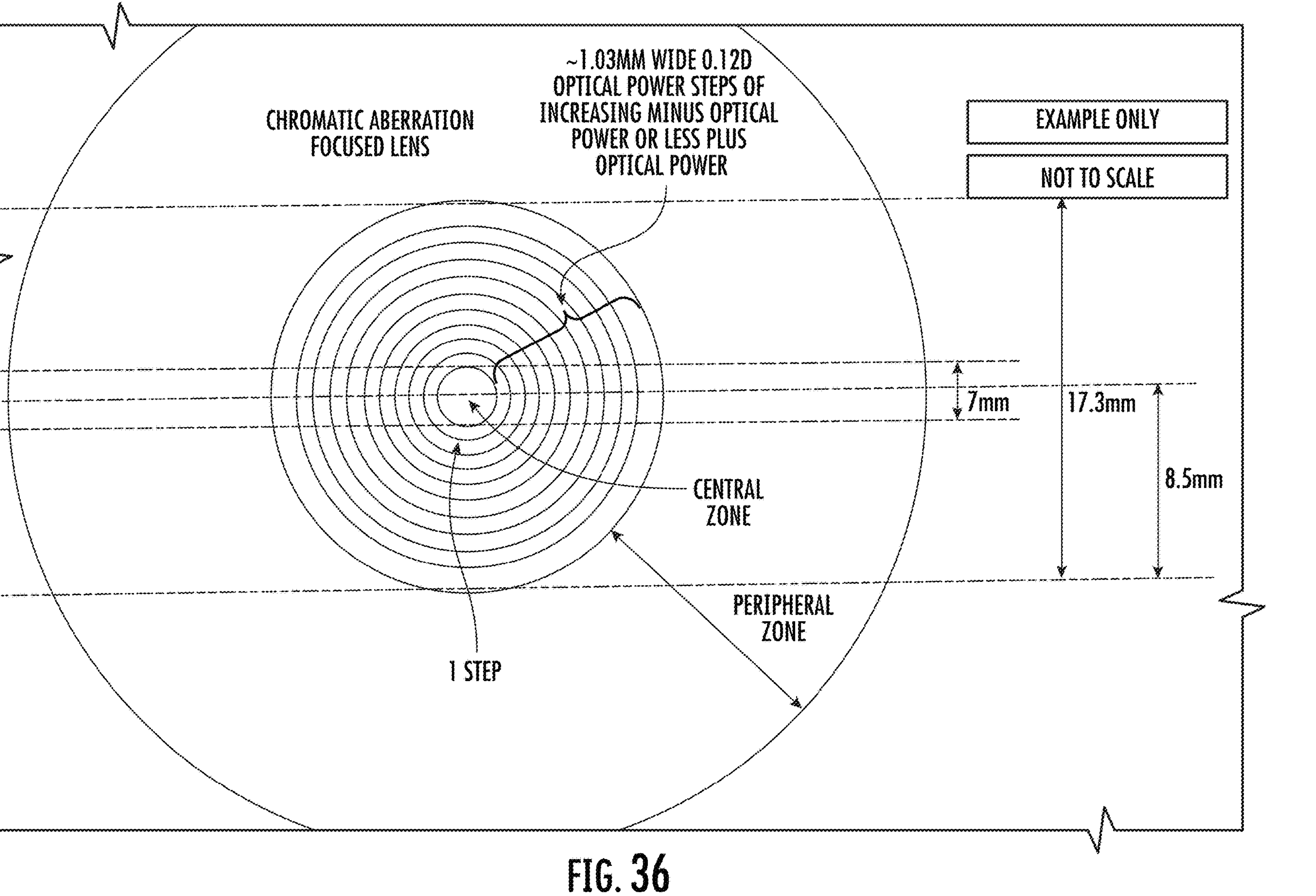
FIG. 36 shows an embodiment of the current invention as described herein.

In reference to FIG. 36, in embodiments of a chromatic aberration focused lens, the central zone can be comprised of a spherical or sphero-cylinder surface curvature causing a spherical or sphero-cylinder optical power, and the peripheral zone can be comprised of a spherical surface curve causing a spherical equivalent optical power. Said another way, a chromatic aberration focused lens that corrects astigmatism of the wearer can comprise an astigmatic correction in the central zone and a spherical equivalent spherical curve (somewhat) in all or part of the peripheral zone. The optical power differential between the central zone, intermediate zone, and peripheral zone can be generated by way of example only, plurality of continuous curvature changes, increasing minus optical progressive curve, a plurality of optical power steps, one optical power step, a micro-lens array, refractive index changes, blended optical power curves or steps, or a combination of any two or more. As shown in FIG. 36, an Intermediate Zone of optical power may comprise 10 Steps of increasing minus optical power or less plus optical power totaling 1.20D of optical power difference from that of the Central zone. In aspects, optical power in a peripheral zone remains either constant from that of the 1.20D of increase in minus or reduction of plus optical power, or can further increase in minus, or decrease in plus optical power by way of a continuous surface curvature change. The steps can be on the convex side, and the progressive plus power region on the concave side of the lens or lens blank. The preference is to have one surface on the convex side.

The optical power change from the central zone compared to either the intermediate zone or peripheral zone is of more minus optical power of less plus optical power. When using changes in continuous curvatures, the surface astigmatism generated is moved to the right and left side of the intermediate zone of the lens and superior to the intermediate zone only if needed. In certain embodiments, 50% of the optical power change from the optical power of the central zone is accomplished at the junction of the intermediate zone and the peripheral zone. For the purposes of this disclosure, plano optical power is considered zero optical power, but still can be utilized to denote the optical power of a section or region of the lens or lens blank.

In certain embodiments, a method for determining a preferred or optimal optical power for the central zone is to measure the distance vision refractive error of a patient while utilizing a green bandpass filter (interference filter). This causes focusing only the green wavelength band on the retina. Thus, by optimizing clarity of the green wavelength band to measure the patient's refractive power needs at far, it will establish the best optical power for seeing 20/20 in the distance. Once that is established, the needed increase in minus optical power or decreased plus optical power can be utilized for the peripheral lens area. This needed increase in minus optical power or decreased plus optical power can be a constant depending upon the material type comprised by the chromatic aberration focused lens. By way of example only, polycarbonate with an abbe of 30, a refractive index of 1.59, and a center thickness of 1.5 mm, will provide one constant number of increased minus or decreased plus optical power in the peripheral region of a chromatic aberration focused lens for most if not all optical powers. By way of example only, CR39 with an abbe of 58, a refractive index of 1.49, and a center thickness of 2.0 mm, will provide a different one constant number of increased minus or decreased plus optical power in the peripheral region of a chromatic aberration focused lens for most if not all optical powers.

Such is the case for all other optical materials having known abbe numbers used for fabricating ophthalmic lenses. So once the central zone optical power and the abbe number is known, lookup table (hard copy or electronic software) can be used to calculate the peripheral zone optical power deviation from that of the central zone optical power. In embodiments, the chromatic aberration focused lens can be clear (without a tint). In certain embodiments, the chromatic aberration focused lens can be tinted.

In certain embodiments a secondary attachable/detachable filtered lens, by way of example only, one or more of, a bandpass filter, interference filter, absorption filter, neutral density filter, notch filter, or optic or eyewear (by way of example only, magnetic attachable, pressure attachable, clip on attachable or a fit over optic), can periodically be worn with the chromatic aberration focused lens to further define the wavelengths of light for stimulating the retina of the wearer. By way of example only, a filtered lens such as a bandpass filter (interference filter) transmitting predominantly within the wavelength range of 480 nm+/−30 nm can be worn to further stimulate the rods and ganglion cells to generate dopamine. By way of example only, such a filter can be applied or used for 10 minutes or less in the morning and 10 minutes or less in the early afternoon.

A chromatic aberration focused lens represents a completely new category of lenses that utilize a clear lens' inherent chromatic aberration in a positive way to increase retinal dopamine, thus increasing choroid thickening to neutralize part or all the force responsible for the elongation of the eye that causes myopia. Such a lens can also be worn by patients with other types of dopamine deficiency disorders. Such lenses are taught within this disclosure. In a chromatic aberration focused lens, the longitudinal chromatic aberration found in the central zone of the lens is inherent in the lens required with the proper optical to achieve the wearer's best distance visual acuity. Thus, the central zone of the lens comprises an optical power which provides the wearer with his or her best visual acuity. However, the peripheral zone of the lens which begins at the outer junction with the central zone of the lens comprises additional minus power or less plus power causing the chromatic aberration wavelength bands to be moved farther away from the lens being worn by the wearer of such a lens, or said another way, deeper into or behind the retina of the eye of the wearer.

However, in aspects, peripheral to the central zone, another set of chromatic aberration can be engineered by the lens design to permit the blue wave bands of chromatic aberration to focus on or within the retina peripheral to the macula of the wearer's eye(s). Such lenses can take ambient light, by way of example only, fluorescent light, incandescent light, LED light, or sun light, and cause the blue light band of chromatic aberration generated by the lens to stimulate one or more of the retinal rods and/or ganglion cells to increase dopamine in the retina and in cases the brain. In certain embodiments it is the retinal rods that cause the largest amount of dopamine to be produced. In certain embodiments the desired level of light is 300 lux or greater. In other embodiments the desired level of light is 1,000 lux or greater. In still other embodiments the desired level of light is 10,000 lux or greater.

Another embodiment is that of a darkened, enhanced version of chromatic aberration focused lens that is worn for brief periods of time independent of one's conventional myopic correcting eyewear or as fit over eyewear in addition one's conventional eyewear. Such an embodiment delivers only the specific wavelengths of light required to produce dopamine in the eye's retina, in aspects. For this reason, this enhanced embodiment can be able to be worn for a little as 5 minutes, 10 minutes, or 15 minutes or less, in the morning and mid-day to slowdown, and contribute to stopping myopia progression. This enhanced chromatic aberration lens can also be worn by patients with other types of dopamine deficiency disorders.

An embodiment of a chromatic aberration focused lens can be a lens or optic that comprises a central zone of optical power, wherein the central zone's optical power can be of an optical power required to correct an individual's distance refraction needs, wherein the optical power peripheral to a central zone can be of more minus optical power or less plus optical power than the optical power of the central zone, and wherein an outer surface of the zone peripheral to the central zone that comprises the increased minus optical power or reduced plus optical power compared to the central zone can be comprised of a smooth continuous curve.

The increase in minus optical power or reduced plus optical power can be of a difference of an optical power (either positive or negative) of 0.35D and 5.00D compared to that of the central zone's optical power. By way of example only, if the central power zone has an optical power of plano, a zone peripheral to the central zone can have an optical power that is within the range of 0.50D to 5.00D more minus optical power. Another example would be, if the central power zone had an optical power of −1.00D a zone peripheral to the central zone could have an optical power of −1.50D up to −6.00D. Still another example would be, if the central power zone had an optical power of +1.00D a zone peripheral to the central zone could have an optical power of +0.50 D up to that of +4.00D.

The central zone can be comprised of an optical power required by one of an emmetrope, myope, hyperope, astigmat, compound astigmat, and/or presbyope. In addition to the optical powers mentioned herein, the lens or optic can comprise one or more bandpass filter(s), interference filter(s), absorption filter(s), and/or notch filters. The central zone of the lens or optic can be of any optical power including plano. The lens or optic can comprise a near focusing optical power that is applied in the form of a bifocal, trifocal or progressive addition lens. The lens or optic can be sunglass tint, colored tint, or of a clear color. The lens or optic can be finished with any optical coating including that of a hard coat and/or antireflective coating. The lens or optic can have a central zone and a peripheral zone. The lens or optic can comprise a central zone, intermediate zone and a peripheral zone. The lens or optic can comprise multiple intermediate zones of different optical power. The lens or optic can comprise a single change of optical power. The lens or optic can comprise multiple changes of optical power. The change(s) of optical power can be continuous. The change(s) of optical power can be blended. The change(s) of optical power can be immediate. The junction between the central zone and a zone that begins immediately at the junction between such zone and the central zone can be lined due to a sharp optical power change, blended, or continuous with the start of an intermediate zone of that of a peripheral zone (see, FIG. 36).

An embodiment can comprise no blended intermediate zone or a blend at the junction of the outer central zone edge and peripheral zone. In certain embodiments a blended junction or smoothed continuous increased minus powered (or less plus power) junction can be present. In still other embodiments if the central zone is of plus optical power an intermediate power zone can be of less plus power than the central zone's optical power, and the peripheral zone can be of even less optical plus power than the intermediate zone. If the central zone is of minus or plano optical power the intermediate zone can be of increased minus optical power and the peripheral zone can be of a greater amount of minus optical power than that of the intermediate zones minus optical power.

The central zone can be of any distance optical power required by an emmetrope, hyperope, myope, astigmat, or any combination thereof. The lens further can comprise an additional positive power for the correction of presbyopia or to assist with near point accommodative stress. The additional optical power can be a lined bifocal, trifocal or progressive addition zone. Given that the peripheral zone is increasing in minus power this causes additional stress on the near point accommodative system of the wearer, thus depending upon the age of the wearer or the amount of near work that is required of the wearer, for a chromatic aberration lens in certain embodiments additional near point optical power can be required. In certain embodiments the increase in minus power can be generated by curvature on one side of the lens or lens blank, while the near addition optical power (added positive optical power) can be generated on the opposite side of the lens or lens blank. In still other embodiments the increase in minus power and the near addition optical power (added positive optical power) can be generated on the same side of the lens or lens blank while the near addition power can be generated on the opposite side of the lens or lens blank.

This embodiment is also a chromatic aberration focused lens, but in addition to the lens design where the central area focuses the distance BVA of the patient, the lens utilizes a filter or filters, by way of example only: a bandpass filter, interference filter, absorptive filter, notch filter, or a combination of any two or more, to permit the largest concentration of visible wavelengths to be within the wavelength ranges of 450 nm-510 nm or 480 nm+/−30 nm. In certain embodiments, but not all, the central zone is left free of a filter or filters, with the filter being peripheral to the central zone. The lenses can take ambient light, by way of example only, fluorescent light, incandescent light, LED light, or sun light, and cause the light transmitted by the filter to stimulate one or more of the retinal rods and/or ganglion cells to increase dopamine in the retina and in cases the brain. In certain embodiments it is the retinal rods that cause the largest amount of dopamine to be produced. The desired level of light is 300 lux or greater. In other embodiments the desired level of light is 1,000 lux or greater. In still other embodiments the desired level of light is 10,000 lux or greater. With this lens, the filtered passed light wavelengths can be designed to be focused on the retina or in the retina, peripheral to the macula, depending upon the optical power peripheral to the central optic zone of the lens. However, in other embodiments the filter or filters are applied across the lens.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of, 460 nm-520 nm, 470 nm to 520 nm, or 480 nm-520 nm, or by utilizing a light source or light emitter that predominately transmits within the wavelength range of at least one of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Embodiments when light wavelengths are generated by way of filtered optics or filtered lenses the transmission peak of the wavelength range that strike the eye's retina falls within the wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina, which fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens.

An embodiment is that of a lens or optic, wherein the central zone maintains its normal focus of chromatic aberration wavelength bands, wherein one or more of the chromatic aberration wavelength bands that are peripheral to the central zone focuses farther from the lens or optic than those of the central zone, and wherein the lens' or optic's optical power that is peripheral to that of the central zone is within the range of 0.50D to 5.00D of increased minus optical power or less plus optical power when compared to the optical power of the central zone of the lens or optic.

Another embodiment is that of a lens or optic, wherein the optical power peripheral to the central zone of the lens or optic is comprised of an increase in minus optical power or a reduction in plus optical power compared to that of the central zone of the lens or optic, and wherein that increase of minus optical power or reduced plus optical power is within the range of 0.50D to 5.00D.

Still another embodiment is that of a lens or optic comprising a central zone and a zone or zones peripheral to the central zone, wherein the central zone comprises a diameter within the range of 6 mm to 12 mm, wherein the central zone has an optical power required for the wearer's best distance visual acuity, and wherein the optical power peripheral to the central zone of the lens or optic is comprised of an increase in minus optical power or a reduction in plus optical power compared to that of the central zone of the lens or optic, and wherein that increase of minus optical power or reduced plus optical power is within the range of 0.50D to 5.00D.

In reference to FIG. 37, it shows an embodiment of a lens or optic that comprises a central zone of optical power, wherein the optical power peripheral to the central zone is more minus optical power than the optical power of the central zone, wherein the lens or optic comprises a downward directional zone or corridor of optical power that is within 0.50D of or equal to the central zone's optical power, and wherein the downward corridor of optical power continues in a length of 5 mm or more. The lens or optic can comprise an optical power peripheral to the central zone ranges between −0.50D to −5.00D more minus optical power. According to this embodiment, one surface of this peripheral zone is that of a smooth continuous curve. In certain embodiments the optical power is constant within the tolerance of +/−0.25D and in other embodiments the optical power can vary. In aspects, the peripheral zone comprises "increased" minus optical power (or "less" plus optical power) within the range of 0.35D to 5.00D compared to that of the Distance Corrected BVA which is the Optical power of the Central Zone. If the central zone power is plano the peripheral zone would be within the range of −0.50D and −5.00D. The central zone can be of any distance optical power required by an emmetrope, hyperope, myope, astigmat or any combination thereof. The lens further can comprise an additional positive power for the correction of presbyopia. The additional optical power can be a lined bifocal, trifocal or progressive addition zone.

The lens or optic can comprise a series of increases of minus optical power steps from the central zone outward. The lens or optic can comprise a series of increases of minus optical power continuous power curves from the central zone outward. The lens or optic can comprise a plurality of minus power lenslets being of more minus power than the central zone outside of the central zone. The lens or optic can comprise a minus power microlens array of more minus power than the central zone outside of the central zone. The lens or optic can comprise a plurality of minus zones having more minus power than the central zone outside of the central zone. The lens or optic can comprise a transition zone of increased optical power between the central zone and a peripheral zone.

The lens or optic can comprise a downward corridor. The downward corridor can be comprised of offsetting positive power. The downward corridor can be positioned below the pupil of the wearer to allow for offsetting all or some of the peripheral minus optical power. The downward corridor can be that of a positive power zone that provides a reduction in the added peripheral minus power of the lens or optic, thus reducing near point accommodative stress of the wearer. The downward corridor can be comprised of increasing positive power compared to that of the peripheral zone's optical power located outside of the downward corridor. The downward corridor can be generated on the front convex surface of the lens. The downward corridor can be generated on the front concave surface of the lens. The lens or optic can comprise surface topography for generating the downward corridor's optical power. Such topography can be located on one side of the lens or optic while the surface topography generating the increasing optical power peripheral to the central zone can be located on the opposite side of the lens or optic.

In reference to FIG. 38, the lens or optic can comprise surface topography for generating the downward corridor's optical power. The lens or optic can comprise surface topography or a zone within in the lens for generating the increasing optical power peripheral to the central zone which can be located on the same side of the lens or optic. The downward corridor can connect to a reading zone. The downward corridor can comprise an optical power equal to that of the central zone. The reading zone can comprise an optical power that is between +0.50D and +3.25D of increased plus optical power compared to that of the central zone's optical power. The downward corridor can comprise an optical power that is contributed by both sides of the lens. The downward corridor can comprise a transition of increased added positive optical power. In aspects, one surface of the peripheral zone is that of a smooth continuous curve. In certain embodiments the optical power is constant within the tolerance of +/−0.25D and in other embodiments the optical power can vary. In aspects, the peripheral zone comprises "increased" Minus Optical Power (or "less" Plus Optical Power) within the range of 0.35D to 5.00D compared to that of the Distance Corrected BVA, which is the Optical power of the Central Zone. If the central zone power is plano the peripheral zone would be within the range of −0.50D and −5.00. The lens further can comprise an additional positive power for the correction of presbyopia 3801. The additional optical power can be a lined bifocal, trifocal or progressive addition zone.

Another embodiment of the lens can be a filtered lens or optic. The filtered lens can comprise one or more of: an interference filter, bandpass filter, absorption filter, notch filter, selective wavelength(s) filter, or neutral density filter. The lens or optic can predominantly transmit wavelengths within the wavelength range of one of: 450 nm-510 nm or 530 nm+/−20 nm or 650 nm+/−30 nm. The filtered lens can comprise a central zone and a defocus zone.

Another embodiment is that of a lens or optic that comprises a central zone of optical power, wherein the central zone's optical power can be of an optical power required to correct an individual's distance refraction needs, wherein the optical power peripheral to a central zone can be of more minus optical power or less plus optical power than the optical power of the central zone, and wherein an outer surface of the zone peripheral to the central zone that comprises the increased minus optical power or reduced plus optical power compared to the central zone is comprised of a smooth continuous curve.

The increase in minus optical power or reduced plus optical power can be of a difference of an optical power (either positive or negative) of 0.35D and 5.00D compared to that of the central zone's optical power. By way of example only, if the central power zone has an optical power of plano, a zone peripheral to the central zone can have an optical power that is within the range of 0.35D to 5.00D more minus optical power. Another example would be, if the central power zone had an optical power of −1.00D a zone peripheral to the central zone could have an optical power of −1.35D up to that of −6.00D. Still another example would be, if the central power zone had an optical power of +1.00D a zone peripheral to the central zone could have an optical power of +0.65D up to that of +4.00D.

The central zone can be comprised of an optical power required by one of an emmetrope, myope, hyperope, astigmat, compound astigmat, and/or presbyope. In addition to the optical powers mentioned herein, the lens or optic can comprise one or more bandpass filter(s), interference filter(s), absorption filter(s), or notch filters. The central zone of the lens or optic can be of any optical power including plano. The lens or optic can comprise a near focusing optical power that is applied in the form of a bifocal, trifocal or progressive addition lens. The lens or optic can be a sunglass tint, colored tint, or of a clear color. The lens or optic can be finished with any optical coating including that of a hard coat and/or antireflective coating. The lens or optic can have a central zone and a peripheral zone. The lens or optic can comprise a central zone, intermediate zone and a peripheral zone. The lens or optic can comprise multiple intermediate zones of different optical power. The lens or optic can comprise a single change of optical power. The lens or optic can comprise multiple changes of optical power. The change(s) of optical power can be continuous. The change(s) of optical power can be blended. The change(s) of optical power can be immediate.

In another embodiment a chromatic aberration focused lens for photo-bio-stimulation can be fabricated by altering the index of refraction between the central zone and other zones of the lens or lens blank. This can be utilized for altering the lens focus power between the central zone, an optional intermediate zone, and a peripheral zone, in such a way that the focus power in the optical intermediate zone and non-optional peripheral zone is more minus focus power or less plus focus power that the central zone. It can also be generated by altering the index of refraction of the central zone, the optional intermediate zone, and the non-optional peripheral zone. In this case the refractive index would be less in the optional intermediate zone and non-optional peripheral zone of the lens or lens blank as compared to the central zone. And it can be caused by a combination of both altering the focal power and the index of refraction.

In reference to FIG. 39, it shows an embodiment of an ocular photo-bio-stimulation filtered defocused lens can be a lens that comprises: a central zone for correcting distance focus for the wearer and small enough to establish an effective functional zone; a selected or chosen fill factor to deliver high efficacy while preserving good wearability; a central zone of 4 mm-6 mm; and added Surface power within the range of −0.50D to −5.00D. In aspects, the fill factor can be of 0.5. In aspects, utilizing this design, the chromatic aberration of outside of the central zone can cause the blue light wavelengths to be focused deeper into the retina, while the central zone's chromatic aberration focuses the blue light wavelengths in front of the retina.

In reference to FIG. 40, it shows an embodiment of an ocular photo-bio-stimulation filtered defocused lens, which can be a lens that comprises: a spectacle lens for myopia correction and control with Highly Aspherical Lenslet Target (H.A.L.T.) Technology; a central optical zone (9 mm) for correcting distance refractive error of the wearer, with surrounding myopia control zone incorporating 1021 contiguous (touching) highly aspherical lenslets (each 1.12 mmø). Each lenslet does not have a single focal power, instead creating a 'volume of defocus' as a slow-down signal for eye growth. Each of the, in aspects, 11 rings of lenslets feature contiguous lenslets of similar asphericity, with successive rings having lenslets with different asphericities. Spaces between the rings of lenslets provide single vision correction. In aspects, added optical power peripheral to the central zone can be within the range of 0.50D to 5.00D more minus or less plus. Utilizing this design the chromatic aberration of outside of the central zone causes the blue light wavelengths to be focused deeper into the retina, while the central zone's chromatic aberration focuses the blue light wavelengths in front of the retina.

In reference to FIG. 41, still Another embodiment of an ocular photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and surrounding treatment zone with honeycomb array of lenslets (each 1.03 mm). In aspects, each lenslet can has a relative negative power within the range of 0.50D to 5.00D more minus or less plus. There can be spaces between the lenslets where the single vision correction is accessible. The precise optical power of the lenslets is selected to move the chromatic aberration blue light wavelengths back into the retina. This occurs while the central zone focuses the chromatic aberration blue light wavelengths in front of the retina.

In reference to FIG. 42, another embodiment of an ocular photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb array of lenslets (each 1.03 mmø). The lenslets can have a relative power within the range of −0.50D to −5.00D. There can be spaces between the lenslets where the single vision correction is accessible. The precise optical power of the lenslets can be selected to focus the chromatic aberration blue light wavelengths into the retina. This occurs while the central zone focuses the chromatic aberration blue light wavelengths in front of the retina. Outside of the intermediate zone there is a peripheral zone comprised of increased negative power or less plus power compared to the central zone of the lens.

In reference to FIG. 43, another embodiment of an ocular photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb micro-lens array of lenslets (each 1.03 mmø). Each lenslet can have a relative negative power within the range of 0.50D to 5.00D more minus or less plus. There can be spaces between the lenslets where the single vision correction is accessible. In this embodiment the lens power outside of the central zone also increases in minus optical power or less plus optical power. In the intermediate zone the precise combined optical power of the lenslets and the lens power is selected to focus the chromatic aberration blue light wavelengths into the retina. This occurs while the central zone focuses the chromatic aberration blue light wavelengths in front of the retina. Outside of the intermediate zone there is a peripheral zone comprised of increased negative power or less plus power compared to the central zone of the lens.

In order to determine the appropriate amount of added minus optical power to the periphery of a chromatic aberration focused optic that is used for ocular photo-bio-stimulation the use of a duo-chrome test can be helpful. An embodiment can be that of a red-blue vision test, or a green-blue vision test. When refracting a patient for their best corrected distance vision, after determining the appropriate best corrected optical power, have the patient use the distance optical power as a base line. Then while testing the patient monocularly, place a red blue see through duochrome in front of the eye. Add minus optical power until the blue side appears to be the best in focus. The optical power that provides the clearest vision when looking through the blue side of the duochrome (when adding minus lenses) should be the point when the blue light wavelengths are focusing on or in the retina. This can also be tested with a green blue duochrome. This test can be performed when looking through a blue tinted optic or lens. This test can also be performed with a blue printed distance eye chart or that of a blue projected eye chart. The amount of increase in minus power that provides the clearest blue image of either the blue duo chrome test or that of a blue eye chart can then be prescribed for the power of the non-central zone (the peripheral zone) of the chromatic aberration focused lens or optic, while measuring and prescribing the optical power required through a clear lens to achieve the BVA distance optical power for that of the central zone of the lens or optic. When testing for the peripheral optical power that will be prescribed (that of the increased minus optical power) the use of the lens material (abbe number) that will be prescribed should be utilized.

An embodiment is that of a look up chart that is calculated in advance. Such an embodiment can show the lens material with the abbe number, the distance optical power for achieving the best corrected distance visual acuity, and/or the increase in minus optical power required to move the blue wavelengths so they will focus on or in the retina for that distance BVA optical power when taking into account the abbe number for the lens material to be used for the lens that will be prescribed. Such a chart can show optical power required for the patient's distance BVA (this being the central zone's optical power) and based upon the lens material to be prescribed (its abbe number), and/or the increased minus optical power over that of the central zone optical power required for the non-central zone. This optical power in the periphery being an increase in minus optical power compared to that of the central zone. Such a look up chart can be a printed chart, manual generated electronic chart, or software automatically generated chart. By way of example only; Distance BVA correction power=−2.00D/Abee Number 30/non-central (or peripheral) optical power=−3.25D.

An embodiment can be that of an ocular photo-bio stimulation look up chart for determining the appropriate optical power for the central zone and the peripheral zone of a chromatic aberration focused lens or optic, wherein the look up chart can be one of: printed, manually electronic generated, or automatic software generated, and wherein to determine the optical power of each the central zone and the peripheral zone the user must locate on the chart or enter electronically the wearer's optical power required to provide the wearer with their distance BVA and the material (or Abee #) of which their lens will be made. Once that is filled in electronically the appropriate non-central zone (or peripheral zone) optical power will be expressed. The optical power required for the distance BVA can be expressed as their distance optical power prescription. The optical power required for the distance BVA can be expressed as their distance optical power spherical equivalent.

Sunglass Lens or Optic that Provides Ocular Photo-Bio-Stimulation

Embodiments when light wavelengths are generated by way of filtered optics or filtered lenses the transmission peak of the wavelength range that strike the eye's retina falls within the wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

An embodiment can be an eyewear apparatus worn by a wearer comprising a filtered lens or filtered optic, wherein the filtered lens or filtered optic of the eyewear apparatus transmits light at a light wavelength transmission rate of 50% or more within a light wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to an eye of the wearer, and wherein the filtered lens or filtered optic of the eyewear apparatus comprises an overall visible light transmission of 40% or less.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens.

Visible light transmission (VLT) is measured as a percentage of the total visible light that strikes the lenses and is affected by a number of factors such as lens material and thickness, the base lens color, and the coatings applied on top. The VLT percentage tells how much light will reach your eyes. The lower the percentage, the darker your glasses will be.

In reference to FIG. 44, there are 5 sunglass categories of VLT. Sunglasses that fall within categories 2 and 3 are the most popular sunglasses. Category 2 transmits visible light between 18%-43%. Categories, such as categories 3 or 4 filter or block most blue light wavelengths.

Figure 45:
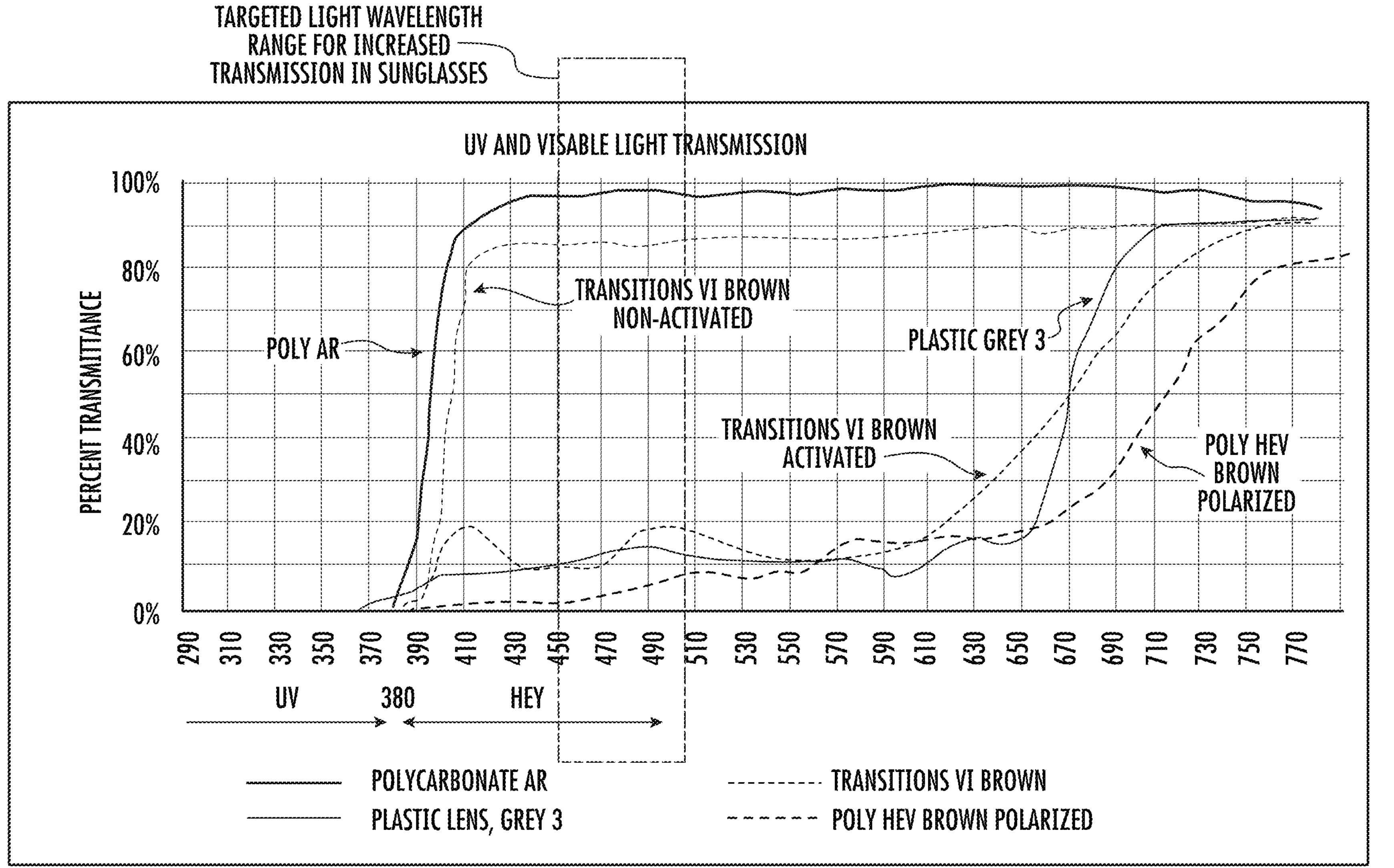
FIG. 45 shows information related to the invention described herein.

In reference to FIG. 45, most sunglass manufacturers lead their marketing by providing information on how much blue light is filtered or blocked with their sunglasses. Unfortunately, sunglasses that fit within categories 3, 4 and 5 provide substantial vision and ocular protection. However, given that they block or filter most blue light and transmit so little, they actually inhibit the production of dopamine in the eye of the wearer and possibly serotonin and dopamine in the brain of the wearer while being worn. This is true of all sunglasses that transmit 43% or less visible light wavelengths including those that are polarized or photochromatic.

Figure 46:
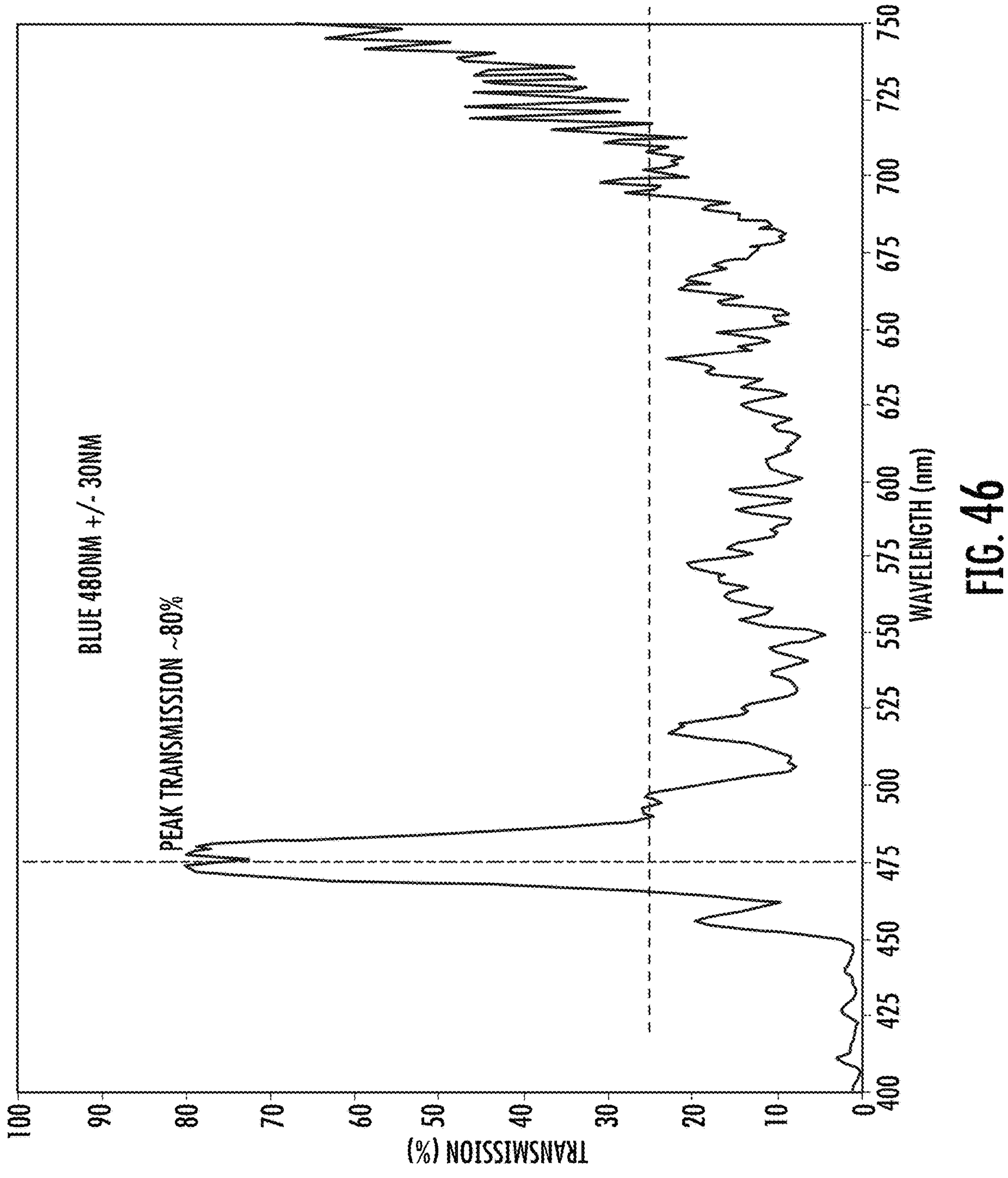
FIG. 46 shows information related to the invention described herein.

In reference to FIG. 46, there is a pressing need for sunglasses having an overall visible light transmission of 40% or less visible light while transmitting 41% or more blue light wavelengths within the range of 480 nm+/−30 nm, and, in addition, that pass color transmission standards/requirements so to be able to permit the wearer to drive and properly identify the colors red and green, by way of example only, on a red light. Sunglasses having a 41% or greater transmission within the wavelength range of 480 nm+/−30 nm would transmit enough of the light wavelengths that are known to stimulate dopamine in the eye's retina and in the brain of the wearer. This then could be most beneficial for individuals suffering from dopamine deficiency disorder.

Figure 47:
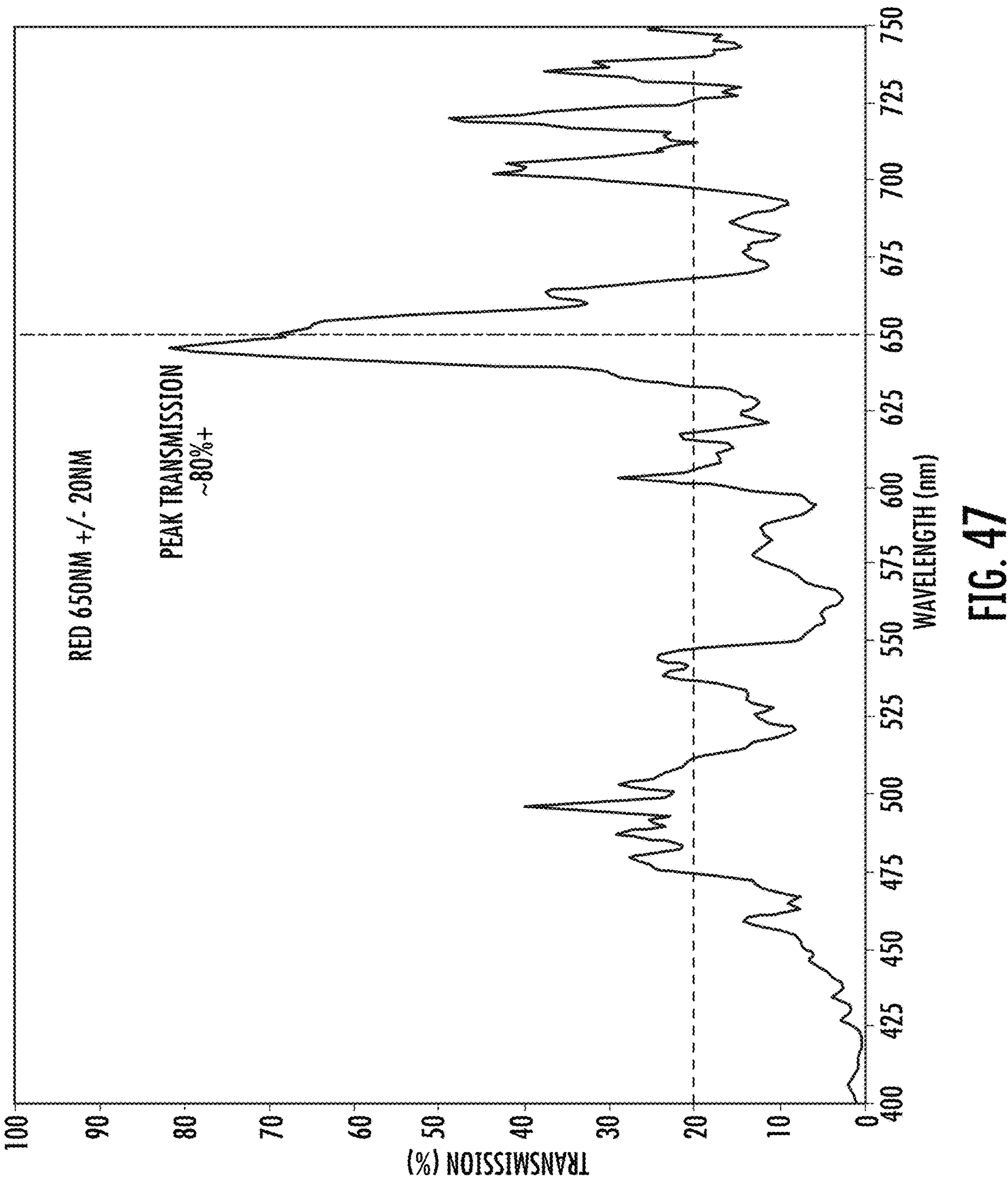
FIG. 47 shows information related to the invention described herein.

In reference to FIG. 47, this shows sunglasses having an overall transmission of 40% or less visible light while transmitting 41% or more red light wavelengths within the range of 650 nm+/−30 nm. In addition, these need to pass color transmission standards/requirements so to be able to permit the wearer to drive and properly identify the colors red and green, by way of example only, on a red light. Sunglasses having a 41% or greater transmission within the wavelength range of 650 nm+/−30 nm would transmit enough of the light wavelengths that are known to stimulate dopamine in the eye's retina and in the brain of the wearer. This then could be most beneficial for individuals suffering from dopamine deficiency disorder.

In certain embodiments a sunglass lens or optic comprises two or more absorptive dyes, wherein one or more of the absorptive dyes filters or blocks light wavelengths within the range of 450 nm downward to 400 nm or lower, and one or more absorptive dyes that filter or block light wavelengths within the range of 490 nn upward to 700 nm or greater, and wherein the light transmission within the range of wavelengths of 450 nm and 490 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic.

In certain embodiments a sunglass lens or optic comprises two or more absorptive dyes, wherein one or more of the absorptive dyes filters or blocks light wavelengths within the range of 440 nm downward to 400 nm or lower, and one or more absorptive dyes filter or block light wavelengths within the range of 500 nn upward to 700 nm or greater, and wherein the light transmission within the range of wavelengths of 440 nm and 510 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic.

In certain embodiments a sunglass lens or optic comprises two or more absorptive dyes, wherein one or more of the absorptive dyes filters or blocks light wavelengths within the range of 450 nm downward to 400 nm or lower, and one or more absorptive dyes filter or block light wavelengths within the range of 490 nn upward to 650 nm or greater, and wherein the light transmission within the range of wavelengths of 450 nm and 510 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic.

In certain embodiments a sunglass lens or optic comprises two or more absorptive dyes, wherein one or more of the absorptive dyes filters or blocks light wavelengths within the range of 440 nm downward to 400 nm or lower, and one or more absorptive dyes filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic.

In certain embodiments a sunglass lens or optic comprises two or more absorptive dyes, wherein one or more of the absorptive coatings filters or blocks light wavelengths within the range of 450 nm downward to 400 nm or lower, and one or more absorptive coatings filter or block light wavelengths within the range of 490 nn upward to 700 nm or greater, and wherein the light transmission within the range of wavelengths of 450 nm and 490 nm is 40% or more and the overall visible light transmission of the sunglass lens is 30% or less. One or more absorptive coatings can be coated on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more absorptive coatings, wherein one or more of the absorptive coatings filters or blocks light wavelengths within the range of 450 nm downward to 400 nm or lower, and one or more absorptive coatings filter or block light wavelengths within the range of 500 nn upward to 700 nm or greater, and wherein the light transmission within the range of wavelengths of 450 nm and 510 nm is 40% or more and the overall visible light transmission of the sunglass lens is 30% or less. One or more absorptive coatings can be coated on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more absorptive coatings, wherein one or more of the absorptive coatings filters or blocks light wavelengths within the range of 450 nm downward to 400 nm or lower, and one or more absorptive coatings filter or block light wavelengths within the range of 490 nn upward to 650 nm or greater, and wherein the visible light transmission within the range of wavelengths of 450 nm and 510 nm is 40% or more and the overall light transmission of the sunglass lens is 30% or less. One or more absorptive coatings can be coating on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more absorptive coatings, wherein one or more of the absorptive coatings filters or blocks light wavelengths within the range of 440 nm downward to 400 nm or lower, and one or more absorptive coatings filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more absorptive coatings can be coated on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more reflective coatings, wherein one or more of the reflective coatings filters or blocks light wavelengths within the range of 450 nm downward to 400 nm or lower, and one or more reflective coatings filter or block light wavelengths within the range of 490 nn upward to 700 nm or greater, and wherein the light transmission within the range of wavelengths of 450 nm and 510 nm is 40% or more and the overall visible light transmission of the sunglass lens is 30% or less. One or more reflective coatings can be coated on one of the surfaces of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more reflective coatings, wherein one or more of the reflective coatings filters or blocks light wavelengths within the range of 440 nm downward to 400 nm or lower, and one or more reflective coatings filter or block light wavelengths within the range of 500 nn upward to 700 nm or greater, and wherein the light transmission within the range of wavelengths of 440 nm and 510 nm is 40% or more and the overall visible light transmission of the sunglass lens is 30% or less. One or more reflective coatings can be coated on one of the surfaces of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface casting.

In certain embodiment a sunglass lens or optic comprises two or more reflective coatings, wherein one or more of the reflective coatings filters or blocks light wavelengths within the range of 450 nm downward to 400 nm or lower, and one or more reflective coatings filter or block light wavelengths within the range of 490 nn upward to 650 nm or greater, and wherein the light transmission within the range of wavelengths of 450 nm and 490 nm is 40% or more and the overall visible light transmission of the sunglass lens is 30% or less. One or more reflective coatings can be coating on one of the surfaces of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more reflective coatings, wherein one or more of the reflective coatings filters or blocks light wavelengths within the range of 440 nm downward to 400 nm or lower, and one or more reflective coatings filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more reflective coatings can be coated on the surface of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more reflective, or absorptive coatings and/or absorptive dyes, wherein one or more of the reflective coatings or absorptive coatings and/or absorptive dyes filters or blocks light wavelengths within the range of 450 nm downward to 400 nm or lower, and one or more reflective coatings or absorptive coatings and/or absorptive dyes filter or block light wavelengths within the range of 490 nn upward to 700 nm or greater, and wherein the light transmission within the range of wavelengths of 450 nm and 490 nm is 40% or more and the overall visible light transmission of the sunglass lens is 30% or less. One or more reflective coatings or absorptive coatings and/or absorptive dyes can be coated and/or imbibed on a surface of the lens or optic. One or more reflective coatings or absorptive coatings and/or absorptive dyes can be coated and/or imbibed on the convex surface of the lens or optic. One or more reflective coatings or absorptive coatings and/or absorptive dyes can be coated and/or imbibed on the concave surface of the lens or optic. The coating(s) can be coated by vacuum deposition. The coating(s) can be coated by spin coating. The coating(s) can be coated by surface casting. The dyes (can) can be imbibed by using a heat bath.

In certain embodiments a sunglass lens or optic comprises two or more reflective coatings or absorptive coatings and/or absorptive dyes, wherein one or more of the reflective coatings or absorptive coatings and/or absorptive dyes filters or blocks light wavelengths within the range of 440 nm downward to 400 nm or lower, and one or more reflective coatings or absorptive coatings and/or absorptive dyes filter or block light wavelengths within the range of 500 nn upward to 700 nm or greater, and wherein the light transmission within the range of wavelengths of 440 nm and 510 nm is 40% or more and the overall visible light transmission of the sunglass lens is 30% or less. One or more reflective coatings or absorptive coatings and/or absorptive dyes can be coated on a surface of the lens or optic. One or more reflective coatings or absorptive coatings and/or absorptive dyes can be coated or imbibed on the convex surface of the lens or optic. One or more reflective coatings can be coated or imbibed on the concave surface of the lens or optic. The coating(s) can be coated by vacuum deposition. The coating(s) can be coated by spin coating. The coating(s) can be coated by surface casting. The dyes(can) can be imbibed by use of a heat bath.

In certain embodiments a sunglass lens or optic comprises two or more reflective coatings or absorptive coatings and/or absorptive dyes, wherein one or more of the reflective coatings or absorptive coatings and/or absorptive dyes filters or blocks light wavelengths within the range of 450 nm downward to 400 nm or lower, and one or more reflective coatings or absorptive coatings and/or absorptive dyes filter or block light wavelengths within the range of 490 nn upward to 650 nm or greater, and wherein the light transmission within the range of wavelengths of 450 nm and 490 nm is 40% or more and the overall visible light transmission of the sunglass lens is 30% or less. One or more reflective coatings or absorptive coatings and/or absorptive dyes can be coated or imbibed on a surface of the lens or optic. One or more reflective coatings or absorptive coatings and/or absorptive dyes can be coated or imbibed on the convex surface of the lens or optic. One or more reflective coatings or absorptive coatings and/or absorptive dyes can be coated or imbibed on the concave surface of the lens or optic. The coating(s) can be coated by vacuum deposition. The coating(s) can be coated by spin coating. The coating(s) can be coated by surface casting. The dyes(can) can be imbibed by use of a heat bath.

In certain embodiments a sunglass lens or optic comprises two or more reflective coatings, or absorptive coatings and/or absorptive dyes, wherein one or more of the reflective coatings, or absorptive coatings and/or absorptive dyes, filters or blocks light wavelengths within the range of 440 nm downward to 400 nm or lower, and one or more reflective coatings or absorptive coatings and/or absorptive dyes filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more reflective coatings or absorptive coatings and/or absorptive dyes can be coated or imbibed on the surface of the lens or optic. One or more reflective coatings or absorptive coatings and/or absorptive dyes can be coated or imbibed on the convex surface of the lens or optic. One or more reflective coatings or absorptive coatings and/or absorptive dyes can be coated or imbibed on the concave surface of the lens or optic. The coating(s) can be coated by vacuum deposition. The coating(s) can be coated by spin coating. The dyes(can) can be imbibed by use of a heat bath. The coating(s) can be coated by surface casting.

An embodiment as described herein is a sunglass lens or optic, wherein the light transmission within the range of wavelengths of 440 nm and 490 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 450 nm and 510 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 460 nm and 500 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 480 nm+/−10 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 480 nm+/−20 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 480 nm+/−30 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

Ocular photo-bio-stimulation sunglasses can be a sunglass lens or optic, wherein the light transmission within the range of wavelengths of 440 nm and 490 nm is 40% or more and the overall visible light transmission of the sunglass lens is 30% or less. A sunglass lens or optic, wherein the light transmission within the range of wavelengths of 450 nm and 510 nm is 40% or more and the overall visible light transmission of the sunglass lens is 35% or less. A sunglass lens or optic, wherein the light transmission within the range of wavelengths of 460 nm and 510 nm is 40% or more and the overall visible light transmission of the sunglass lens is 35% or less. A sunglass lens or optic, wherein the light transmission within the range of wavelengths of 475 nm+/−20 nm is 40% or more and the overall light visible transmission of the sunglass lens is 35% or less. A sunglass lens or optic, wherein the light transmission within the range of wavelengths of 475 nm+/−30 nm is 40% or more and the overall light visible transmission of the sunglass lens is 35% or less. A sunglass lens or optic, wherein the light transmission within the range of wavelengths of 480 nm+/−30 nm is 40% or more and the overall light visible transmission of the sunglass lens is 35% or less. A sunglass lens or optic, wherein the light transmission within the range of wavelengths of 480 nm+/−30 nm is 40% or more and the overall light visible transmission of the sunglass lens is 30% or less. A sunglass lens or optic, wherein the light transmission within the range of wavelengths of 480 nm+/−30 nm is 40% or more and the wherein the overall light visible transmission of the sunglass lens is 25% or less.

Ocular photo-bio-stimulation sunglasses can be a sunglass lens or optic, wherein the light transmission within the range of wavelengths of 470 nm and 520 nm is 40% or more, and the overall visible light transmission of the sunglass lens is 30% or less. Another embodiment includes a sunglass lens or optic, wherein the light transmission within the range of wavelengths of 480 nm and 520 nm is 40% or more, and the overall visible light transmission of the sunglass lens is 35% or less. Another embodiment is a sunglass lens or optic, wherein the light transmission within the range of wavelengths of 490 nm and 520 nm is 40% or more and the overall visible light transmission of the sunglass lens is 35% or less. Another embodiment is a sunglass lens or optic, wherein the light transmission within the range of wavelengths of 500 nm+/−20 nm is 40% or more and the overall visible light transmission of the sunglass lens is 35% or less. Another embodiment is a sunglass lens or optic, wherein the light transmission within the range of wavelengths of 490 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall light visible transmission of the sunglass lens is 35% or less. Another embodiment is a sunglass lens or optic, wherein the visible light transmission within the range of wavelengths of 470 nm+/−30 nm is 40% or more and the overall visible light transmission of the sunglass lens is 30% or less. Another embodiment is a sunglass lens or optic, wherein the light transmission within the range of wavelengths of 485 nm+/−30 nm is 40% or more and the overall visible light transmission of the sunglass lens is 25% or less.

Ocular photo-bio-stimulation sunglasses can be a sunglass lens or optic, wherein the light transmission within the range of wavelengths of 480 nm+/−30 nm is 40% or more, and the overall visible light transmission of the sunglass lens is 30% or less. Another embodiment includes a sunglass lens or optic, wherein the light transmission within the range of wavelengths of 480 nm+/−30 nm is 40% or more, and the overall visible light transmission of the sunglass lens is 35% or less. Another embodiment is a sunglass lens or optic, wherein the light transmission within the range of wavelengths of 480 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall light visible transmission of the sunglass lens is 35% or less. Another embodiment is a sunglass lens or optic, wherein the visible light transmission within the range of wavelengths of 480 nm+/−30 nm is 40% or more and the overall visible light transmission of the sunglass lens is 30% or less. Another embodiment is a sunglass lens or optic, wherein the light transmission within the range of wavelengths of 480 nm+/−30 nm is 40% or more and the overall visible light transmission of the sunglass lens is 25% or less. Another embodiment is a sunglass lens or optic, wherein the light transmission within the range of wavelengths of 480 nm+/−30 nm is 40% or more and the overall visible light transmission of the sunglass lens is 20% or less.

Ocular photo-bio-stimulation sunglasses can be a sunglass lens or optic, wherein the light transmission within the range of wavelengths of 500 nm+/−30 nm is 40% or more, and the overall visible light transmission of the sunglass lens is 30% or less. Another embodiment includes a sunglass lens or optic, wherein the light transmission within the range of wavelengths of 500 nm+/−30 nm is 40% or more, and the overall visible light transmission of the sunglass lens is 35% or less. Another embodiment is a sunglass lens or optic, wherein the light transmission within the range of wavelengths of 500 nm+/−30 nm is 40% or more and the overall visible light transmission of the sunglass lens is 35% or less.

Another embodiment is a sunglass lens or optic, wherein the light transmission within the range of wavelengths of 500 nm+/−30 nm is 40% or more and the overall visible light transmission of the sunglass lens is 35% or less. Another embodiment is a sunglass lens or optic, wherein the light transmission within the range of wavelengths of 500 nm+/−30 nm is 40% or more and the overall visible light transmission of the sunglass lens is 35% or less. Another embodiment is a sunglass lens or optic, wherein the light transmission within the range of wavelengths of 500 nm+/−30 nm is 40% or more and the overall light visible transmission of the sunglass lens is 35% or less. Another embodiment is a sunglass lens or optic, wherein the visible light transmission within the range of wavelengths of 500 nm+/−30 nm is 40% or more and the overall visible light transmission of the sunglass lens is 30% or less. Another embodiment is a sunglass lens or optic, wherein the light transmission within the range of wavelengths of 500 nm+/−30 nm is 40% or more and the overall visible light transmission of the sunglass lens is 25% or less. Another embodiment is a sunglass lens or optic, wherein the light transmission within the range of wavelengths of 500 nm+/−30 nm is 40% or more and the overall visible light transmission of the sunglass lens is 20% or less.

Ocular photo-bio-stimulation sunglasses can be a sunglass lens or optic, wherein the light transmission within the range of wavelengths of 650 nm+/−30 nm or 700 nm+/−30 nm is 40% or more, and the overall visible light transmission of the sunglass lens is 30% or less. Another embodiment includes a sunglass lens or optic, wherein the light transmission within the range of wavelengths of 650 nm+/−30 nm or 700 nm+/−30 nm is 40% or more, and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall light visible transmission of the sunglass lens is 35% or less. Another embodiment is a sunglass lens or optic, wherein the visible light transmission within the range of wavelengths of 650 nm+/−30 nm or 700 nm+/−30 nm is 40% or more and the overall visible light transmission of the sunglass lens is 30% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 25% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 20% or less.

In reference to FIG. 48, another embodiment is that of a sunglass lens or optic, wherein the sunglass lens comprises two wavelength peaks of transmission, wherein one wavelength peak of transmission is within the wavelength range of 480 nm+/−30 nm and a second wavelength peak of transmission is within the wavelength range of 650 nm+/−30 nm or 700 nm+/−30 nm, and wherein the light transmission of each peak is 40% or greater and wherein the overall visible light transmission of the sunglass lens is 40% or less. Another embodiment is one wherein one wavelength peak of transmission is within the wavelength range of 480 nm+/−30 nm and a second wavelength peak of transmission is within the wavelength range of 650 nm+/−30 nm or 700 nm+/−30 nm, and wherein the light transmission of each peak is 40% or greater and wherein the overall visible light transmission of the sunglass lens is 30% or less. Another embodiment is wherein one wavelength peak of transmission is within the wavelength range of 480 nm+/−30 nm and a second wavelength peak of transmission is within the wavelength range of 650 nm+/−30 nm or 700 nm+/−30 nm, and wherein the light transmission of each peak is 50% or greater and wherein the overall visible light transmission of the sunglass lens is 40% or less.

Another embodiment is that of a sunglass lens or optic, wherein the sunglass lens or optic comprises a peak of visible wavelength transmission, wherein the visible wavelength peak of transmission is within the wavelength range of 480 nm+/−30 nm, and wherein the transmission peak of the wavelengths within the range of 480 nm+/−30 nm is 40% or greater.

XR Devices for Ocular Photo-Bio-Stimulation

Figure 49:
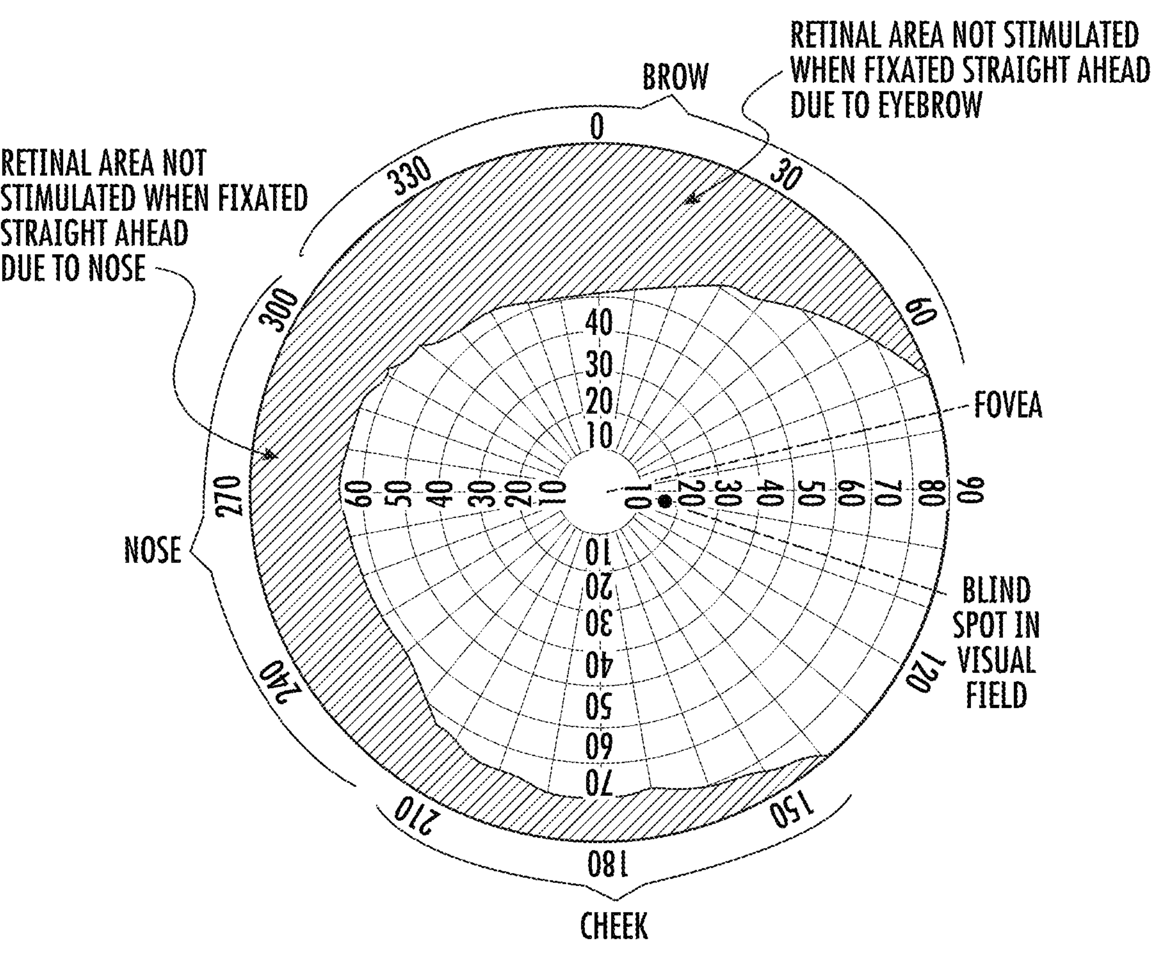
FIG. 49 shows information related to the invention described herein.

In reference to FIG. 49, the retina is comprised of a central zone, mid peripheral zone and a far peripheral zone. Approximately an estimated 20%-30% of each eye's retina is not stimulated by light when looking straight ahead. This is because one's nose and eyebrow interfere with light rays that could stimulate portions of the peripheral retina. Given the more retina of an eye that is stimulated the more robust the ocular photo-bio-stimulation response may be, or the greater efficacy it may have, it is important to apply the ocular photo-bio-stimulation light therapy to as much of the retina as possible. In addition, certain eye diseases, for example only, retinitis pigmentosa, that could be treated with ocular photo-bio-stimulation occur in the far periphery of the retina. There is a need for a way to be able to stimulate and/or treat areas of the retina that under normal circumstances are rarely stimulated with light. The inventive embodiments disclosed herein allow for this to occur.

Embodiments when light wavelengths are generated by way of filtered optics or filtered lenses the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina falling within the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Figure 50:
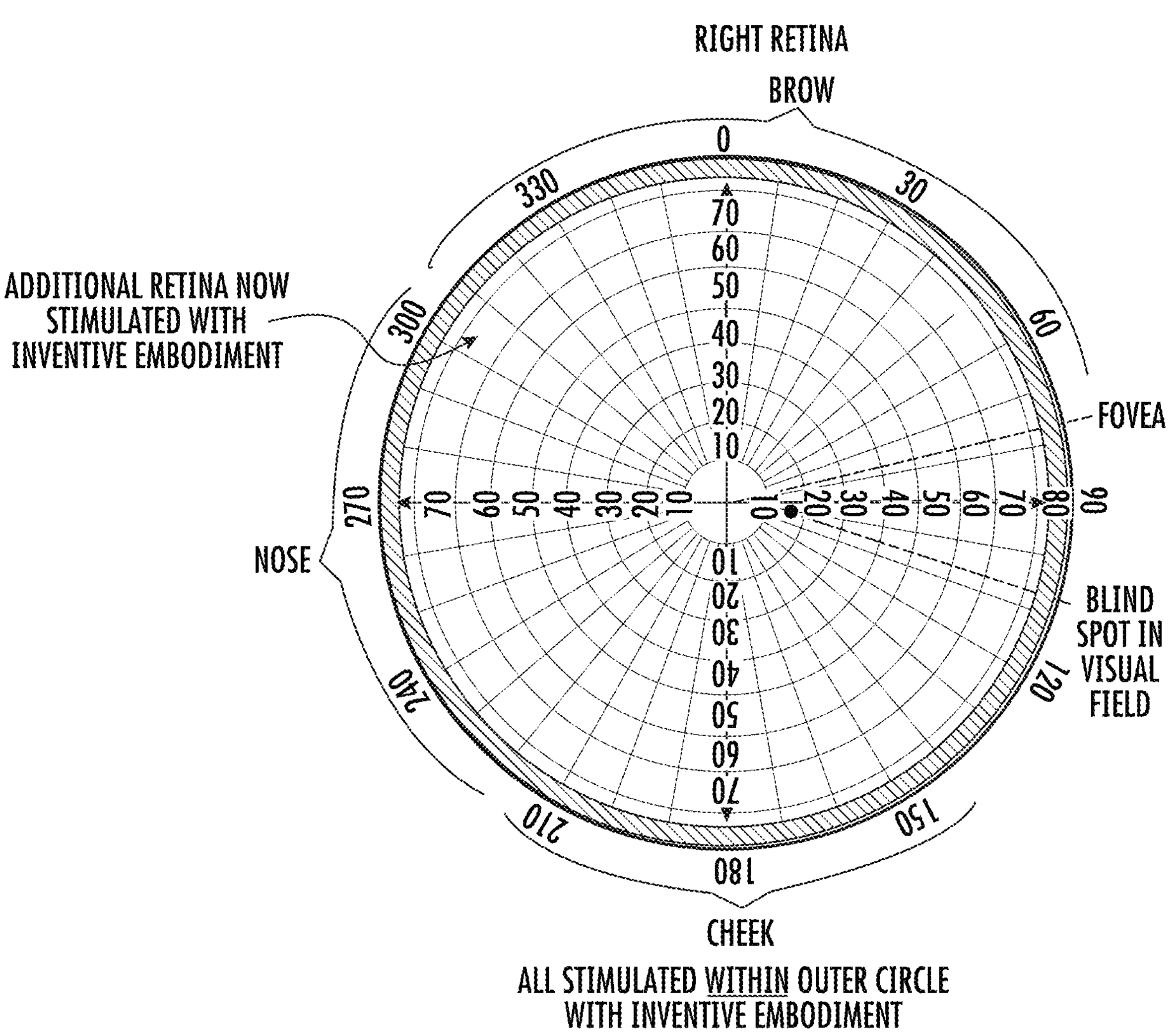
FIG. 50 shows information related to the invention described herein.

In reference to FIG. 50, with XR inventive embodiments disclosed herein it is possible to stimulate areas of the retina of an eye by way of ocular photo-bio-stimulation in such a manner to stimulate the 20%-30% that is normally not stimulated. This is due to the embodiments disclosed herein that cause the painting of all areas of the retina with the desired ocular photo-bio-stimulation wavelengths of light. Such desired wavelengths of light can be, by way of example only, one within the range of wavelengths of at least one of: 480 nm+/−30 nm, 480 nm+/−20 nm, 500 nm+/−30 nm, 500 nm+/−20 nm, 510 nm+/−30 nm, 510 nm+/−20 nm, 530 nm+/−20 nm, or 650 nm+/−30 nm, or 700 nm+/−30 nm. In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm, 470 nm to 520 nm, or 480 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens.

In ocular photo-bio-stimulation embodiments, the virtual image as seen with AR, VR, MR, Modified Reality, and/or XR eyewear as described herein is one or more of a blue light image (with wavelengths within the range of 480 nm+/−30 nm), a green light image (with wavelengths within the range of 530 nm+/−20 nm), and/or a red-light image (with wavelengths within the range of 650 nm+/−30 nm or 700 nm+/−30 nm). In certain embodiments of VR eyewear, the device embodiment can comprise a filter or a combination of filters for transmitting one or two virtual images. In certain embodiments of AR, MR, VR, Modified Reality, XR eyewear as described herein, they can comprise a filter, or a combination of filters, for transmitting the real image and/or virtual images. The filter or filters can be one or more of a bandpass filter, interference filter, absorptive filter, selective light filter, notch filter, and/or neutral density filter. The filter or filters can transmit light wavelengths, by way of example only, within one or more of the ranges of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. In certain ocular photo-bio-stimulation embodiments of the current invention, the real image that passes through a filter(s) can be of any color, but a color that allows for the user to see the real image comprising wavelengths within the range of 480 nm+/−30 nm in the morning and by switching the filter(s) red wavelengths of 650 nm+/−30 nm in the afternoon. The filter(s) can cause the real image to have a light transmission of 80% or less, 50% or less, or 40% or less. The lower overall visible light transmission through the XR device to the eye, while at the same time transmitting the desired range of wavelengths for ocular photo-bio-stimulation, can enlarge the pupil diameter of the user of the XR device. By way of example only, in certain embodiments a virtual image can be of a black spot that moves around within the virtual image. By way of example only, in certain embodiments the virtual image can be of a black spot that moves around within the real image. By way of example only, in certain embodiments the real image can be of an image that moves around within the virtual image. By way of example only, in certain embodiments the virtual image can be of a colored (which includes black) or white spot that moves around within the real image. In certain other embodiments one virtual image can comprise, by way of example only, a moving black spot that is moving within the perimeter of a second virtual image. In certain other embodiments one virtual image can comprise, by way of example only, a moving black spot that is moving within the perimeter of the same virtual image. In certain embodiments, the virtual image with the moving black spot that moves within the perimeter of the virtual image is part of the same virtual image. Thus, there is only one virtual image. In other embodiments the virtual image with the moving black spot that moves within the perimeter of the virtual image is a separate virtual image that appears within the perimeter but is really an overlapping virtual image. Thus, in this case there would be two virtual images.

Filter(s) can cause the real image to have a light transmission of 50% or less. The filter(s) can cause the real image to have a light transmission of 25% or less. A real image can be an image of a solid color or black. A virtual image can be an image of a color(s) including black. In certain cases, the real image and the virtual image can both be images seen distance separated along the Z axis from the wearer's eye. In cases, the real image is the distance image, and the virtual image is the nearer image, and vice versa. In certain cases of XR, AR, MR, and Modified reality eyewear, the eyes can be fixated on the real image as it moves within the virtual image. In certain cases of XR, AR, MR, Modified reality eyewear, the eyes can be fixated on the real image as it moves within the virtual image.

In certain cases of VR or Modified Reality, the eyes can be fixated on one virtual image as it moves within, around, or in reference to a different virtual image. Still in some cases with Modified Reality, a virtual image can comprise two or more parts with one part moving within the second part. Said another way, one portion of the virtual image can move while the other portion of the same virtual image can be stationary. The eye of a user can fixate on the moving image while the stationary image paints the retina of the eye, or the eye can fixate on the stationary image while the moving image paints the retina of an eye of the user.

In some ocular photo-bio-stimulation embodiments, the eyewear comprises an electronic display attached to the eyewear that projects blue light, or green light, or red-light, through a wave guide to an optic housed within the eyewear. In some embodiments the eyewear comprises an electronic display attached or integrated within a wave guide to an optic housed within the eyewear. In some embodiments the eyewear comprises an electronic display that is attached to or integrated within an optic housed or supported by the eyewear. In some cases, the eyewear houses or supports an optic that incorporates an electronic display and wherein the wearer looks through the electronic display while the electronic display projects blue, or green, or red-light. In various AR, MR, VR, and/or Modified Reality embodiments, a non-see-through near eye display can be utilized to generate a lighted virtual reality image. In some cases, two non-see-through near eye displays are utilized to generate lighted virtual reality images. In some cases, a see-through near eye display can be utilized to generate a lighted virtual reality image. In some cases, two-see-through near eye display can be utilized to generate lighted virtual reality images. In some cases, a non-see-through near eye display optically aligned or in optical communication with a micro-lens array can be is utilized to generate a lighted virtual reality image. In some cases, two non-see-through near eye displays optically aligned or in optical communication with micro-lens arrays are utilized to generate lighted virtual reality images. In some cases, a see-through near eye display optically aligned or in optical communication with a micro-lens array can be utilized to generate a lighted virtual reality image. In certain cases, the micro-lens array can comprise a filtering agent(s). The filtering agent(s) can be coated on to the micro-lens array. The filtering agent(s) can be embedded in the matrix of the microlens array. The filtering agent(s) can be imbibed within the micro-lens array.

In some cases, a see-through near eye display optically aligned or in optical communication with a micro-lens array can be utilized to generate a lighted virtual reality image. In some cases, a see-through near eye display optically aligned or in optical communication with a micro-lens array can be utilized in optical communication with a see-through near eye display to generate a lighted virtual reality image. In some cases, a non-see-through near eye display optically aligned or in optical communication with micro-lens array can be utilized in optical communication (but slightly offset) with a second see-through near eye display to generate a lighted virtual reality image. In some cases, a non-see-through near eye display optically aligned or in optical communication with a micro-lens array can be utilized in optical communication (but slightly offset) with a see-through near eye display that can be aligned with a second micro-lens array to generate a lighted virtual reality image. In some cases, a see-through near eye display optically aligned or in optical communication with a micro-lens array can be in optical communication (but slightly offset) with a second see-through near eye display, which is aligned and in optical communication with a second microlens array, to generate a lighted virtual reality image.

In some cases, a see-through near eye display optically aligned or in optical communication with a micro-lens array can be in optical communication (but slightly offset) with a second see-through near eye display which is aligned and in optical communication with a second microlens array, to generate a lighted virtual reality image while permitting the viewing of a real image through both see-through near eye displays and both microlens arrays.

In some cases, the electronic display provides diffuse blue, green, or red-light all over. In some cases, the electronic display allows the wearer to see an object, image or words, displayed on the display, which is surrounded by blue, or green or red-light, or comprises blue, or green, or red-light peripheral to the object, image, or words being displayed. In certain embodiments, by way of example only, VR (Virtual Reality) or AR (Augmented Reality), or MR (Mixed Reality), or modified reality, the blue, or green, or red light, can be provided in a diffused manner. In other embodiments, especially with VR, AR, MR eyewear, a targeting image or video that caused movement can cause the eyes to gaze while seeing the blue, or green, or red diffused light. In certain embodiments, especially with VR or AR, the blue, or green, or red light, can be provided as the background light, by way of example only, a blue sky or blue ocean, or green grass, or a red sun. By way of example only, a real image can be the object being viewed in the distance and the diffused and/or defocused light can be that of the virtual image. By utilizing this approach, it permits the pupil of the eye to be less constricted.

Figure 51:
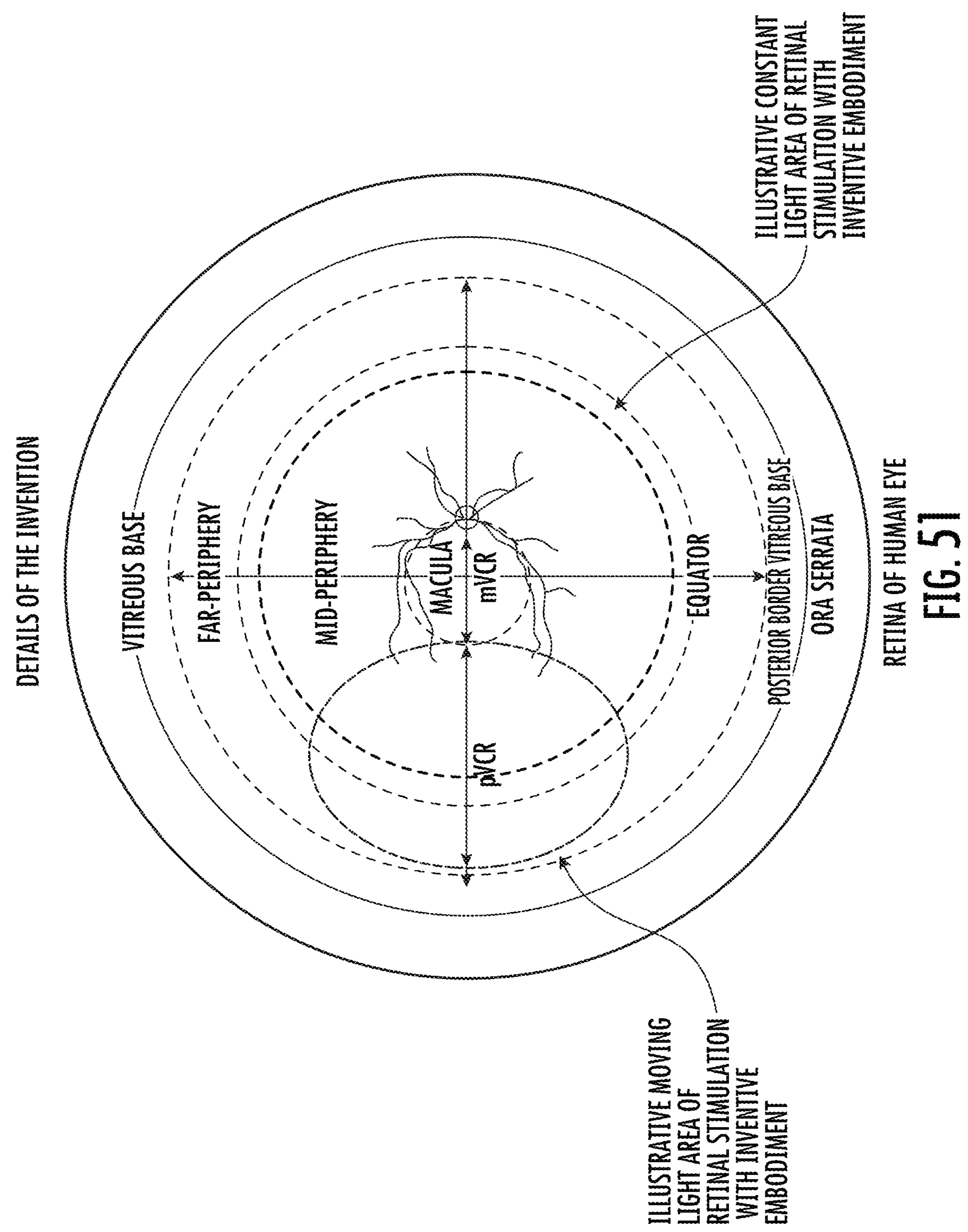
FIG. 51 shows information related to the invention described herein.

In reference to FIG. 51, in most, but not all cases of XR according to the present invention, the image that is stationary is the image or scene that is providing the ocular photo-bio-stimulation to the retina as the eye moves in reference to this stationary image or scene. In most, but not all cases of XR for the invention described herein, the moving image on which the eye is fixated on, is a moving image that focuses on the fovea or macula, while the stationary image or scene is the image that is stimulating the one or more of rods, ganglion cells, or cones of the retina. In addition, generally but not always, the fixated image is smaller than the stationary image that is painting portions of the retina as the eye follows the moving fixated image. For clarity, in most cases the stationary image provides the light of the desired wavelength and intensity for stimulating one or more of the rods, ganglion cells, or cones. The stationary image paints with a band of desired wavelengths of light (by way of example only, 480 nm+/−30 nm or 650 nm+/−30 nm, or 700 nm+/−30 nm) a portion or most of the peripheral retina because the eye is moving relative to the stationary image. In certain cases, both images are moving, however the user fixates on one image as it moves relative to the other. In this case the image that paints with a desired band of light wavelengths the peripheral retina or a portion thereof, is the image that is not fixated by the user's macula, or fovea.

In reference to FIG. 51, by way of example only, for increasing dopamine in the eye's retina as the eye follows the moving image, the fovea or macula will be fixated on that moving image causing the eye to move relative to the stationary image. This allows the light that makes up the stationary image to paint the retina. By way of example only, the stationary image can be a blue image having wavelengths of light within the range of 450 nm-500 nm with over a 300-lux intensity or a red image of 500 lux intensity or greater having wavelengths of light within the range of 650 nm+/−30 nm or 700 nm+/−30 nm, and the moving image can be of any color that stands out against the blue image or red image, including that of black or white. By way of example only, for treating retinitis pigmentosa and increasing the number of healthy mitochondria in the periphery of the eye, the stationary image can be a red image having wavelengths of light within the range of 650 nm-700 nm or near IR of 830 nm+/−30 nm, and the moving image can be of any color that stands out against the red image including that of black or white.

However, by way of another example only, for treating macular degeneration, the fixated moving image or that of a fixated stationary image whereby the fovea and or macula is fixated can be a red image having wavelengths of light within the range of 650 nm-700 nm, 700 nm+/−30 nm, or 830 nm+/−30 nm. In certain embodiments the image that moves and is fixated on by one's fovea can be that of black, dark grey, or red. When using black or dark grey, there is less light stimulation for causing the pupil of the eye of the viewer to constrict fully. Likewise, a red fixation target can allow for the pupil of the eye to be slightly larger. By utilizing the embodiments disclosed herein it is possible to provide ocular photo-bio-stimulation therapy to each of the retina's macula, fovea, optic nerve head, central zone, mid periphery zone, and far periphery zone.

Figure 52:
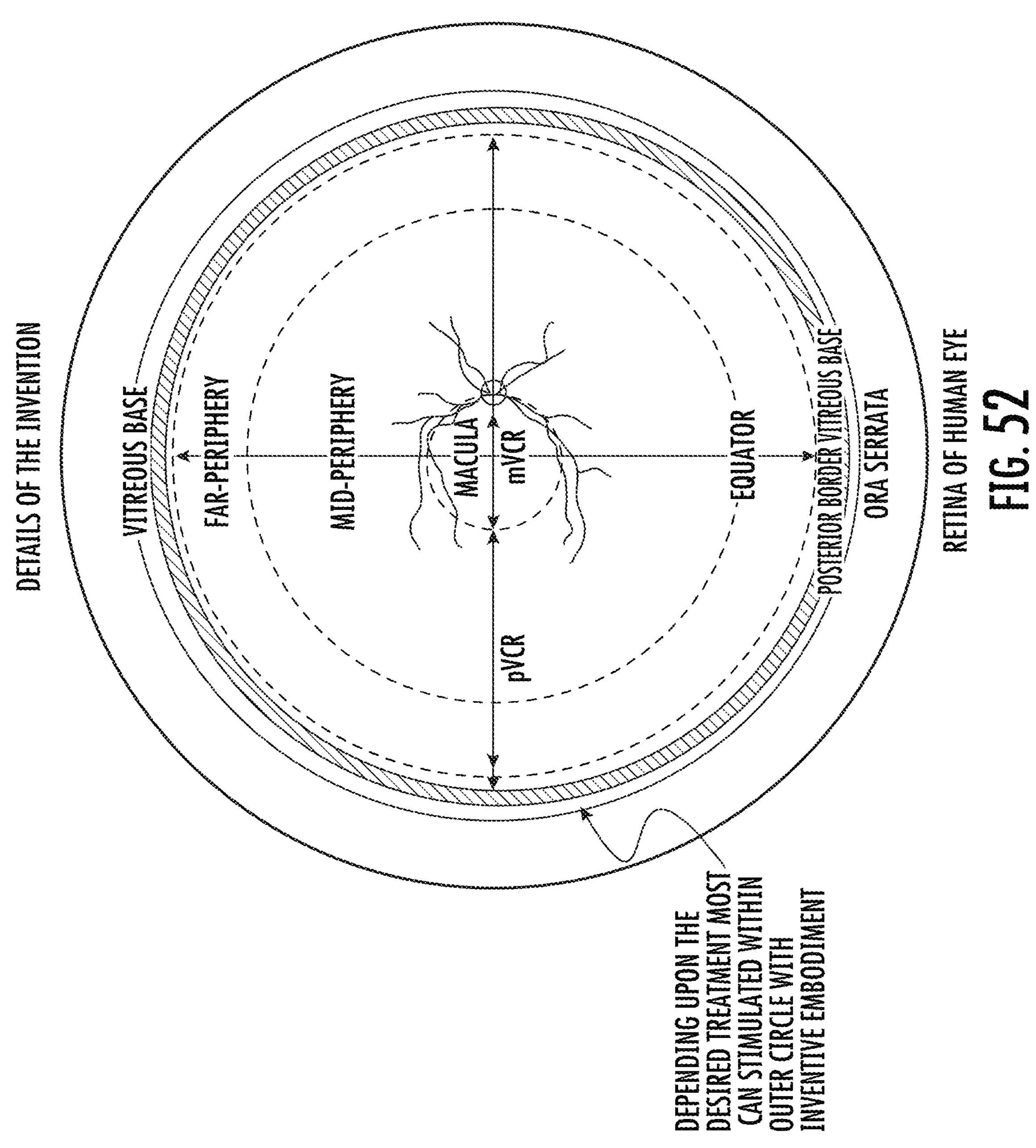
FIG. 52 shows information related to the invention described herein.

In reference to FIG. 52, embodiments of defocused light can be used for generating an image. In certain embodiments focused light can be used for generating an image. In certain embodiments one image can be generated with focused light and the other with defocused light. By using defocused light, it is possible to stimulate more (or a larger area) of the retina at one time with a light stimulus. This is true for a fixed image or an image that is moving relative to a fixed image. Such a defocused image can be generated by a plus lens that focuses in front of the retina or a minus lens that focuses behind the retina. In certain cases, focused light can be used. By way of example, a chromatic aberration focused lens can cause blue light wavelengths to move the focus from in front of the retina of the user's eye, to on or in the retina of the user's eye. In certain cases, a focused lens being of a slight increase in plus power can move the focus of red wavelengths of light from the back of the retina to focusing within the retina.

Embodiments of software that enable the appropriate ocular photo-bio-stimulation for one of a XR, AR, MR, or Modified Reality device, can be available by download to the device. Embodiments envisioned or covered by this invention disclosure can include one or more of the following; 1) appropriate light source(s) that provides wavelengths of light desired for the ocular photo-bio-stimulation 2) the use of light source and one or more filter combinations, 3) a light source or sources of the appropriate intensity to achieve the desired ocular photo-bio-stimulation results, 4) the appropriate timing of the ocular photo-bio-stimulation to achieve the desired results, 5) the appropriate movement of one image relative to another to achieve the desired ocular photo-bio-stimulation results, 6) in the case of treating a fovea and/or macula disorder, the appropriate light source fixation on the fovea and/or macula, 7) the use of defocused or focused light, 8) appropriate optics to achieve the desired outcome from the ocular photo-bio-stimulation, and/or 9) appropriate modulation or flicker of the light source(s) by way of example, 5 Hz-15 Hz, 10 Hz, or 40 Hz, or 40 Hz+/−20 Hz, if such modulation or flicker is desired.

For examples of one of XR, AR, MR, or Modified Reality eyewear devices described herein, the light source that generates the real image, virtual image or both, can be generated, by way of example only, by one or more of, LED, OLED, TOLED, iLED, quantum dots, fluorescent, incandescent, sun light, laser, television set, electronic display screen. For a VR, or Modified Reality eyewear device, the light source for either the first virtual image, or the second virtual image, or both, can be, by way of example only, LED, TOLED, OLED, iLED, quantum dots, fluorescent, incandescent, sun light, electronic display screen, and/or laser.

In certain XR embodiments (e.g., AR, MR, VR, and/or Modified Reality), a system for maximizing the stimulation of dopamine and serotonin in the brain of an individual using the system can comprise using a combination of two or more of light, color, sound, aroma, and/or taste. In certain embodiments for stimulating dopamine and/or serotonin, a combination of light and sound are utilized. In certain embodiments for stimulating dopamine and/or serotonin, a combination of light and color are utilized. In certain embodiments for stimulating dopamine and/or serotonin, a combination of light and aroma are utilized. In certain embodiments, for stimulating dopamine and/or serotonin, a combination of light and taste are utilized. In order to detect if the brain is generating an increased level of dopamine and/or serotonin, biofeedback can be sensed or measured. Such sensing can be, by way of example only, sensing or measuring for an increase in the blink rate of the eye of the user of the XR device. Such sensing can be, by way of example only, sensing or measuring for an increase in the pupil diameter of the eye of the user of the XR device The light can comprise wavelengths of light that are predominantly or substantially light wavelengths within the ranges of one or more of: 480 nm+/−30 nm, 530 nm+/−20 nm, and/or 650 nm+/−30 nm. Such a system can comprise any two or more of light, color, sound, aroma, and/or taste. The sound can be, by way of example only, love songs. The aroma can be by, way of example only, cookies being baked. The taste can be, by way of example only, chocolate. In certain embodiments an XR system is utilized. An XR system can be one or more of AR, MR, VR, and/or Modified Reality. An XR system can be utilized on, in, or around the eyes of a wearer or user. The XR system can be one or more of: AR, MR, and/or VR when used in combination with one or more of light, color, sound, aroma, and/or taste. The XR system can comprise or display light. The XR system can display color. The color can be one or more, by way of example only, that of: red, yellow, and/or orange. The XR system can comprise audio. The XR system can comprise an odor emitting component. In certain embodiments smart eyewear can be utilized. Smart eyewear can be used in combination with one or more light, sound, aroma, and/or taste. Smart eyewear can comprise or display light. Smart eyewear can display color. The color can be one or more of, for example only, that of red, yellow, and/or orange. The smart eyewear can comprise audio. Smart eyewear can comprise an odor emitting component.

In certain embodiments an ocular photo-bio-stimulation instrument can be utilized. The instrument can be used in combination with one or more of: light, color, sound, aroma, and/or taste. The instrument can comprise or display light. The instrument can display color. The color can be one of: red, yellow, and/or orange. The instrument can comprise audio. The instrument can comprise an odor emitting component. The light can comprise wavelengths of light that are predominantly or substantially light wavelengths within the ranges of one or more of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The color can be one or more of, by way of example only, that of red, yellow, and/or orange. The sound can be, by way of example only, love songs. The aroma can be by, way of example only, cookies being baked. The taste can be, by way of example only, chocolate. In certain embodiments an XR helmet or XR eyewear comprising a display can be utilized. The helmet or eyewear comprising a display can be used in combination with one or more of light, color, sound, aroma, and/or taste. The helmet or eyewear comprising a display can comprise or display light. A helmet or eyewear can display color. The color can be one or more of red, yellow, and/or orange. The helmet or eyewear comprising a display can comprise audio aspects. The helmet or eyewear comprising a display can comprise an odor emitting component.

The light can comprise wavelengths of light that are predominantly or substantially light wavelengths within the ranges of one or more of: 480 nm+/−30 nm, 530 nm+/−20 nm, 630 nm+/−20 nm, 650 nm+/−30 nm, and/or 700 nm+/−30 nm. Colors can be one or, by way of example only, that of red, yellow, orange. The sound can be, by way of example only, love songs. In each of these embodiments, the light, or color, or sound, or smell, or a combination thereof, can be modulated within the range of one of, 5 Hz-15 Hz, 10 Hz-20 Hz, 40 Hz+/−10 Hz or 40 Hz+/−20 Hz, by way of example.

In certain ocular photo-bio-stimulation embodiments, an XR device (e.g., AR, MR, VR, or Modified Reality) comprising a display can be used in combination with one or more of light, color, sound, aroma, and/or taste. The XR device comprises a display that can comprise or display light. The XR device can display color. The color can be one of red, yellow, and/or orange. The XR device comprising a display can comprise audio aspects(s). The XR device comprising a display can comprise an odor emitting component. The light can comprise wavelengths of light that are predominantly or substantially light wavelengths within the ranges of one or more of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. Colors can be one or more of, by way of example only, that of red, yellow, and/or orange. In each of these embodiments the light, or color, or sound, or smell, or a combination thereof, can be modulated within the range of one of 5 Hz-15 Hz, 40 Hz+/−10 Hz or 40 Hz+/−20 Hz, by way of example.

In an embodiment of the invention as described herein, an XR device provides or comprises a first lighted image and a second lighted image, wherein the first lighted image is moved relative to the second lighted image, wherein the first image is generated by a first light source, wherein the second image is generated by a second light source (or absence thereof) forming a black spot, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 630 nm-700 nm, or 650 nm+/−30 nm, or 700 nm+/−30 nm, and wherein the wavelengths of light that fall within the peak transmission band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 630 nm-700 nm, or 650 nm+/−30 nm, or 700 nm+/−30 nm, paint portions of the retina peripheral to the macula of the user of the XR device as the user views an image with the XR device. The XR device can provide ocular photo-bio-stimulation to the eye or eye's retina. One of the lights can comprise a band of wavelengths of light having a transmission peak of 50% or greater than any other transmission peak of visible light for that light. The first image can move relative to a stationary second image. The second image can move relative to the stationary first image. The first image can move relative to a moving second image. The first image can move relative to a moving second image. The first image and the second image can both move. In certain cases, the virtual image can be black (this can be formed by a combination of colored pixels or the lack of light). In certain cases, both images are virtual images. The black image can be a spot. The black spot can be of any size or shape. The black spot can move within or relative to the real image. The real image can paint the retina as the eye follows the movement of the black spot. When the light source generates a virtual image, the light source can be, by way of example only, that of a non-see-through near eye display comprising light emitters. When the light source generates a virtual image, the light source can be, by way of example only, that of a see-through near eye display comprising light emitters. When the image is that of a real image, the real image can be generated by, by way of example, a light source of one or more of: sun, ambient light, television, or an electronic display of a remote computerized device.

In an embodiment of the invention as described herein, an XR device provides or comprises a first lighted image and a second lighted image, wherein the first image is moved relative to the second image, wherein the first image is generated by a first light source, wherein the second image is generated by a second light source (or absence thereof) forming a black spot, wherein the predominant wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, and wherein the predominant wavelengths of light that fall within the transmission band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, paint portions of the retina peripheral to the macula of the user of the XR device as the user views an image with the XR device. The XR device can provide ocular photo-bio-stimulation to the eye or eye's retina. One of the light sources can generate a band of wavelengths of light having a transmission of the predominant wavelengths being 50% or greater than any other transmission of visible light for that light. The first image can move relative to a stationary second image. The second image can move relative to the stationary first image. The first image can move relative to a moving second image. The first image can move relative to a moving second image. The first image and the second image can both move. In certain cases, the virtual image can be black (this can be formed by a combination of colored pixels or the lack of light). In certain cases, both images are virtual images. The black image can be a spot. The black spot can be of any size or shape. The black spot can move within or relative to the real image. The real image can paint the retina as the eye follows the movement of the black spot. When the light source generates a virtual image, the light source can be, by way of example only, that of a non-see-through near eye display comprising light emitters. When the light source generates a virtual image, the light source can be, by way of example only, that of a see-through near eye display comprising light emitters. When the image is that of a real image the real image can be generated by way of example by a light source of one or more of, sun, ambient light, television, or electronic display of a remote computerized device.

Figure 53C:
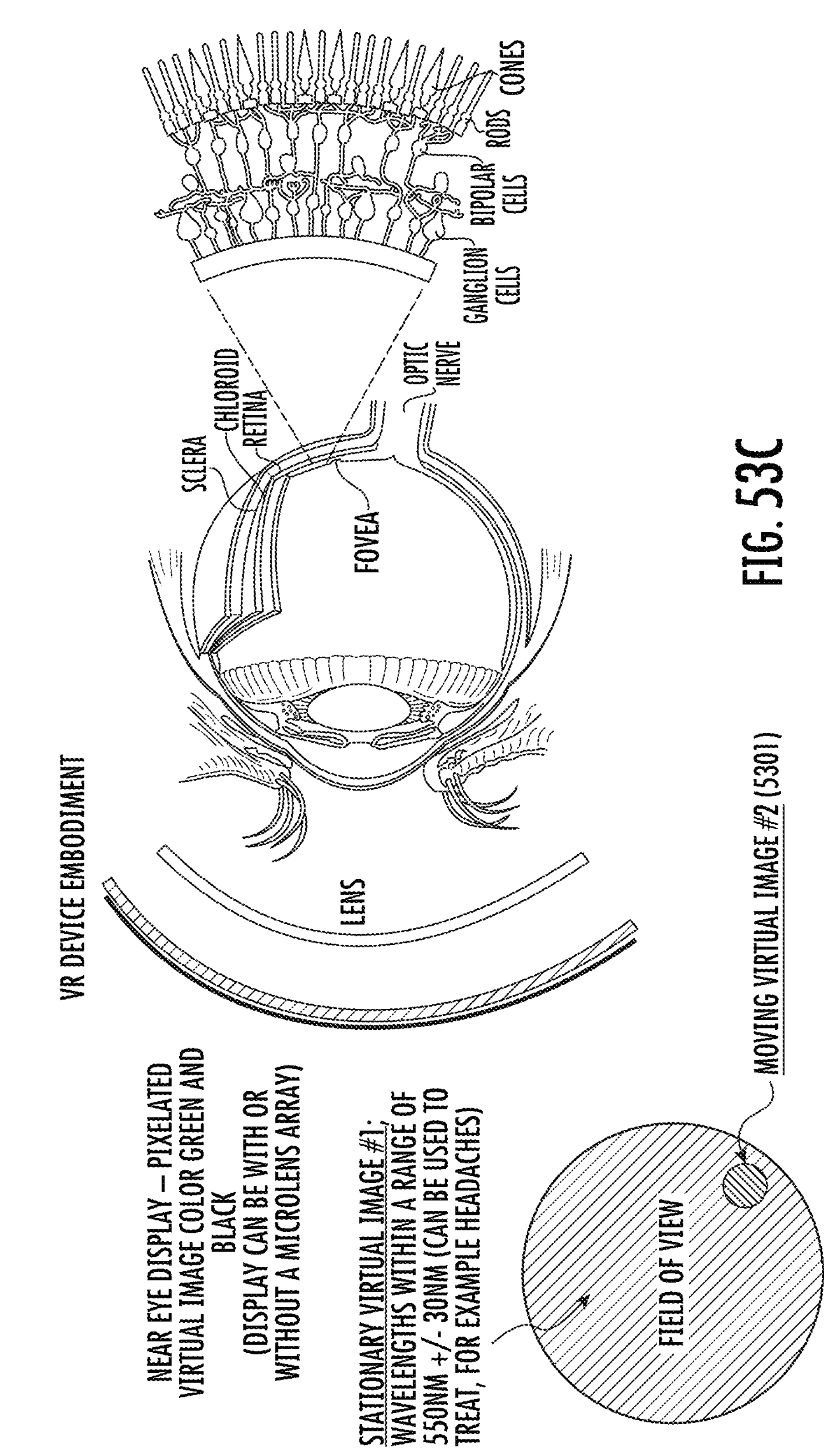

In reference to FIG. 53A, a VR or Modified Reality device can be capable of painting with desired light wavelengths to most of the retina peripheral to the macula or fovea. By way of example, the VR device can provide focused, non-focused, scattered light. Illumination can be within the range of 400 lux to 20,000 lux. Pixels can be comprised by way of example only one of: OLEDs, TOLEDs, microOLEDs, iLeds, Quantum Dots, or LEDs. With respect to the moving virtual image #2 5301, it can be, by way of example only, one of continuous, periodic, intermittent movement from place to place of any desired colored dot including black, grey or white. In aspects, the moving image can be comprised of, by way of example, a combination of colors, lack of light, and/or lack of color. Such ocular photo-bio-stimulation treatment can be done on a monocular basis or a binocular basis.

FIGS. 53, 54, and 55, show how, by way of example only, a non-see-through near eye display or a see-through near eye display can be curved to conform with the eyewear lens(es). Not shown is the curved micro-lens array that can be in alignment with and in optical communication with either the appropriate non-see-though near eye display or a see-through near eye display. By curving a non-see-through near eye display or a see-through near eye display along with a micro-lens array, it is possible to cause light from the pixels of the display to cover or stimulate a larger area of the retina of the eye of the wearer.

In embodiments, the first image can be a real image fixated on by the fovea of the user's eye. The second image can be a virtual image. The second image can paint portions of the far peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the far peripheral retina with light wavelengths.

The moving image (whether a virtual image or a real image) can be by way of example only, one of continuous, periodic, or intermittent movement, from place to place of any desired colored dot (including black, grey, or white). Such ocular photo-bio-stimulation treatment can be done on a monocular basis or a binocular basis.

The image (whether a virtual image or real image) which is painting the retina of an eye can be generated by a light emitter or emitters, by way of example only, having illumination within the range of 400 lux to 20,000 lux. In certain embodiments, when an electronic display is utilized for XR (such as by example only, one of a see-through near eye display, a near eye display, and/or a non-see-through near eye display), the electronic display can be located directly in front of the eye within the line of sight of the eye when the eye is looking straight ahead. In certain embodiments when an electronic display is utilized for XR (such as by example only, one of a see-through near eye display, a near eye display, and/or a non-see-through near eye display), the electronic display can be located in front of the eye but offset with regards to the line of sight of the eye when the eye is looking straight ahead. The electronic display pixels can be comprised of, by way of example only: OLEDs, TOLEDs, micro-OLEDs, iLEDs, Quantum Dots, and/or LEDs. The light can be that of focused, non-focused or scattered light. When an electronic display is remote from the lens or optic or located on the eyewear or the edge of the lens or optic, a waveguide can be utilized to cause the light to be directed into the eye, the electronic display pixels can be, by way of example only: OLEDs, TOLEDs, micro-OLEDs, iLEDs, Quantum Dots, and/or LEDs. The light can be that of focused, non-focused or scattered light. The light emitter or emitters, by way of example only, can have illumination within the range of 400 lux to 20,000 lux.

The XR eyewear can utilize one or more of a near eye display, see-through near eye display, non-see-through near eye display, or waveguide. Any one or more of those will allow for the embodiment of moving a first light that forms an image that is fixed upon by the eye of a user/wearer, while another the light that forms a second image paints the retina. In certain embodiments both images are virtual images. In other embodiments one image (the moving fixated image) is that of a real image and the second image (stationary image) is that of a virtual image. In still other embodiments one image (the moving fixated image) is that of a virtual image and the second image (stationary image) is that of a real image.

The XR device can be a VR or Modified Reality device (see, e.g., FIGS. 53A-D and 54A-B). With the VR device the first image and the second image can be virtual images. In certain cases, one of the virtual images can be black (this can be formed by a combination of colored pixels or the lack of light) The first light can be focused light. The black image can be a spot. The black spot can be of any size or shape. The black spot can move within or relative to the second virtual image. The second virtual image can paint the retina as the eye follows the movement of the black spot. The first light can be focused light. The second light can be defocused light. The first light can be defocused light. The second light can be focused light. The first light can be filtered light. The second light can be filtered light. The light wavelength band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 700 nm+/−30 nm, or 830 nm+/−30 nm, and it can be generated by way of the use one or more of: an interference filter, absorption filter, neutral density filter, bandpass filter, and/or notch filter.

The image movement can be continuous. The image movement can be intermittent. The image movement can be periodic. The first light can be one of generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, and/or electronic display. The second light can be generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, and/or electronic display.

The first image can modulate within the range of one of: 5 Hz-15 Hz, 10 Hz+20 Hz, 40 Hz+/−10 Hz, or 40 Hz+/−20 Hz. The second image can modulate within the range of: 5 Hz−15 Hz, 10 Hz+20 Hz, 40 Hz+/−10 Hz, or 40 Hz+/−20 Hz. The first light can flicker. The second light can flicker. The first light can have an intensity of 300 lux or greater. The second light can have an intensity of 300 lux or greater. The time of ocular photo-bio-stimulation exposure can be for each treatment session, 5 minutes or less, 15 minutes or less, or 1 hour or less. A filter or filters that block or filter light wavelengths within the wavelength range of 449 nm-380 nm can be utilized.

The light that paints the peripheral retina can target rods. The light that paints the peripheral retina can target ipRGCs (melanopsin containing ganglion cells). The light that paints the peripheral retina can target amacrine cells. The XR device can provide two or more of the following, each chosen with the goal of stimulating dopamine in the human body: light, color, sound, and/or smell. Taste can be added to further stimulate dopamine in the human body.

Another embodiment of the invention is that of an XR device (again, AR, MR, VR, or Modified Reality) comprising a first image and a second image, wherein the first image is generated by a first light, wherein the second image is generated by a second light, wherein one of the lights comprise a band of wavelengths of light having a transmission peak 2X or greater compared to any other transmission peak of visible light for that particular light, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm. 480 nm+/−30 nm, 480 nm+/−20 nm, 500 nm+/−30 nm, 500 nm+/−20 nm, 510 nm+/−30 nm, 510 nm+/−20 nm, 530 nm+/−20 nm, or 650 nm+/−30 nm, or 700 nm+/−30 nm, and wherein the wavelengths of light that fall within the peak transmission band stimulate portions of the retina peripheral to macula of the user of the XR device as the user views an image with the XR device.

The XR device can provide ocular photo-bio-stimulation to the eye's or both eyes' retina. One of the lights can comprise a band of wavelengths of light having a transmission peak of 50% or greater than any other transmission peak of visible light for that light. The first image can move relative to a stationary second image. The second image can move relative to the first image. The first image and the second image can both move.

In reference to FIG. 54, in regards to the XR device, the first image can be a real image fixated on by the fovea of the user's eye. The second image can be a virtual image. The second image can paint portions of the peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the peripheral retina with light wavelengths. The XR device can be a VR device.

With the VR or Modified Reality device the first image and the second image can be virtual images. The first light can be focused light. The second light can be defocused light. The first light can be defocused light. The second light can be focused light. The first light can be filtered light. The second light can be filtered light. The light wavelength band of one of: 480 nm+/−30 nm, 530 nm+/−20 nm, 575 nm+/−30 nm, 630 nm-700 nm, 650 nm+/−30 nm, 700 nm+/−30 nm, or 830 nm+/−30 nm, can be generated by way of the use one or more of: an interference filter, absorption filter, neutral density filter, bandpass filter, and/or notch filter.

Figure 54A:
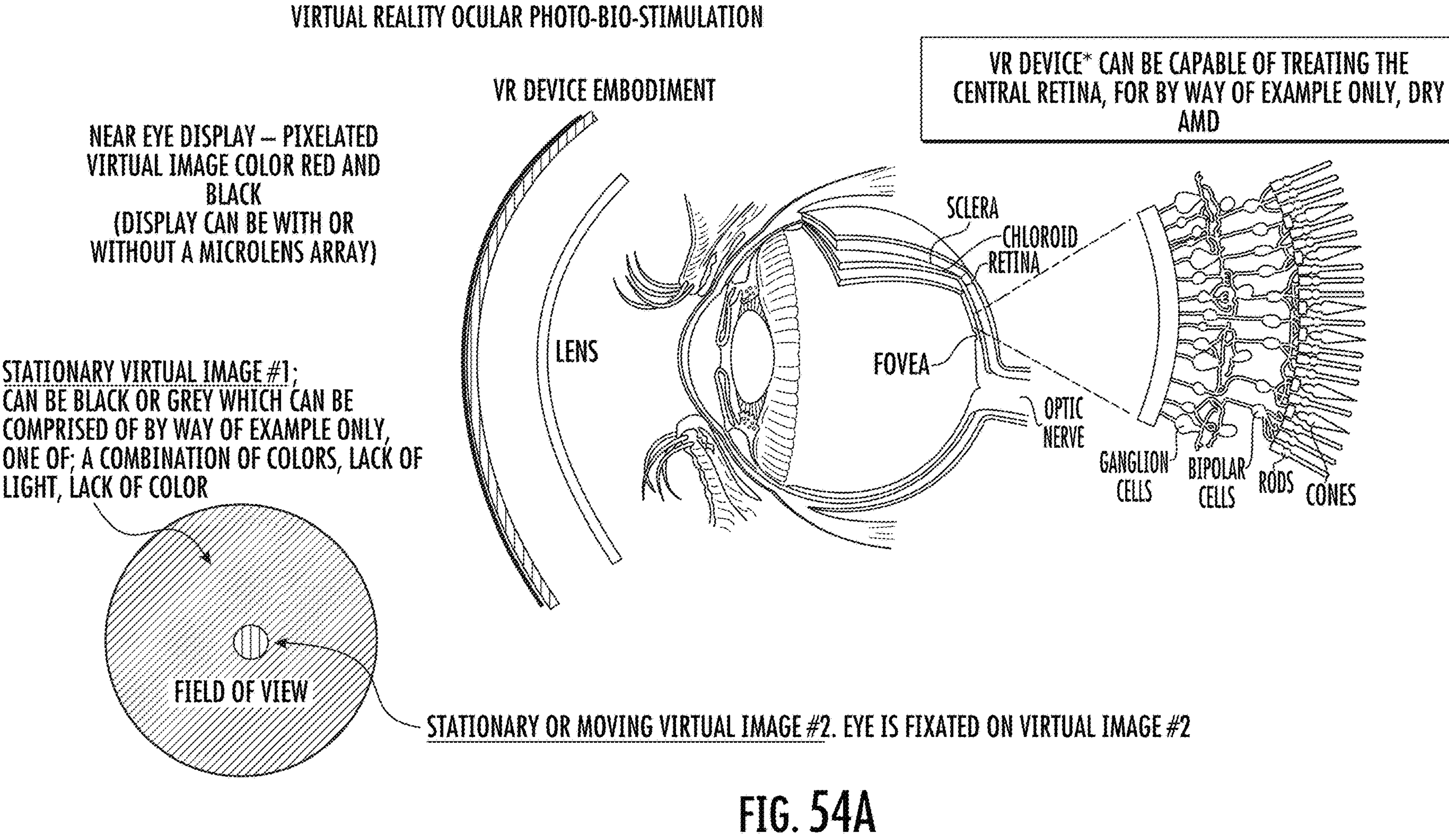

In reference to FIG. 54A, the light wavelengths can be by way of example only within the range of 650 nm+/−30 nm or 620 nm to 700 nm, for treating the macula or fovea for slowing or stopping the progression of dry AMD. Such ocular photo-bio-stimulation treatment in most but not all cases is performed on a monocular basis. In aspects, by way of example, the devices in FIG. 54 can provide focused, non-focused, and/or scattered light. Illumination can be within the range of 400 lux to 20,000 lux. Pixels can be comprised by way of example only one or more of: OLEDs, TOLEDs, microOLEDs, iLeds, Quantum Dots, or LEDs. Real world light can include, by way of example, LED, OLEDs, fluorescent light, incandescent light, ambient sun light, television, electronic display of a remote computerized device, etc.

In reference to FIG. 54B, the device can be used to treat the ganglion cells axons of optic nerve head or surrounding ipRGCs. Wavelengths of virtual image #2 can be by way of example only within the range of one of 475 nm+/−30 nm or 650 nm+/−30 nm for treating the optic nerve head to generate retinal dopamine to slow or stop myopia progression. When treating the optic nerve head using ocular photo-bio-stimulation, the eye is to remains centrally fixated on image #1 which can be moving or stationary. Virtual Image #2 is offset from virtual image #1 so that if the wearer fixates on virtual image #1 the optic nerve head is being treated by virtual image #2 or its light. By first turning on and off the pixels that form virtual image #2, it is possible to ensure that the image is aligned and solely targeting the optic nerve head. If when fixating on virtual image #1, it is possible to see virtual image #2, then the alignment is not correct and different pixels can be activated until virtual image #2 is not able to be seen. Such alignment must be done on a monocular basis, in cases. In aspects, a stationary virtual image #1, the image for central fixation, can be comprised of a black dot. The black dot can be comprised of by way of example only, one of; a combination of colors, lack of light, or lack of color (red wavelengths can be within the range of 600 nm-700 nm. Virtual image #2, which treats the optic nerve head with ocular photo-bio-stimulation, can be comprised of light wavelengths within the wavelength range of one of 480 nm+/−30 nm or 650 nm+/−30 nm.

Figure 55A:
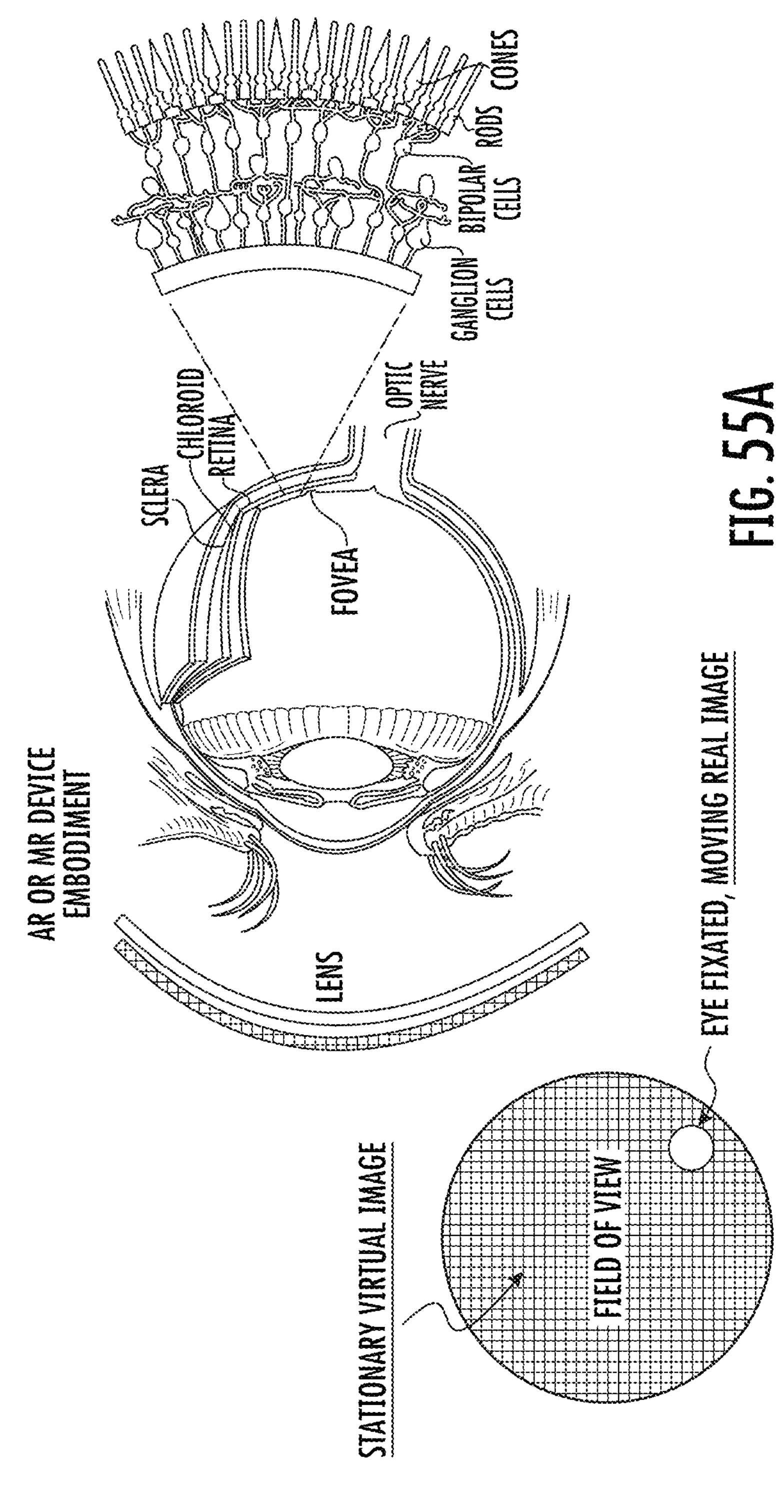
FIG. 55A-I shows an embodiment of the current invention as described herein.

In reference to FIG. 55A, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated, full color display, which can be with or without a microlens array. The microlens array can focus the virtual image one of: in front of the retina, in the retina, or behind the retina. In regard to the stationary virtual image, in embodiments, the wavelengths may be within a range of: 450 nm-510 nm, or 520 nm-580 nm, or 620 nm-680 nm. Regarding the moving real image, it can be one of continuous, periodic, and/or intermittent movement from place to place of the real-world image. The movement can be a constant continuous movement or a movement that jumps from one place to another. The image can appear as a moving hole showing a real image or the real world or real-world image within the virtual image. Such ocular photo-bio-stimulation treatment can be performed monocularly or binocularly. In aspects, by way of example, the devices in FIG. 55*a* can provide one of, focused, non-focused, and/or scattered light. The illumination that generates the virtual image can be within the range of 300 lux to 20,000 lux or greater. The pixel light emitters which generate the virtual image can be comprised by way of example only one or more of: OLEDs, TOLEDs, microOLEDs, iLeds, Quantum Dots, or LEDs. The real-world light that generates the real image can include, by way of example, one or more of, remote LED, OLEDs, fluorescent light, incandescent light, ambient sunlight, television, or display of a remote computerized device, which are capable of generating a real image seen at far, etc. The real image movement can be continuous. The image movement can be intermittent. The image movement can be periodic. In aspects, the moving real image will appear as a moving hole filled in with a real distance image. As the eye fixates on the real moving image the virtual image will paint the retina of the user.

Figure 55B:
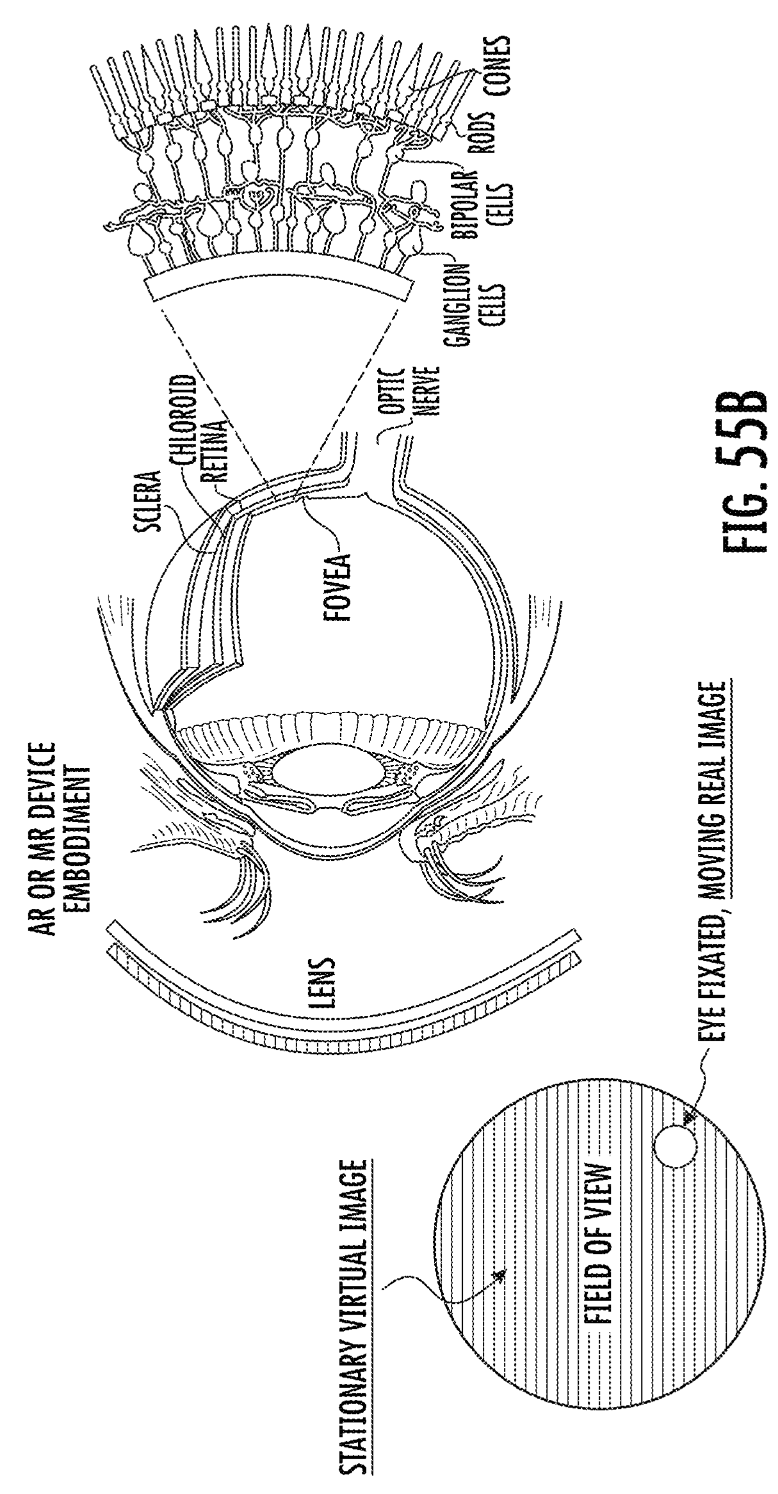

In reference to FIG. 55B, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated, blue monochrome, which can be with or without a microlens array. The microlens array can focus the virtual image one of: in front of the retina, in the retina, or behind the retina. A stationary virtual image can include wavelengths within a range of 450 nm-510 nm (can be used to treat, for example, myopia). In cases, the real-world image can be seen through the virtual image. In aspects, the eye fixates on a moving real image, the movement of which can be continuous, periodic, or intermittent movement from place to place of a real-world image. The movement can be a constant continuous movement or a movement that jumps from one place to another. The moving image can appear as a moving hole showing a real image within the virtual image. Such photo-bio-stimulation treatment can be performed monocularly or binocularly.

Figure 55C:
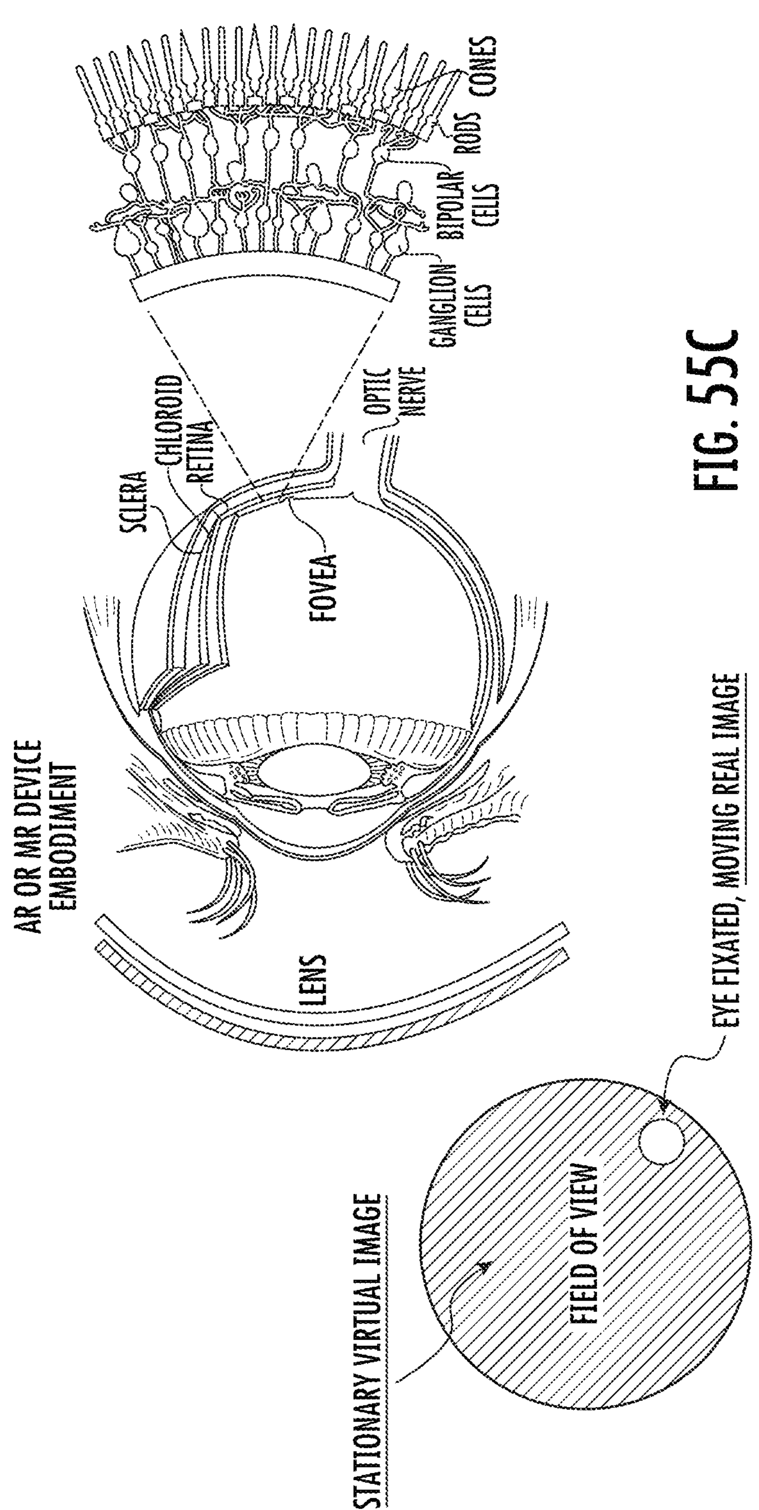

In reference to FIG. 55C, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated, green monochrome, which can be with or without a microlens array. The microlens array can focus the virtual image one of: in front of the retina, in the retina, or behind the retina. A stationary virtual image can include wavelengths within a range of 550 nm+/−30 nm (can be used to treat, for example, headaches). In cases, the real-world image can be seen through the virtual image. In aspects, the eye fixates on a moving real image, the movement of which can be continuous, periodic, or intermittent movement from place to place of a real-world image. The movement can be a constant continuous movement or a movement that jumps from one place to another. The moving image can appear as a moving hole showing a real image within the virtual image. Such ocular photo-bio-stimulation treatment can be performed monocularly or binocularly.

Figure 55D:
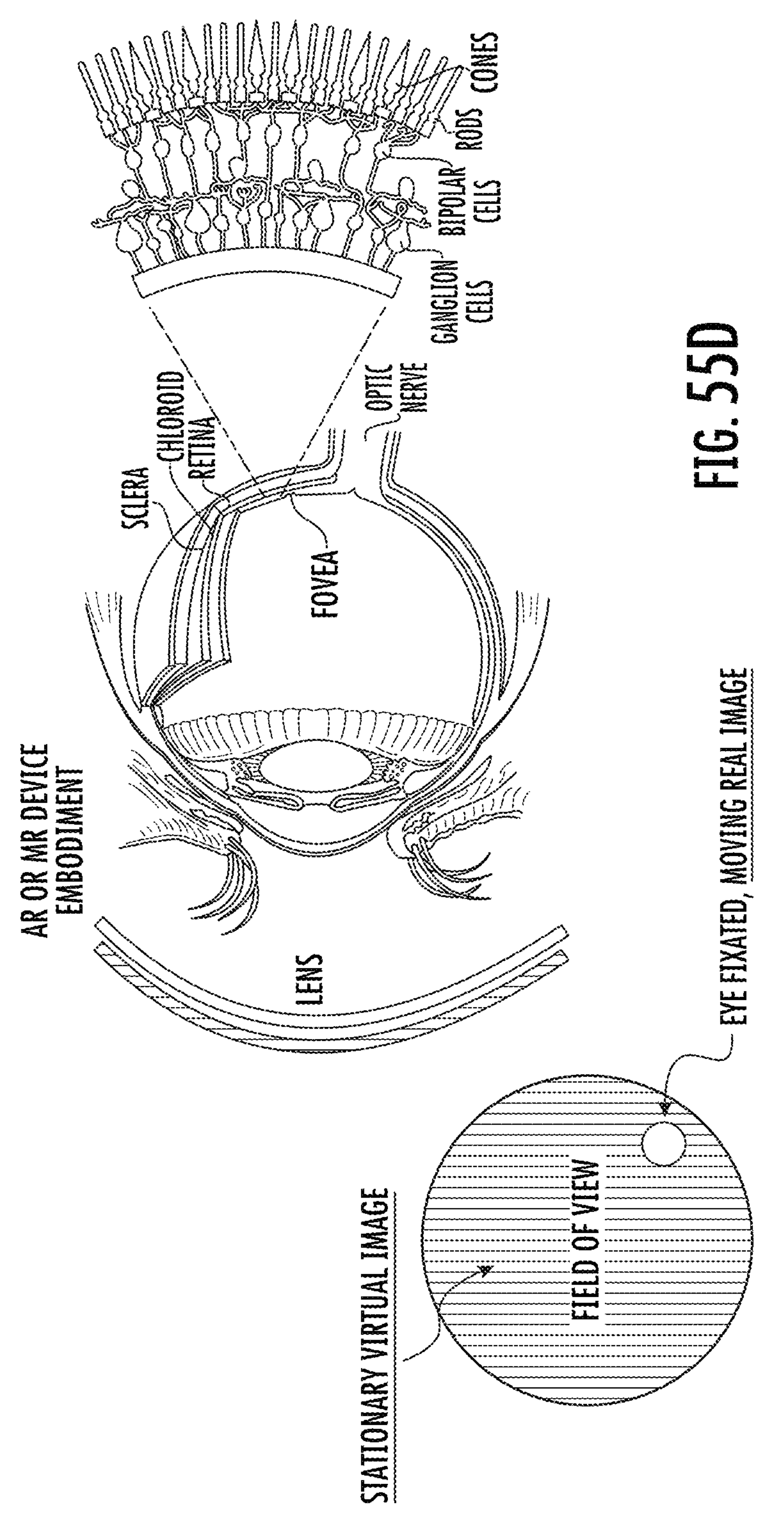

In reference to FIG. 55D, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated red monochrome, which can be with or without a microlens array. The microlens array can focus the virtual image one of: in front of the retina, in the retina, or behind the retina. A stationary virtual image can include wavelengths within a range of 650 nm+/−30 nm (can be used to treat, for example, retinitis pigmentosa or diabetic retinopathy). In cases, the real-world image can be seen through the virtual image. In aspects, the eye fixates on a moving real image, the movement of which can be continuous, periodic, or intermittent movement from place to place of a real-world image. The movement can be a constant continuous movement or a movement that jumps from one place to another. The moving image can appear as a moving hole showing a real image within the virtual image. Such photo-bio-stimulation treatment can be performed monocularly or binocularly.

Figure 55E:
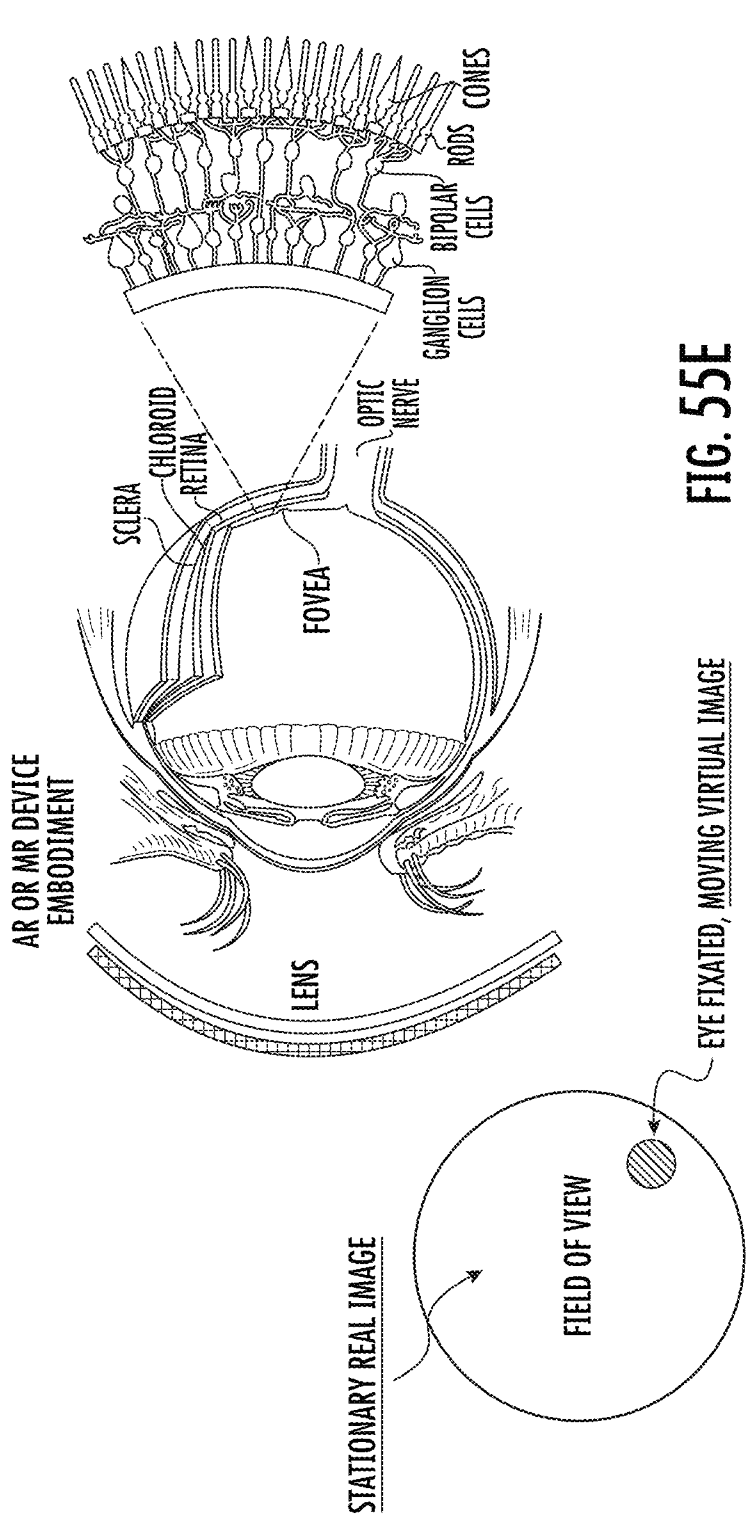

In reference to FIG. 55E, it shows that one of an AR, MR, or Modified Reality ocular photo-bio-stimulation device can be capable of painting with desired light wavelengths most of the retina peripheral to the macula or fovea. In aspects, a "see through" near-eye display can be used to generate light, such as a pixelated, full color display, which can be with or without a microlens array. The microlens array can focus the virtual image one of: in front of the retina, in the retina, or behind the retina. A stationary real image can include, by way of example, light wavelengths within the visible range of 380 nm-700 nm (sunlight). It can be used to treat, for example, myopia. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55F:
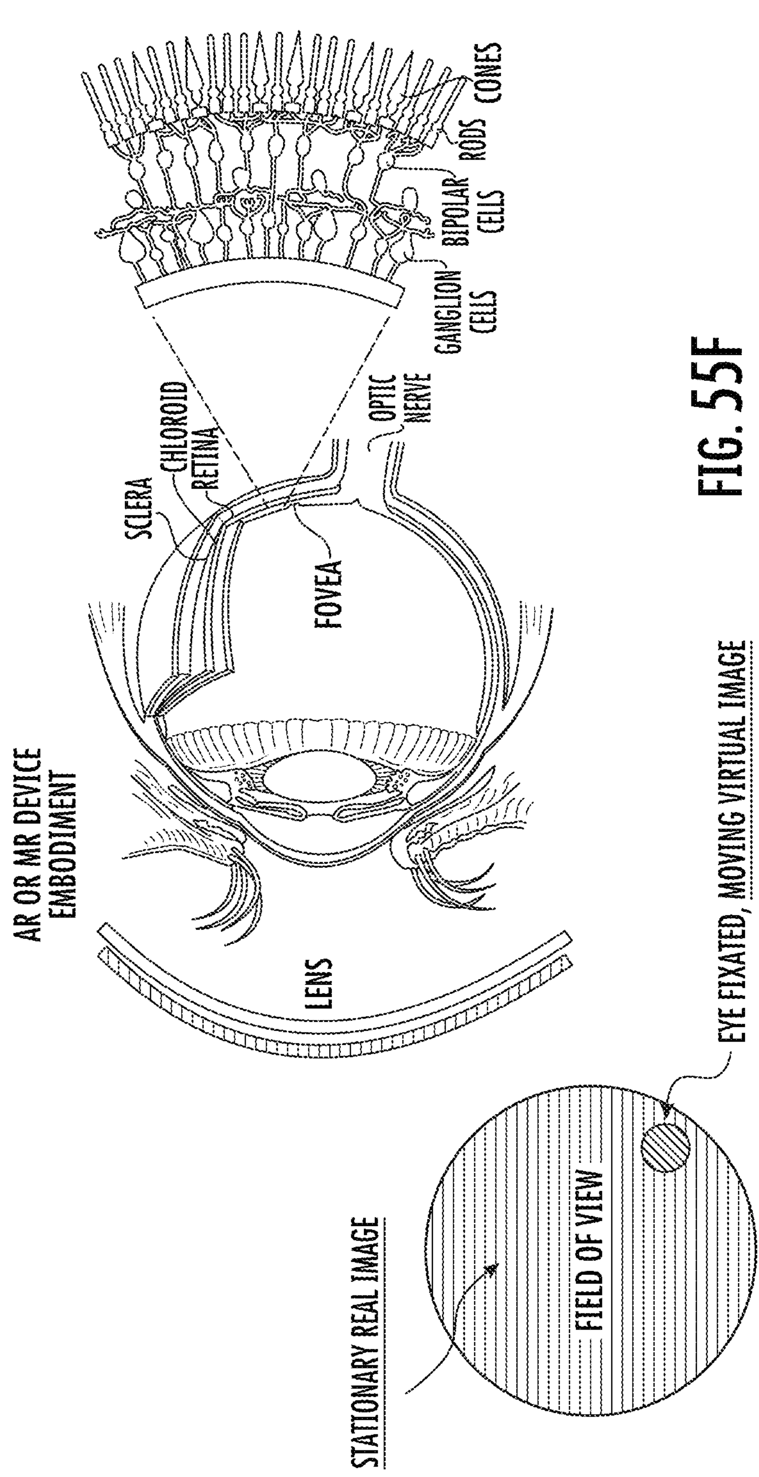

In reference to FIG. 55F, it shows that one of an AR, MR, or Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that is filtered to allow blue wavelengths to pass. A stationary real image can use a "filtered lens" allowing for wavelengths within the range of 450 nm-510 nm or 475 nm+/−20 nm to strike/paint the retina. It can be used to treat, for example, myopia. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55G:
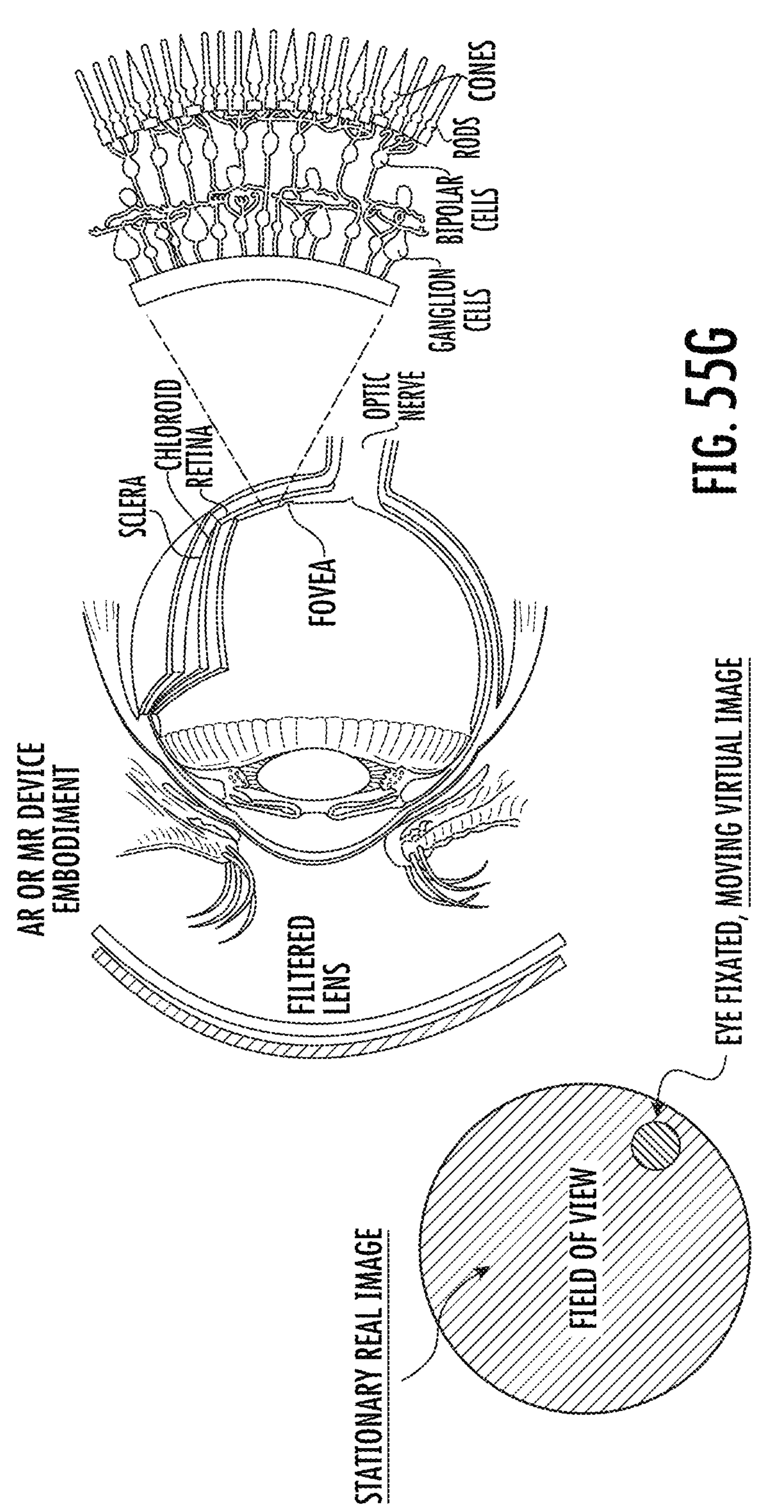

In reference to FIG. 55G, it shows that one of, an AR, MR, Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that is filtered to allow green wavelengths to pass. A stationary real image can use a "filtered lens" allowing for wavelengths within the range of 550 nm+/−30 nm or 510+/−20 nm to strike/paint the retina. It can be used to treat, for example, headaches. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55H:
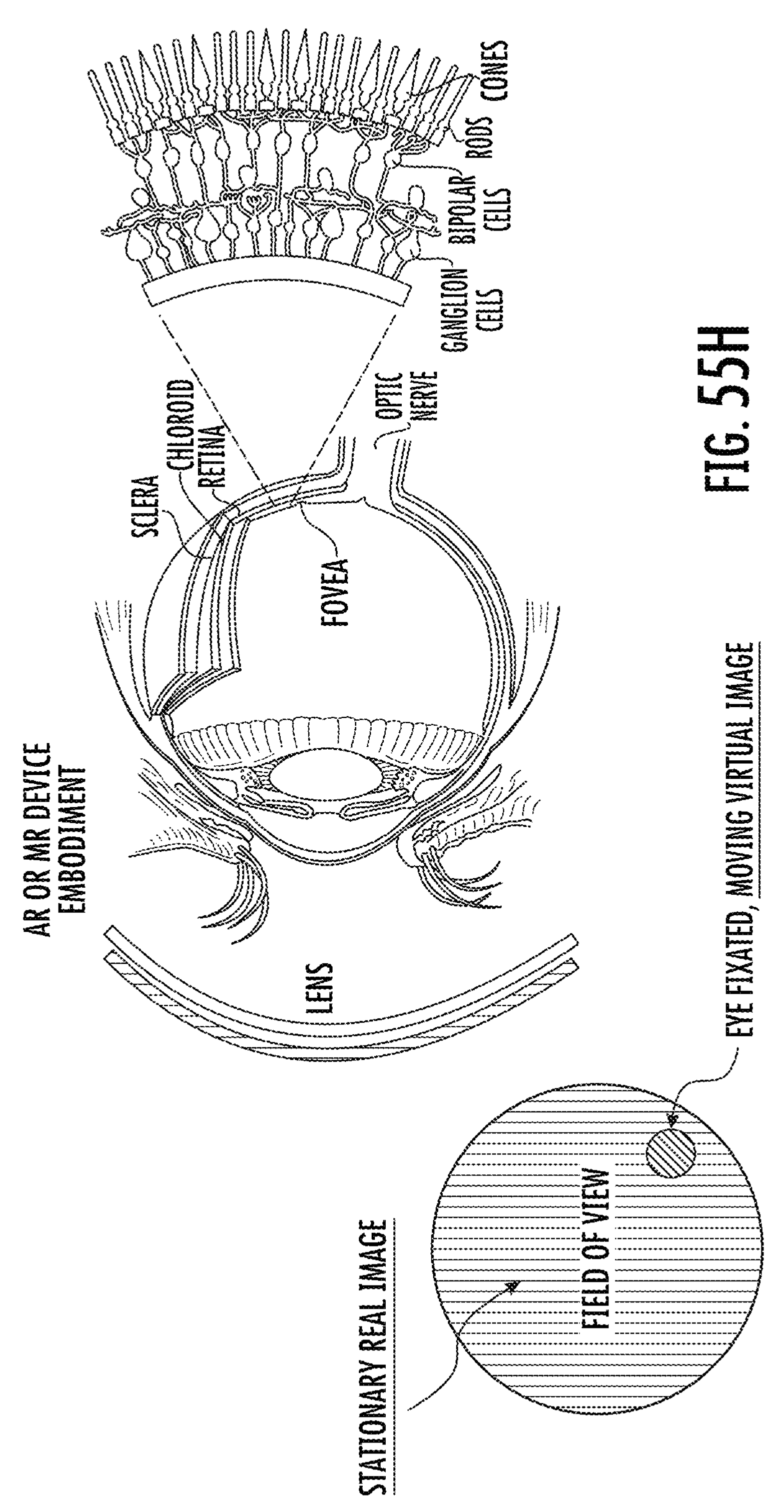

In reference to FIG. 55H, it shows that one of an AR, MR, or Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that is filtered to allow red wavelengths to pass. A stationary, or 700 nm+/−30 nm, real image can use a "filtered lens" allowing for wavelengths within the range of 650 nm+/−30 nm or 700 nm+/−30 nm to strike/paint the retina. It can be used to treat, for example, retinitis pigmentosa or diabetic retinopathy. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55I:
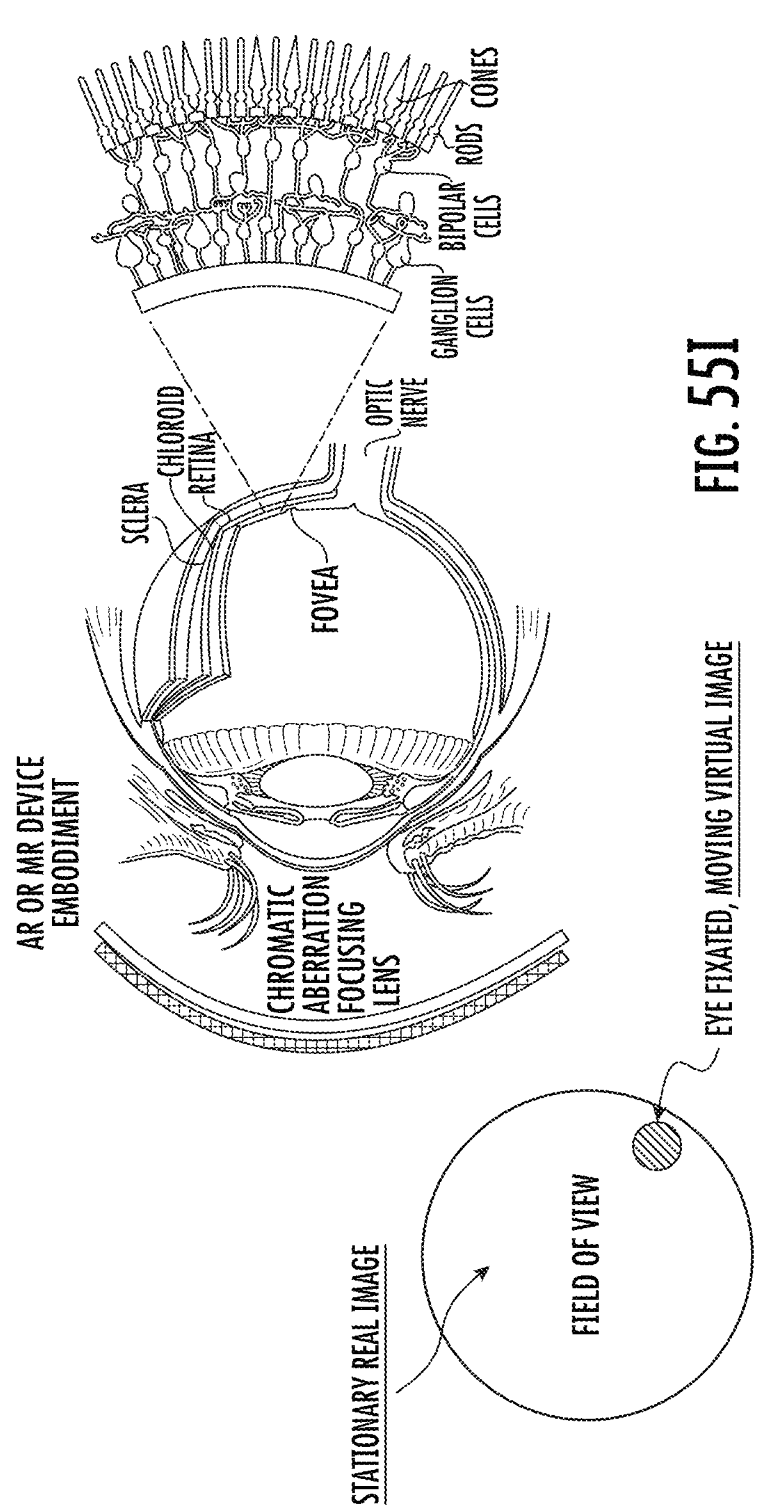

In reference to FIG. 55I, it shows that one of an AR, MR, or Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that when focused by the lens peripheral to the central zone can cause blue wavelengths to strike/paint the periphery of the retina. In aspects, a stationary real image uses ambient light, such that the chromatic aberration focusing lens causes wavelengths within the range of 450 nm-510 nm or 475 nm+/−20 nm to strike/paint the retina. It can be used to treat, for example, myopia. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

In aspects, the first image can modulate within the range of one of, 5 Hz-15 Hz, 10 Hz+20 Hz, 40 Hz+/−10 Hz, or 40 Hz+/−20 Hz. The second image can modulate within the range one of, 5 Hz-15 Hz, 10 Hz+20 Hz, 40 Hz+/−10 Hz, or 40 Hz+/−20 Hz. The first light can flicker. The second light can flicker. The first light can have an intensity of 400 lux or greater. The second light can have an intensity of 300 lux or greater. The time of ocular photo-bio-stimulation exposure for each treatment session can be 5 minutes or less, 15 minutes or less, or 1 hour or less. The light that paints the peripheral retina can target cones. The light that paints the peripheral retina can target rods. The light that paints the peripheral retina can target ganglion cells. The light that paints the peripheral retina can target melanopsin ganglion cells. The light that paints the peripheral retina can target amacrine cells. The XR device can provide two or more of the following, each chosen with the goal of stimulating dopamine in the human body: light, color, sound, and/or smell. Taste can be added to further stimulate dopamine in the human body.

Still another embodiment of the invention is of an XR device being one of, AR, MR, VR, or Modified Reality, comprising a first image and a second image, wherein the first image is generated by a first light source, wherein the second image is generated by a second light source, wherein one of the lights comprise a band of wavelengths of light having a transmission peak 2X or greater than any other visible light transmitted by the XR device to the eye of the user of the XR device, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 630 nm-700 nm, and wherein the wavelengths of light that fall within the peak transmission band stimulate the macula or fovea of the user of the XR device as the user views an image with the XR device. The XR device can provide ocular photo-bio-stimulation of the eye or eyes' retina. One of the lights can comprise a band of wavelengths of light having a transmission peak for the light transmitted to the eye of the user of 50% or greater than any other transmission peak of visible light for that light.

The first image can move relative to a stationary second image. The second image can move relative to the first image. The first image and the second image can both move. The XR device can be one of an AR, MR, or Modified Reality device. The first image can be a real image fixated on by the fovea of the user's eye. The second image can be a virtual image. The second image can paint portions of the peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the peripheral retina with light wavelengths while the second image stimulates the macula or fovea. The first image can paint portions of the peripheral retina with light wavelengths while the eye fixates centrally on the second image. The first image can move. The second image can move. The first image can move relative to the second image. The second image can move relative to the first image. The second image can paint portions of the peripheral retina with light wavelengths while the first image stimulates the macula or fovea. The XR device can be VR or Modified Reality. With the VR device the first image and the second image can be virtual images. The first light can be focused light. The second light can be defocused light. The first light can be defocused light. The second light can be focused light. The first light can be filtered light. The second light can be filtered light.

The light wavelength band can be 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 700 nm+/−30 nm, or 830 nm+/−30 nm, which can be generated by way of one or more of: an interference filter, absorption filter, neutral density filter, bandpass filter, or notch filter. The image movement can be continuous. The image movement can be intermittent. The image movement can be periodic. The first light can be one of: LED, OLED, iLED, quantum dots, fluorescent, incandescent, sun light, laser, plasma display, TV display, tablet display, cell phone display, computer display, or electronic display. The second light can be one of: LED, TOLED, OLED, iLED, quantum dots, fluorescent, incandescent, sunlight, laser, plasma display, TV display, tablet display, cell phone display, computer display, or electronic display.

The first image can modulate within the range of one of, 5 Hz−15 Hz, 10 Hz+20 Hz, 40 Hz+/−10 Hz, or 40 Hz+/−20 Hz. The second image can modulate within the range of one of, 5 Hz−15 Hz, 10 Hz+20 Hz, 40 Hz+/−10 Hz, or 40 Hz+/−20 Hz. The first light can flicker. The second light can flicker. The light that is providing the ocular photo-bio-stimulation treatment or therapy can be 400 lux or more, 700 lux, or more 1000 lux or more, or 5,000 lux or more. The time of ocular photo-bio-stimulation stimulation exposure for each treatment session can be 5 minutes or less, 15 minutes or less, or 1 hour or less. The light that paints the peripheral retina can target rods. The light that paints the peripheral retina can target ganglion cells (ipRGCs). The light that paints the peripheral retina can target amacrine cells. The light that targets the macula or fovea can target mitochondria. The XR device (being one of AR, MR, VR, or Modified Reality device) can provide light within the wavelength range 650 nm+/−30 nm, 700 nm+/−30 nm, or 830 nm+/−30 nm, for increasing the number of healthy mitochondria within the eye. The XR device can provide two or more of the following, each chosen with the goal of stimulating dopamine in the human body: light, color, sound, and/or smell. Taste can be added to further stimulate dopamine in the human body.

Still another embodiment of the invention is of an XR device being one of AR, MR, VR, or Modified Reality, comprising a first image and a second image, wherein the first image is generated by a first light source, wherein the second image is generated by a second light source, wherein one of the lights comprise a band of wavelengths of light having a light transmission peak percentage of light wavelengths transmitted to the eye of a user of the XR device that can be 2× or greater than any other light wavelength transmission peak percentage of visible light wavelengths for that particular light that are transmitted to the eye of a user, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 630 nm-700 nm, or 700 nm+/−30 nm, and wherein the wavelengths of light that fall within the peak transmission percentage wavelength band stimulate the macula or fovea of the user of the XR device as the user views an image with the XR device.

The XR device can provide ocular photo-bio-stimulation to the eye or eye's retina. One of the lights can comprise a band of wavelengths of light having a transmission peak 50% or greater than any other transmission peak of visible light wavelengths for that light. The first image can move relative to a stationary second image. The second image can move relative to the first image. The first image and the second image can both move. The first image can be a real image fixated on by the fovea of the user's eye. The second image can be a virtual image. The second image can paint portions of the peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the peripheral retina with light wavelengths while the second image stimulates the macula or fovea. The second image can paint portions of the peripheral retina with light wavelengths while the first image stimulates the macula or fovea. The first image can paint portions of the peripheral retina with light wavelengths while the eye is fixated on the second image. The second image can paint portions of the peripheral retina with light wavelengths while the eye is fixated on the first image.

The XR device can be a VR or a Modified Reality device. With the VR device the first image and the second image can be virtual images. The first light can be focused light. The second light can be defocused light. The first light can be defocused light. The second light can be focused light. The first light can be filtered light. The second light can be filtered light. The light wavelength band of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 630 nm-700 nm, 700 nm+/−30 nm or 830 nm+/−30 nm, can be generated by way of the use one or more of an interference filter, absorption filter, neutral density filter, bandpass filter, or notch filter.

The image movement can be continuous. The image movement can be intermittent. The image movement can be periodic. The first light can be LED, OLED, TOLED, iLED, quantum dots, fluorescent, incandescent, sun light, laser, plasma display, TV display, tablet display, cell phone display, computer display, or electronic display. The second light can be LED, OLED, iLED, quantum dots, fluorescent, incandescent, sun light, laser, plasma display, TV display, tablet display, cell phone display, computer display, or electronic display.

The first image can modulate within the range one of, 5 Hz−15 Hz, 10 Hz+20 Hz, 40 Hz+/−10 Hz, or 40 Hz+/−20 Hz. The second image can modulate within the range of one of, 5 Hz−15 Hz, 10 Hz+20 Hz, 40 Hz+/−10 Hz, or 40 Hz+/−20 Hz. The first light can flicker. The second light can flicker. The light that is providing the ocular photo-bio-stimulation treatment or therapy can be 300 lux or more, 700 lux or more, 1000 lux or more, or 5,000 lux or more. The light that paints the peripheral retina can target rods. The light that paints the peripheral retina can target ganglion cells. The light that paints the peripheral retina can target amacrine cells. The light that targets the macula or fovea can target mitochondria. The XR device can provide light within the wavelength range 650 nm+/−30 nm, 700 nm+/−30 nm, or 830 nm+/−30 nm, for increasing the number of healthy mitochondria within the eye.

In still other embodiments of XR for the purposes of treating the fovea or macula, the light used for the treatment can be of a light wavelength not visible to the human eye, such as, by way of example only, 830 nm+/−30 nm. The second image can be that of black or dark grey. By using this combination, it is possible to have the pupil naturally dilate for darkness while the ocular photo-bio-stimulation treatment is taking place. In certain embodiments a mild mydriatic eye drop can be used.

Figure 56:
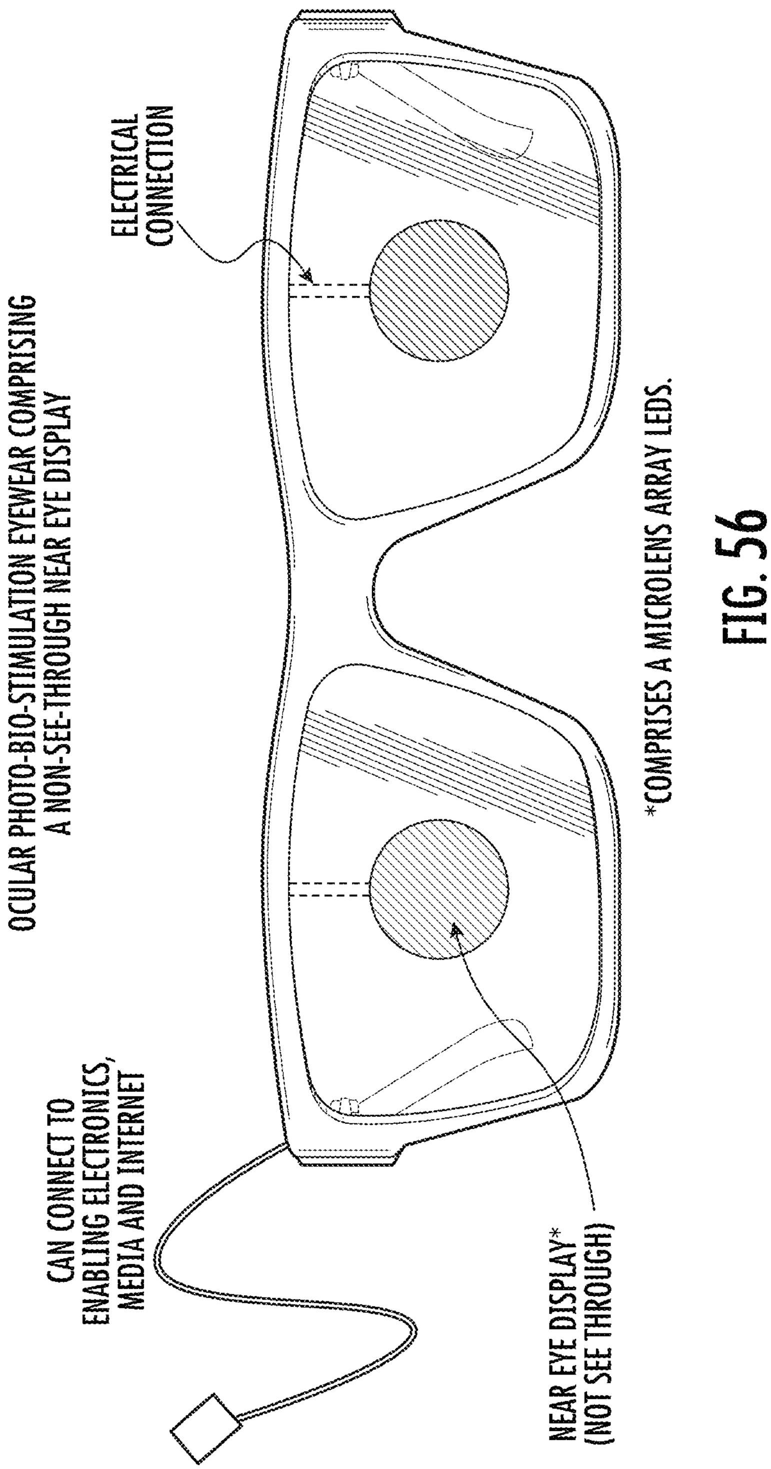
FIG. 56 shows an embodiment of the current invention as described herein.
Figure 57:
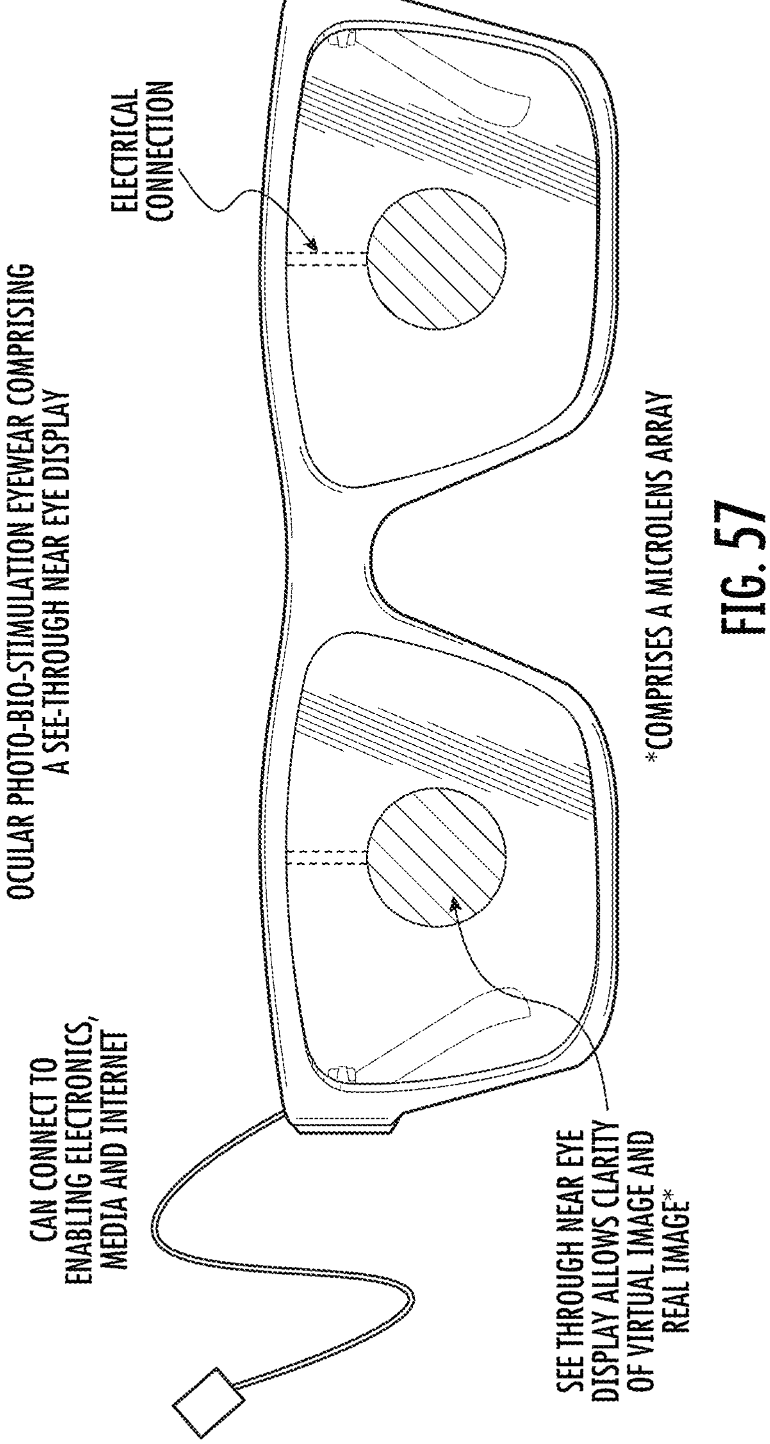
FIG. 57 shows an embodiment of the current invention as described herein.
Figure 58:
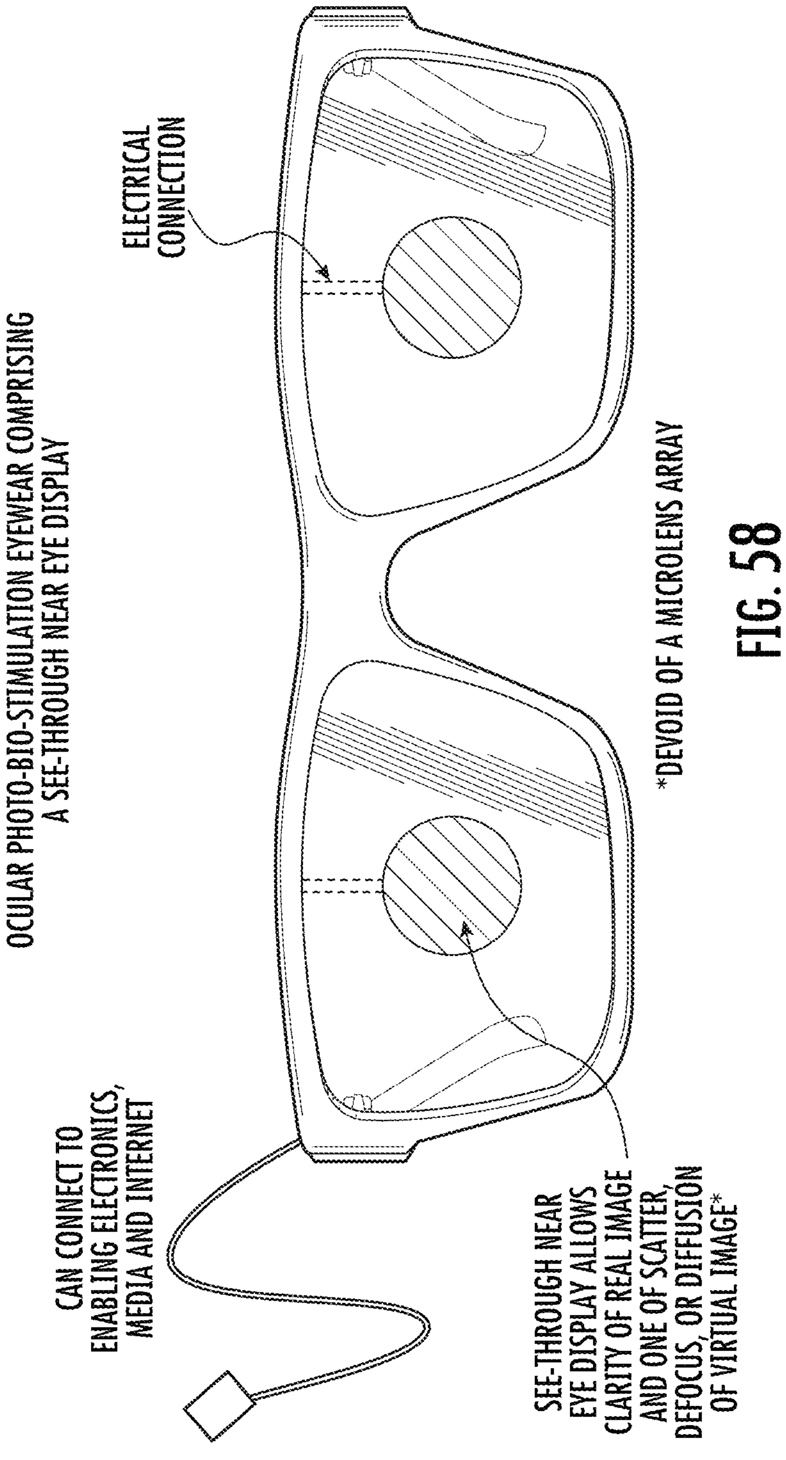
FIG. 58 shows an embodiment of the current invention as described herein.

In reference to FIGS. 56-58, the display diameter can be any dimension within the range of 10 mm to 50 mm in diameter. By way of example, the display can provide a focused or a non-focused virtual image. The view through this device is devoid of a real image. Illumination can be within the range of 300 lux to 20,000 lux. Display Pixels can be comprised by way of example one or more of: LEDs, OLEDs, TOLEDs, microOLEDs, iLeds, or quantum dots. In aspects, the device can transmit blue wavelengths within the range of 450 nm-500 nm, or 460 nm+/−20 nm, or 480 nm+/−30 nm; the device can transmit green wavelengths within the range of 520 nm+/−10 nm or 530 nm+/−20 nm; or the device can transmit red wavelengths within the range of 660 nm+/−20 nm, 630 nm+/−30 nm, or 700 nm+/−30 nm.

Such ocular photo-bio-stimulation treatments can be, by way of example only, for dry AMD. In still other embodiments of XR for the purposes of treating the fovea or macula, the light used for the treatment can be of a light wavelength to which the human eye is caused less pupil constriction, such as, by way of example only, 650 nm-700 nm. The second image can be that of black or dark grey. By using this combination, it is possible to have the pupil less constricted while the ocular photo-bio-stimulation stimulation treatment is taking place. Such treatments can be, by way of example only, for dry AMD.

In still other embodiments of XR for the purposes of treating a degenerative condition in the peripheral retina (including the far periphery), such as by way of example only, retinitis pigmentosa or diabetic retinopathy, a first moving image (which can be a black or dark grey image) being fixated on by the fovea which moves relative to the second image, while the second image which is used for the treatment can be of light wavelengths to which the human eye causes less pupil constriction, such as, by way of example only, 650 nm-700 nm. This allows for the second image or light to paint the peripheral retina as the eye moves. By using this combination, it is possible to have the pupil less constricted while the ocular photo-bio-stimulation treatment is taking place. It is worth noting that this inventive embodiment permits a light source or lighted image to treat the peripheral retina while not stimulating, treating, or harming the fovea or macula. To further enhance peripheral stimulation coverage the second image can comprise defocused light.

In still other embodiments of XR for the purposes of treating a degenerative condition in the peripheral retina, such as by way of example only, retinitis pigmentosa or diabetic retinopathy, a first moving image being fixated on by the fovea which moves relative to the second image can be a black or dark grey image, while the second image which is used for the treatment can be of light wavelengths to which the human eye does not see, such as, by way of example only, 830 nm+/−30 nm. This allows for the second image or light to paint the peripheral retina as the eye moves. By using this combination, it is possible to have the pupil mostly dilated while the ocular photo-bio-stimulation treatment is taking place. To further enhance peripheral stimulation coverage the second image can comprise defocused light.

As used herein a band is a band of light wavelengths that run concurrently with a beginning wavelength and ending wavelength. A transmission peak is the peak light wavelength or wavelengths having the highest light transmission that fall within a band of light wavelengths. As used herein, an image can be generated by light or by the absence of light (in the case of a black image). As used herein the term eyewear can be any eyewear that is used on, in, or about the eye of the user of the eyewear. By way of example only, eyewear can be any of dress eyewear, designer eyewear, safety eyewear, industrial eyewear, military eyewear, shooting eyewear, driving eyewear, sunglasses, googles, face shield, helmet with face shield, or contact lenses. The light can be that of 300 lux or more. The light can be that of 700 lux or more. The light can be that of 1000 lux of more.

As used herein, black can be a color. As used herein black can be generated by a plurality of colored pixels. As used herein black can be generated by a devoid of light or lack of light. The term paint as used herein means that light wavelengths strike and stimulate areas of the retina of one's eye as either the eye moves relative to a light, or the light moves relative to the eye. The use of the word target means to aim for the purposes of striking. Ocular photo-bio-stimulation as used herein comprises the use of light for the purposes of eliciting a neurological change or response, or a physiological change.

As used herein, an XR device can comprise lenses of optical power or no optical power. As used herein an XR device can comprise a wearer's best corrected optical prescription lens or lenses. Embodiments can stimulate or provide ocular photo-bio-stimulation treatment to one or more of the three photoreceptors as desired: Cones, Rod, Ganglion Cells, including melanopsin Ganglion cells. Embodiments can provide ocular photo-bio-stimulation treatment of amacrine cells. A real image light source can be that of a plasma display, TV display, tablet display, cell phone display, computer display, electronic display, or outdoor or indoor ambient lighting. In certain embodiments the user watches a distance separated electronic display through their XR eyewear. Such a display can give off the appropriate level of light intensity. The light can be that of 300 lux or more. The light can be that of 700 lux or more. The light can be that of 1000 lux of more. As used herein, light which stimulates any of the three photoreceptors of an eye first enters through the pupil of the eye. As used herein, light which stimulates the retina of an eye first enters through the pupil of the eye. As used herein an XR device can be that of one of AR, MR, VR, or Modified Reality eyewear, or one of AR, MR, VR, or Modified Reality contact lenses, or one of AR, MR, VR, or Modified Reality intra-ocular lens, or a combination of any of the three. In certain embodiments a prism can be added to the light or image that paints the retina prior to entering the pupil of the eye being ocular photo-bio-stimulation treated.

Embodiments of XR devices for providing ocular photo-bio-stimulation of the eye of the user can comprise appropriate safety guards. Such safety concerns can be addressed by one or more of: a timer, alarm, timed light switch, eye location sensor(s), retinal location sensor(s), cornea location sensor(s), and/or iris location sensor(s). A timer can be set by either the user, automatically by the software for the XR device, or by a remote professional monitoring the treatment approach of the user. An alarm being that of a light, sound, or vibration, can alert the user to turn off or take off the XR device. The light or lights which provide the ontogenetic stimulation can be timed to turn off after a set time. This set time can be set by either the user, automatically by the software for the XR device, or by a remote professional monitoring the treatment approach of the user. The location of retinal stimulation can be monitored by way of one or more of: cornea light reflex location sensor(s) or iris light reflex location sensor(s). The sensors can include a camera. The intensity of the light source and image can be monitored to ensure that the appropriate intensity of the ocular photo-bio-stimulation treatment is being provided.

Such monitoring can be checked by the user or remotely by a third party. The wavelengths of light being provided for the ocular photo-bio-stimulation treatment can be monitored by the user or by a remote third party. The ability to monitor a specific area of the retina being painted or stimulated can be confirmed and calibrated for the XR device in advance of being dispensed for a user to use remotely from that of the eye care professional, neurologist, physician or other technician or professional. Such calibration can be performed individually for each user of an XR device. The use of the XR device by the user can be communicated in real time to the monitoring professional or remote third party. The use of the XR device by the user can be communicated periodically to the monitoring professional. This allows for a remote third party to monitor the user's compliance with the ocular photo-bio-stimulation treatment. Messages can be communicated from the monitoring professional or remote third party to the user of the XR device by way of an image shown or displayed on the XR device. Messages can be communicated from the monitoring professional or remote third party to the user of the XR device by way of sound or audio heard from the XR device. The communication from the XR device to the professional or from the professional to the XR device can be provided by way of wired or wireless communication. Such communication can be in part or whole by way of the internet.

The XR device can comprise all required electronics for enabling the use of the XR device as well as any form of communication needed. Downloaded software can provide updated treatment programs. Such programs can affect the user experience, the treatment procedure or protocol, and/or the mechanical operation of the XR device. The XR device can comprise all required electronic components to accomplish any one or all the preceding XR device modalities of use or performance.

An embodiment of a biomarker (by way of example only) can be that of causing blue light (within the wavelengths of 480 nm+/−30 nm) to strike the eye's retina of a subject. If the subject's pupil enlarges this can be a biomarker that additional dopamine is being generated in the subject's brain. One of the embodiments of this invention is by monitoring the pupil diameter of the eye(s) of the subject being treated it is possible to objectively tell that the desired ocular photo-bio-stimulation effect is occurring either in one or more of the eye, the body or the brain of the individual being treated with light. By way of example only, an ocular photo-bio-stimulation treatment of the retina of eye of the subject being treated can be stopped when the pupil diameter shows an increase in size/diameter. Such monitoring can be accomplished, by way of example only, by a vision system, pupilometer, handheld measurement tool, corneal topographer that captures dimensions of pupil, or device comprising one or more IR sensors.

The method can first measure the patient pupils prior to or at the start of the ocular photo-bio-stimulation treatment and immediately either before or after ceasing the ocular photo-bio-stimulation treatment. In certain cases, the ocular photo-bio-stimulation treatment can be stopped within a period of time after the enlargement of the wearer's pupils first occurs. Such a measurement device or components can be built into, be attached to, or separately used to monitor the enlargement of the pupil of the subject. In certain cases, the device can automatically communicate an alarm once the pupil is enlarged. The alarm can be that of a sound, voice, vibration, or light signal. By way of example only, eyewear, smart eyewear, or XR eyewear can comprise a means to detect and measure the blink rate of a subject that wears such eyewear in response to ocular photo-bio-stimulation treatment.

Another bio-marker embodiment can be that of utilizing a subject's blink rate. If the subject's blink rate increases after (by way of example only) blue light (within the wavelength range of 480 nm+/−30 nm) is utilized to strike the subject's retina, the result can be that of a biomarker that dopamine is being generated in the subject's brain. Once again this can be monitored and measured objectively. Such measuring equipment for blink rate, by way of example only, includes computerized vision system that monitors the eye and lids, eyewear or equipment having light or lights that shine on the cornea to generate a corneal light reflection and sensors that measure the on off of the reflection coming from the cornea, or certain eye tracking instruments.

The method can first measure the subject's blink rate prior to or at the start of the ocular photo-bio-stimulation treatment and immediately either before or after ceasing the ocular photo-bio-stimulation treatment. In certain cases, the ocular photo-bio-stimulation treatment can be stopped within a period of time after the enlargement of the subject's blink rate first occurs. Such a measurement device or components can be built into, be attached to, or separately used to monitor the blink rate of the subject. In certain cases, the device can automatically communicate an alarm once the blink rate increases from the base line measured prior to the ocular photo-bio-stimulation treatment. The alarm can be that of a sound, voice, vibration, or light signal. By way of example only one of, eyewear, smart eyewear, or XR eyewear can comprise a means to detect and measure the blink rate of a subject that wears such eyewear in response to ocular photo-bio-stimulation treatment.

The XR ocular photo-bio-stimulation embodiments disclosed herein can utilize all required enabling components. By way of example only, eye tracking, vision measurement/monitoring system, see-through near eye display, near eye display, microlens array, filters, filter lens(es), lens(es) comprising the wearer's proper correction for his or her distance refractive error, chromatic aberration correcting lens comprising a power increase within the range of −0.35D to −5.00D additional increase in minus power peripheral to the central zone of the lens, timer, appropriate additional XR hardware (AR, MR, VR) such as by way of example only, controller, CPU, rechargeable battery, ability to be wired or wireless to one's cell phone or mobile phone. The embodiments disclosed herein can utilize all required software and communication components such as by way of example only, Wi-Fi and/or Bluetooth.

In certain ocular photo-bio-stimulation XR embodiments when looking at an electronic display screen (by way of example only, a large thin plasma screen, OLED screen, iLED screen, or LED screen), software can be downloaded to the AR or MR device and or the electronic display screen, or to a VR device. In certain embodiments software in the form of, by way of example only, one or more YouTube videos can be created so that when loaded or communicating to the remote electronic display screen it shows movement of an image or images to be in coordination with the AR or MR device. In certain embodiments software in the form of, by way of example only, one or more YouTube videos can be created so that when loaded or communicating to the AR or MR device that is worn, the AR or MR device shows movement of an image or images to be in coordination with the electronic display screen. And still in other cases software in the form of, by way of example only, YouTube videos can be downloaded or communicated to each the AR or MR device and the remote electronic display screen.

In certain ocular photo-bio-stimulation XR embodiments comprising a near eye display, the microarray can cause light to become defocused when it strikes the retina. This can occur by focusing in front of the retina or behind the retina. In other XR embodiments comprising a near eye display, the microarray can cause light to focus within the retina. In certain XR embodiments the correcting lens for myopia can focus centrally for far vision, and peripheral to the central zone causing a defocus or light scatter. In certain XR embodiments the correcting lens for myopia can focus centrally for far vision and peripheral to the central zone causing the band of blue light wavelengths to strike the retina as opposed to conventional lenses having chromatic aberration where the blue light wavelength band focuses in front of the retina. As used herein when an image (virtual or real) is referred to, it is the light that forms the image that provides the ocular photo-bio-stimulation treatment. So, an image should be thought of as a light, or lack of a light when a black image.

Ocular photo-bio-stimulation XR eyewear can comprise a see-through near eye display without a microlens array, a non-see-through near eye display without a microlens array, see through near eye display with a microlens array, and/or a non-see-through near eye display with a microlens array. Such a microlens array permits with AR and MR the virtual image of a near eye display to be seen clearly. Without a microlens array the virtual image will be one or more of, out of focus, scattered, or dispersed. For the purposes of spreading light within a desired wavelength band across the retina, using the device with or without a micro lens array can work. The same is true with VR, however with VR both virtual images without a microlens array would appear out of focus, scattered, and/or dispersed. However, with a microlens array the virtual images will appear clear.

In reference to FIGS. 56-58, the see-through near eye display and the non-see-through near eye display can be comprised with a curved electronic display and a curved microlens array. A near eye display can be curved. The see-through near eye display and the non-see-through near eye display can be comprised with a flat electronic display and a flat microlens array. A near eye display can be flat. The eyewear can comprise a see-through near eye display. The eyewear can comprise a non-see-through near eye display. The display can comprise or be in optical alignment with a micro-lens array. The display can transmit the desired wavelengths of light through the micro-lens array and in focus for seeing a virtual image clearly. The display can be devoid of a microlens array. The microlens array can transmit the desired wavelengths of light and cause light defocus or light scatter. The display can transmit the desired wavelengths of light and cause light defocus or light scatter. The eyewear that supports AR, MR, VR, or Modified Reality components can be wrapped around eyewear. The eyewear that supports AR, MR, VR, or Modified Reality components can be conventional around eyewear. The eyewear that supports AR, MR, VR, or Modified Reality components can comprise side shields for the purposes of blocking peripheral light rays.

Figure 59A:
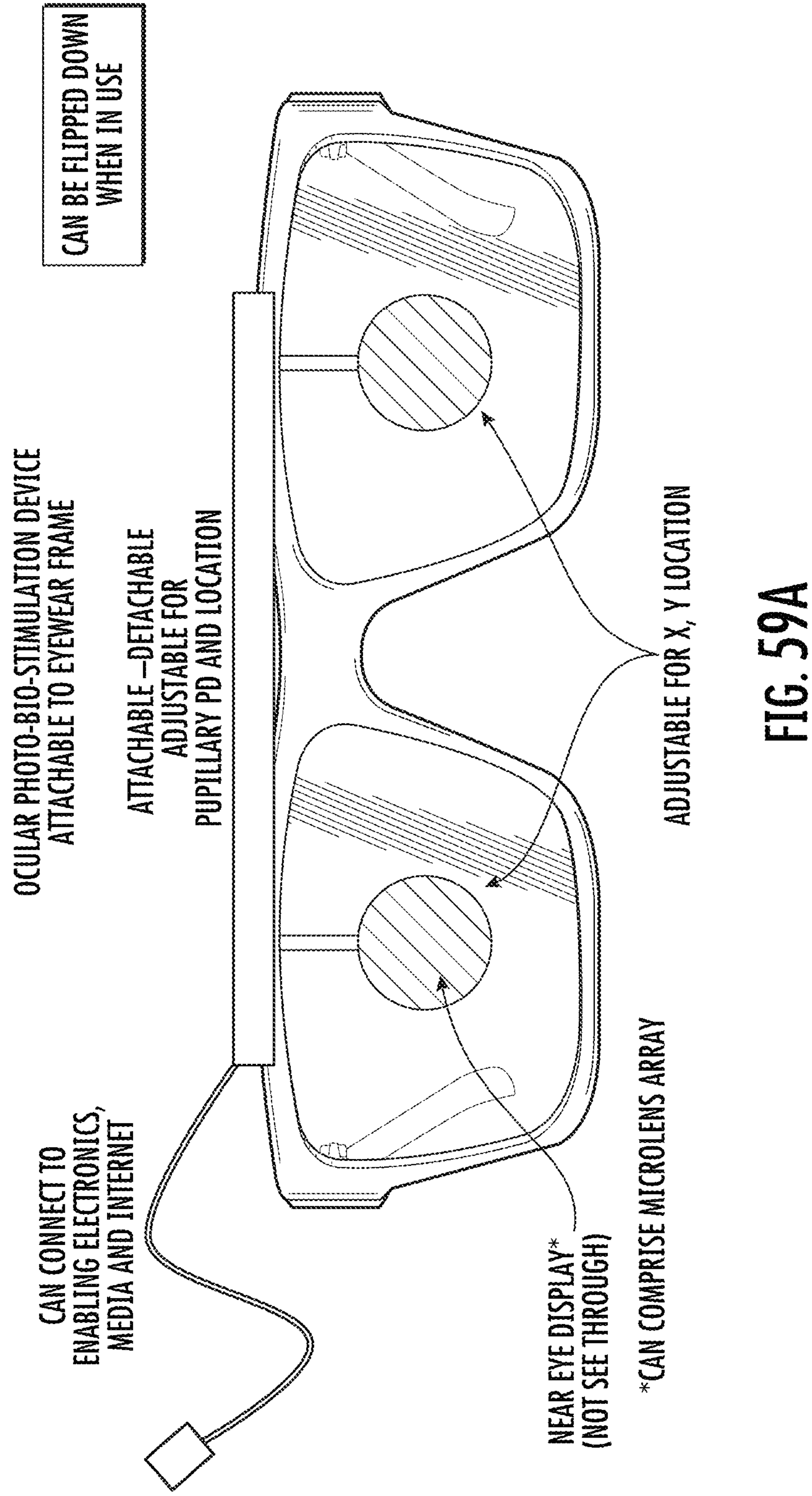
FIG. 59A-B shows an embodiment of the current invention as described herein.
Figure 59B:
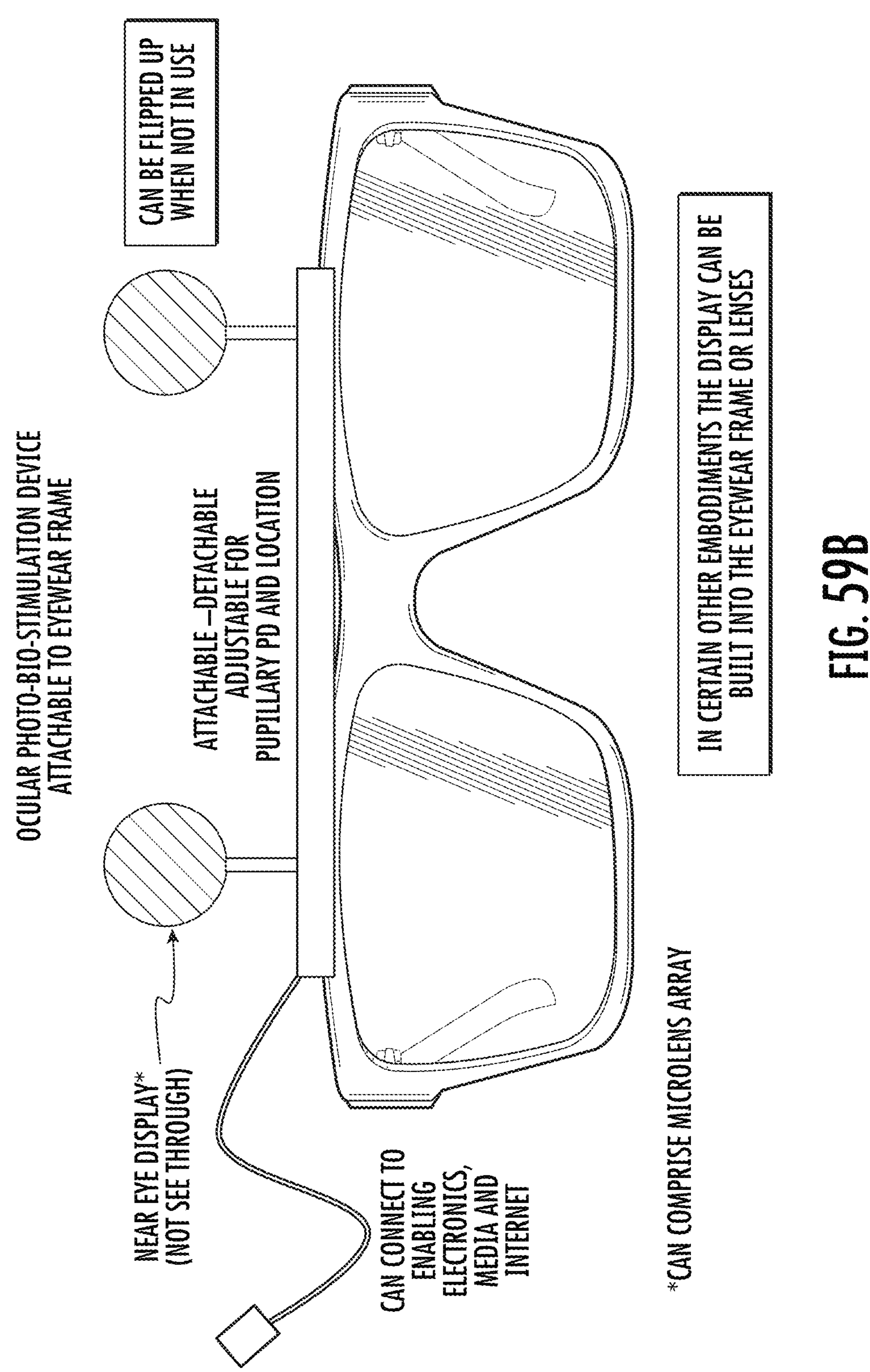
Figure 60A:
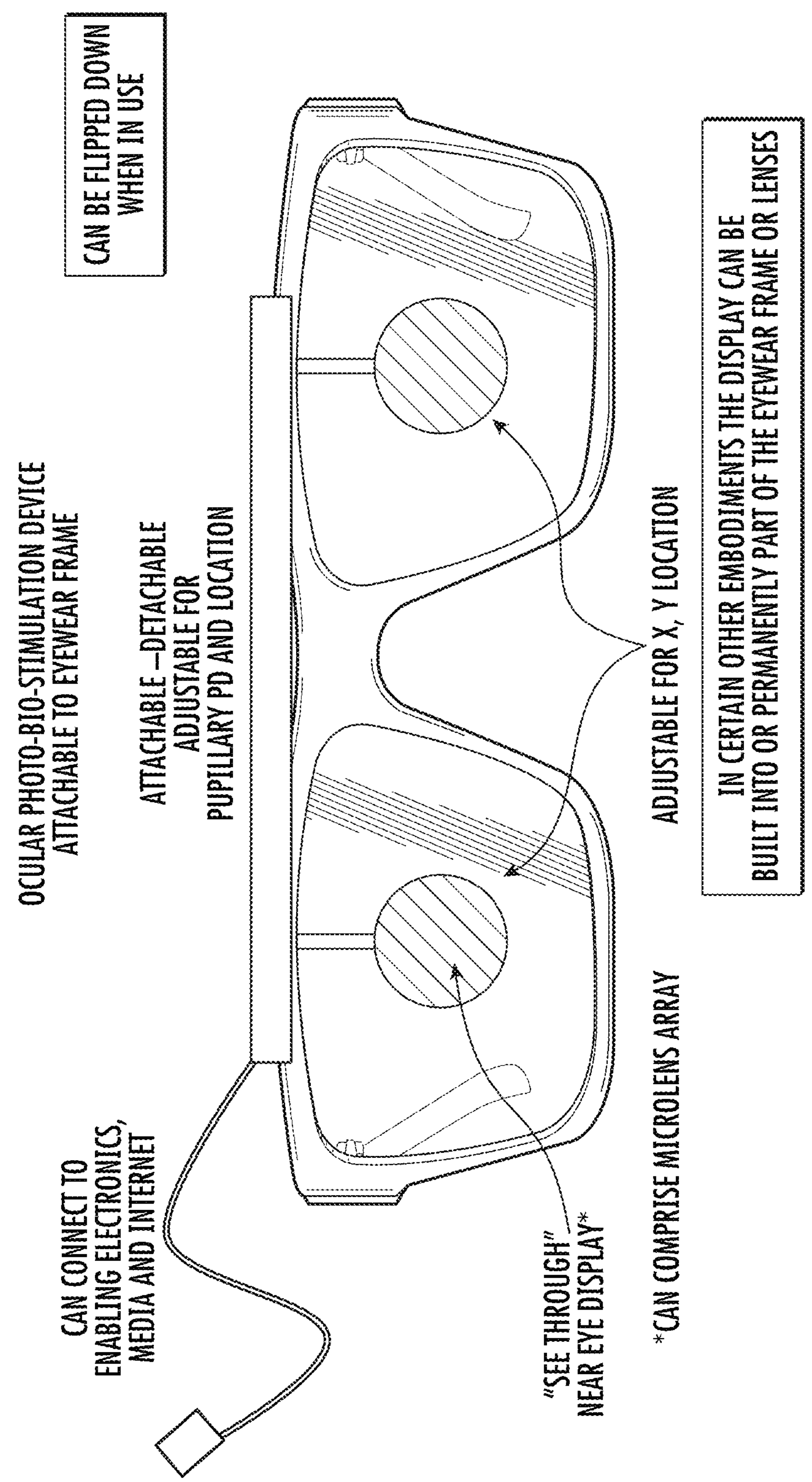
FIG. 60A-B shows an embodiment of the current invention as described herein.
Figure 60B:
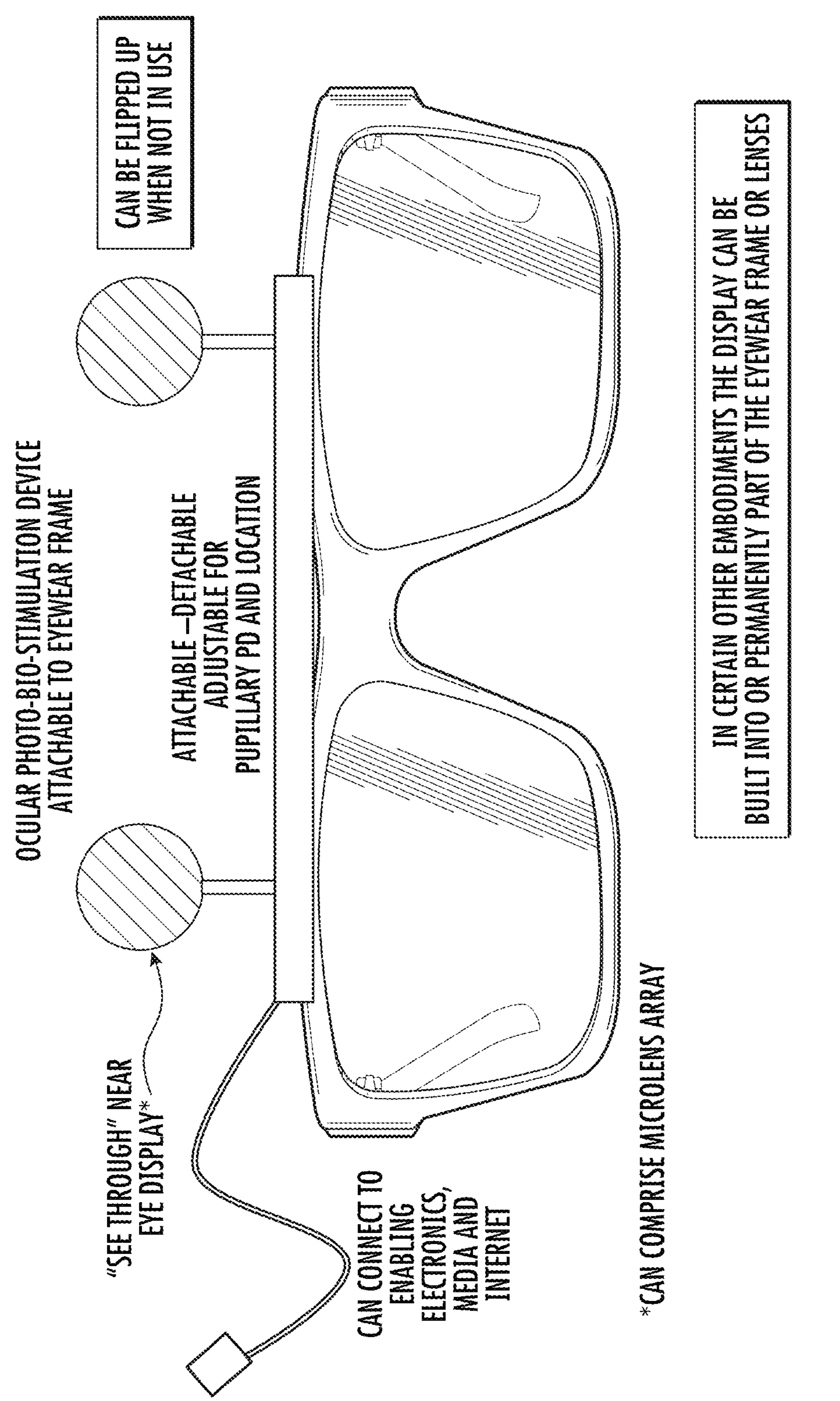

In reference to FIGS. 59A and 60A, the display diameter can be any dimension within the range of 10 mm to 50 mm in diameter. By way of example, the display can provide a focused or a non-focused virtual image. The view through this device is devoid of a real image. Illumination can be within the range of 300 lux to 20,000 lux. Display Pixels can be comprised by way of example, one of: OLEDs, TOLEDs, microOLEDs, iLeds, or quantum dots. In certain embodiments the XR device is attachable and detachable to one's conventional eyeglasses. Such an attachable XR device (one of AR, MR, VR, or Modified Reality) can be adjustable to align with the wearer's pupils. Such a device can comprise a means so that the near eye displays can be rotated out of position when not being used. The see-through near eye display and the non-see-through near eye display can be comprised with a flat electronic display and a flat microlens array. A near eye display can be flat. The XR device can comprise a see-through near eye display. The XR device can comprise a non-see-through near eye display. The display can comprise or be in optical alignment with a micro-lens array. The display can transmit the desired wavelengths of light through the micro-lens array and in focus for seeing a virtual image clearly. The display can be devoid of a microlens array. The microlens array can transmit the desired wavelengths of light and cause light defocus or light scatter. The display can transmit the desired wavelengths of light and cause light defocus or light scatter. (See, FIGS. 59B and 60B.) The see through near eye displays can be flipped out of position so not to be in the way of the wearer's line of sight when not XR ocular photo-bio-stimulation is not being used.

The moving fixation target can be that of a dot, circle or similar shape. In aspects, the size of the target is no larger than the size of the user's macula calculated and enlarged for the distance from the macula of the eye of the user to that of where the virtual image is located along the Z axis in space. The average size of the macula of the eye is approximately 5 mm in diameter.

With certain ocular photo-bio-stimulation VR or Modified Reality embodiments, when a central vision virtual fixation target moves, it will move across or within another virtual image comprising the wavelengths of light desired for painting the peripheral retina or retinas of the user. With certain AR, MR, or Modified Reality embodiments, the central vision fixation target could be a real image that moves, in which case it would be the virtual image that paints the desired wavelengths on the peripheral retina or retinas of the AR, MR, Mixed Reality wearer/user, or with AR, MR, Mixed Reality, the central vision fixation target could also be that of a virtual image that moves, in which case it would be the real image which paints the desired wavelengths on the peripheral retina or retinas of the wearer/user. Depending upon the ocular photo-bio-stimulation physiological effect desired, either the virtual image or the real image can paint the peripheral retina with light wavelengths within the wavelength range of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, while the eye of the wearer/user centrally fixates on a moving target. By way of example only, for increasing dopamine in the eye's retina and the brain, blue light wavelengths within the range of 480 nm+/−30 nm can be used to paint the peripheral retina while the central region of the wearer/user's eye is fixated on a moving black or grey dot.

As used herein the peripheral retina is retina that is peripheral to the outer edge of the central retina. As used herein the central retina would be that of the macula. Furthermore, the peripheral retina can be further subdivided into that of the mid peripheral zone and the far peripheral zone. For the purposes of this disclosure when stating periphery or peripheral to the central zone this would include all retina peripheral to the central zone thus the term peripheral retina can also include all or some of the mid periphery and or far periphery.

In embodiments where the ocular photo-bio-stimulation treatment is intended for treating the central region of the retina of an eye or that of the fovea and/or macula, the desired wavelengths can be applied whether the central image is that of a moving image or a fixed still image, so long as the eye of the wearer/user remains fixated at the target that is applying the light stimulation. By way of example only, when central fixation is fixed on either a moving target or that of a fixed stationary (fixation) target, 650 nm+/−30 nm can be applied for treating dry macular degeneration. For VR or Modified Reality, the fixation target would be one of the virtual images. For AR, MR, or Mixed Reality, the fixation target could be that of a real image or a virtual image. As used herein the peripheral retina is retina that is peripheral the outer edge of the central retina In certain XR ocular photo-bio-stimulation embodiments, the light/image that is painting the peripheral retina can be wavelengths within the wavelength range of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm. The light/image that acts as the fixation target can be preferably a color of black, grey, or red. While any colored fixation target can be used, by using black, grey or red as the fixation target (whether moving or stationary) the pupil of the wearer's eye can remain larger in size as compared to using yellow, blue, orange, or white, for the fixation target. It is also preferable in embodiments that the fixation target is a distance fixation target so it does not cause an accommodative pupil constriction, thus keeping the pupil diameter as large as possible.

In certain XR ocular photo-bio-stimulation embodiments, in addition to with VR or Modified Reality the two virtual images moving relative to one another, or with AR, MR or Modified Reality, the virtual image moving relative to the real image, the ocular photo-bio-stimulation XR (one of AR, MR, VR, or Modified Reality) embodiment can comprise a defocusing lens or a prism optic. In certain XR (one of AR, MR, VR, or Modified Reality) ocular photo-bio-stimulation embodiments, in addition to with VR, or Modified Reality, the two virtual images moving relative to one another, or with AR, MR or Modified Reality, the virtual image moving relative to the real image, the ocular photo-bio-stimulation XR embodiment can comprise a moving or rotating mirror that further enhances the painting of the peripheral retina of the user/wearer. Such a mirror can be a pin mirror. In certain embodiments multiple mirrors can be utilized. Still in other XR ocular photo-bio-modulation embodiments, in addition to with VR or Modified Reality, the two virtual images moving relative to one another, or with AR, MR or Modified Reality, the virtual image moving relative to the real image, the ocular photo-bio-stimulation XR embodiment can comprise a moving or rotating mirror and a defocusing lens or a prism optic that further enhances the painting of the peripheral retina for the user/wearer.

The average monocular visual field consists of central vision, which includes the inner 30 degrees of vision and central fixation, and the peripheral visual field, which extends to 100 degrees laterally, 60 degrees medially, 60 degrees upward, and 75 degrees downward. An estimated 20%-30% of a monocular retina is not stimulated when fixated on a stationary distance object straight ahead. While binocular vision increases the size of the visual field, it does not increase the amount of light stimulation of the retina of each eye. Three different embodiments follow: move the eye relative to the light source, the light source relative to the eye, or the eye and the light source relative to each other.

The inventive embodiment which utilizes one light source being fixated while the other light source paints the retina permits approximately an additional 20%-30% of each retina to be stimulated or treated with light of the appropriate wavelength. In the case of treating myopia, it is light wavelengths within the range of 480 nm+/−30 nm, 450 nm-500 nm, or 650 nm+/−30 nm. In the case of treating retinitis pigmentosa or diabetic retinopathy it is wavelengths within the range of 650 nm+/−30 nm, 700 nm+/−30 nm or 830 nm+/−30 nm.

Different Inventive ocular photo-bio-stimulation XR embodiments disclosed herein permit stimulation or treatment with light of all regions of the retina including, fovea, macula, optic nerve head, mid periphery and most of the far-periphery. This allows for ocular photo-bio-stimulation light treatment for each of the three photoreceptors (as desired); Cones, Rods, and/or ipRGC Ganglion Cells.

In the case of treating myopia with ocular photo-bio-stimulation, the entire retina, or a portion of the retina, or the optic nerve head, can be stimulated or treated with light within the range of light wavelengths of 480 nm+/−30 nm, 650 nm+/−30 nm, or 700 nm+/−30 nm.

In the case of treating dry AMD with ocular photo-bio-stimulation, the fovea and a large portion of the macula can be treated with light within the range of light wavelength of 630 nm-700 nm, 650 nm+/−30 nm, or 830 nm+/−30 nm.

In the case of retina retinitis pigmentosa or diabetic retinopathy in the mid and far periphery any ocular photo-bio-stimulation treatment can be with light within the range of light wavelengths of 650 nm+/−30 nm, 700 nm+/−30 nm, or 830 nm+/−30 nm. In the case of retina retinitis pigmentosa or diabetic retinopathy in the mid and far periphery any ocular photo-bio-stimulation treatment can be with light within the range of light wavelengths of 650 nm+/−30 nm or 830 nm+/−30 nm. And in the case of treating myopia and additional dopamine deficient disorders with light, an embodiment can treat most of the retina (including the mid and far-peripheral region) or just the optic nerve head with light wavelengths within the range of 450 nm+/−30n or 650 nm+/−30 nm. Certain embodiments disclosed herein permit stimulating or treating the fovea and/or macula, but not the remainder of the retina.

In other embodiments disclosed herein the retina peripheral to the macula can be treated while the macula and fovea are not treated. In still other embodiments the most or all of the retina is treated. Treatment is that of ocular photo-bio-stimulation light treatment or therapy. The objective for treating dry AMD and/or retinitis pigmentosa and diabetic retinopathy with light is to increase the number of healthy mitochondria. The objective for treating myopia with light is to increase dopamine in the retina. This is also the case of many other dopamine disorders as by increasing dopamine in the retina, dopamine and/or serotonin can be increased in the brain.

In the case of treating dry eye with ocular photo-bio-stimulation, the use of one of the wavelength bands within the range of 630 nm-700 nm, 650 nm+/−30 nm, 700 nm+/−30 nm, or 830 nm+/−30 nm, targeting the eye lids meibomian glands can be utilized.

Figure 61:
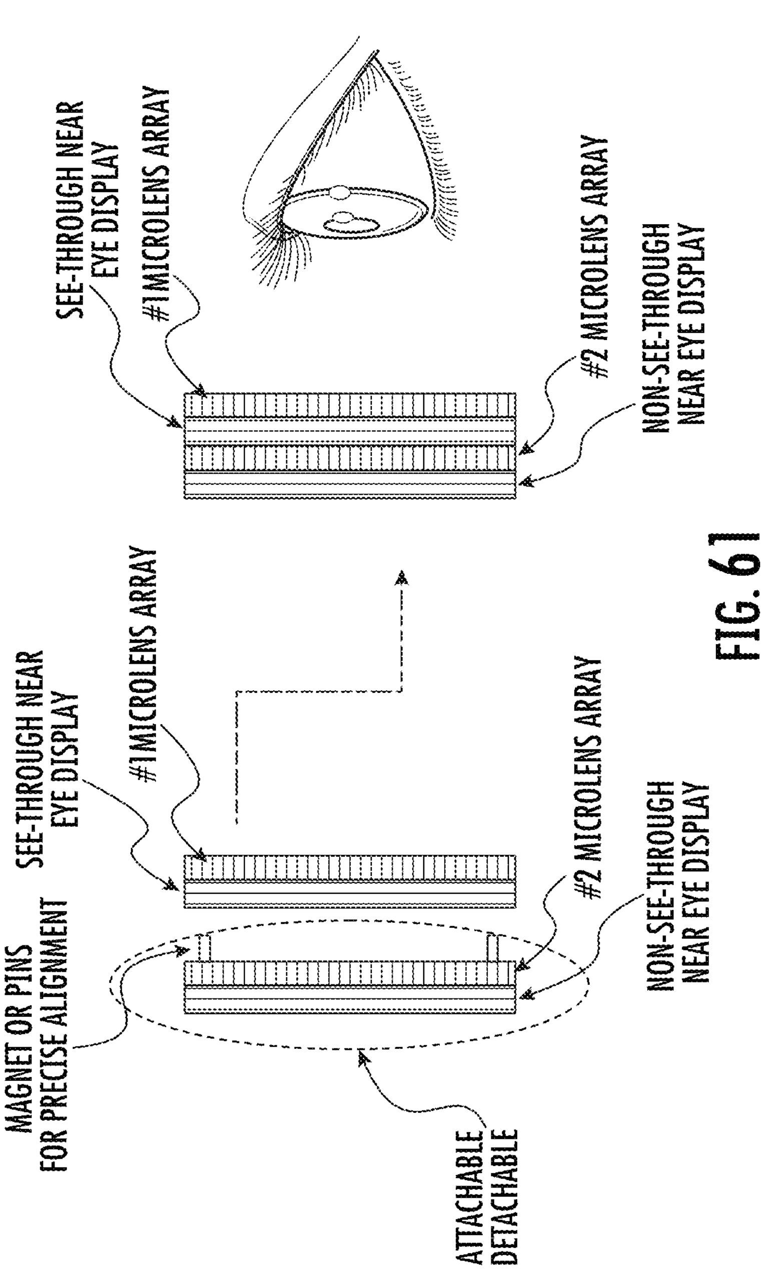
FIG. 61 shows an embodiment of the current invention as described herein.

In reference to FIG. 61, it shows a conversion of an AR device to a VR device, and back to AR. The non-see-through near eye display aligned with its microlens array can be slightly offset with the see-through near eye display and its aligned microlens array. The reason for the offset is to allow for the light generating the virtual image seen by the eye to pass between or through the pixels of the see-though near eye display. Even though there is an offset, the non-see-through near eye display, its aligned microlens array, and the see through near eye display, remain in optical communication, thus allowing light to be projected to the retina of the eye of a user.

Figures 62A, 62B, 62C:
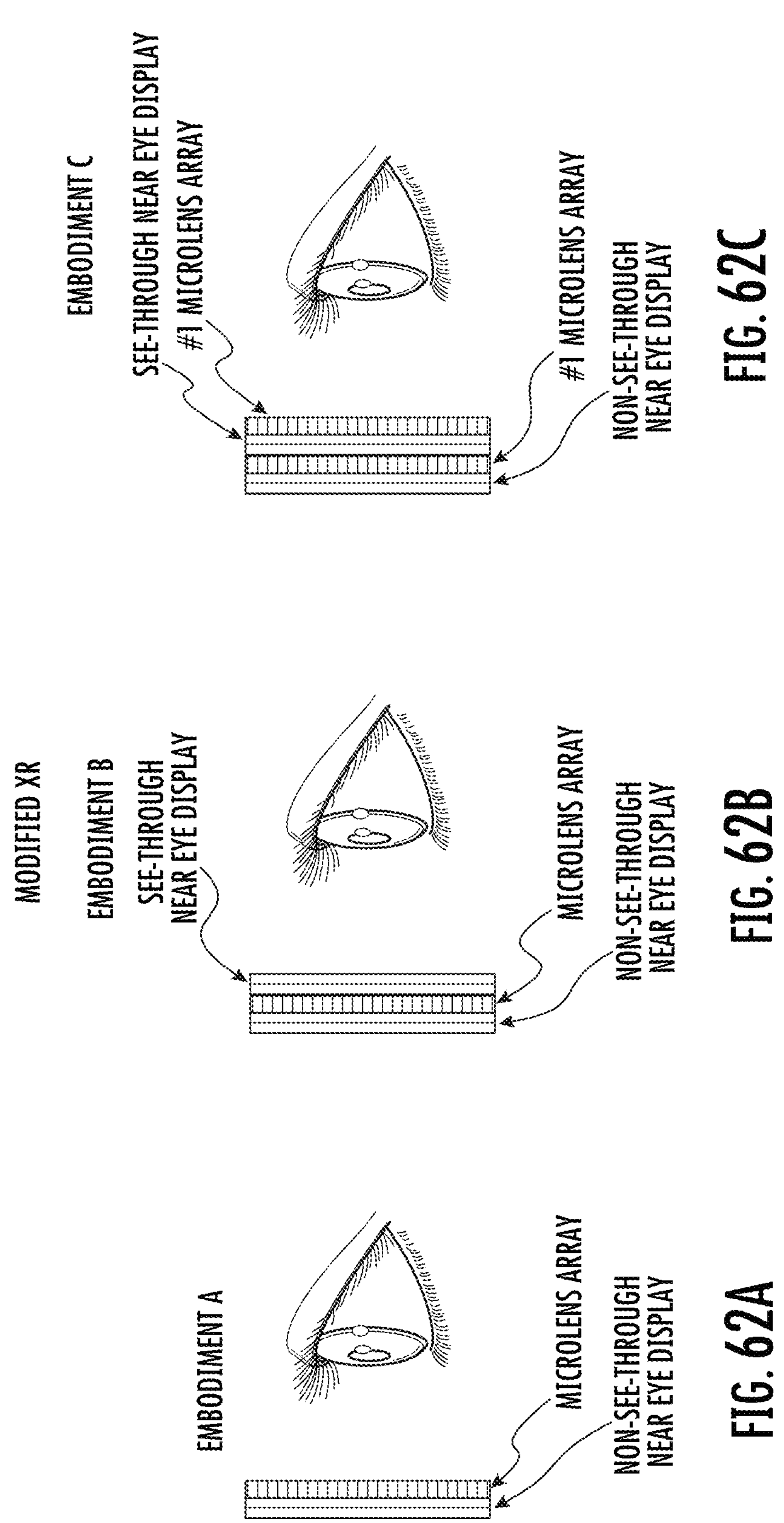
FIG. 62A-C shows an embodiment of the current invention as described herein.
Figure 63:
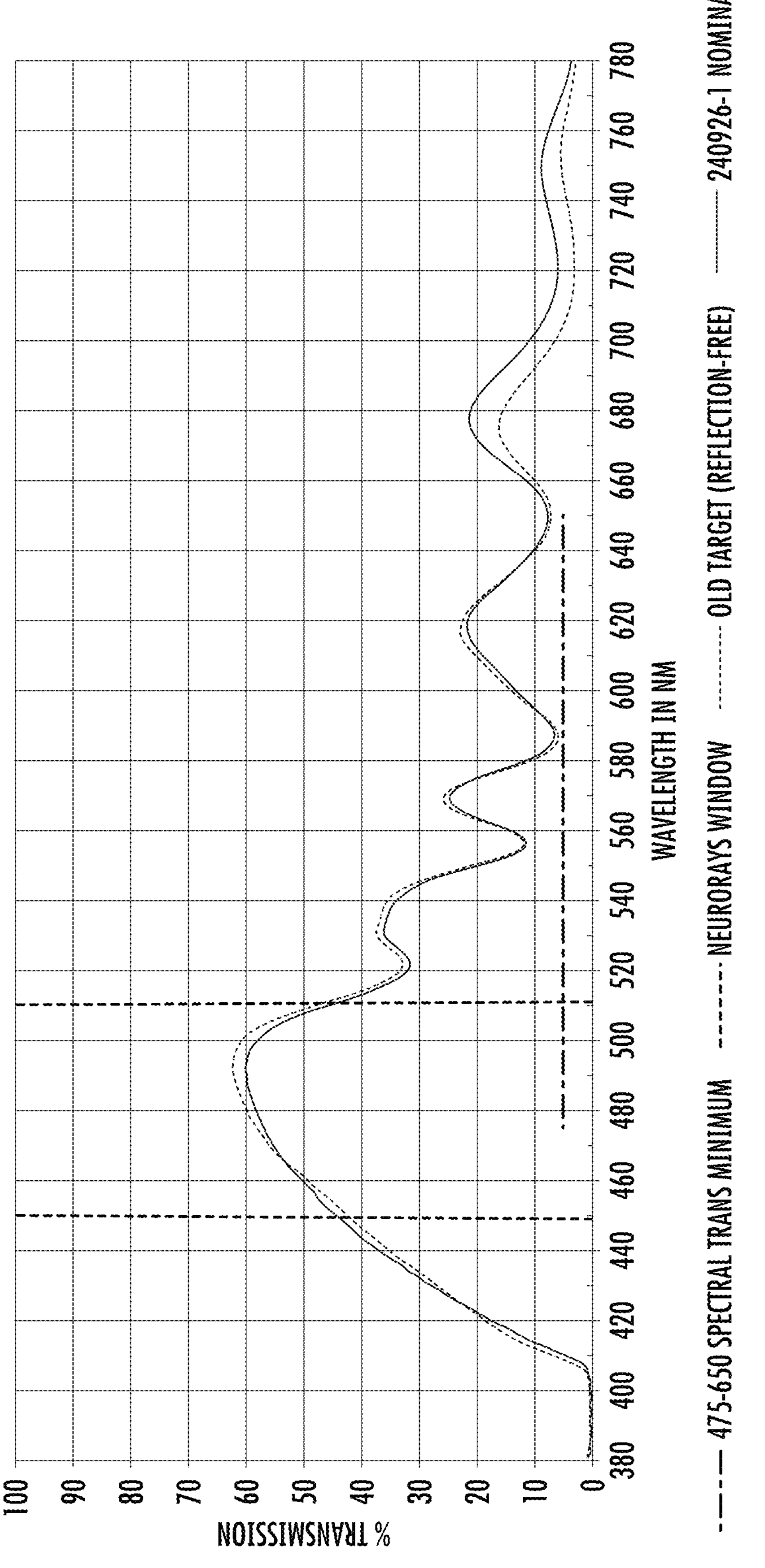
FIG. 63 is a graph showing functionality of the current invention as described herein.
Figure 64:
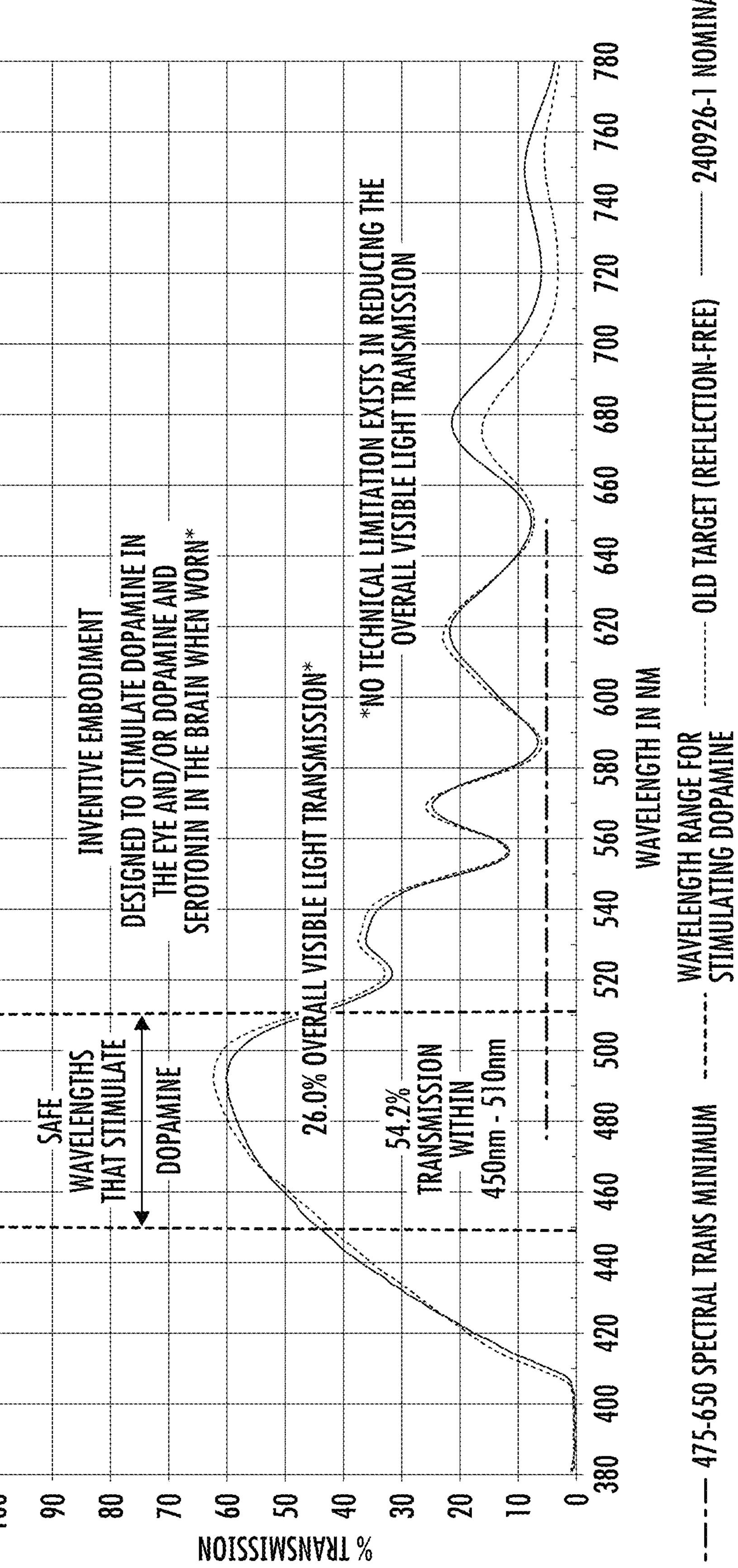
FIG. 64 is a graph showing functionality of the current invention as described herein.
Figure 65:
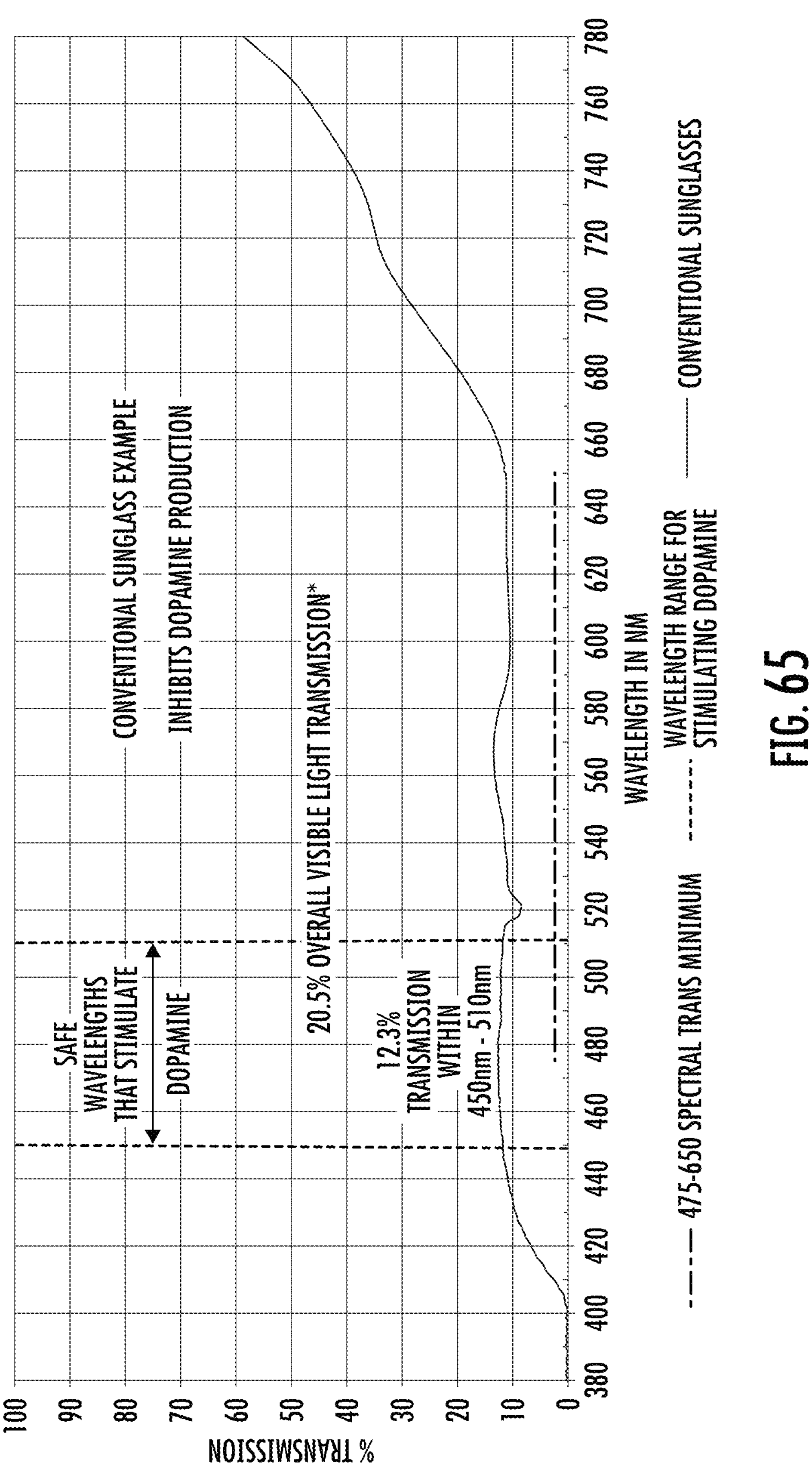
FIG. 65 is a graph showing functionality of the current invention as described herein.
Figure 66:
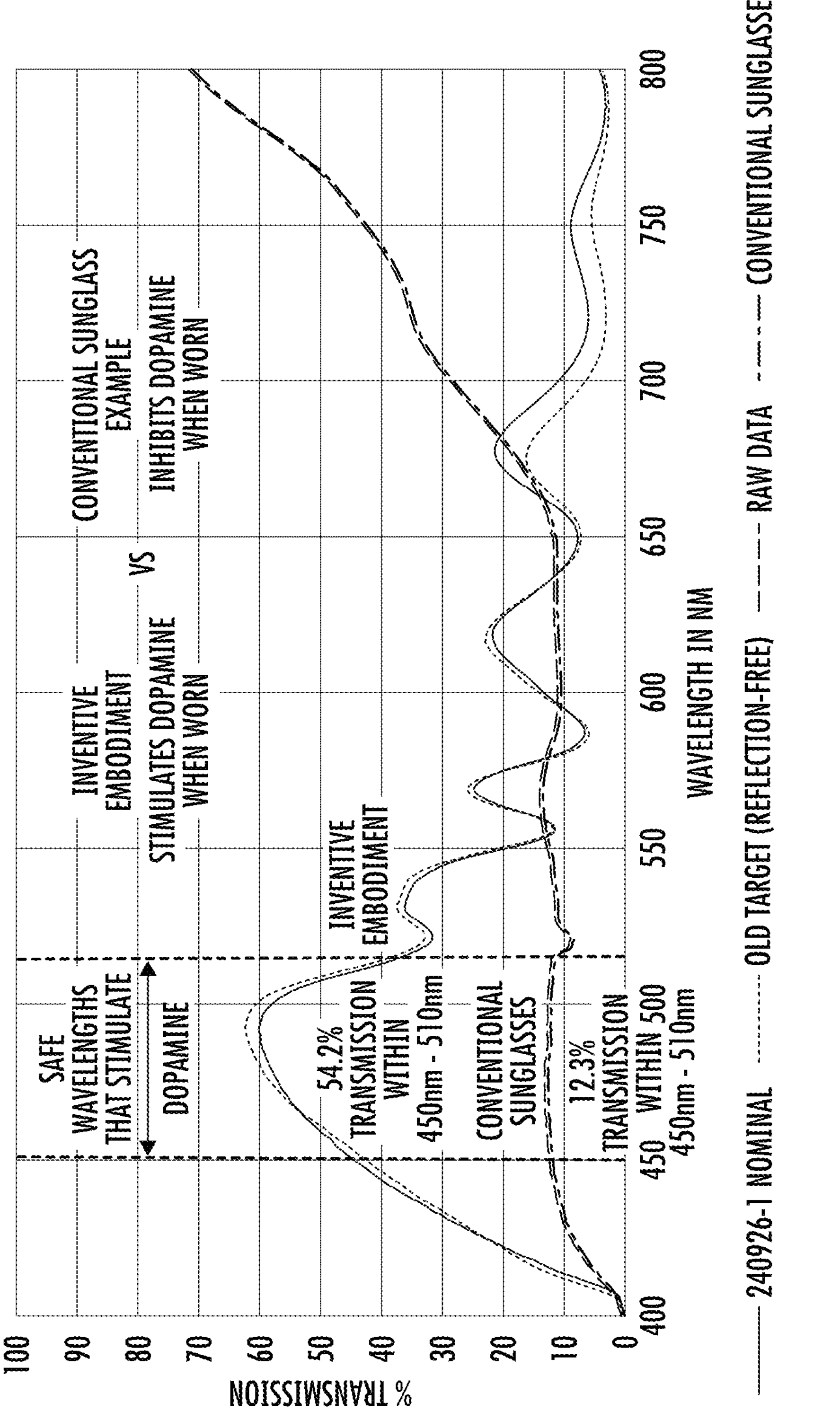
FIG. 66 is a graph showing functionality of the current invention as described herein.

In FIGS. 62B and 62C, the non-see-through near eye display aligned with its microlens array can be slightly offset with the see-through near eye display and its aligned microlens array. The reason for the offset is to allow for the light generating the virtual image seen by the eye to pass between or through the pixels of the see-though near eye display and its aligned microlens array. Even though there is an offset, the non-see-through near eye display, its aligned microlens array, and the see through near eye display, remain in optical communication, thus allowing light to be projected to the retina of the eye of a user. An embodiment can be that of an XR (one of AR, MR, VR, or Modified Reality) device wherein the XR device utilizes two light sources, wherein one light source generates a lighted real image and another light source generates a lighted virtual image, wherein the real image is that of a digital image or video and wherein the virtual image is that of a light that paints or stimulates areas of the retina of the eye of the wearer or user of the XR device. The virtual image can be generated by a see-through near eye display that allows the real image to be seen through the near eye display. In certain embodiments the virtual image can be generated by a non-see-through near eye display that comprises a see-through central zone devoid of pixels or electronic components so as to have peripheral pixels that can be formed as one of, a ring, partial ring, or series of separated pixels. Whether that of a non-see-through near eye display or a see-through near eye display, the central zone that allows the real image to be seen can be of a diameter within the range of 6 mm-12 mm in diameter. In certain embodiments the see-through near eye display can permit the real image to be seen without limitation to a central zone. The see-through central zone can be filtered to cause the pupil of the eye to enlarge. The virtual image can be generated by a filtered or non-filtered light source that projects wavelengths predominantly within the wavelengths range of one of, 480 nm+/−30 nm, 530 nm+/−20 nm, or 650 nm+/−30 nm. The light source for the real image can be one of, a computerized digital display device, television, computer electronic display, cell phone electronic display, tablet electronic display, and/or digital movie screen. This embodiment permits the user of the XR device to watch a video, movie or read text while the retina(s) of his or her eye can be being painted/treated with ocular photo-bio-stimulation. In certain embodiments, different pixels light for the purposes of painting the retina. In other embodiments the same pixels are lighted as the user's line of sight looks through the central clear zone. These pixels project light at various angles to the user's line of sight thus painting or stimulating non-central areas of the retina of the eye of the user.

An embodiment is that of a device for providing extended reality (one of AR, MR, VR, or Modified Reality), comprising a light source providing light to stimulate a retina of an eye of a user of the device, wherein the light is chosen to result in a physiological response in the user's eye or a body of the user, wherein the device causes the user to see a first lighted image and a second lighted image with a user's same eye, wherein the device projects the first lighted image having light wavelengths that are substantially within a wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, wherein at a same time as the user fixates on the second lighted image with the user's same eye, the first lighted image paints light wavelengths substantially within the wavelength range of at least one of 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, across or on different areas of the retina of the user's same eye. The first lighted image can be a virtual image. The second lighted image can be a real image. The first lighted image can be a real image. The second lighted image can be a virtual image. The second lighted images can be virtual images. The device is one of augmented reality eyewear, mixed reality eyewear, or virtual reality eyewear. The device can comprise a see-through near eye display. The device can comprise a non-see-through near eye display. The XR device can comprise an electronic display comprised of a plurality of pixels. The device can comprise a waveguide. The device can comprise a microlens array. The light of the first lighted image can be defocused light. The light of the first lighted image can be a diffused light. The light of the first lighted image can be focused light. The light of the first lighted image can be filtered light. The light of the second lighted image can be focused light. The light of the second lighted image can be defocused light. The light of the second lighted image can be diffused light. The light of the second lighted image can be filtered light. The first lighted image can be stationary/non-moving. The second lighted image can be moving. The first lighted image can be moving. The second lighted image can be stationary/non-moving. The second lighted image can be red, black, or grey. The first lighted image and/or the second lighted image can be generated with light from one or more of the following light emitters: light-emitting diodes (LEDs), organic light-emitting diodes (OLEDs), transparent organic light-emitting diodes, micro-OLEDs, micro-LEDs, ionic liquids for electrochemical devices (iLEDs), micro-iLEDS, quantum dots, florescent lights, ambient light, or incandescent lights. The light generating the first and/or second lighted images can be filtered by the filter or filters, and wherein the filter or filters can be one or more of: a bandpass filter, an interference filter, an absorption filter, a selective wavelengths filter, a notch filter, or a neutral density filter. The physiological response can be one or more of, a generation of additional dopamine, additional serotonin, improved mitochondria function, and/or reduction of age-related inflammation in the eye of the user. The physiological response can be a generation of additional dopamine or serotonin in the brain of the user. The first and second lighted images can modulate, by way of example only, within the range of 5 Hz and 15 Hz. The device can comprise one or more of a timer, a wireless communication component, or an alarm. The device can comprise one or more sensors for sensing and/or receiving biofeedback from the user. The device can be capable of delivering to the user sound, smell, vibration, or combinations thereof. The device can be capable of receiving biofeedback from the user. Biofeedback can include, increased blink rate, measuring blink rate, increased pupil size, and/or measuring pupil size.

Another embodiment is of an XR device (VR or Modified Reality) for providing light to stimulate a retina of a user's eye, the device comprising a non-see-through near eye display for providing the light and a microlens array for focusing or defocusing all or some of the light provided by the non-see-through near eye display, wherein the non-see-through near eye display produces a first lighted image, wherein a fixation target is seen within a perimeter of the first lighted image, wherein the first lighted image is substantially comprised of light wavelengths within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, and wherein light wavelengths within the range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, and can stimulate a portion of the user's retina or all of the retina as the user's eye fixates on the fixation target, and wherein such stimulation initiates a physiological response in the user. The device can be eyewear. The device can comprise a see-through near eye display located on the front-side of the non-see-through near eye display closest to the eye of the user. The non-see-through near eye display can produce a second lighted image. In front of the see-through near eye display on the side closest to the eye of the user, can be a second micro-lens array. The see-through near eye display provides a second light that generates a second lighted image. The first lighted image can be a virtual image. The second lighted image can be a virtual image. The light generating the first lighted image can be defocused light. The light generating the first lighted image can be diffused light. The light generating the first lighted image can be focused light. The light generating the first lighted image can be filtered light. The light generating the second lighted image can be defocused light. The light generating the second lighted image can be diffused light. The light generating the second lighted image can be focused light. The light generating the second lighted image can be filtered light. One or both of the first lighted image and/or the second lighted image can modulate between 5 Hz and 15 Hz. The fixation target can be stationery/non-moving. The fixation target can move. The fixation target can move relative to the first lighted image. The fixation target can move relative to a second lighted image. The fixation target color can be one of red, black, or grey. The fixation target can be the first lighted image. The fixation target can be the second lighted image. The fixation target can be a third lighted image. The second lighted image can be substantially comprised of light wavelengths within the wavelength range of one of: 480 nm+/−30 nm, 475 nm+/−20 nm, 530 nm+/−20 nm, or 650 nm+/−30 nm. One or both of the first lighted image and/or the second lighted image can be generated from one or more of the following light emitters: light-emitting diodes (LEDs), organic light-emitting diodes (OLEDs), transparent organic light-emitting diodes, micro-OLEDs, micro-LEDs, ionic liquids for electrochemical devices (iLEDs), micro-iLEDS, quantum dots, florescent lights, ambient light, or incandescent lights. One or both of the first lighted image and/or the second lighted image can be generated by light that has been filtered by one or more of: a bandpass filter, an interference filter, an absorption filter, a selective wavelengths filter, a notch filter, or a neutral density filter. The physiological response can be a generation of additional dopamine or serotonin in the eye of the user, in a brain of the user, or both. The physiological response can be one of, improved mitochondria function, or reduction of age-related inflammation in the eye of the user, the retina of the eye of the user, or both. The device can comprise one or more of a timer, a wireless communication component, or an alarm. The device can comprise one or more sensors for sensing and/or receiving biofeedback from the user. The device can be capable of delivering to the user in addition to light, one of, sound, smell, vibration, or combinations thereof. The device can be capable of receiving biofeedback from the user. Biofeedback can be increased blink rate, measuring blink rate, increased pupil size, and/or measuring pupil size. The light can modulate at a rate within the range of 5 Hz and 15 Hz.

A physiological response can be the generation of additional dopamine or serotonin in an eye of the user and/or in the brain of the user. Such additional dopamine in the retina of an eye of the user's eye can, one of, prevent, slow, or stop, myopia. Such additional dopamine or serotonin in the brain can help with many neurological dopamine deficiency disorders. The physiological response can also be the generation of improved mitochondria function or reduction of age-related inflammation in the eye in a section of the retina of the eye of the user. By way of example only, for dry AMD improved mitochondria function or reduction of age-related inflammation in the eye can occur around or within the macula area. For retinitis pigmentosa such improved mitochondria function or reduction of age-related inflammation in the eye can occur in the mid periphery or far periphery of the user's retina. For diabetic retinopathy such improved mitochondria function or reduction of age-related inflammation in the eye can occur in the mid periphery of the user's retina. Another physiological response can be the improvement of dry eye of a user of the devices taught herein, whereby the meibomian gland(s) are treated through the use of ocular photo-bio-stimulation therapy.

The device can comprise one or more of, a timer, wireless communication, or alarm. The ocular photo-bio-stimulation therapy can be timed not to exceed a certain amount of time. Should the time be exceeded an alarm can advise the user. The device can communicate with a remote third party so to keep the remote third party informed about the status of the ocular pho-bio-stimulation therapy. The device can receive biofeedback from the user. The biofeedback can be an enlarged pupil, or an increased blink rated, both of which can signal additional dopamine or serotonin being produced in the brain of the user. The device can deliver to the user one or more sounds, smell, or vibration, in addition to light.

The following are XR (can be one of AR, MR, VR, or Modified Reality) ocular photo-bio-stimulation embodiments taught herein.

Aspect 1: XR eyewear comprising a see-through near eye display comprising a micro-lens array, for ocular photo-bio-stimulation therapy (stimulating all or part of the retina for the purposes of obtaining a desired physiological response)

Said ocular photo-bio-stimulation therapy or treatment for stimulating one or more of, the optic nerve head, macula/foveal area, or peripheral retina.

Said XR eyewear can be one of, AR eyewear, MR eyewear, VR, or Modified Reality eyewear.

Optionally comprising a means to identify or measure a biomarker, such as by way of example only, blink rate or pupil enlargement.

Optionally comprising a filter or filters to reduce or block high energy blue wavelengths of light within the wavelength ranges of one or both: 449 nm-421 nm and 419 nm-400 nm.

Optional timer.

Optional alarm or component to alert the user; and

Optional communication means for communicating to a third party.

Aspect 2: XR (can be one of AR, MR, VR, or Modified Reality) eyewear comprising a see-through near eye display, devoid of a microlens array, for ocular photobio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of AR eyewear, MR eyewear, VR, or Modified Reality eyewear;

Optionally comprising a means to identify or measure a biomarker, such as by way of example only, blink rate or pupil enlargement;

Optionally comprising a filter or filters to reduce or block blue light high energy wavelengths of light within the wavelength ranges of one or both: 449 nm-421 nm and 419 nm-400 nm;

Optional timer;

Optional alarm or component to alert the user; and

Optional communication means for communicating with a third party.

Aspect 3: XR (can be one of AR, MR, VR, or Modified Reality) eyewear comprising a non-see-through near eye display comprising a microlens array, for ocular photo-bio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of AR eyewear, MR eyewear, VR, or Modified Reality eyewear;

Optionally comprising a means to identify or measure a biomarker, such as by way of example only, blink rate or pupil enlargement;

Optionally comprising a filter or filters to reduce or block blue light high energy wavelengths of light within the wavelength ranges of one or both: 449 nm-421 nm and 419 nm-400 nm;

Optional timer;

Optional alarm or component to alert the user; and

Optional communication means for communicating with a third party.

Aspect 4: (Can be one of AR, MR, VR, or Modified Reality) XR eyewear comprising a non-see-through near eye display, devoid of a microlens array, for ocular photo-bio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of, AR eyewear, MR eyewear, VR, or Modified Reality eyewear;

Optionally comprising a means to identify or measure a biomarker, such as by way of example only, blink rate or pupil enlargement;

Optionally comprising a filter or filters to reduce or block certain blue light high energy wavelengths of light within the wavelength ranges of one or both: 449 nm-421 nm and 419 nm-400 nm;

Optional timer;

Optional alarm or component to alert the user; and

Optional communication means for communicating with a third party.

Aspect 5: (Can be one of AR, MR, VR, or Modified Reality) XR eyewear comprising a waveguide, for ocular photo-bio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of, AR eyewear, MR eyewear, VR, or Modified Reality eyewear;

Said XR eyewear comprising a means to identify or measure a biomarker, such as by way of example only, blink rate or pupil enlargement;

Optionally comprising a filter or filters to reduce or block blue light high energy wavelengths of light within the wavelength ranges of one or both: 449 nm-421 nm and 419 nm-400 nm;

Optional timer;

Optional alarm or component to alert the user; and

Optional communication means for communicating with a third party.

An XR (can be one of AR, MR, VR, or Modified Reality) eyewear near eye display diameter can be any dimension within the range of 10 mm to 70 mm in diameter. The near eye display can provide focused or a non-focused virtual image. For viewing a focused clear virtual image, a micro-lens array can be optically aligned with the near eye display and the combination is thus utilized. For viewing a non-focused virtual image such a micro-lens array, in certain embodiments a micro-lens array is not utilized. In other embodiments a defocused micro-lens array can be utilized and in still other embodiments a light scattering micro-lens array can be utilized. The illumination intensity from the near eye display can be within the range of 300 lux to 20,000 lux. Display Pixels can be comprised by way of example only, one of, OLEDs, TOLEDs, microOLEDs, iLeds, Quantum Dots, and/or LEDs. The near eye display can be see-through or non-see through (opaque). For VR the near eye display can be a non-see-through near eye display. For AR and MR, the near eye display can be a see-through near eye display.

For viewing a real image with XR (AR, MR, or Modified Reality) while utilizing a near eye display, the near eye display needs to be see-through and thus is transparent or largely transparent. This permits, along with the proper alignment of a microlens array, the ability to see a real distance image through the see-through near eye display and also that of the micro-lens array. The illumination intensity from the near eye display can be within the range of 300 lux to 20,000 lux. Display Pixels can be comprised by way of example only, one of: OLEDs, TOLEDs, microOLEDs, iLeds, Quantum Dots, or LEDs. In certain see-through near eye display embodiments the wearer/user views the real image between the pixels and the microlenses of the micro-lens array. In other embodiments the viewer views the real image through transparent pixels.

An embodiment includes an XR device (can be one of AR, MR, VR, or Modified Reality) comprising a first image and a second image, wherein the first image is generated by a first light, wherein the second image is generated by a second light, wherein one of the lights comprise a band of wavelengths of light having a transmission peak 2X or greater than any other transmission peak of visible light for that particular light, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 830 nm+/−30 nm, and wherein the wavelengths of light that fall within the peak transmission band stimulates portions of the retina peripheral to macula of the user of the XR device as the user views an image with the XR device.

An embodiment includes an XR device comprising a first image and a second image, wherein the first image is generated by a first light, wherein the second image is generated by a second light, wherein one of the lights comprise a band of wavelengths having a predominant transmission with at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 830 nm+/−30 nm, and wherein the wavelengths of light that fall within the predominant transmission band stimulates the macula or fovea of the user of the XR device as the user views an image with the XR device.

An embodiment includes an XR device comprising a first image and a second image, wherein the first image is moved relative to the second image, wherein the first image is generated by a first light (or absence thereof), wherein the second image is generated by a second light (or absence thereof), wherein the predominant transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, and wherein the wavelengths of light that fall within the predominant transmission band paint portions of the retina peripheral to macula of the user of the XR device as the user views an image with the XR device.

In aspects, the first image can move relative to a stationary second image. The first image and the second image can both move. The first image can be a real image fixated on by the fovea of the user's eye. The second image can be a virtual image. The second image can paint portions of the far peripheral retina with light. The second image can move relative to a stationary first image. The first image can be a virtual image. The second image can be a real image fixated on by the fovea of the user's eye. The first image can paint portions of the far peripheral retina with light.

The XR device can be a VR or Modified Reality device. The first and second images can be virtual images. The first light can form a real image. The first light can form a virtual image. The second light can form a real image. The second light can form a virtual image. Both the first and second light can form two virtual images. The first light can be focused light. The second light can be defocused light. The first light can be defocused light. The second light can be focused light. The first light can be filtered light. The second light can be filtered light. Wavelengths can be within the light wavelength band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 830 nm+/−30 nm, and can be generated by way of the use one or more of: interference filter, absorption filter, neutral density filter, bandpass filter, notch filter, and/or selective wavelength filter.

An image movement can be continuous. An image movement can be intermittent. An image movement can be periodic. The first light can be generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, or electronic display. The second light can be generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, or electronic display. The first image can modulate within the range of one of 10 Hz+20 Hz or 40 Hz+/−10 Hz or 40 Hz+/−20 Hz. The second image can modulate within the range of 10 Hz+20 Hz or 40 Hz+/−10 Hz or 40 Hz+/−20 Hz. The first image can flicker. The second image can flicker. The first light can flicker. The second light can flicker. The first light can have an intensity of 300 lux or greater. The second light can have an intensity of 300 lux or greater. The XR device can provide two or more of the following, light, color, sound, smell.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purposes only.

It is to be understood that while certain of the illustrations and figure may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. A wearable eyewear device comprising a filtered lens or filtered optic, wherein the filtered lens or filtered optic provides a light transmission of 40% or more of ocular photo-bio-stimulation light through and measured within a light wavelength range of at least one of 480 nm+/−30 nm or 500 nm+/−20 nm, to an eye of a wearer of the wearable eyewear device, wherein the filtered lens or filtered optic further provides a visible light transmission (VLT) of 30% or less, and wherein the filtered lens or filtered optic provides for a visible light transmission percentage for a light wavelength range of 451 nm-495 nm that is 1.5 times or greater than a visible light transmission percentage for a light wavelength range of 496 nm-570 nm, and wherein a visible light transmission percentage for the light wavelength range of 496 nm-570 nm is 2.5 times or greater than a visible light transmission percentage for a light wavelength range of 571 nm-780 nm.

2. The wearable eyewear device of claim 1, wherein the ocular photo-bio-stimulation light transmitted by the filtered lens or filtered optic increases a production of dopamine, serotonin, or both, in an eye and/or a brain of the wearer of the wearable eyewear device as compared to conventional sunglasses.

3. The wearable eyewear device of claim 1, wherein the wearable eyewear device can be utilized on its own for daily wear and is a first eyewear, or wherein the first eyewear fits over, behind, or around, a second eyewear frame or a lens of the second eyewear frame, or wherein the wearable eyewear device is supported by or releasably attachable to the second eyewear frame or the lens of the second eyewear frame.

4. The wearable eyewear device of claim 3, wherein the eyeglass lens of the wearable device or the second eyewear frame comprises a central zone for correcting distance vision of the wearer of the wearable eyewear device, and wherein the eyeglass lens of the wearable device or the second eyewear frame comprises or is a lens comprising one or more of: H.A.L.T. technology (Highly Aspheric Lenslet Target), D.I.M.S. technology (Defocus Incorporated Multiple Segments), alternating optical rings for focus and defocus, light dispersion or diffusion, increased minus optical power of a peripheral zone of the eyeglass lens of the second eyewear frame compared to an optical power of the central zone, or a myopia control lens.

5. The wearable eyewear device of claim 3, wherein the eyeglass lens of the wearable device or the second eyewear frame comprises one or more of: rings of optical defocus, Fresnel rings, chromatic aberration focused lens technology, aspheric lenslets, micro-lenslets, a lenslet micro-array, nanoparticles or micro structured materials, or optical islands causing defocus or lack of focus.

6. The wearable eyewear device of claim 3, wherein the eyeglass lens of the second eyewear frame comprises optical power, and wherein the filtered lens or filtered optic of the wearable eyewear device comprises a plano optical power in a central zone.

7. The wearable eyewear device of claim 3, wherein the lens of the second eyewear frame corrects a wearer's vision, wherein the first eyewear fits around or over the second eyewear frame or the lens of the second eyewear frame, or wherein the first eyewear is supported by or attached to the second eyewear frame or the lens of the second eyewear frame.

8. The wearable eyewear device of claim 1, wherein the filtered lens or filtered optic comprises one or more of: an interference filter, an absorption filter, a light absorber, dye, a neutral density filter, a bandpass filter, a notch filter, or blue light filter.

9. The wearable eyewear device of claim 1, wherein the filtered lens or filtered optic primarily filters light within the light wavelength range of 480 nm+/−30 nm, and also filters light within light wavelength ranges of 580 nm+/−20 nm or 600 nm+/−30 nm, and wherein the filtered lens or filtered optic comprises a reddish-brown color tone or a greenish color tone.

10. The wearable eyewear device of claim 1, wherein the wearable eyewear device is one of: fit-over eyewear, disposable eyewear, clip-on eyewear, magnetically attachable eyewear, pressure-mounted eyewear, rollable eyewear, statically attachable eyewear, or eyewear.

11. The wearable eyewear device of claim 1, wherein the wearable eyewear device is sunglasses.

12. The wearable eyewear device of claim 1, wherein the filtered lens or filtered optic has an optical power or is plano (devoid of optical power).

13. The wearable eyewear device of claim 1, wherein the light intensity of the transmitted wavelengths within the range of 480 nm+/−30 nm or 500 nm+/−20 nm that passes through a last surface of the filtered lens or filtered optic closest to an eye of the wearer is 300 lux or greater.

14. The wearable eyewear device of claim 1, wherein ocular photo-bio-stimulation light transmitted through the filtered lens or filtered optic increases choroidal thickness and/or reduces or slows axial elongation of an eye of the wearer of the wearable eyewear device.

15. The wearable eyewear device of claim 1, wherein the ocular photo-bio-stimulation light transmitted through the filtered lens or filtered optic slows down myopia progression of an eye of the wearer of the wearable eyewear device.

16. The wearable eyewear device of claim 1, wherein the ocular photo-bio-stimulation light transmitted through the filtered lens or filtered optic excites rhodopsin and/or melanopsin of an eye of the wearer of the wearable eyewear device.

17. The wearable eyewear device of claim 1, further comprising one or more of: a timer, an alarm, a sound alarm, a vibration alarm, a light alarm, a light switch, wired or wireless communication to a remote third party, a computer processing unit, a sensor(s) for monitoring a physiological response of the wearer, or one or more sensors providing biofeedback of or from the wearer.

18. The wearable eyewear device of claim 1, further comprising a biofeedback component, wherein the biofeedback is a measurement of a size of a pupil or a blink rate of the wearer.

19. The wearable eyewear device of claim 1, wherein the filtered lens or filtered optic comprises an imbibed tint or a dye.

20. The wearable eyewear device of claim 1, wherein the filtered lens or filtered optic comprises a deposition coating or spin coating.

21. The wearable eyewear device of claim 1, wherein the filtered lens or filtered optic is a single vision lens or single vision optic or a multifocal lens or multifocal optic.

22. The wearable eyewear device of claim 1, wherein the filtered lens or filtered optic comprises a surface cast layer that filters light.

23. The wearable eyewear device of claim 1, wherein the filtered lens or filtered optic comprises a progressive addition lens topography.

24. The wearable eyewear device of claim 1, wherein the wearable eyewear device is one of spectacle eyewear, extended reality (XR) eyewear, modified reality eyewear, a Fresnel lens or optic, a contact lens, an intraocular lens, or a corneal implant.

25. The wearable eyewear device of claim 1, wherein the filtered lens or filtered optic comprises a blue light transmission percentage for the light wavelength range of 451 nm-495 nm that is 1.5 times or greater than the visible light transmission (VLT) through the filtered lens or filtered optic, and wherein the blue light transmission percentage is 1.5 times or greater than a green light transmission percentage within the range of 496 nm-570 nm.

26. The wearable eyewear device of claim 1, wherein the filtered lens or filtered optic complies with traffic signal light standards so that a wearer of the wearable eyewear device can sufficiently identify colors of stop lights, traffic lights, and/or other road signs or signals.

27. The wearable eyewear device of claim 1, further comprising one or more of: H.A.L.T. technology (Highly Aspheric Lenslet Target); D.I.M.S. technology (Defocus Incorporated Multiple Segments); alternating optical rings for focus and defocus; Fresnel optics or Fresnel rings; light dispersion or diffusion; the filtered lens or optic, wherein the filtered lens or optic has a central zone and at least one peripheral zone, wherein the at least one peripheral zone has one or more of increased minus optical power or increased plus optical power when compared to an optical power of the central zone; or a myopia control lens.

28. The wearable eyewear device of claim 1, wherein the photo-bio-stimulation light is emitted from at least one of: a light emitter, light emitters, light-emitting diodes ("LEDs"), organic LEDs (OLEDs), transparent organic LEDs, micro-organic LEDs (micro-oLEDs), micro-LEDs, ionic liquids for electrochemical devices ("iLEDs"), micro-iLEDSs, organic LEDs, quantum dots, fluorescent light, incandescent light, particles that fluoresce, ambient light, sunlight, or an electronic display.

* * * * *